United States Patent [19]
Galemmo, Jr. et al.

[11] Patent Number: 5,998,424
[45] Date of Patent: Dec. 7, 1999

[54] INHIBITORS OF FACTOR XA WITH A NEUTRAL P1 SPECIFICITY GROUP

[75] Inventors: Robert A. Galemmo, Jr., Collegeville, Pa.; Celia Dominguez, Westlake Village, Calif.; John M. Fevig, Lincoln University, Pa.; Qi Han, Wilmington, Del.; Patrick Y. Lam, Chadds Ford, Pa.; Donald J. P. Pinto, Newark, Del.; James R. Pruitt, Landenberg, Pa.; Mimi L. Quan, Newark, Del.

[73] Assignee: DuPont Pharmaceuticals Company, Wilmington, Del.

[21] Appl. No.: 09/099,752

[22] Filed: Jun. 18, 1998

Related U.S. Application Data

[60] Provisional application No. 60/050,219, Jun. 19, 1997, and provisional application No. 60/076,691, Feb. 27, 1998.

[51] Int. Cl.$^6$ .................. A01N 43/54; C07D 403/12; C07D 211/32; C07D 277/64
[52] U.S. Cl. .................. 514/269; 514/326; 514/365; 514/367; 514/400; 514/406; 544/295; 546/272.7; 546/190; 548/180; 548/200; 548/338.1; 548/374.1
[58] Field of Search .............. 548/374.1, 338.1; 544/295; 514/269, 406; 546/190

[56] References Cited

U.S. PATENT DOCUMENTS

| | | | |
|---|---|---|---|
| 4,214,090 | 7/1980 | Happatz | 548/377 |
| 4,950,668 | 8/1990 | Okada et al. | 514/232.2 |
| 5,082,949 | 1/1992 | Sohn et al. | 548/378 |
| 5,550,147 | 8/1996 | Matsuo et al. | 514/406 |
| 5,677,319 | 10/1997 | Chihiro et al. | 514/365 |

FOREIGN PATENT DOCUMENTS

| | | |
|---|---|---|
| 9676985 | 5/1997 | Australia . |
| 4247081 | 3/1992 | Japan . |
| 9732583 | 9/1997 | WIPO . |

OTHER PUBLICATIONS

Jaszberenyi et al., Enzyme Inhibitor Interactions, Sejtosztodas Farmakol. 10(1) pp. 75–92 (see abstract), Dec. 1992.

*Primary Examiner*—Johann Richter
*Assistant Examiner*—Dominic Keating
*Attorney, Agent, or Firm*—David H. Vance

[57] ABSTRACT

The present application describes inhibitors of factor Xa with a neutral P1 specificity group of formula I:

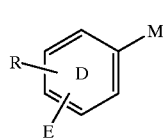

I or pharmaceutically acceptable salt forms thereof, wherein R and E may be groups such as methoxy and halo.

23 Claims, No Drawings

INHIBITORS OF FACTOR XA WITH A NEUTRAL P1 SPECIFICITY GROUP

This application is a continuation of U.S. Provisional Application Ser. Nos. 60/050,219 filed Jun. 19, 1997 and 60/076,691 filed Feb. 27, 1998.

FIELD OF THE INVENTION

This invention relates generally to novel inhibitors of factor Xa with a neutral P1 specificity group, pharmaceutical compositions containing the same, and methods of using the same as anticoagulant agents for treatment and prevention of thromboembolic disorders.

BACKGROUND OF THE INVENTION

WO 96/28427 describes benzamidine anticoagulants of the formula:

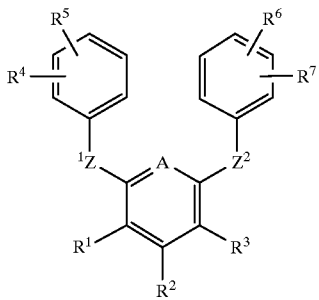

wherein $Z^1$ and $Z^2$ are O, N(R), S or $OCH_2$ and the central ring may be phenyl or a variety of heterocycles. The presently claimed compounds do not contain the $Z^1$ linker or the substitution pattern of the above compounds.

WO 95/13155 and PCT International Application US 96/07692 describe isoxazoline and isoxazole fibrinogen receptor antagonists of the formula:

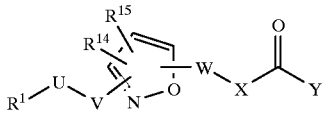

wherein $R^1$ may be a basic group, U—V may be a six-membered aromatic ring, W—X may be a variety of linear or cyclic groups, and Y is an oxy group. Thus, these compounds all contain an acid functionality (i.e., W—X—C(=O)—Y). In contrast, the presently claimed compounds do not contain such an acid functionality.

EP 0,513,387 depicts active oxygen inhibitors which are oxazoles or thiazoles of the formula:

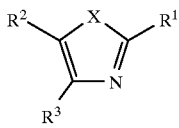

wherein X is O or S, $R^2$ is preferably hydrogen, and both $R^1$ and $R^3$ are substituted cyclic groups, with at least one being phenyl. The presently claimed invention does not relate to these types of oxazoles or thiazoles.

WO 95/18111 addresses fibrinogen receptor antagonists, containing basic and acidic termini, of the formula:

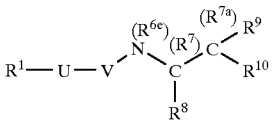

wherein $R^1$ represents the basic termini, U is an alkylene or heteroatom linker, V may be a heterocycle, and the right hand portion of the molecule represents the acidic termini. The presently claimed compounds do not contain the acidic or basic termini of WO 95/18111.

In U.S. Pat. No. 5,463,071, Himmelsbach et al depict cell aggregation inhibitors which are 5-membered heterocycles of the formula:

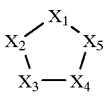

wherein the heterocycle may be aromatic and groups A-B-C-and F-E-D-are attached to the ring system. A-B-C-can be a wide variety of substituents including a basic group attached to an aromatic ring. The F-E-D-group, however, would appear to be an acidic functionality which differs from the present invention. Furthermore, use of these compounds as inhibitors of factor Xa is not discussed.

Baker et al, in U.S. Pat. No. 5,317,103, discuss 5-$HT_1$ agonists which are indole substituted five-membered heteroaromatic compounds of the formula:

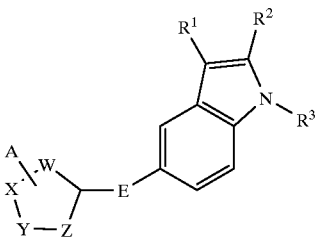

wherein $R^1$ may be pyrrolidine or piperidine and A may be a basic group including amino and amidino. Baker et al, however, do not indicate that A can be a substituted ring system like that contained in the presently claimed heteroaromatics.

Baker et al, in WO 94/02477, discuss 5-$HT_1$ agonists which are imidazoles, triazoles, or tetrazoles of the formula:

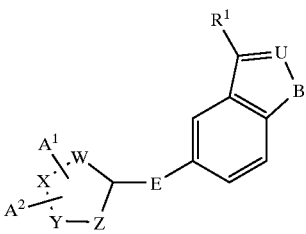

wherein $R^1$ represents a nitrogen containing ring system or a nitrogen substituted cyclobutane, and A may be a basic group including amino and amidino. But, Baker et al do not indicate that A can be a substituted ring system like that contained in the presently claimed heteroaromatics.

Tidwell et al, in *J. Med. Chem.* 1978, 21(7), 613–623, describe a series of diarylamidine derivatives including 3,5-bis (4-amidinophenyl)isoxazole. This series of compounds was tested against thrombin, trypsin, and pancreatic kallikrein. The presently claimed invention does not include these types of compounds.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of pro-thrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel inhibitors of factor Xa with a neutral P1 specificity group or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

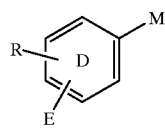

I or pharmaceutically acceptable salt forms thereof, wherein D, E, M, and R are defined below, are effective factor Xa inhibitors.

DETAILED DESCRIPTION OF PREFERRED EMBODIMENTS

[1] Thus, in a first embodiment, the present invention provides novel compounds of formula I:

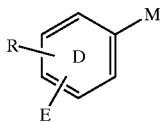

I or stereoisomers or pharmaceutically acceptable salts thereof, wherein;

ring D is phenyl or pyridyl:

E is selected from F, Cl, Br, I, OH, $C_{1-3}$ alkoxy, SH, $C_{1-3}$ alkyl-S, $S(O)R^{3b}$, $S(O)_2R^{3a}$, $S(O)_2NR^2R^{2a}$, and $OCF_3$;

R is selected from H, F, Cl, Br, I, $OR^3$, $SR^3$, $CO_2R^3$, $NO_2$, and $CH_2OR^3$;

alternatively, E and R combine to form methylenedioxy or ethylenedioxy;

M is selected from the group:

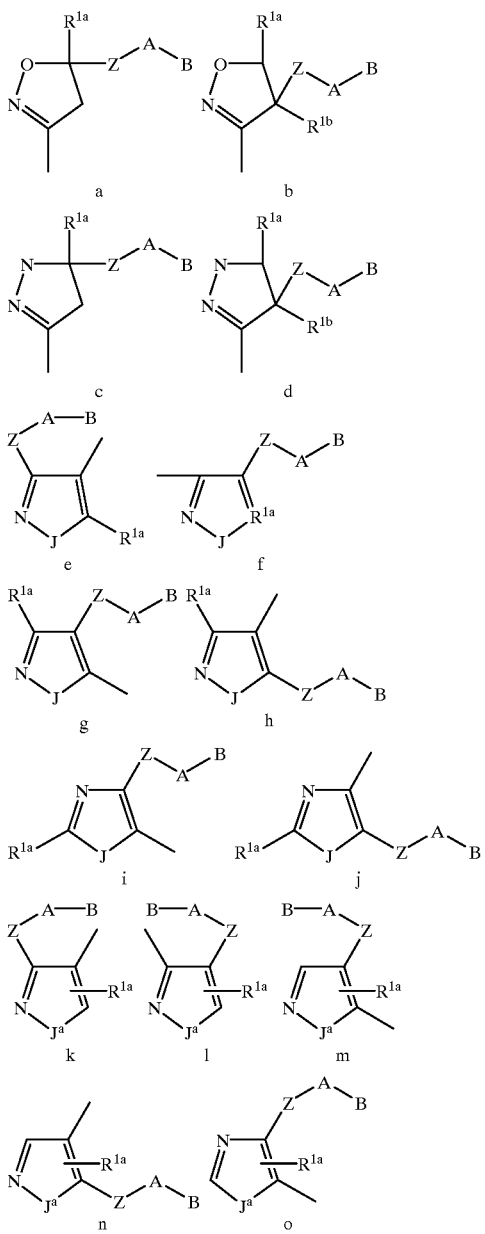

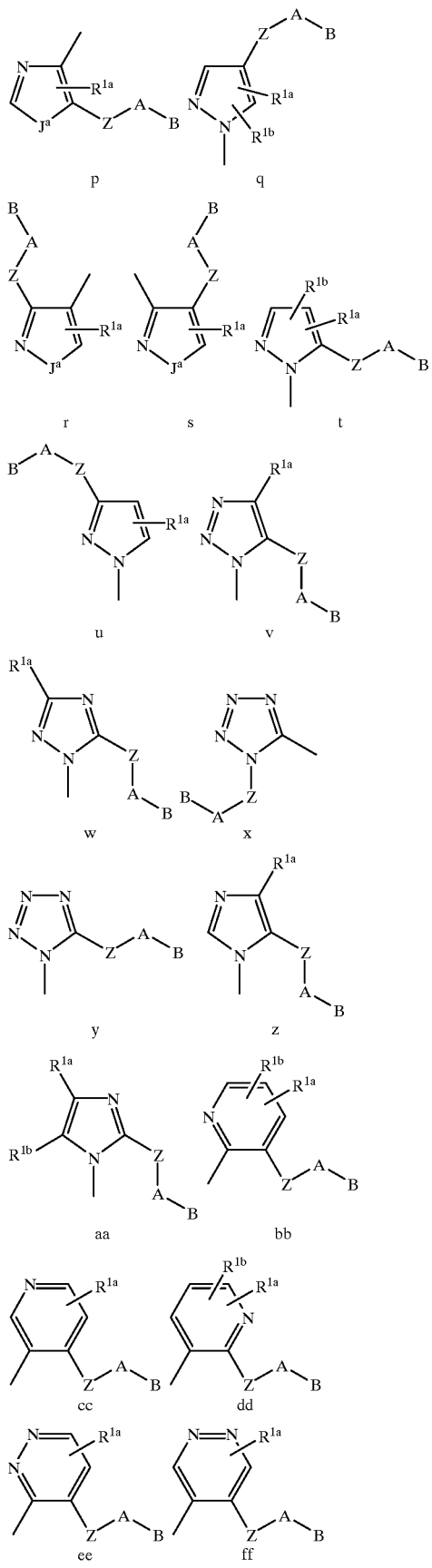
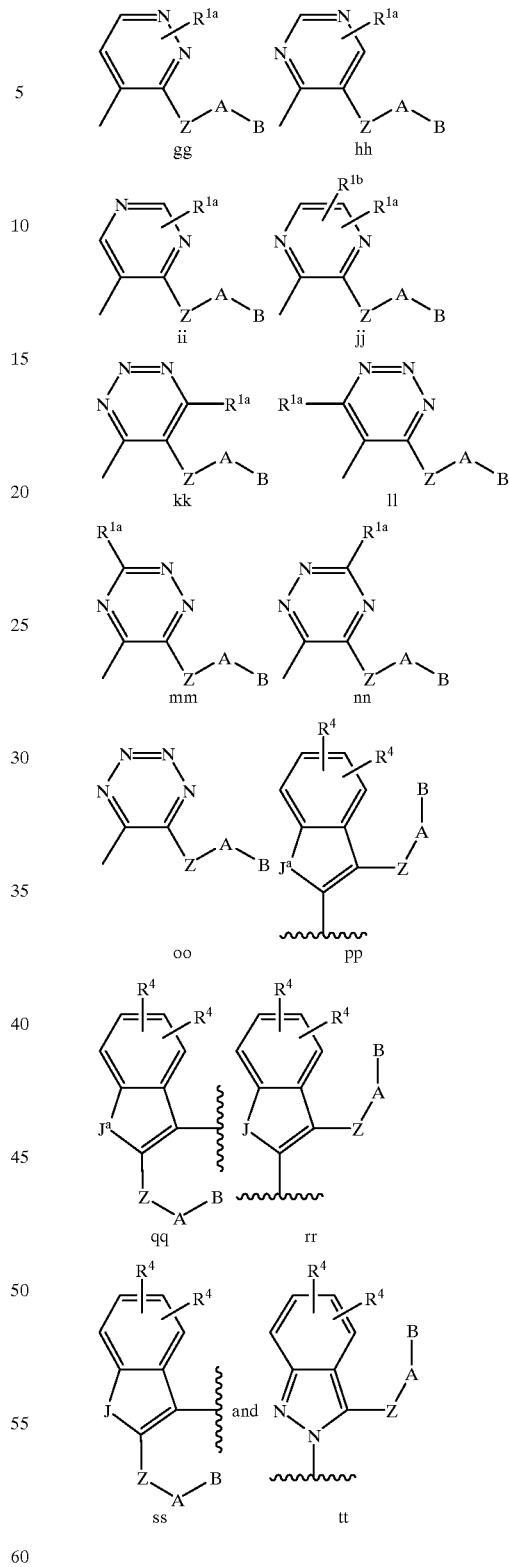
J is O or S;
$J^a$ is NH or $NR^{1a}$;
Z is selected from a bond, $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_r NR^3C(O)(CH_2)_r$, $(CH_2)_rOC(O)O(CH_2)_r$, $(CH_2)_rOC(O)NR^3(CH_2)_r$, $(CH_2)_rNR^3C(O)O(CH_2)_r$, $(CH_2)_rNR^3C(O)$ NR$^3$(CH$_2$)$_r$, (CH$_2$)$_r$S(O)$_p$(CH$_2$)$_r$, (CH$_2$)$_r$SO$_2$NR$^3$(CH$_2$)$_r$, (CH$_2$)$_r$NR$^3$SO$_2$(CH$_2$)$_r$, and (CH$_2$)$_r$NR$^3$SO$_2$NR$^3$(CH$_2$)$_r$, provided that Z does not form a N—N, N—O, N—S, NCH$_2$N, NCH$_2$O, or NCH$_2$S bond with ring M or group A;

R$^{1a}$ and R$^{1b}$ are independently absent or selected from —(CH$_2$)$_r$—R$^{1'}$, —CH=R$^{1'}$, NCH$_2$R$^{1''}$, OCH$_2$R$^{1''}$, SCH$_2$R$^{1''}$, NH(CH$_2$)$_2$(CH$_2$)$_r$R$^{1'}$, O(CH$_2$)$_2$(CH$_2$)$_r$R$^{1'}$, and S(CH$_2$)$_2$(CH$_2$)$_r$R$^{1'}$;

alternatively, R$^{1a}$ and R$^{1b}$, when attached to adjacent carbon atoms, together with the atoms to which they are attached form a 5–8 membered saturated, partially saturated or saturated ring substituted with 0–2 R$^4$ and which contains from 0–2 heteroatoms selected from the group consisting of N, O, and S;

alternatively, when z is C(O)NH and R$^{1a}$ is attached to a ring carbon adjacent to Z, then R$^{1a}$ is a C(O) which replaces the amide hydrogen of Z to form a cyclic imide;

R$^{1'}$ is selected from H, C$_{1-3}$ alkyl, F, Cl, Br, I, —CN, —CHO, (CF$_2$)$_r$CF$_3$, (CH$_2$)$_r$OR$^2$, NR$^2$R$^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, CH(=NR$^{2c}$)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocyclic residue substituted with 0–2 R$^4$, and 5–10 membered heterocyclic system containing from 1–4 heteroatoms selected from the group consisting of N, O, and S substituted with 0–2 R$^4$;

R$^{1''}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$; R$^2$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

R$^3$, at each occurrence, is selected from H, C$_{1-4}$ alkyl, and phenyl;

R$^{3a}$, at each occurrence, is selected from H, C$_{1-4}$ alkyl, and phenyl;

R$^{3b}$, at each occurrence, is selected from H, C$_{1-4}$ alkyl, and phenyl;

R$^{3c}$, at each occurrence, is selected from C$_{1-4}$ alkyl, and phenyl;

A is selected from:
C$_{3-10}$ carbocyclic residue substituted with 0-2 R$^4$, and
5–10 membered heterocyclic system containing from 1–4 heteroatoms selected from the group consisting of N, O, and S substituted with 0–2 R$^4$;

B is selected from: H, Y, and X—Y;

X is selected from C$_{1-4}$ alkylene, —CR$^2$(CR$^2$R$^{2b}$)(CH$_2$)$_t$—, —C(O)—, —C(=NR$^{1''}$)—, —CR$^2$(NR$^{1''}$R$^2$)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S(O)$_2$—, —NR$^2$S(O)$_2$CR$^2$R$^{2a}$—, —CR$^2$R$^{2a}$S(O)$_2$NR$^2$—, —NR$^2$S(O)$_2$NR$^2$—, —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)O—, —OC(O)NR$^2$—, —NR$^2$C(O)NR$^2$—, —NR$^2$—, NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from:
(CH$_2$)$_r$NR$^2$R$^{2a}$, provided that X—Y do not form a N—N, O—N, or S—N bond,
C$_{3-10}$ carbocyclic residue substituted with 0–2 R$^{4a}$, and 5–10 membered heterocyclic system containing from 1–4 heteroatoms selected from the group consisting of N, O, and S substituted with 0–2 R$^{4a}$;

R$^4$, at each occurrence, is selected from H, =O, (CH$_2$)$_r$OR$^2$, F, Cl, Br, I, C$_{1-4}$ alkyl, —CN, NO$_2$, (CH$_2$)$_r$NR$^2$R$^{2a}$, (CH$_2$)$_r$C(O)R$^{2c}$, N$^2$C(O)R$^{2b}$, C(O)NR$^2$R$^{2a}$, NR$^2$C(O)NR$^2$R$^{2a}$, CH(=NR$^2$)NR$^2$R$^{2a}$, CH(=NS(O)$_2$R$^5$)NR$^2$R$^{2a}$, NHC(=NR$^2$)NR$^2$R$^{2a}$, C(O)NHC(=NR$^2$)NR$^2$R$^{2a}$, SO$_2$NR$^2$R$^{2a}$, NR$^2$ SO$_2$NR$^2$R$^{2a}$, NR$^2$SO$_2$—C$_{1-4}$ alkyl, NR$^2$SO$_2$R$^5$, S(O)$_p$R$^5$, (CF$_2$)$_r$CF$_3$, NCH$_2$R$^{1''}$, OCH$_2$R$^{1''}$, SCH$_2$R$^{1''}$, N(CH$_2$)$_2$(CH$_2$)$_r$R$^{1'}$, O(CH$_2$)$_2$(CH$_2$)$_{tR}$$^{1'}$, and S(CH$_2$)$_2$(CH$_2$)$_r$R$^{1'}$, alternatively, one R$^4$ is a 5–6 membered aromatic heterocycle containing from 1–4 heteroatoms selected from the group consisting of N, O, and S;

provided that if B is H, then R$^4$ is other than tetrazole, C(O)-alkoxy, and C(O)NR$^2$R$^{2a}$;

R$^{4a}$, at each occurrence, is selected from H, =O, (CH$_2$)$_r$OR$^2$, (CH$_2$)$_r$—F, (CH$_2$)$_r$—Br, (CH$_2$)$_r$—Cl, I, C$_{1-4}$ alkyl, —CN, NO$_2$, (CH$_2$)$_r$NR$^2$R$^{2a}$, (CH$_2$)$_r$NR$^2$R$^{2b}$, (CH$_2$)$_r$C(O)R$^{2c}$, NR$^2$C(O)R$^{2b}$, C(O)NR$^2$R$^{2a}$, C(O)NH(CH$_2$)$_2$NR$^2$R$^{2a}$, NR$^2$C(O)NR$^2$R$^{2a}$, CH(=NR$^2$)NR$^2$R$^{2a}$, NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, C(O)NHSO$_2$—C$_{1-4}$ alkyl, NR$^2$SO$_2$R$^5$, S(O)$_p$R$^5$, and (CF$_2$)$_r$CF$_3$;

alternatively, one R$^{4a}$ is a 5–6 membered aromatic heterocycle containing from 1–4 heteroatoms selected from the group consisting of N, O, and S and substituted with 0–1 R$^5$;

R$^{4b}$, at each occurrence, is selected from H, =O, (CH$_2$)$_r$OR$^3$, F, Cl, Br, I, C$_{1-4}$ alkyl, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O)NR$^3$R$^{3a}$, CH(=NR$^3$)NR$^3$R$^{3a}$, NH$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—Cl$_{1-4}$ alkyl, NR$^3$SO$_2$CF$_3$, NR$^3$SO$_2$—phenyl, S(O)$_p$CF$_3$, S(O)$_p$—C$_{1-4}$ alkyl, S(O)$_p$—phenyl, and (CF$_2$)$_r$CF$_3$;

R$^5$, at each occurrence, is selected from CF$_3$, C$_{1-6}$ alkyl, phenyl substituted with 0–2 R$^6$, and benzyl substituted with 0–2 R$^6$;

R$^6$, at each occurrence, is selected from H, OH, (CH$_2$)$_r$OR$^2$, F, Cl, Br, I, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, CH(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

n is selected from 0, 1, 2, and 3;
m is selected from 0, 1, and 2;
p is selected from 0, 1, and 2;
r is selected from 0, 1, 2, and 3;
s is selected from 0, 1, and 2; and,
t is selected from 0 and 1.

[2] In a preferred embodiment, the present invention provides novel compounds, wherein M is selected from the group:

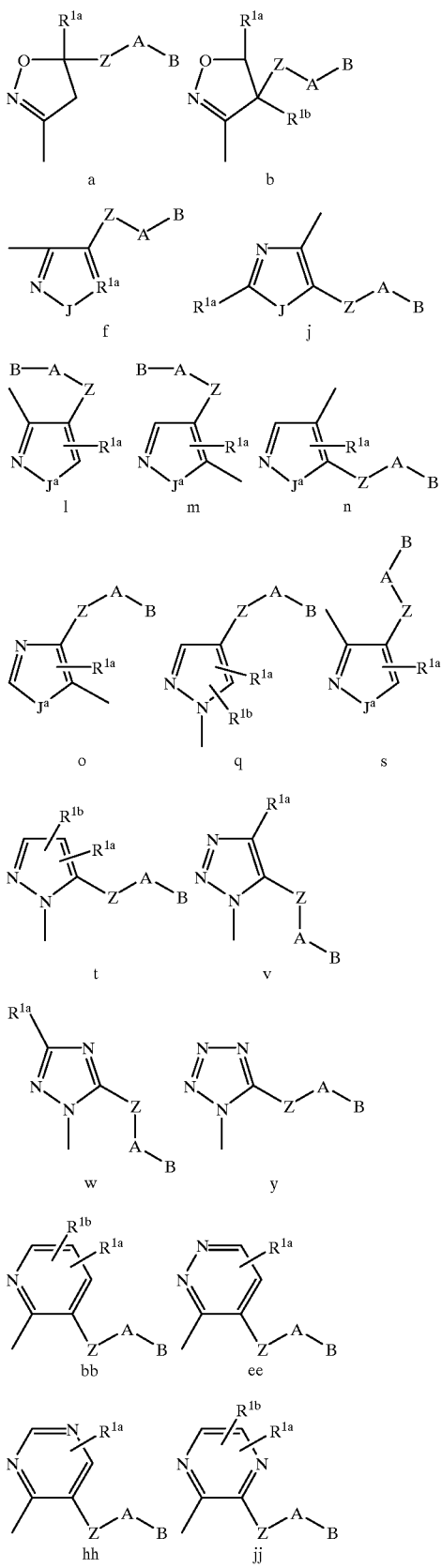

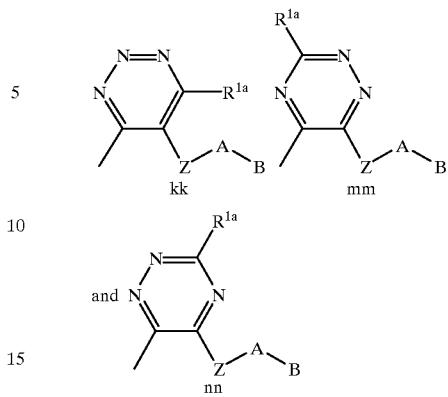

Z is selected from $(CH_2)_rC(O)(CH_2)_r$, $(CH_2)_rC(O)O(CH_2)_r$, $(CH_2)_rC(O)NR^3(CH_2)_r$, $(CH_2)_rS(O)_p(CH_2)_r$, and $(CH_2)_rSO_2NR^3(CH_2)_r$; and, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

Y may also be selected from the following bicyclic heteroaryl ring systems:

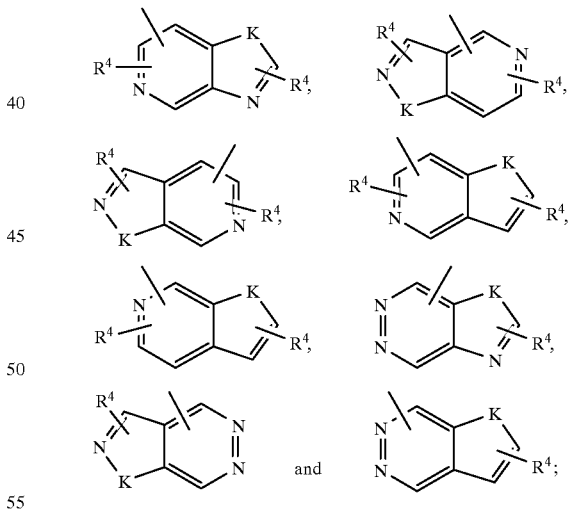

K is selected from O, S, NH, and N.

[3] In a more preferred embodiment, the present invention provides novel compounds of formula Ia or Ib:

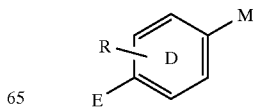

-continued

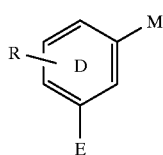

wherein;

ring D is phenyl or pyridyl:

E is selected from F, Cl, Br, and $C_{1-3}$ alkoxy;

R is selected from H, F, Cl, Br, $OR^3$, and $CH_2OR^3$;

H is selected from the group:

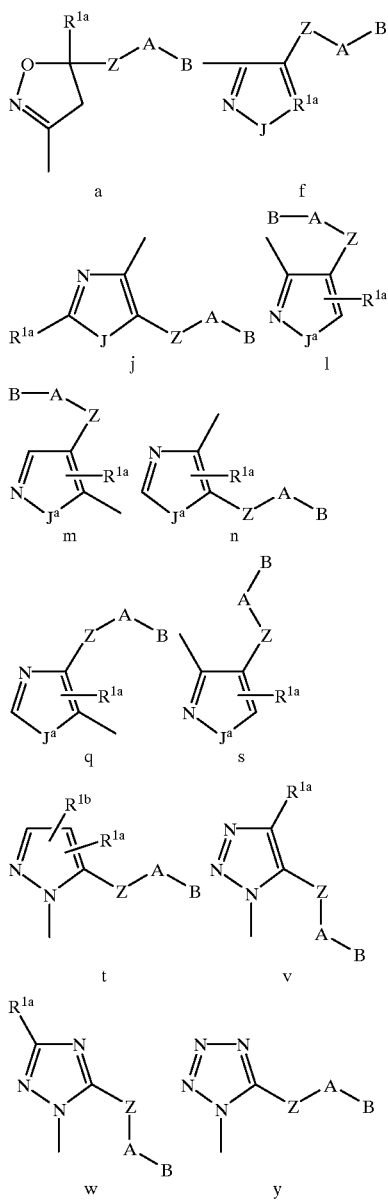

-continued

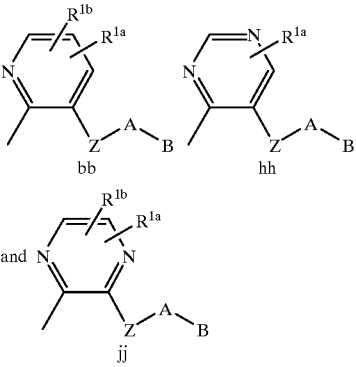

Z is selected from $(CH_2)_rC(O)(CH_2)_r$ and $(CH_2)_rC(O)NR^3(CH_2)_r$; and,

Y is selected from one of the following carbocyclic and heterocyclic systems which are substituted with 0–2 $R^{4a}$; phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole.

[4] In an even more preferred embodiment, the present invention provides novel compounds of formula Ia, wherein;

ring D is phenyl;

E is selected from F, Cl, Br, and $OCH_3$;

R is selected from H, F, Cl, and Br;

M is selected from the group:

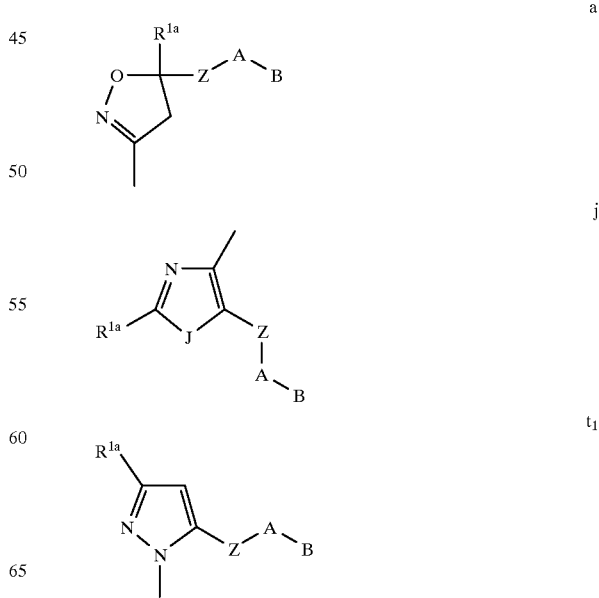

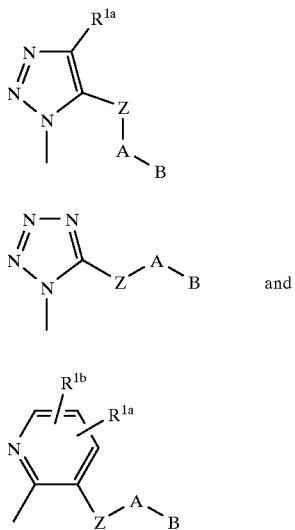

A is selected from:
C$_{5-6}$ carbocyclic residue substituted with 0–2 R$^4$, and 5–6 membered heterocyclic system containing from 1–4 heteroatoms selected from the group consisting of N, O, and S substituted with 0–2 R$^4$;

Y is selected from one of the following carbocyclic and heterocyclic systems which are substituted with 0–2 R$^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole;

R$^2$, at each occurrence, is selected from H, CF$_3$, C$_{1-6}$ alkyl, benzyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$, together with the atom to which they are attached, combine to form a ring selected from imidazolyl, morpholino, piperazinyl, pyridyl, and pyrrolidinyl, substituted with 0–2 R$^{4b}$;

R$^4$, at each occurrence, is selected from H, =O, OR$^2$, CH$_2$$_O$R$^2$, F, Cl, C$_{1-4}$ alkyl, NR$^2$R$^{2a}$, CH$_2$NR$^2$R$^{2a}$, C(O)R$^{2c}$, CH$_2$C(O)R$^{2c}$, C(O)NR$^2$R$^{2a}$, CH(=NR$^2$)NR$^2$R$^{2a}$, CH(=NS(O)$_2$R$^5$)NR$^2$R$^{2a}$, SO$_2$R$^{2a}$, NR$^2$SO$_2$—C$_{1-4}$ alkyl, S(O)$_2$R$^5$, and CF$_3$ provided that if B is H, then R$^4$ is other than tetrazole, C(O)-alkoxy, and C(O)NR$^2$R$^{2a}$;

R$^{4a}$, at each occurrence, is selected from H, =O, (CH$_2$)$_r$OR$^2$, F, Cl, C$_{1-4}$ alkyl, NR$^2$R$^{2a}$, CH$_2$NR$^2$R$^{2a}$, NR$^2$R$^{2b}$, CH$_2$NR$^2$R$^{2b}$, (CH$_2$)$_r$C(O)R$^{2c}$, NR$^2$C(O)R$^{2b}$, C(O)NR$^2$R$^{2a}$, C(O)NH(CH$_2$)$_2$NR$^2$R$^{2a}$, NR$^2$C(O)NR$^2$R$^{2a}$, SO$_2$NR$^2$R$^{2a}$, S(O)$_2$R$^5$, and CF$_3$; and, R$^{4b}$, at each occurrence, is selected from H, =O, (CH$_2$)$_r$OR$^3$, F, Cl, C$_{1-4}$ alkyl, NR$^3$R$^{3a}$, CH$_2$NR$^3$R$^{3a}$, C(O)R$^3$, CH$_2$C(O)R$^3$, C(O)OR$^{3c}$, C(O)NR$^3$R$^{3a}$, CH(=NR$^3$)NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(0)$_2$CF$_3$, S(O)$_2$—C$_{1-4}$ alkyl, S(O)$_2$-phenyl, and CF$_3$.

[5] In a further even more preferred embodiment, the present invention provides novel compounds selected from:
3-Methyl-1-phenyl-1H-pyrazole-5-(N-(2'-aminosulfonyl-[1,1']-biphen-4-yl))carboxyamide;
3-Methyl-1-(2-methoxy)phenyl-1H-pyrazole-5-(N-(2'-aminosulfonyl-[1,1']-biphen-4-yl)carboxyamide;
3-Methyl-1-(3-methoxy)phenyl-1H-pyrazole-5-(N-(2'-aminosulfonyl-[1,1']-biphen-4-yl)carboxyamide;
3-Methyl-1-(4-methoxy)phenyl-1H-pyrazole-5-(N-(2'-aminosulfonyl-[1,1']-biphen-4-yl)carboxyamide;
3-Methyl-1-(2-hydroxy)phenyl-1H-pyrazole-5-(N-(2'-aminosulfonyl-[1,1']-biphen-4-yl)carboxyamide;
3-Methyl-1-(3-hydroxy)phenyl-1H-pyrazole-5-(N-(2'-aminosulfonyl-[1,1']-biphen-4-yl)carboxyamide;
3-Methyl-1-(4-hydroxy)phenyl-1H-pyrazole-5-(N-(2'-aminosulfonyl-[1,1']-biphen-4-yl)carboxyamide;
3-Methyl-1-(4-methoxyphenyl)-1H-pyrazole-5-(N-(3-fluoro-(2'-aminosulfonyl-[1,1']-biphen-4-yl)carboxyamide;
3-Methyl-1-(4-methoxyphenyl)-1H-pyrazole-5-(N-(3-bromo-4-(2'-aminosulfonyl-[1,1']-biphen-4-yl)carboxyamide;
3-Methyl-1-(4-methoxyphenyl)-1H-pyrazole-5-(N-(3-iodo-(2'-aminosulfonyl-[1,1']-biphen-4-yl)carboxyamide;
3-Methyl-1-(4-methoxyphenyl)-1H-pyrazole-5-(N-(3-methyl-(2'-aminosulfonyl-[1,1']-biphen-4-yl)carboxyamide;
3-Methyl-1-(4-methoxyphenyl)-1H-pyrazole-5-(N-(4-N-carboxyldimethylamine)phenyl)carboxyamide;
3-Methyl-1-(4-methoxyphenyl)-1H-pyrazole-5-(N-(4-N-pyrrolidinocarbonyl)phenyl)carboxyamide;
3-Methyl-1-(4-methoxyphenyl)-1H-pyrazole-5-(N-(4-a-methyl-N-pyrrolidino)phenyl)carboxyamide;
3-Trifluoromethyl-1-(4-methoxyphenyl)-1H-pyrazole-5-(N-(2'-aminosulfonyl-[1,1']-biphen-4-yl)carboxyamide;
3-Trifluoromethyl-1-(4-methoxyphenyl)-1H-pyrazole-5-(N-(4-N-pyrrolidinocarbonyl)phenyl)carboxyamide;
3-Trifluoromethyl-1-(4-methoxyphenyl)-1H-pyrazole-5-(N-(5-(2-methanesulfonyl)phenyl)pyridin-2-yl)carboxyamide;
3-Trifluoromethyl-1-(4-methoxyphenyl)-1H-pyrazole-5-(N-(5-N-pyrrolidinocarbonyl)pyridin-2-yl)carboxyamide;
3-Methyl-1-(4-methoxyphenyl)-1H-pyrazole-5-(N-(5-N-pyrrolidinocarbonyl)pyridin-2-yl)carboxyamide;
3-Methyl-1-(4-methoxyphenyl)-1H-pyrazole-5-(N-(5-(2-sulfonamido)phenyl)pyridin-2-yl)carboxyamide;
3-Methyl-1-(4-methoxyphenyl)-1H-pyrazole-5-N-(4-(N-carboxyl-3-hydroxypyrrolidino)phenyl)carboxyamide;
2-Amino-4-(4-methoxyphenyl)-5-[(2'-aminosulfonyl-[1,1']-biphen-4-yl)aminocarbonyl]thiazole;
2-Bromo-4-(4-methoxyphenyl)-5-[(2'-aminosulfonyl-[1,1']-biphen-4-yl)aminocarbonyl]thiazole;
2-Chloro-4-(4-methoxyphenyl)-5-[(2'-aminosulfonyl-[1,1']-biphen-4-yl)aminocarbonyl]thiazole;

2-Chloro-4-(4-phenoxy)-5-[(2'-aminosulfonyl-[1,1']-biphen-4-yl)aminocarbonyl]thiazole;

2-Methoxy-4-(4-methoxyphenyl)-5-[(2'-aminosulfonyl-[1,1']-biphen-4-yl)aminocarbonyl]thiazole;

2-Thiomethyl-4-(4-methoxyphenyl)-5-[(2'-aminosulfonyl-[1,1']-biphen-4-yl)aminocarbonyl]thiazole;

2-Methylsulfoxide-4-(4-methoxyphenyl)-5-[(2'-aminosulfonyl-[1,1']-biphen-4-yl)aminocarbonyl]thiazole;

2-Methylsulfone-4-(4-methoxyphenyl)-5-[(2'-aminosulfonyl-[1,1']-biphen-4-yl)aminocarbonyl]thiazole;

2-Cyano-4-(4-methoxyphenyl)-5-[(2'-aminosulfonyl-[1,1']-biphen-4-yl)aminocarbonyl]thiazole;

2-N,N-Dimethylamino-4-(4-methoxyphenyl)-5-[(2'-aminosulfonyl-[1,1']-biphen-4-yl)aminocarbonyl]thiazole;

2-(1-Pyrrole)-4-(4-methoxyphenyl)-5-[(2'-aminosulfonyl-[1,1']-biphen-4-yl)aminocarbonyl]thiazole;

3-(4-Methoxyphenyl)-5-[5-(2'-aminosulfonylphenyl-1-yl)pyridin-2-yl]aminocarbonyl-5-carbomethoxymethyl-isoxazoline;

3-(4-Methoxyphenyl)-5-[5-(2'-aminosulfonylphenyl-1-yl)pyridin-2-yl]aminocarbonyl-5-carboxymethyl-isoxazoline;

3-(4-Methoxyphenyl)-5-[5-(2'-aminosulfonylphenyl-1-yl)pyridin-2-yl]aminocarbonyl-5-(N-carbomethoxymethyl)carboxamidomethyl-isoxazoline;

3-(4-Methoxyphenyl)-5-[5-(2'-aminosulfonylphenyl-1-yl)pyridin-2-yl]aminocarbonyl-5-(1,2,4-triazol-1-yl)methyl-isoxazoline;

1-(4-Methoxyphenyl)-5-[(2'-aminosulfonyl-[1,1']-biphen-4-yl)aminocarbonyl]tetrazole;

3-Methyl-1-(4-methoxy-3-chloro)phenyl-1H-pyrazole-5-(N-(2'-aminosulfonyl-[1,1']-biphen-4-yl)carboxyamide;

3-Methyl-1-(4-trifluoromethoxy)phenyl-1H-pyrazole-5-(N-(2'-aminosulfonyl-[1,1']-biphen-4-yl)carboxyamide;

1-(3-Bromophenyl)-3-methyl-1H-pyrazole-5-[(2'-aminosulfonyl-[1,1']-biphen-4-yl)carboxyamide;

1-(3-Iodophenyl)-3-methyl-1H-pyrazole-5-[(2'-aminosulfonyl-[1,1']-biphen-4-yl)carboxyamide;

1-(3,4-Methylenedioxanephenyl)-3-methyl-1H-pyrazole-5-[(2'-aminosulfonyl-[1,1']-biphen-4-yl)carboxyamide;

1-(4-Methoxyphenyl)-3-hydroxylmethylene-1H-pyrazole-5-(4'-pyrrolidinocarbonyl)anilide;

1-(4-Methoxyphenyl)-3-formaldehyde-1H-pyrazole-5-(4'-pyrrolidinocarbonyl)anilide;

1-(4-Methoxyphenyl)-5-(4'-pyrrolidinocarbonyl)anilide-3-pyrazolecarboxylic acid;

1-(4-Methoxyphenyl)-3-methylcarboxylate-1H-pyrazole-5-(4'-pyrrolidinocarbonyl)anilide;

1-(4'-Chlorophenyl)-3-methyl-1H-pyrazole-5-[(2'-aminosulfonyl-[1,1']-biphen-4-yl)carboxyamide;

1-(4'-Chlorophenyl)-3-methyl-1H-pyrazole-5-[(2'-aminosulfonyl-[1-pyridyl-1'-phenyl]-4-yl)carboxyamide;

1-(3',4'-Dichlorophenyl)-3-methyl-1H-pyrazole-5-[(2'-aminosulfonyl-[1,1']-biphen-4-yl)carboxyamide;

1-(3'-Chlorophenyl)-3-methyl-1H-pyrazole-5-[(2'-aminosulfonyl-[1,1']-biphen-4-yl)carboxyamide;

2-Amino-4-phenyl-5-[(2'-aminosulfonyl-[1,1']-biphen-4-yl)aminocarbonyl]thiazole;

2-Chloro-4-phenyl-5-[(2'-aminosulfonyl-[1,1']-biphen-4-yl)aminocarbonyl]thiazole;

2-Amino-4-[3-(bromo)-4-(fluoro)-phenyl]-5-[(2'-aminosulfonyl-[1,1']-biphen-4-yl)aminocarbonyl]thiazole;

2-Amino-4-[4-fluorophenyl]-5-[(2'-aminosulfonyl-[1,1']-biphen-4-yl)aminocarbonyl]thiazole;

2-Amino-4-[3-bromophenyl]-5-[(2'-aminosulfonyl-[1,1']-biphen-4-yl)aminocarbonyl]thiazole;

2-Chloro-4-[3-bromophenyl]-5-[(2'-aminosulfonyl-[1,1']-biphen-4-yl)aminocarbonyl]thiazole;

N-(2'-Aminosulfonyl-[1,1']-biphen-4-yl)-1-(4-methoxyphenyl)-3-(methylthio)pyrazole-5-carboxamide;

1-(4-Methoxyphenyl)-3-(methylsulfonyl)-N-(5-(2'-methylsulfonylphenyl)pyrimid-2-yl)pyrazole-5-carboxamide;

N-(2'-Aminosulfonyl-[1,1']-biphen-4-yl)-1-(4-methoxyphenyl)-3-(methylsulfonyl)-1H-pyrazole-5-carboxamide;

N-(4-Benzoylpyrrolidino)-1-(4-methoxyphenyl)-3-(methylthio)-1H-pyrazole-5-carboxamide;

1-(4-Methoxyphenyl)-N-(5-(2'-methylsulfonylphenyl)pyrimid-2-yl)-3-(methylthio)-1H-pyrazole-5-carboxamide;

N-(4-Benzoylpyrrolidino)-1-(4-methoxyphenyl)-3-(methylsulfonyl)-1H-pyrazole-5-carboxamide;

N-(2'-Aminosulfonyl-[1,1']-biphen-4-yl)-1-(4-methoxyphenyl)-3-(methoxymethyl)-1H-pyrazole-5-carboxamide;

N-(2'-Aminosulfonyl-[1,1']-biphen-4-yl)-1-(4-methoxyphenyl)-3-carbomethoxy-1H-pyrazole-5-carboxamide;

N-(2'-Aminosulfonyl-[1,1']-biphen-4-yl)-1-(4-methoxyphenyl)-3-(methylsulfonylmethyl)-1H-pyrazole-5-carboxamide;

3-Trifluoromethyl-1-(4-methoxyphenyl)-1H-pyrazole-5-(N-(5-(2-methanesulfonyl)phenyl)pyrimidin-2-yl)carboxyamide;

3-Methyl-1-(4-methoxyphenyl)-1H-pyrazole-5-N-(4-(N-carboxyl-2-carbomethoxypyrrolidino)phenyl)carboxyamide;

3-Methyl-1-(4-methoxyphenyl)-1H-pyrazole-5-N-(4-(N-carboxyl-3-aminopyrrolidino)phenyl)carboxyamide;

3-Methyl-1-(4-methoxyphenyl)-1H-pyrazole-5-N-(4-(N-carboxyl-3-methoxypyrrolidino)phenyl)carboxyamide;

3-Trifluoromethyl-1-(4-methoxyphenyl)-1H-pyrazole-5-(N-(5-(2-aminosulfonyl)phenyl)pyridin-2-yl)carboxyamide;

3-Trifluoromethyl-1-(4-methoxyphenyl)-1H-pyrazole-5-(N-(4-amidino)phenyl)carboxyamide;

3-Trifluoromethyl-1-(4-methoxyphenyl)-1H-pyrazole-5-(N-(4-(N-pyrrolidino)formylimino)phenyl)carboxyamide;

3-Trifluoromethyl-5-(N-(2'-aminosulfonyl-[1,1']-biphen-4-yl))-1-(4-methoxyphenyl)pyrrolo[3,4-d]pyrazole-4,6-(1H,5H)-dione;

3-Trifluoromethyl-1-(4-methoxyphenyl)-1H-pyrazole-5-carbomethoxy-(N-(2'-aminosulfonyl-[1,1']-biphen-4-yl))carboxyamide;

3-Trifluoromethyl-1-(4-methoxyphenyl)-1H-pyrazole-5-hydoxymethyl-(N-(2'-aminosulfonyl-[1,1']-biphen-4-yl))carboxyamide;

3-Trifluoromethyl-1-(4-methoxyphenyl)-1H-pyrazole-5-(N-2-fluoro(4-(N-pyrrolidino)formylimino)phenyl)carboxyamide;

3-Trifluoromethyl-1-(4-methoxyphenyl)-1H-pyrazole-5-(N-(4-(N-pyrrolidino)formyl-N-((2-propyl)methylcarbamoyl)imino)phenyl)carboxyamide;

3-Trifluoromethyl-1-(4-methoxyphenyl)-1H-pyrazole-5-(N-(4-(N-pyrrolidino)formyl-N-(methanesulfamoyl)imino)phenyl)carboxyamide;

3-Trifluoromethyl-1-(4-methoxyphenyl)-1H-pyrazole-5-(N-((4-amidino)phenyl)inethyl)carboxyamide;

3-Trifluoromethyl-1-(4-methoxyphenyl)-1H-pyrazole-5-(N-((4-(N-pyrrolidino)formylimino)phenyl)methyl)carboxyamide;

3-Trifluoromethyl-1-(4-methoxyphenyl)-1H-pyrazole-5-(N-((1-benzyl)piperidin-4-yl)carboxyamide;
3-Trifluoromethyl-1-(4-methoxyphenyl)-1H-pyrazole-5-(N-((1-(pyridin-2-yl)methyl)piperidin-4-yl)carboxyamide;
3-Trifluoromethyl-1-(4-methoxyphenyl)-1H-pyrazole-5-(N-(4-(2-methylimidazo-1-yl))phenyl)carboxyamide;
3-Methyl-(4-methoxy)phenyl-1H-pyrazole-5-(N-{4-(5-methyl-imidazol-1-yl}phenyl)carboxyamide;
3-Methyl-(4-methoxy)phenyl-1H-pyrazole-5-(N-{4-(4-methyl-imidazol-1-yl}phenyl)carboxyamide;
3-Trifluoromethyl-(4-methoxy)phenyl-1H-pyrazole-5-(N-{4-(5-carbomethoxy-imidazol-1-yl}phenyl)carboxyamide;
3-Trifluoromethyl-(4-methoxy)phenyl-1H-pyrazole-5-(N-{4-(5-carboxy-imidazo-1-yl}phenyl)carboxyamide;
1-(4'-Methoxyphenyl)-3-hydroxylmethyl-1H-pyrazole-5-N-(4'-pyrrolidinocarbonyl)phenyl)carboxyamide;
1-(4'-Methoxyphenyl)-3-formaldehyde-1H-pyrazole-5-N-(4'-(pyrrolidinocarbonyl)phenyl)carboxyamide;
1-(4'-Methoxyphenyl)-5-N-(4'-(pyrrolidinocarbonyl)anilide)-1H-pyrazol-3-yl-carboxylic acid;
1-(4'-Methoxyphenyl)-3-methylcarboxylate-1H-pyrazole-5-N-(4'-pyrrolidinocarbonyl)phenyl)carboxyamide;
1-(4'-Methoxyphenyl)-3-cyanomethyl-1H-pyrazole-5-N-(4'-pyrrolidinocarbonyl)phenyl)carboxyamide;
2-(1'-(4"-Methoxyphenyl)-5'-(4"-pyrrolidinyl-one)anilide-1H-pyrazol-3'-yl)acetic acid;
1-(4'-Methoxyphenyl)-3-bromomethyl-1H-pyrazole-5-N-(2'-aminosulfonyl-[1,1']-biphen-4-yl)carboxyamide;
1-(4'-Methoxyphenyl)-3-aminomethyl-1H-pyrazole-5-N-(2'-aminosulfonyl-[1,1']-biphen-4-yl)carboxyamide;
1-(4'-Methoxyphenyl)-3-(N-methylsulfonylamino)methyl-1H-pyrazole-5-N-(2'-aminosulfonyl-[1,1']-biphen-4-yl)carboxyamide;
1-(4'-Methoxyphenyl)-3-(imidazol-1-yl)methyl-1H-pyrazole-5-N-(2'-aminosulfonyl-[1,1']-biphen-4-yl)carboxyamide;
1-(4'-Methoxyphenyl)-3-hydroxylmethyl-1H-pyrazole-5-N-(2'-aminosulfonyl-[1,1']-biphen-4-yl)carboxyamide;
1-(4'-Methoxyphenyl)-3-trifluoroacetylhydroxylmethyl-1H-pyrazole-5-N-(2'-aminosulfonyl-[1,1']-biphen-4-yl)carboxyamide;
1-(4'-Methoxy-2'-methoxycarbonylphenyl)-3-trifluoromethyl-1H-pyrazole-5-N-(2'-methylsulfonyl-[1,1']-biphen-4-yl)carboxyamide;
1-(4'-Methoxy-2'-hydroxycarbonylphenyl)-3-trifluoromethyl-1H-pyrazole-5-N-(2'-methylsulfonyl-[1,1']-biphen-4-yl)carboxyamide;
1-(4'-Methoxy-2'-methoxycarbonylphenyl)-3-trifluoromethyl-1H-pyrazole-5-N-(2'-aminosulfonyl-[1,1']-biphen-4-yl)carboxyamide;
1-(4'-Methoxy-2'-hydroxycarbonylphenyl)-3-trifluoromethyl-1H-pyrazole-5-N-(2'-tert-butylaminosulfonyl-[1,1']-biphenyl)carboxyamide;
1-(4'-Methoxy-2'-hydroxycarbonylphenyl)-3-trifluoromethyl-1H-pyrazole-5-N-(2'-aminosulfonyl-[1,1']-biphen-4-yl)carboxyamide;
1-(4'-Methoxy-2'-hydroxylmethylphenyl)-3-trifluoromethyl-1H-pyrazole-5-N-(2'-aminosulfonyl-[1,1']-biphen-4-yl)carboxyamide;
1-(4'-Methoxyphenyl)-3-methyl-1H-pyrazole-5-N-(4'-sec-butyl)phenyl)carboxyamide;
1-(4'-Methoxyphenyl)-3-methyl-1H-pyrazole-5-N-(4'-(3"-methyl-3"-pyrazolin-5"-one-2"-yl)phenyl)carboxyamide;
1-(4'-Methoxyphenyl)-3-methyl-1H-pyrazole-5-N-(4'-(6"-methylbenzothiazol-2 "-yl)phenyl)carboxyamide;
1-(4'-Methoxyphenyl)-3-methyl-1H-pyrazole-5-N-(3',4'-dibromophenyl)carboxyamide;
1-(4'-Methoxyphenyl)-3-methyl-1H-pyrazole-5-N-(4'-n-butyl)phenyl)carboxyamide;
1-(4'-Methoxyphenyl)-3-methyl-1H-pyrazole-5-N-(4'-(4"-methylpiperidino)phenyl)carboxyamide;
1-(4'-Methoxyphenyl)-3-methyl-1H-pyrazole-5-N-(4'-(2"-methylimidazol-1"-yl)phenyl)carboxyamide;
3-Trifluoromethyl-1-(4-methoxyphenyl)-1H-pyrazole-5-(N-(4-carboxy(N-methylimidazo-2-yl)phenyl)carboxyamide;
3-Trifluoromethyl-1-(4-methoxyphenyl)-1H-pyrazole-5-(N-(4-hydroxymethyl(2-(imidazol-2-yl)phenyl)))carboxyamide;
3-Trifluoromethyl-1-(4-methoxyphenyl)-1H-pyrazole-5-(N-(4-hydroxymethyl(2-(1-benzyl-imidazol-2-yl)phenyl)))carboxyamide;
1-(4-Methoxyphenyl)-3-trifluoromethyl-1H-pyrazole-5-(N-(4-(2-carboxy(imidazol-2-yl)phenyl)))carboxyamide;
3-Trifluoromethyl-1-(4-methoxyphenyl)-1H-pyrazole-5-(N-(4-(N-(4-methoxyphenyl)amino-(2-thiazolyl)methyl)phenyl)))carboxyamide;
1-(4-Methoxyphenyl)-3-trifluoromethyl-1H-pyrazole-5-(N-(4-(2-carboxy-(4,5-dihyrothiazol-2-yl)phenyl)))carboxyamide;
1-(4-Methoxyphenyl)-3-trifluoromethyl-1H-pyrazole-5-N-4-(2-(4',5'-dihydro-1'H-imidazol-2'yl)phenyl)carboxyamide;
1-(4-Methoxyphenyl)-3-trifluoromethyl-1H-pyrazole-5-N-(4-(N-2'-aminoethylenecarboxyamide)phenyl)carboxyamide;
1-(4-Methoxyphenyl)-3-trifluoromethyl-1H-pyrazole-5-[4-(1,4,5,6-tetrahydro-pyrimid-2-yl)-phenyl]carboxyamide;
1-(4-Methoxyphenyl)-3-trifluoromethyl-1H-pyrazole-5-[4-(N-methyl-4,5,6-trihydro-pyrimid-2-yl)-phenyl]carboxyamide;
1-(4-Methoxyphenyl)-3-trifluoromethyl-1H-pyrazole-5-N-1-(2-fluoro-4-imadazolinephenyl)carboxyamide;
1-(4-Methoxyphenyl)-3-trifluoromethyl-1H-pyrazole-5-N-1-(2-fluoro-4-N-methylimadazolinephenyl)carboxyamide;
1-(4-Methoxyphenyl)-3-trifluoromethyl-1H-pyrazole-5-N-[4-(4,5-dihydro-1-N-methyl-imidazo-2-yl)phenyl]carboxyamide;
1-(4-Methoxyphenyl)-3-trifluoromethyl-1H-pyrazole-5-N-[4-carbonylguanidine)phenyl]carboxyamide;
1-(4-Methoxyphenyl)-3-trifluoromethyl-1H-pyrazole-5-N-[4-(pyrimidin-2-yl)phenyl]carboxyamide;
2-(Carboxyamide)-4-[(4-methoxy)phenyl]-5-[(2'-aminosulfonyl-[1,1']-biphen-4-yl)carboxyamide]thiazole;
2-(2-Methoxyethylamino)-4-[(4-methoxy)phenyl]-5-[(2'-aminosulfonyl-[1,1']-biphen-4-yl)carboxyamide]thiazole;
2-(3-Hydroxypropylamino)-4-[(4-methoxy)phenyl]-5-[(2'-aminosulfonyl-[1,1']-biphen-4-yl)carboxyamide]thiazole;
2-(2-Cyanoethylamino)-4-[(4-methoxy)phenyl]-5-[(2'-aminosulfonyl-[1,1']-biphen-4-yl)carboxyamide]thiazole;
2-(3-Methoxypropylamino)-4-[(4-methoxy)phenyl]-5-[(2'-aminosulfonyl-[1,1']-biphen-4-yl)carboxyamide]thiazole;
2-(N-b-Alanyl)-4-[(4-methoxy)phenyl]-5-[(2'-aminosulfonyl-[1,1']-biphen-4-yl)carboxyamide]thiazole;
2-(Isopropylamino)-4-[(4-methoxy)phenyl]-5-[(2'-aminosulfonyl-[1,1']-biphen-4-yl)carboxyamide]thiazole;
2-(1,3-Dihydroxy-2-propylamino)-4-[(4-methoxy)phenyl]-5-[(2'-aminosulfonyl-[1,1']-biphen-4-yl)carboxyamide]thiazole;
2-[(Methoxycarbonyl)methylamino]-4-[(4-methoxy)phenyl]-5-[(2'-aminosulfonyl-[1,1']-biphen-4-yl)carboxyamide]thiazole;

2-(N-Glycyl)-4-[(4-methoxy)phenyl]-5-[(2'-aminosulfonyl-[1,1']-biphen-4-yl)carboxyamide]thiazole;
1-[(4-Methoxy)phenyl]-3-(ethoxycarbonyl)-1H-pyrazole-5-[(4-(N-pyrrolidinocarbonyl)phenyl)carboxyamide;
1-[(4-Methoxy)phenyl]-3-(carboxyamide)-1H-pyrazole-5-[(4-(N-pyrrolidinocarbonyl)phenyl)carboxyamide;
1-[(4-Methoxy)phenyl]-3-[(2-hydroxyethyl)carboxyamide]-1H-pyrazole-5-[(4-(N-pyrrolidinocarbonyl)phenyl)carboxyamide;
1-[(4-Methoxy)phenyl)-1H-pyrazole-5-[(4-(N-pyrrolidinocarbonyl)phenyl)carboxyamide-3-hydroxamic acid;
1-[(4-Methoxy)phenyl]-3-[phenylcarboxyamide]-1H-pyrazole-5-[(4-(N-pyrrolidinocarbonyl)phenyl)carboxyamide;
1-[(4-Methoxy)phenyl]-3-[(3-hydroxypropyl)carboxyamide]-1H-pyrazole-5-[(4-(N-pyrrolidinocarbonyl)phenyl)carboxyamide;
1-[(4-Methoxy)phenyl]-3-[methylcarboxyamide]-1H-pyrazole-5-[(4-(N-pyrrolidinocarbonyl)phenyl)carboxyamide;
1-[(4-Methoxy)phenyl]-3-[(benzyl)carboxyamide]-1H-pyrazole-5-[(4-(N-pyrrolidinocarbonyl)phenyl)carboxyamide;
1-[(4-Methoxy)phenyl]-3-[(dimethyl)carboxyamide]-1H-pyrazole-5-[(4-(N-pyrrolidinocarbonyl)phenyl)carboxyamide;
1-[(4-Methoxy)phenyl]-3-[(phenylethyl)carboxyamide]-1H-pyrazole-5-[(4-(N-pyrrolidinocarbonyl)phenyl)carboxyamide;
1-[(4-Methoxy)phenyl]-3-[(2-hydroxyphenyl)carboxyamide]-1H-pyrazole-5-[(4-(N-pyrrolidinocarbonyl)phenyl)carboxyamide;
1-[(4-Methoxy)phenyl]-3-[(3-hydroxyphenyl)carboxyamide]-1H-pyrazole-5-[(4-(N-pyrrolidinocarbonyl)phenyl)carboxyamide;
1-[(4-Methoxy)phenyl]-3-[(4-hydroxyphenyl)carboxyamide]-1H-pyrazole-5-[(4-(N-pyrrolidinocarbonyl)phenyl)carboxyamide;
1-[(4-Methoxy)phenyl]-3-[(methoxycarbonyl)amino]-1H-pyrazole-5-[(2'-aminosulfonyl-[1,1']-biphen-4-yl)carboxyamide;
1-[(4-Methoxy)phenyl]-3-amino-1H-pyrazole-5-[(2'-aminosulfonyl-[1,1']-biphen-4-yl)carboxyamide;
1-[(4-Methoxy)phenyl]-3-[(methoxycarbonyl)methylamino]-1H-pyrazole-5-[(2'-aminosulfonyl-[1,1']-biphen-4-yl)carboxyamide;
1-[(4-Methoxy)phenyl]-3-[(2-hydroxy)ethylamino]-1H-pyrazole-5-[(2'-aminosulfonyl-[1,1']-biphen-4-yl)carboxyamide;
1-[(4-Methoxy)phenyl]-3-[E-2-(methoxycarbonyl)ethenyl] 1H-pyrazole-5-[(2'-aminosulfonyl-[1,1']yl)carboxyamide;
1-[(4-Methoxy)phenyl]-3-[2-(methoxycarbonyl)ethyl]-1H-pyrazole-5-[(2'-aminosulfonyl-[1,1']-biphen-4-yl)carboxyamide;
1-[(4-Methoxy)phenyl]-3-[E-2-(carboxy)ethenyl]-1H-pyrazole-5-[(2'-aminosulfonyl-[1,1']-biphen-4-yl)carboxyamide;
1-[(4-Methoxy)phenyl]-3-[2-(carboxy)ethyl]-1H-pyrazole-5-[(2'-aminosulfonyl-[1,1']-biphen-4-yl)carboxyamide;
1-[(4-Methoxy)phenyl]-3-[E-2-(carboxyamide)ethenyl]-1H-pyrazole-5-[(2'-aminosulfonyl-[1,1']-biphen-4-yl)carboxyamide;
1-[(4-Methoxy)phenyl]-3-[E-2-(hydroxymethyl)ethenyl]-1H-pyrazole-5-[(2'-aminosulfonyl-[1,1']-biphen-4-yl)carboxyamide;
1-[(4-Methoxy)phenyl]-3-(3-hydroxypropyl)-1H-pyrazole-5-[(2'-aminosulfonyl-[[1,1']-biphen-4-yl)carboxyamide;
1-[(4-Methoxy)phenyl]-3-propyl-1H-pyrazole-5-[(21'-aminosulfonyl-[1,1']-biphen-4-yl)carboxyamide;
1-[(4-Methoxy)phenyl]-3-(trifluoromethyl)-4-cyano-1H-pyrazole-5-[(2'-methylsulfonyl-3-fluoro-[1,1']-biphen-4-yl)carboxyamide;
1-[(4-Methoxy)phenyl]-3-(trifluoromethyl)-4-(amidino)-1H-pyrazole-5-[(2'-methylsulfonyl-3-fluoro-[1,1']-biphen-4-yl)carboxyamide;
1-[(4-Methoxy)phenyl]1-3-(trifluoromethyl)-4-(N-hydroxyamidino)-1H-pyrazole-5-[(2'-methylsulfonyl-3-fluoro-[1,1']-biphen-4-yl)carboxyamide;
1-[(4-Methoxy)phenyl]-3-(trifluoromethyl)-4-(ethoxycarbonyl)-1H-pyrazole-5-[(2'-methylsulfonyl-3-fluoro-[1,1']-biphen-4-yl)carboxyamide; and,
1-[(4-Methoxy)phenyl]-3-(trifluoromethyl)-1H-pyrazole-5-[(2'-methylsulfonyl-3-fluoro-[1,1']-biphen-4-yl)carboxyamide-4-carboxylic acid;
and pharmaceutically acceptable salts thereof.

[6] In a second embodiment, the present invention provides novel compounds of formula II:

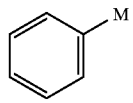

II or stereoisomers or pharmaceutically acceptable salts thereof, wherein;

M is selected from the group:

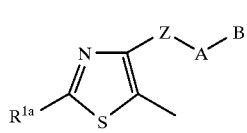

$i_1$

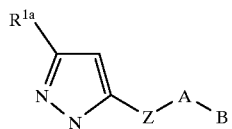

$t_1$

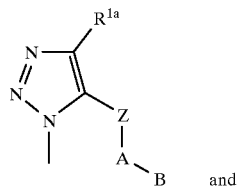

v and

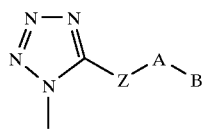

y

Z is selected from $C(O)CH_2$ and $C(O)NR^3$;
$R^{1a}$ is —$(CH_2)_r$—$R^1$;
$R1^{1'}$ is selected from H, $C_{1-3}$ alkyl, F, Cl, Br, $CH(CH_2OR^2)_2$, $(CF_2)_rCF_3$, $(CH_2)_rOR^2$, $NR^2R^{2a}$, $S(O)_pR^{2b}$, $NR^2(CH_2)_r$ $OR^2$, $NR^2C(O)R^{2b}$, $C(O)NR^{2b}$, $C(O)NR^2R^{2a}$, $C(O)NR^2(CH_2)_rOR^2$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^4$, and 5–6 membered heterocyclic system containing from 1–4 heteroatoms selected from the group consisting of N, O and S substituted with 0–2 $R^4$;

$R^2a$, at each occurrence, is selected from H, $CF_3$, $C_{1-6}$ alkyl, benzyl, $C_{3-6}$ carbocyclic residue substituted with 0–2 $R^4$, and 5–6 membered heterocyclic system containing from 1–4 heteroatoms selected from the group consisting of N, O, and S substituted with 0–2 $R^4$;

$R^2b$, at each occurrence, is selected from $CF_3$, $C_{1-4}$ alkoxy, $C_{1-6}$ alkyl, $C_{3-6}$ carbocyclic residue substituted with 0–2 $R^4$, and 5–6 membered heterocyclic system containing from 1–4 heteroatoms selected from the group consisting of N, O and S substituted with 0–2 $R^4$;

alternatively, $R^2$ and $R^{2a}$, together with the atom to which they are attached, combine to form a 5 or 6 membered saturated, partially saturated or unsaturated ring substituted with 0–2 $R^4$ which contains from 0–1 additional heteroatoms selected from the group consisting of N, O, and S; $R^3$, at each occurrence, is selected from H, $C_{1-4}$ alkyl, and phenyl;

A is selected from phenyl, pyridyl, and pyrimidyl, and A is substituted with 0–2 $R^4$;

B is selected from: H and Y;

Y is selected from phenyl, pyridyl, tetrazolyl, and morpholino, and Y is substituted with 0–2 $R^4a$;

$R^4$, at each occurrence, is selected from F, Cl, Br, I, $C(O)NR^2R^{2a}$, and $(CF_2)_rCF3$;

$R^{4a}$, at each occurrence, is selected from F, Cl, Br, I, $C_{1-4}$ alkyl, $C(O)NR^2R^{2a}$, $SO_2NR^2R^{2a}$, $NR^2SO_2$-$C_{1-4}$ alkyl, $S(o)lR^5$, and $(CF2)_rCF_3$;

$R^5$, at each occurrence, is selected from $CF_3$, $C_{1-6}$ alkyl, phenyl, and benzyl;

p is selected from 0, 1, and 2; and, r is selected from 0, 1, 2, and 3.

[7] In another more preferred embodiment, the present invention provides novel compounds selected from:

3-Methyl-1-phenyl-1H-pyrazole-5-(N-(2-aminosulfonyl-[1,1']-biphen-4-yl)carboxyamide;

2-Amino-4-phenyl-5-[(2'-aminosulfonyl-[1,1']-biphen-4-yl)aminocarbonyl]thiazole; and, 2-Chloro-4-phenyl-5-[(2'-aminosulfonyl-[1,1']-biphen-4-yl)aminocarbonyl]thiazole;

and pharmaceutically acceptable salts thereof.

In a third embodiment, the present invention provides novel pharmaceutical compositions, comprising: a pharmaceutically acceptable carrier and a therapeutically effective amount of a compound of formula (I) or a pharmaceutically acceptable salt form thereof.

In a fourth embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0-2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5-to 7-membered monocyclic or bicyclic or 7-to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water -or in an organic solvent, or in a mixture of the two; -generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

Preparation of Compounds of FORMULA I With a Five-Membered Heterocyclic Core General syntheses for compounds of Formula I are outlined in Schemes 1a–b. The M ring may be N-linked or C-linked to the ring referred to in the following scheme as ring D. B' and $R^f$ are protected functional groups that can be converted to R, B and $R^{1a}$ respectively. It is understood that group E may or may not be protected or a precursor to E of Formula I, depending upon the demands of the chemistry involved. The compounds can also be obtained by changing the sequences of the reaction steps as described in Scheme 1. For N-linked M ring, the appropriate amine-substituted ring D is treated under conditions described in "The Chemistry of Heterocyclic Compounds, Weissberger, A. and Taylor, E. C. Ed.,John Wiley & Sons" or as described later in the synthesis section to give N-linked ring M. Further modifications and deprotections give N-linked ring M with R, Z—A—B and $R^{1a}$ substituents.

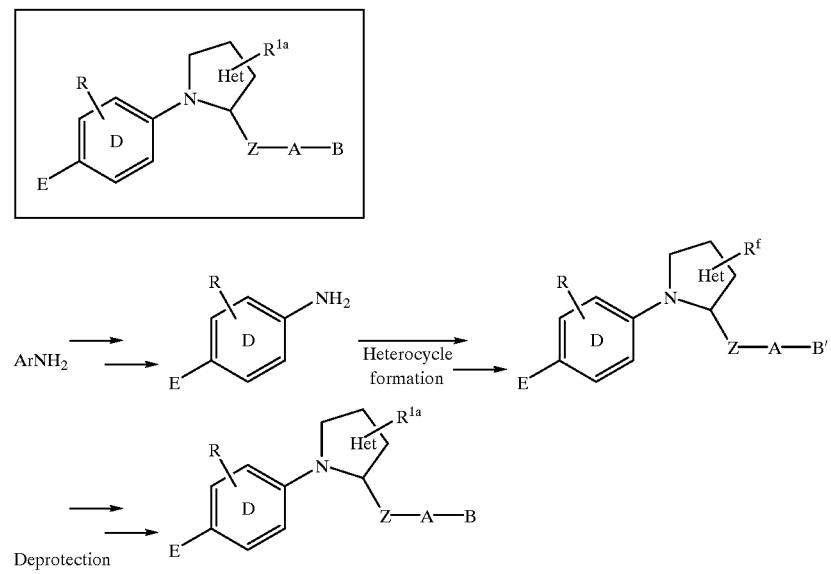

Scheme 1a

For C-linked five-membered ring M, the above aniline is diazotized with nitrous acid and treated with NaBr to give the heterocyclic bromide. Treatment with n-BuLi followed by DMF gives aldehyde which can be converted to ring M as described in "The Chemistry of Heterocyclic Compounds, Weissberger, A. and Taylor, E. C. Ed., John Wiley & Sons" or as described later in the synthesis section. Other precursor functional groups like acid, cyanide, methylketone, etc. can also be used to form the ring M. Further modifications and deprotections can yield five-membered ring M substituted with R, Z—A—B and $R^{1a}$. The corresponding C-linked six-membered ring M can be obtained by converting the above bromide with n-butyl lithium and triisopropyl borate to give the heterocyclic boronic acid. Suzuki coupling with the appropriate heterocyclic bromide, followed by modifications and deprotections gives the C-linked six-membered ring M with R, Z—A—B and $R^{1a}$ substituents.

SCHEME 1b

For carbon-linked heterocycle M.

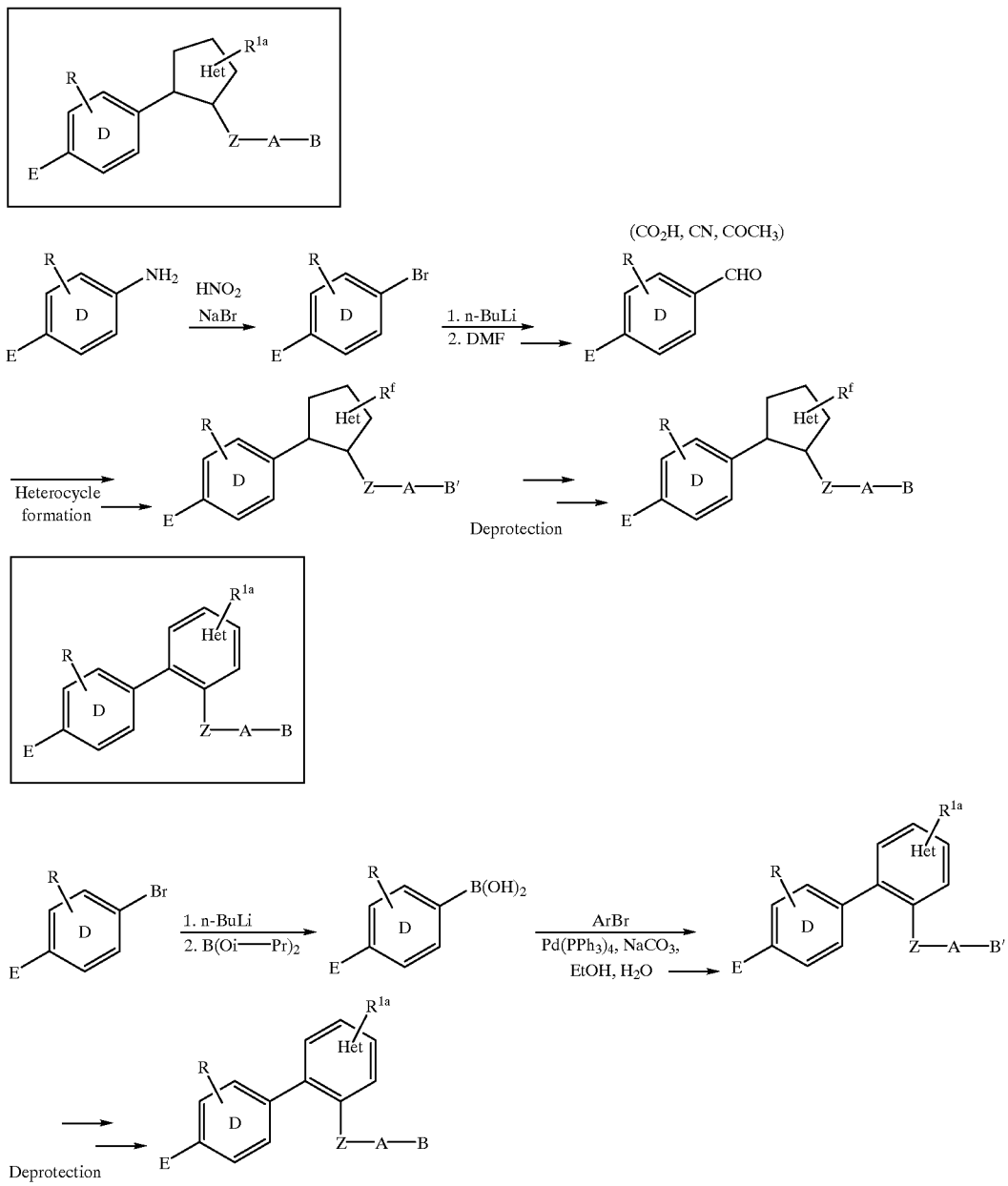

The compounds of the present invention in which the M-thiadiazolyl, is thiazole can be prepared according to the procedures described in Scheme 2. The appropriate ring D bromide can be converted into a beta-keto ester in several ways. One preferred method involves transmetallation with an alkyllithium reagent followed by quenching with DMF to afford the corresponding aldehyde. Addition of ethyl diazoacetate in the presence of tin (II) chloride affords the beta-ketoester directly. Other methods are available for this conversion, one of which involves Reformatsky reaction of the aldehyde followed by oxidation to the beta-keto ester.

Scheme 2

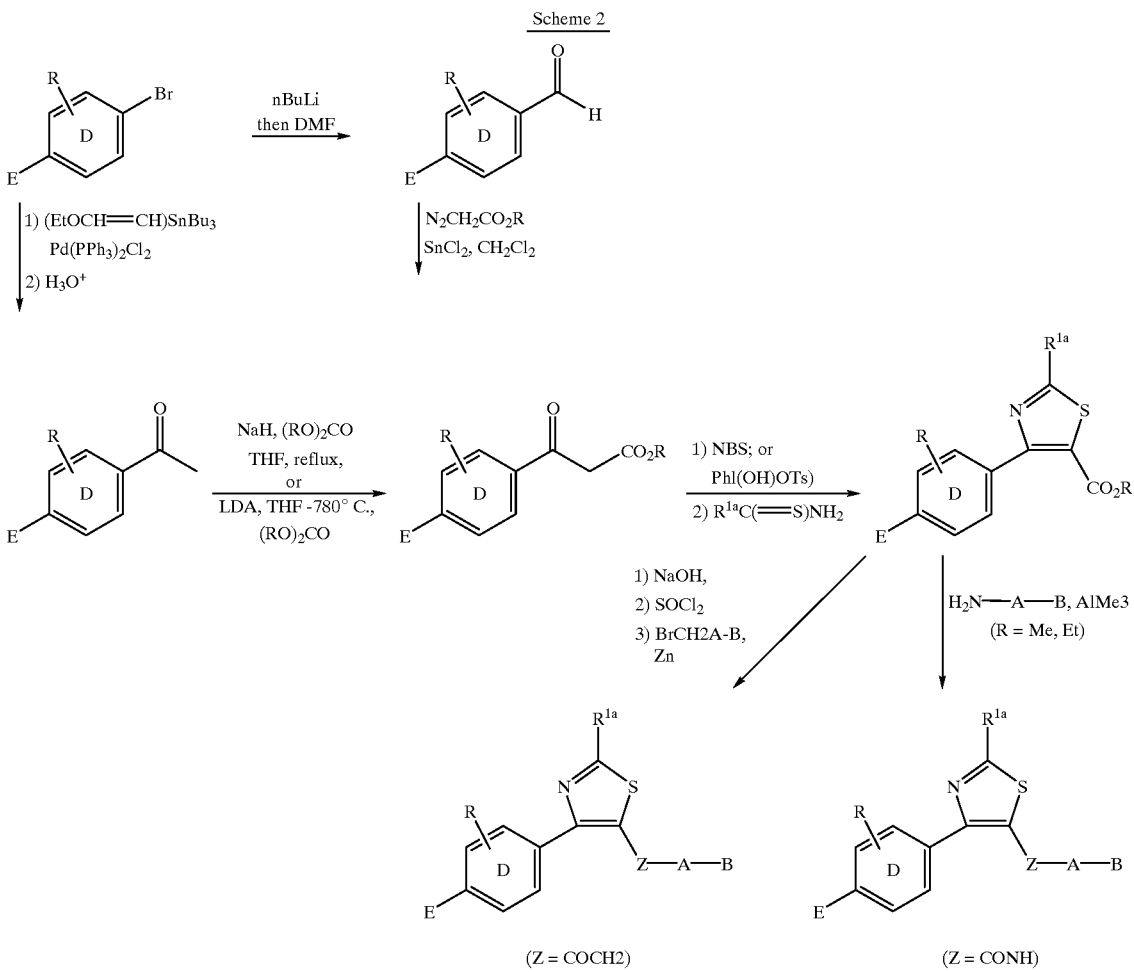

A second preferred method for converting the bromide into a beta-keto ester involves palladium catalysed coupling with (ethoxyvinyl)tributyltin followed by acidic hydrolysis to afford the corresponding acetyl derivative. Many methods exist for conversion of the acetyl derivative to the beta-ketoester, one preferred method of which involves reacting the acetyl derivative with a dialkyl carbonate in the presence of a base such as sodium hydride or lithium diisopropylamide. The beta-ketoester can be converted into the corresponding thiazole derivatives by bromination with NBS followed by cyclization with an appropriate thiourea or thioamide in a solvent such as ethanol or tetrahydrofuran. A one pot method for this conversion involves treating the beta-ketoester with hydroxytosyloxyiodobenzene in acetonitrile, which forms an intermediate alpha-tosyloxy-beta-ketoester, followed by addition of a thiourea or thioamide to effect cyclization to the corresponding thiazole. Manipulation of the ester group of these thiazoles can then afford the compounds containing an appropriate Z—A—B group. Where Z=CONH, standard methods of peptide coupling with an appropriate amine can be employed, such as reaction of the ester with an aluminum reagent derived from the amine. Where Z=COCH2, formation of the acid chloride by standard methods can be followed by addition of an appropriate zinc reagent. The $R^{1a}$ group on the thiazole ring can also be manipulated to provide a variety of different groups. For example, when thiourea is used as the cyclization partner, a 2-aminothiazole is produced. This amino group can be readily diazotized and displaced with the appropriate copper halide to afford 2-halothiazoles. The halogen atom can then be readily displaced by a variety of carbon, nitrogen, oxygen and sulfur nucleophiles to produce a wide variety of alkyl, aryl, heteroatom, and heterocyclic derivatives of $R^{1a}$.

The tetrazole compounds of this invention where Z is —CONH— can be prepared as exemplified in Scheme 3. An appropriately substituted amine (E—D—$NH_2$) is acylated with ethyl oxalyl chloride. The resulting amide can be converted to the tetrazole either by the methods described by Duncia (*J. Org. Chem.* 1991, 2395–2400) or Thomas (*Synthesis* 1993, 767–768, 1993). The amide can be converted to the iminoyl chloride first and the reacted with $NaN_3$ to form the 5-carboethoxytetrazole (*J. Org. Chem.* 1993, 58, 32–35 and *Bioorg. & Med. Chem. Lett.* 1996, 6, 1015–1020). The 5-carboethoxytetrazole is then coupled with an appropriate amine ($BANH_2$) by the method described by Weinreb (*Tetr. Lett.* 1977, 48, 4171–4174). Final deprotection as described before yields the desire product.

The tetrazole compounds of this invention where Z is —CO— can also be prepared via iminoyl chloride (*Chem. Ber.* 1961, 94, 1116 and *J. Org. Chem.* 1976, 41, 1073) using an appropriately substituted acyl chloride as starting material.

The ketone-linker can be reduced to compounds where Z is alkyl.

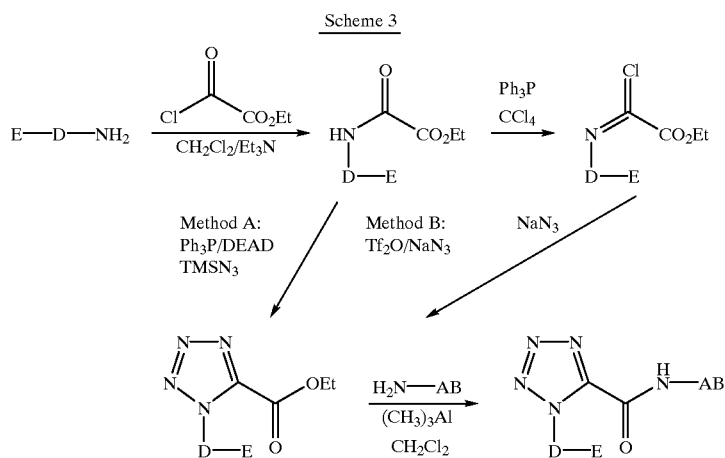

Scheme 3

The tetrazole compounds of this invention where Z is—$SO_2NH$—,—S—,—$S(O)$, $SO_2$—can be prepared as exemplified in Scheme 4. Appropriately substituted thioisocyanate is reacted with sodium azide to give the 5-thiotetrazole (*J. Org. Chem.* 1967, 32, 3580–3592). The thio-compound can be alkylated (*J. Org. Chem.* 1978, 43, 1197–1200) and then oxydized to the sulfoxide or sulfone. The thio-compound can also be converted to the sulfonyl chloride and the reacted with an amine to give the desired sulfonamide. The tetrazole compounds of this invention where Z is—O—can be prepared via the same method described in Scheme 4 by using appropriately substituted isocyanate as the starting material.

The tetrazole compounds of this invention where Z is—NH—,—NHCO—,—$NHSO_2$—can be prepared from 5-aminotetrazole, which can be prepared by Smiles Rearrangement as shown in Scheme 5. The thio-compound prepared as described in Scheme 4 is alkylated with 2-chloroacetamide. The resulting compound is then refluxed in ethanolic sodium hydroxide to give the corresponding 5-amino-tetrazole (*Chem. Pharm. Bull.* 1991, 39, 3331–3334). The resulting 5-amino-tetrazole can then be alkylated or acylated to form the desired products.

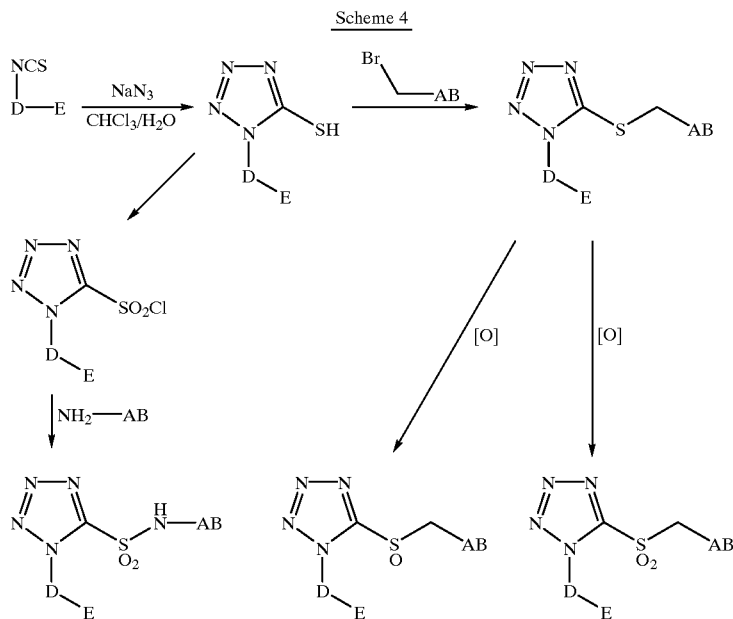

Scheme 4

Scheme 5

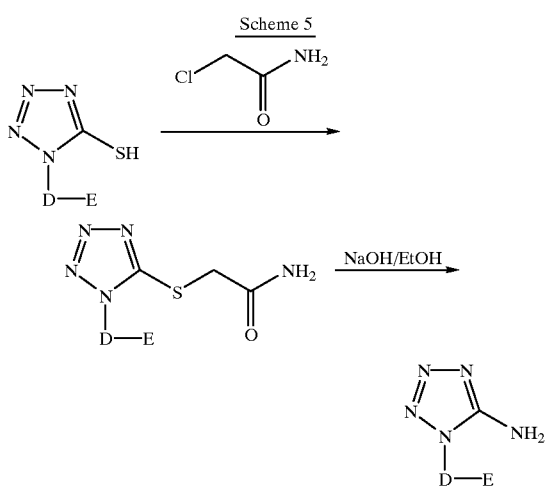

The N-linked imidazole ring M can be synthesized by the synthetic route shown in Scheme 6. Alkylation of E—D—NH₂ with 2-bromoethylacetate followed by reaction with Gold's reagent in the presence of a base, such as NaOMe, or LDA, forms imidazole ring M.

Scheme 6

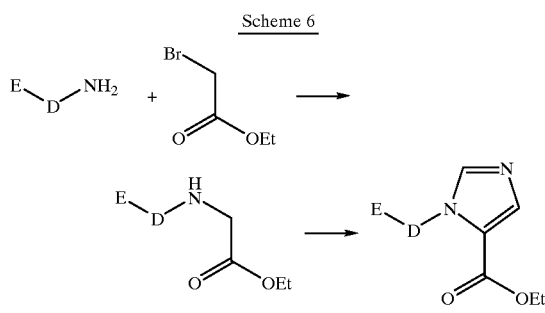

The general procedure to make C-linked imidazole ring M is described in Scheme 7. Aldehyde E—D—CHO from Scheme 1 can be converted into cyano compound by treatment with hydroxyamine and then dehydration with POCl3. The amidine can be obtained from cyano compound by Pinner reaction, which can be cyclized with alpha-halo ester, ketone or aldehyde to form imidazole ring M. Alkylation or acylation of imidazole ring M for further modification as described in Scheme 1.

Scheme 7

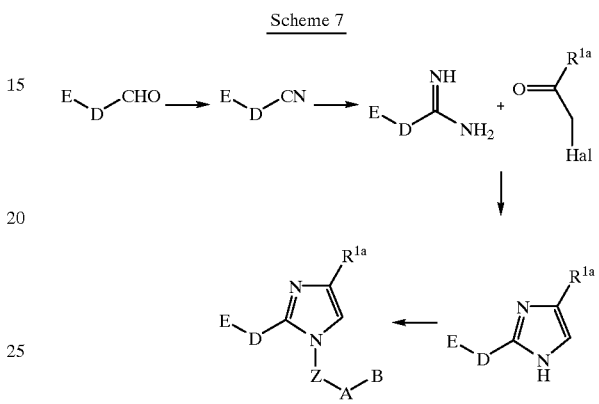

As shown in Scheme 8, pyrazole ring M of the general Formula I such as those described in Scheme 1 can be prepared by the condensation of an appropriately substituted hydrazine with a variety of diketo esters. Condensations of this type typically afford a mixture of pyrazole regioisomers which can be effectively separated via silica gel column chromatography. Hydrolysis of the esters followed by coupling with an appropriate amine can afford the desired amide intermediate. Various substituents on the pyrazole N1 can then be manipulated to afford a variety of benzo, heterocyclic and bicylic compounds

Scheme 8

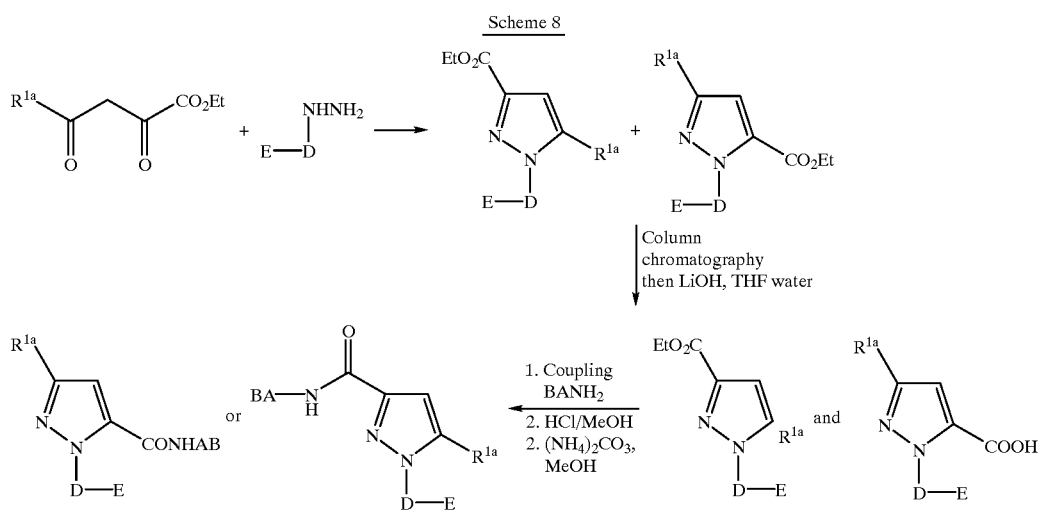

The above methodology when applied to diketo derivatives also affords a mixture of pyrazole regioisomers. These can be further manipulated to afford the compounds of Formula I as shown in Scheme 9.

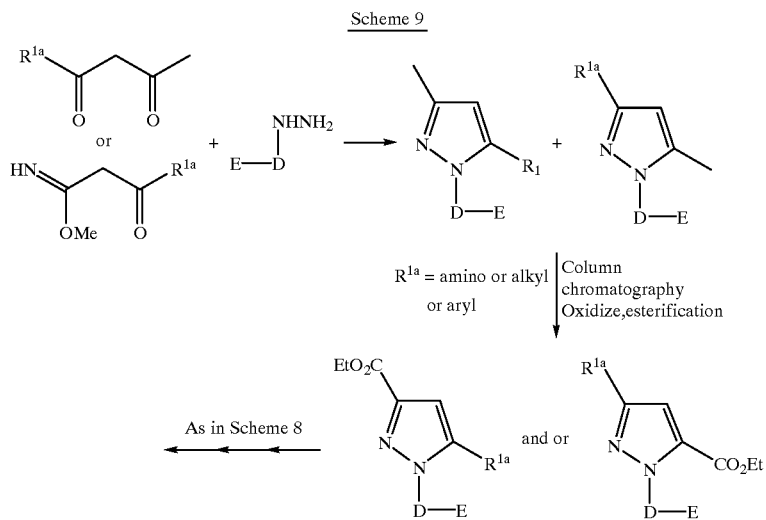

When ketoimidates are used for condensations with hydrazines the corresponding pyrazole amino esters regio-adducts are obtained (Scheme 9). Conversion of these intermediates to the final compounds of formula I can then be accomplished by the protection of the amino functionality with a suitable protecting group commonly known to those in the art or by derivatization (such as a sulfonamide as in Scheme 10) then following the general synthetic strategy to prepare the compounds of this invention.

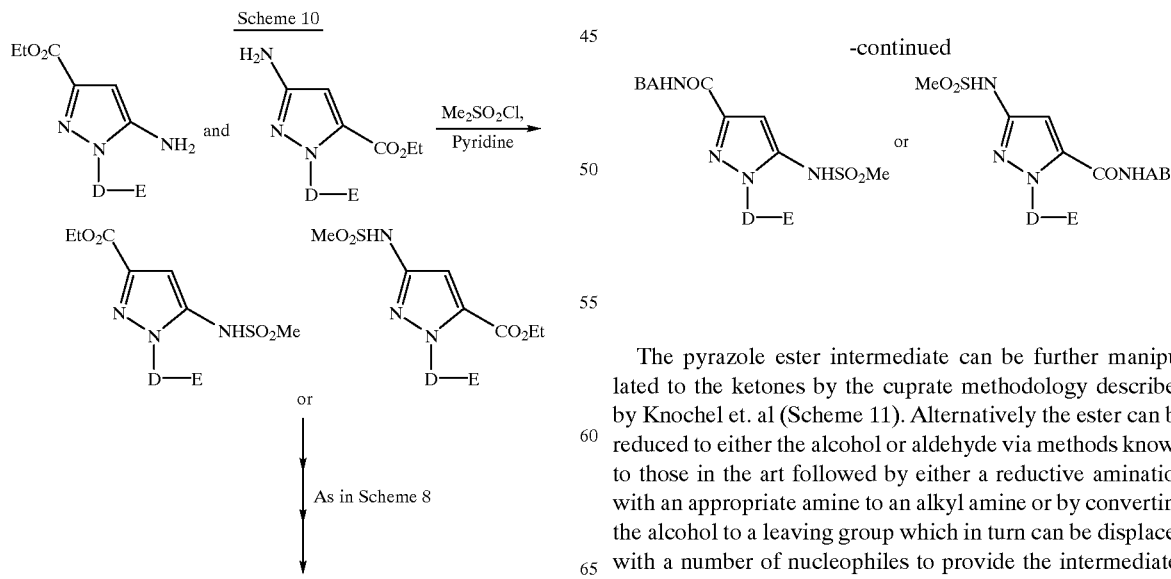

The pyrazole ester intermediate can be further manipulated to the ketones by the cuprate methodology described by Knochel et. al (Scheme 11). Alternatively the ester can be reduced to either the alcohol or aldehyde via methods known to those in the art followed by either a reductive amination with an appropriate amine to an alkyl amine or by converting the alcohol to a leaving group which in turn can be displaced with a number of nucleophiles to provide the intermediates which on further manipulations should afford the compounds of this invention.

Scheme 11
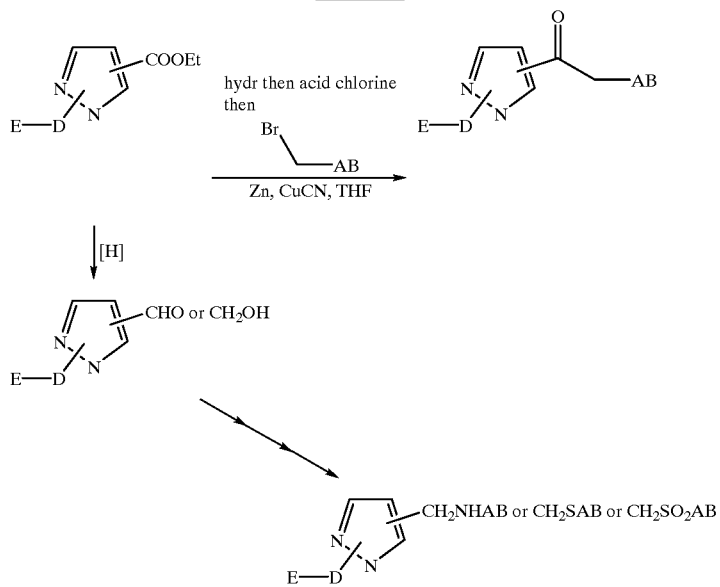
Thio compounds such as those described in Scheme 12 can be easily prepared by the conversion of 5-hydroxy pyrazole to its thiol by treatment with Lawesson's reagent in refluxing toluene.
Compounds of this invention wherein the pyrazole ring M is replaced with a 1,2,3-triazole can be prepared as outlined in Scheme 13.
Scheme 12
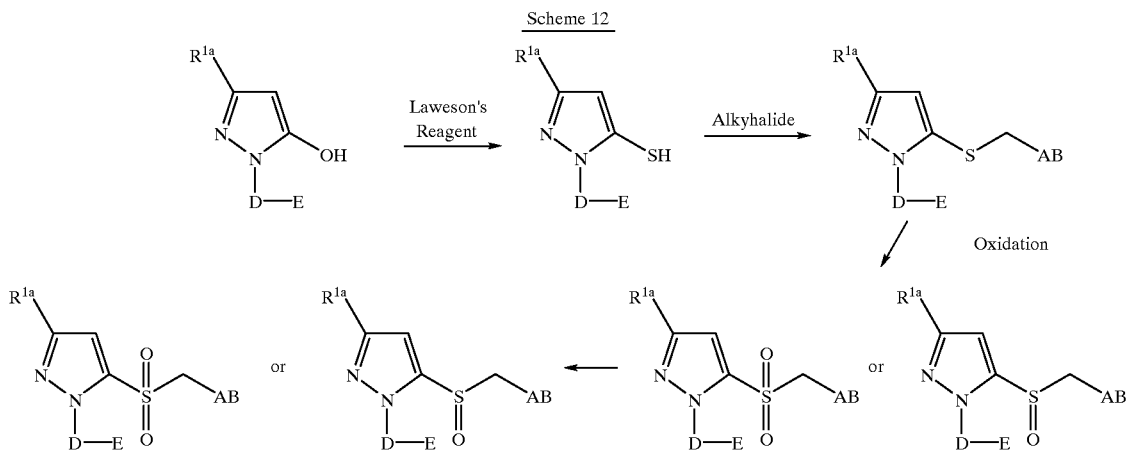

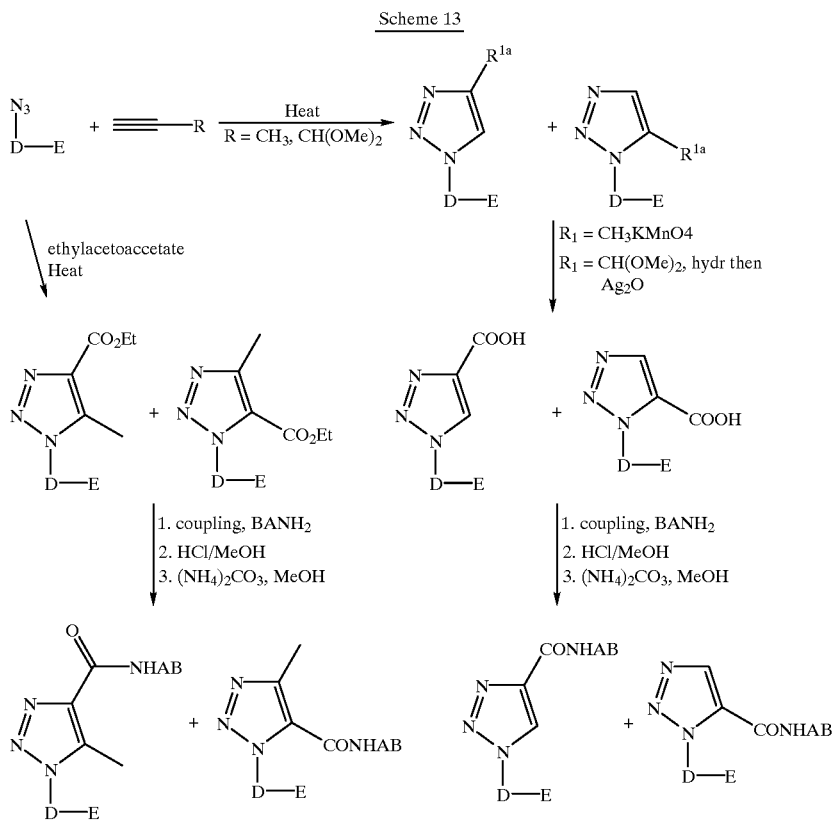

The compounds of this invention where the ring M is 1,2,4-triazole can be easily obtained by the methodology of Huisgen et. al. (*Liebigs Ann. Chem.* 1962, 653, 105) by the cycloaddition of nitriliminium species (derived from the treatment of triethylamine and chloro hydrazone) and an appropriate nitrile dipolarophile as in Scheme 14.

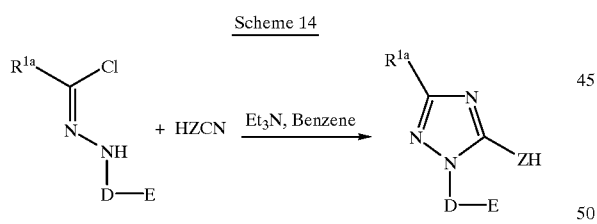

This methodology provides a wide variety of 1,2,4 triazoles with a varied substitution pattern at the 1,3 and 5 positions. Alternatively the 1,2,4 triazoles can also be prepared by the methodology of Zecchi et. al. (*Synthesis* 1986, 9, 772) via an aza Wittig condensation (Scheme 15).

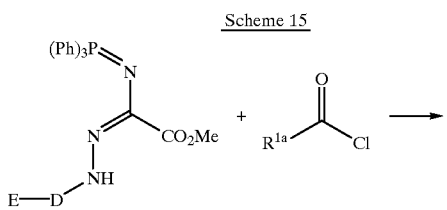

-continued

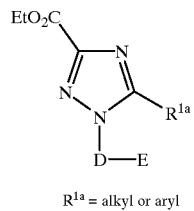

$R^{1a}$ = alkyl or aryl

Alternatively the 1,2,4 triazoles can also be prepared via the methodology of Sauer et. al. (*Tetr. Lett.* 1968, 325) by the photolysis of a cyclic carbonate with an appropriate nitile (Scheme 16).

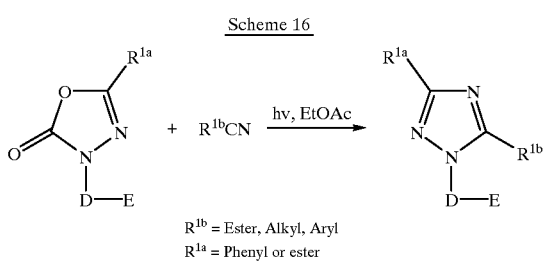

$R^{1b}$ = Ester, Alkyl, Aryl
$R^{1a}$ = Phenyl or ester

For compounds of this invention the esters can be converted to the amide intermediates via the Weinreb methodology (*Tetr. Lett.* 1977, 48, 4171), i.e. the condensation of an appropriate amine aluminum complex with the ester (Scheme 17).

Scheme 17

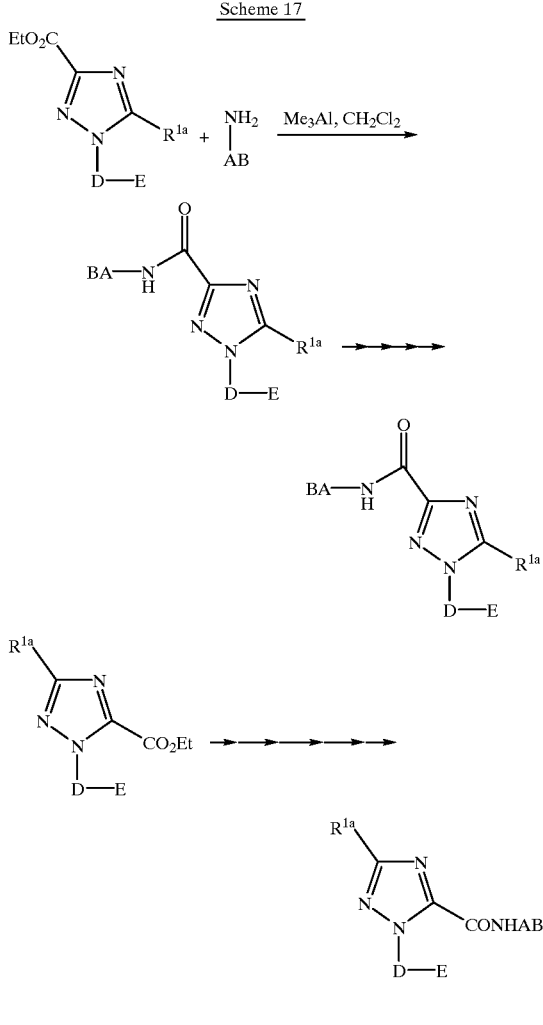

Isoxazoline ring M of the general formula I wherein the 4 and 5 positions are substituted can be prepared following the 1,3-dipolar cycloaddition methodology outlined in Scheme 18. An appropriate benzhydroximinoyl chloride or heterocyclic oximinoylchloride or the oxime when subjected to the 1,3-dipolar cycloaddition protocol with a suitable 1,2-disubstituted olefin as a dipolarophile should afford a mixture of regioisomers. Separation of the regioisomers by column chromatography followed by the sequence of reactions as described previously should then afford the compounds of choice. Optically active isoxazolines can also be obtained by enzymatic resolution on the regioisomeric esters or by the use of an appropriate chiral auxilliary on the dipolarophile as described by Olsson et al (*J. Org. Chem.* 1988, 53, 2468).

Scheme 18

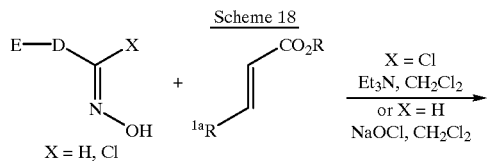

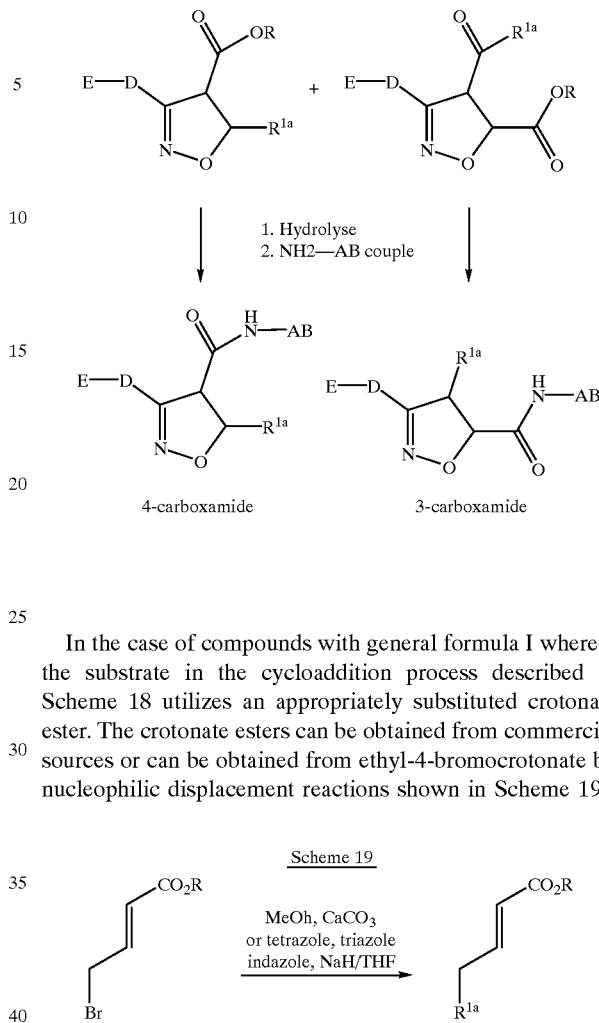

In the case of compounds with general formula I wherein the substrate in the cycloaddition process described in Scheme 18 utilizes an appropriately substituted crotonate ester. The crotonate esters can be obtained from commercial sources or can be obtained from ethyl-4-bromocrotonate by nucleophilic displacement reactions shown in Scheme 19.

Scheme 19

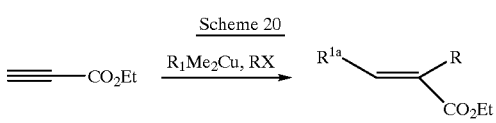

Trisubstituted olefins as dipolarophiles can be obtained from ethylpropiolate by the cuprate chemistry (Scheme 20) according to the method described by Deslongchamps et. al. (*Synlett* 1994, 660).

Scheme 20

≡—CO$_2$Et $\xrightarrow{R_1Me_2Cu, RX}$ R$^{1a}$\\=/R, CO$_2$Et

Compounds of this invention with 1,3,4-triazole ring M can be easily obtained via the methodology of Moderhack et. al. (*J. Prakt. Chem.* 1996, 338, 169) as in Scheme 21.

Scheme 21

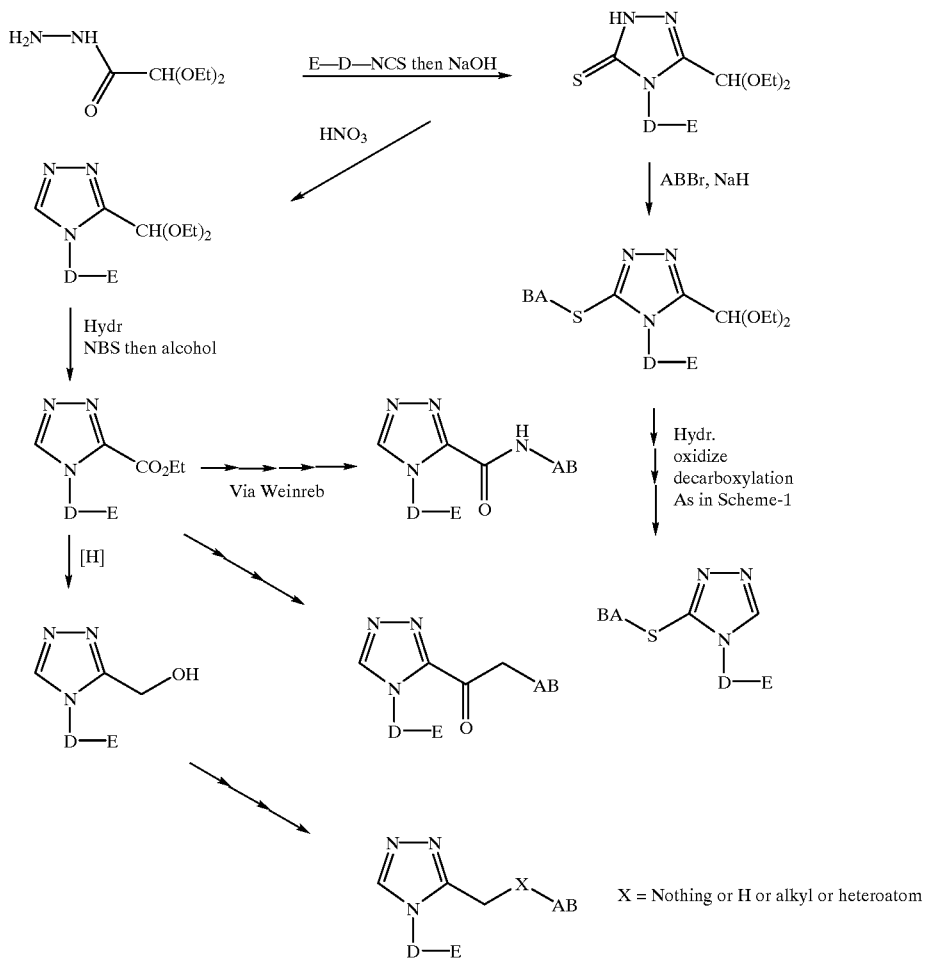

This reaction involves the condensation of a carbazide with an appropriately substituted commercially available thio isocyanate to the cyclic thiourea derivative as described previously. Alkylation or nucleophilic displacement reactions on the thiono intermediate then affords a thio alkyl or aryl intermediate which can be hydrolysed, oxidized and decarboxylated to the 5-H 2-thio triazole intermediate which can be effectively converted to the compounds of this invention. Alternatively the thiono urea intermediate can be oxidized directly to the 2-H triazole which can then be converted to the ester and then subjected to a variety of reactions shown above to obtain the compounds of this invention. The esters can also be converted to the amine via the Hoffmann rearrangement and this methodology provides a variety of analogs similar to those shown previously. The cyclic thiono urea intermediate can also be oxidized to the sulfonyl chloride by methods shown in early examples. This in turn can provide the sulfonamides shown in Scheme 22.

Scheme 22

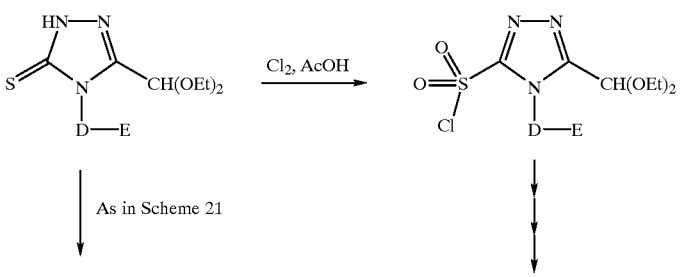

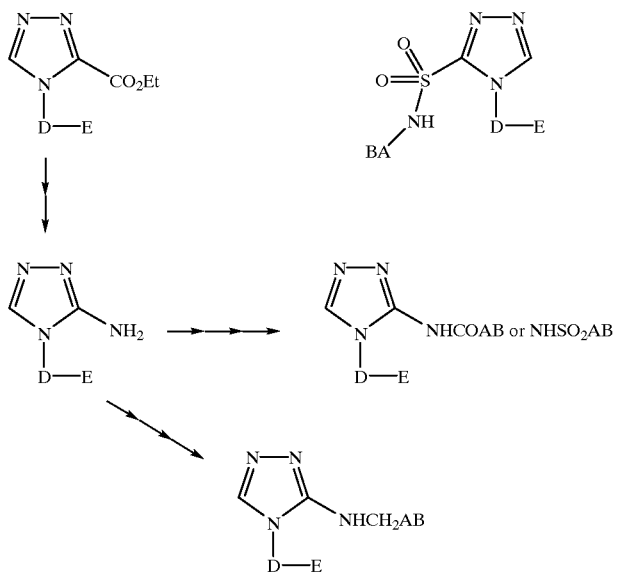

Scheme 23 describes the general synthesis for pyrazoles which have thio and oxidized sulfur derivatives. An appropriately substituted amine is alkylated with ethyl bromoacetate and hydrolyzed to the glycine derivative.

Preparation of the N-nitroso compound was easily achieved with sodium nitrite (*J. Chem. Soc.* 1935, 899). Cyclization to the syndone using acetic anhydride (*J. Chem. Soc.* 1935, 899) was following by the introduction of the sulfide unit using a sulfoxide as solvent and acetyl chloride as a activating reagent (*Tetr.* 1974, 30, 409). Photolytic cleavage of the sydnone in the presence of an acetylenic compound the 1,3,5 trisubstituted pyrazole as the major regioisomer (*Chem. Ber.* 1979, 112, 1206). These can be carried on, as described before, to the final compounds containing the sulfide, sulfoxide or sulfone functionality.

Scheme 23

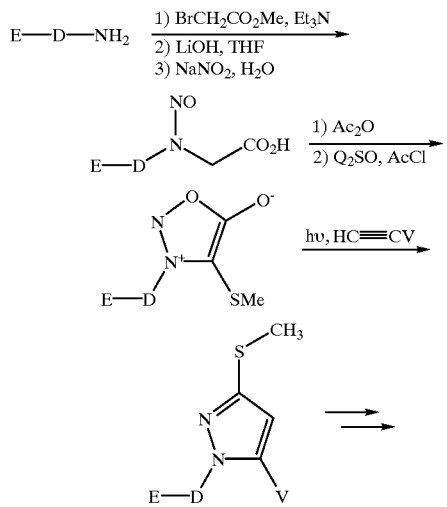

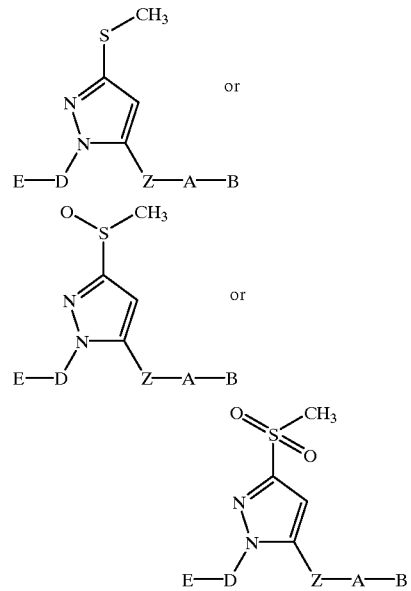

Where V = $NO_2$, $SO_2NR_2$ or $CO_2Me$

Scheme 24 shows one possible synthesis of isoxazoles. Substituted benzaldehydes are reacted with hydroxyl amine then chlorinated to give the hydroximinoyl chloride according to the procedure of (*J. Org. Chem.* 1980, 45, 3916). Preparation of the nitrile oxide in situ with triethylamine and cycloaddition with a substituted alkyne gives a mixture of regioisomeric isoxazoles as shown by H. Kawakami (*Chem. Lett.* 1987, 1, 85). Preparation of the disubstituted alkyne is achieved by nucleophilic attack of the alkynyl anion on an electrophile as shown by Jungheim et al (*J. Org. Chem.* 1987, 57, 4007).

Alternatively, one could make the hydroxyiminoyl chloride of the $R^{1a}$ piece and react it with an appropriately substituted alkyne to give another set of regioisomeric isoxazoles which as separated chromatographically.

Scheme 24

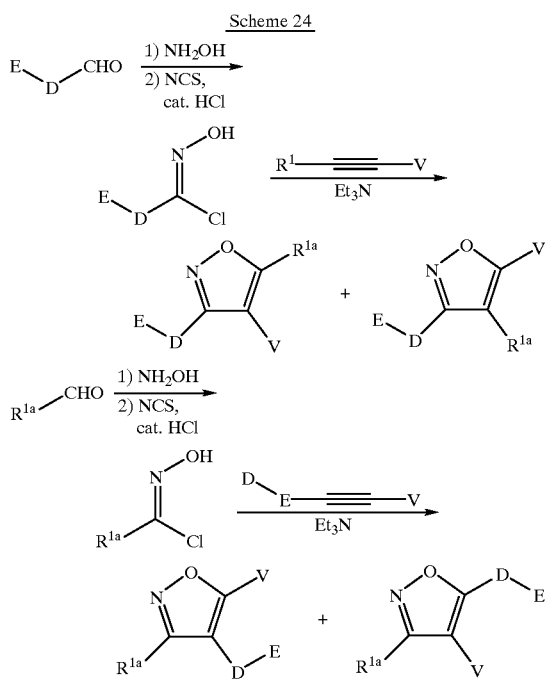

Where V = No₂, SO₂NR₂ or CO₂Me, synthetic precursor to —Z—A—B

An alternate procedure which produces only one regioisomer is described in Scheme 25. The methylated form of V can be deprotonated and silylated. Chlorination with carbon tetrachloride or fluorination with difluorodibromomethane under triethylborane catalysis give the geminal dihalo compound as shown by Sugimoto (*Chem. Lett.* 1991, 1319). Cuprate-mediated conjugate addition-elimination give the desired alkene as in Harding (*J. Org. Chem.* 1978, 43, 3874).

Alternatively, one can acylate with an acid chloride to form a ketone as in Andrews (*Tetr. Lett.* 1991, 7731) followed by diazomethane to form the enol ether. Each of these compounds can be reacted with a hydroximinoyl chloride in the presence of triethylamine to give one regioisomeric isoxazole as shown by Stevens (*Tetr. Lett.* 1984, 4587).

Scheme 25

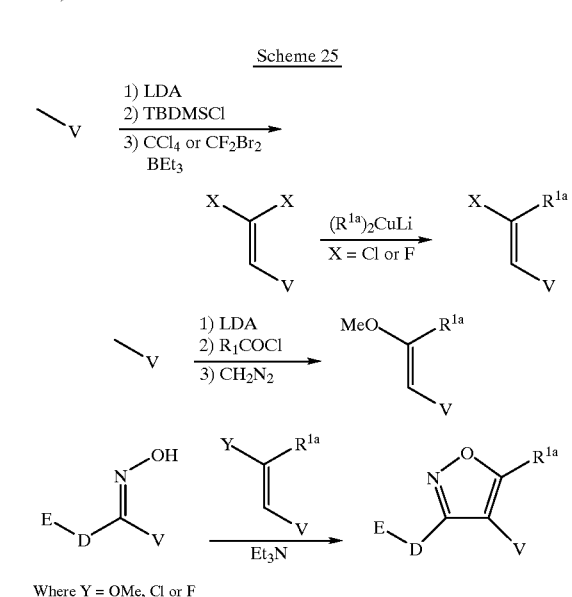

Where Y = OMe, Cl or F
V = NO₂, SO₂NR₂ or CO₂Me, synthetic precursor to —Z—A—B

When core substitutent $R^{1a}$ is $CH_2Q$, the synthesis is shown in Scheme 26. After being treated with LDA, the ketone starting material reacts with $PhSSO_2Ph$ to give the phenylthiolated compound which reacts with hydrazine in acetic acid to form pyrazole derivative. The pyrazole ester reacts with an amine or aniline (previously treated with AlMe3) to provide amide. Oxidation of the sulfide with mCPBA gives the corresponding sulfone. Deprotonation of the sulfone with base, followed by trapping with an electrophile (Q-X) and treatment with $SmI_2$ provided the desired compound after deprotection.

Scheme 26

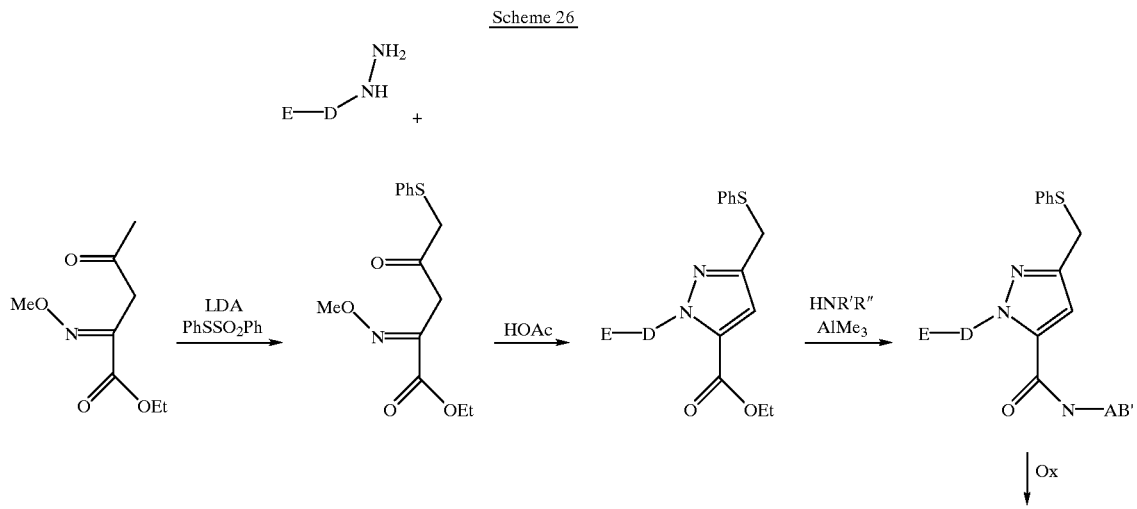

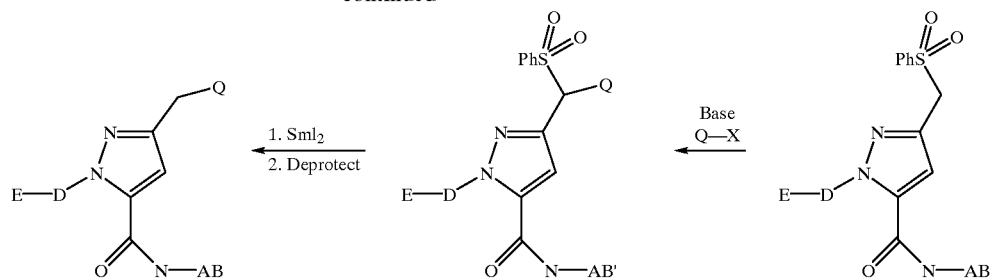

Scheme 27 shows other methods of synthesis for $R^{1a}=$ CH$_2$Q or COQ. Protection of the hydroxyl group of hydroxyacetone with a benzyl halide and treatment with a base and CO(CO$_2$Et)$_2$ gives the tricarbonyl compound. Refluxing with NH2OMe.HCl in pyridine and ethanol in the presence of molecular sieve 3 Å gives the oxime. Cyclization of oxime with E—D—NHNH2 provided pyrazole, which can be converted into the corresponding amide by reacting with an amine or aniline (previously activated with AlMe$_3$). Debenzylation by catalytic hydrogenation provides the alcohol. The alcohol is converted into the tosylate with TsCl, followed by replacement with a nucleophile to provide the desired compound. The alcohol can also be oxidized to the corresponding aldehyde or acid, or further converted to ester or amide.

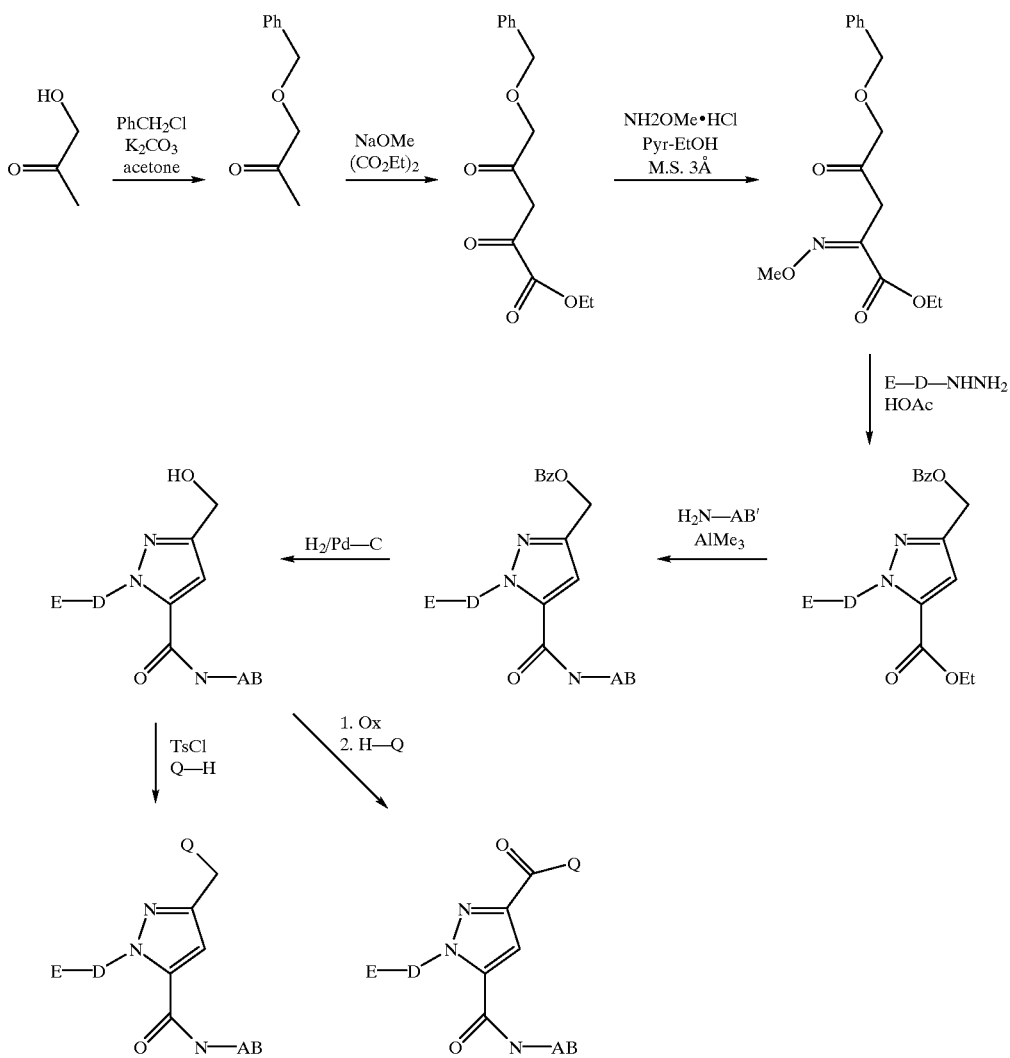

Preparation of Compounds of Formula I With a Six-Membered Heterocyclic Core

Scheme 28 describes the synthesis of compounds wherein M is a benzene ring and V is a nitro, protected sulfonamide or ester group and precursor of group Z of Formula I. The V group is placed on an appropriately substituted phenol either via nitration as shown by Poirier et al. (*Tetrahedron* 1989, 45(5), 1415), sulfonylation as shown by Kuznetsov (*Akad. Nauk SSSR Ser. Khim* 1990,, 8, 1888) or carboxylation by Sartori et al. (*Synthesis* 1988, 10, 763). Bromination with triphenylphosphine and bromine (*J. Am. Chem. Soc.* 1964, 86, 964) gives the desired bromide. Suzuki coupling with the appropriate boronic acid provides the desired substituted pyridine.

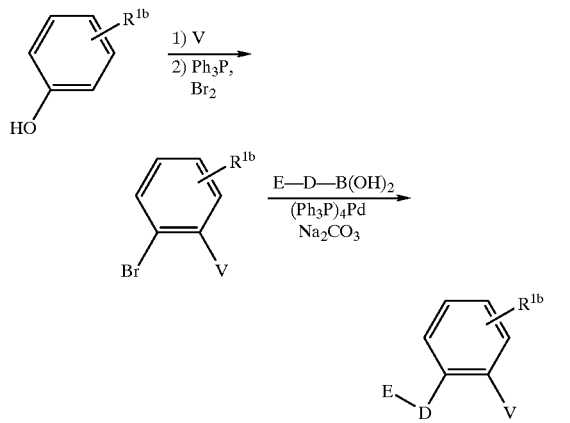

Scheme 29 thru 32 describe the synthesis of compounds wherein M is pyridine. Each scheme represents a different substitution pattern for the pyridine ring. In Scheme 29, a suitably protected aldehyde is subjected to base-catalyzed condensation with an activated ester to give after deprotection the desired aldehyde. Refluxing with ammonium chloride as shown by Dornow and Ische (*Chem. Ber.* 1956, 89, 876) provides the pyridinol which is brominated with POBr₃ (Tjeenk et al. *Rec. Trav. Chim.* 1948, 67, 380) to give the desired 2-bromopyridine. Suzuki coupling with the appropriate boronic acid provides the desired substituted pyridine.

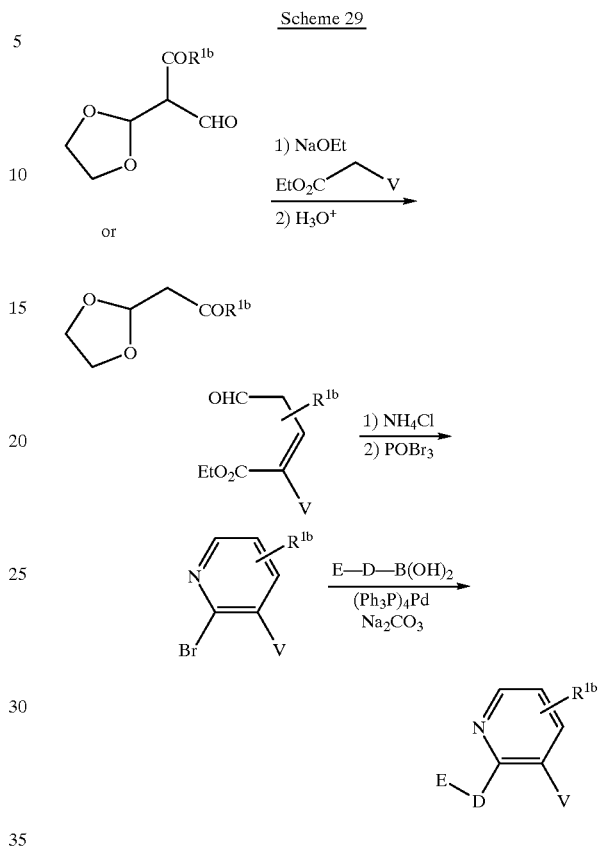

Treatment of an appropriately substituted 5-ethoxyoxazole with an alkene as shown by Kondrat'eva et al. (*Dokl. Akad. Nauk SSSR* 1965, 164, 816) provides a pyridine with the V substituent at the para position. Bromination at the 3-position as shown by van der Does and Hertog (*Rec. Trav. Khim. Pays-Bas* 1965, 84, 951) followed by palladium-catalyzed boronic acid coupling provides the desired substituted pyridine.

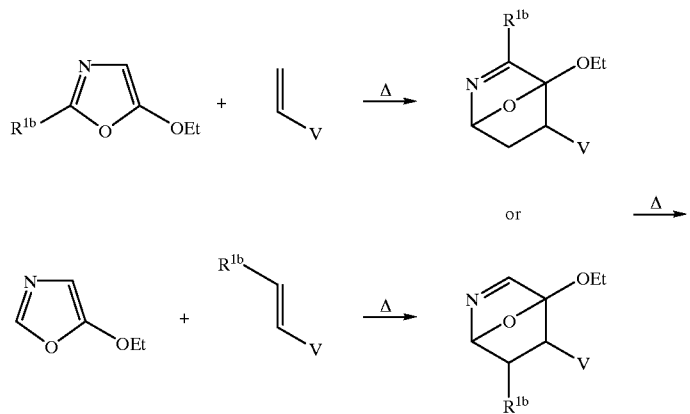

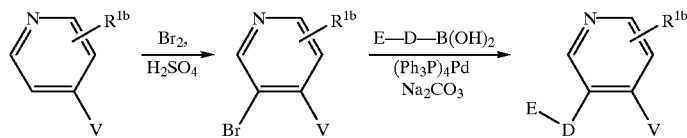

Scheme 31 describes a synthesis of a third substitution pattern on a pyridine ring. The appropriate tricarbonyl compound which can be prepared by methods described in Scheme 29 is treated with ammonium chloride to form the pyridinol which is subsequently brominated. Palladium-catalyzed coupling provides the desired substituted pyridine.

Scheme 31

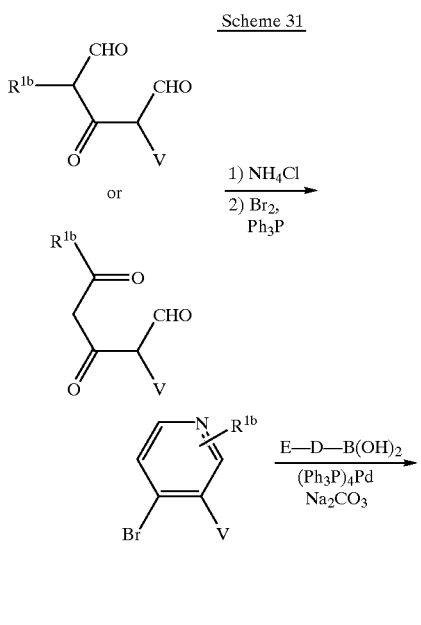

Scheme 32 takes a suitably substituted dicarbonyl compound and by chemistry illustrated in Schemes 29 and 31, reacts it with ammonium chloride. Bromination gives the 3-bromopyridine which upon palladium-catalyzed coupling provides the desired substituted pyridine.

Scheme 32

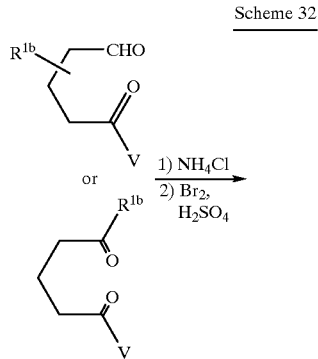

-continued

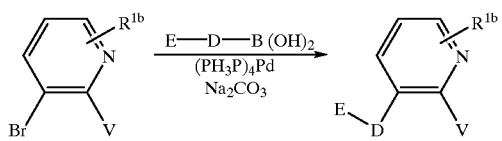

Scheme 33 thru 35 describe the synthesis of compounds wherein M is pyridazine. Each scheme represents a different substitution pattern for the pyridazinering. In Scheme 33 an activated ester is reacted with an appropriately substituted α-keto aldehyde and hydrazine as shown by Schmidt and Druey (*Helv. Chim. Acta* 1954, 37, 134 and 1467). Conversion of the pyridazinone to the bromide using POBr$_3$ and palladium-catalyzed coupling provides the desired substituted pyridazine.

Scheme 33

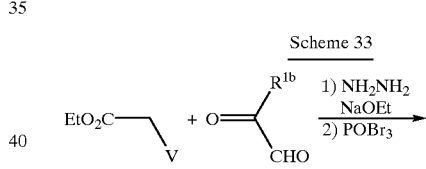

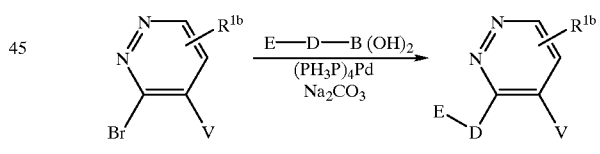

In Scheme 34, glyoxal can react under basic conditions with an activated ketone and subsequently brominated/dehydro-brominated to give the desired ketoaldehyde. Alternatively, a protected ketone can react with an activated aldehyde, undergo bromination/dehydrobromination, be deprotected and oxidized to give the regioisomeric ketoaldehyde. Cyclization as shown by Sprio and Madonia (*Ann. Chim.* 1958, 48, 1316) with hydrazine followed by palladium-catalyzed coupling provides the desired substituted pyridazine.

Scheme 34

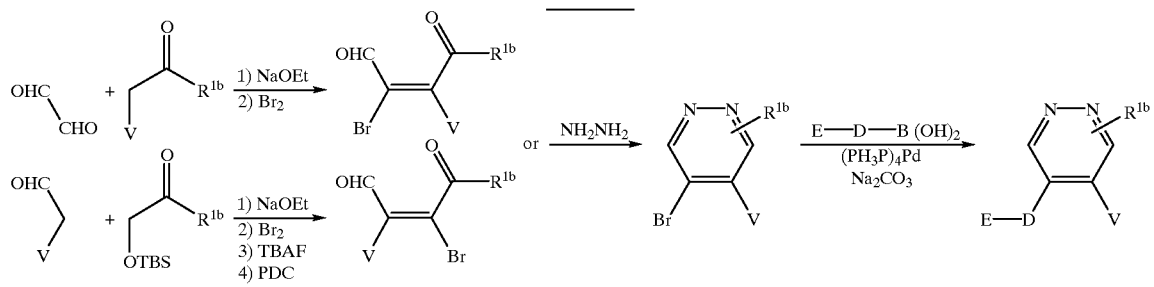

By analogy to Scheme 34, in Scheme 35 a aldehyde can be reacted with an activated ketone, brominated, dehydrobrominated and deprotected to give the desired diketone. Alternatively, a regioisomeric ketone can be placed through the same reaction sequence to produce an isomeric keto aldehyde. Reaction with hydrazine followed by palladium-catalyzed coupling provides the desired substituted pyridazine.

Scheme 35

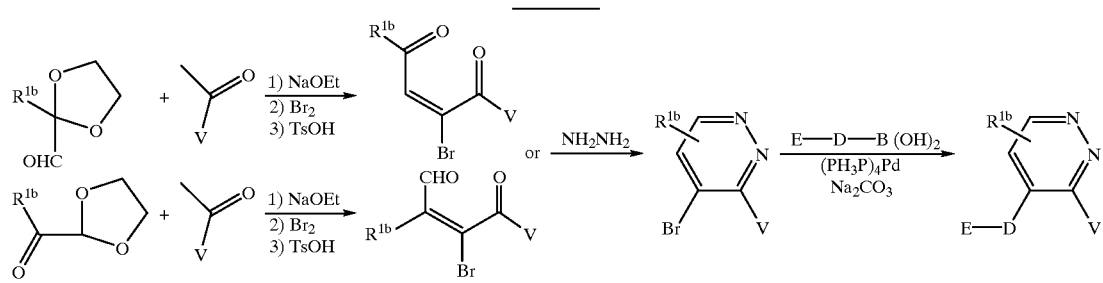

Scheme 36 and 37 describe the synthesis of compounds wherein M is pyrimidine. Each scheme represents a different substitution pattern for the pyrimidine ring. In Scheme 36, a condensation with an appropriately substituted acid chloride and an activated ester followed by conjugate reduction by tin hydride (Moriya et al. *J. Org. Chem.* 1986, 51, 4708) gives the desired 1,4 dicarbonyl compound. Cyclization with formamidine or a substituted amidine followed by bromination gives the desired regioisomeric pyrimidine. Palladium-catalyzed coupling provides the desired substituted pyrimidine.

Scheme 36

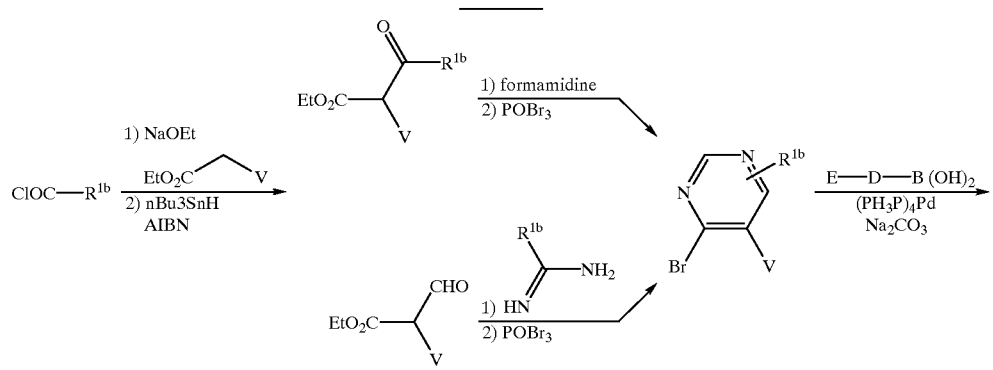

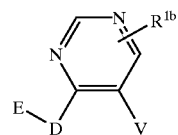

Using similar chemistry, Scheme 37 shows how an amidine can be condensed with a 1,3-dicarbonyl compound and subsequently brominated in the 5-position (*J. Het. Chem.* 1973, 10, 153) to give a specific regioisomeric bromopyrimidine. Palladium-catalyzed coupling provides the desired substituted pyrimidine.

Scheme 37

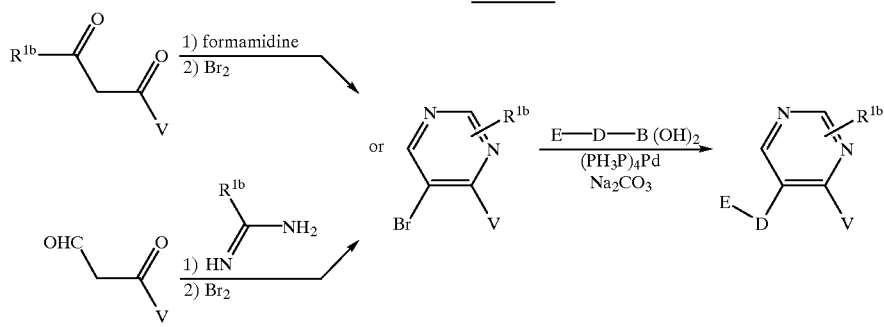

Using the same ketoaldehyde from Scheme 37, cyclization with an appropriately substituted 1,2-diamine (*Chimia* 1967, 21, 510) followed by aromatization (*Helv. Chim. Acta* 1967, 50, 1754) provides a regioisomeric mixture of pyrazines as illustrated in Scheme 38. Bromination of the hydrobromide salt (U.S. Pat. No. 2,403,710) yields the intermediate for the palladium-catalyzed coupling step which occurs as shown above.

Scheme 38

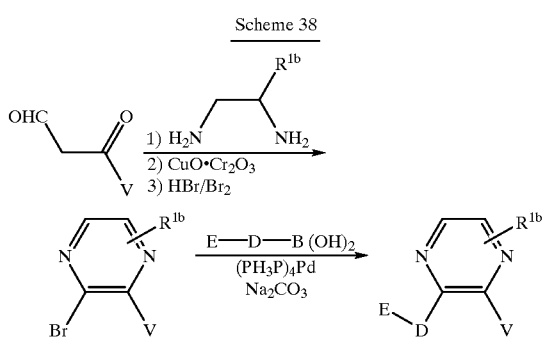

Scheme 39 and 40 describe the synthesis of compounds wherein M is a 1,2,3-triazine. In Scheme 39, a vinyl bromide is palladium coupled to a molecule containing the substituent $R^{1b}$. Allylic bromination followed by azide displacement provide the cyclization precursor. Triphenylphosphine-mediated cyclization (*J. Org. Chem.* 1990, 55, 4724) give the 1-aminopyrazole which is subsequently brominated with N-bromosuccimide. Lead tetraacetate mediated rearrangement as shown by Neunhoeffer et al. (*Ann.* 1985, 1732) provides the desired regioisomeric 1,2,3-triazine. Palladium-catalyzed coupling provides the substituted triazine.

Scheme 39

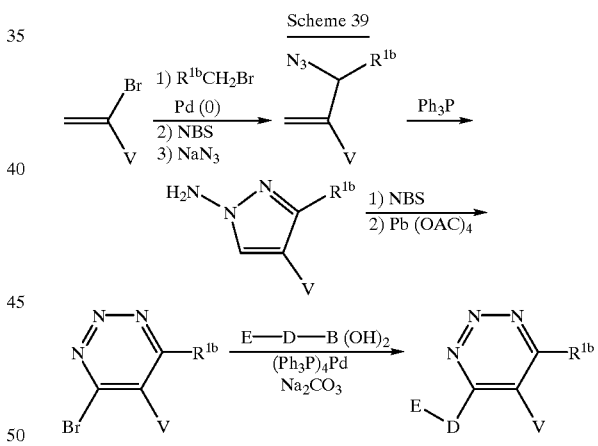

In Scheme 40, an alkene is allylically brominated and the bromide is displaced to give a regioisomer of the azide in Scheme 39. Following the same reaction sequence as shown above, cyclization provides the 1-aminopyrazole. Bromination followed by lead tetraacetate mediated rearrangement give the 1,2,3-triazine. Palladium-catalyzed coupling provides the other desired triazine.

Scheme 40

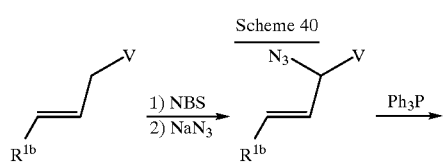

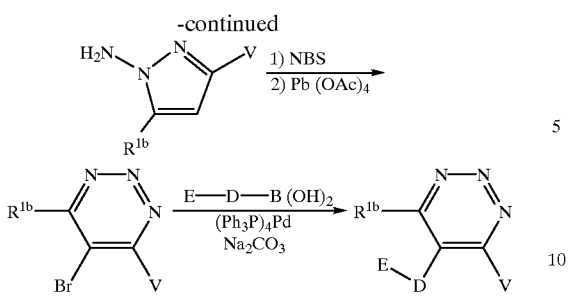

Scheme 41 and 42 describe the synthesis of compounds wherein M is a 1,2,4-triazine. In Scheme 41, a nitrile is converted using hydrazine to give the amidrazone which is condensed with a α-ketoester to give the triazinone as shown by Paudler and Lee (*J. Org. Chem.* 1971, 36, 3921). Bromination as shown by Rykowski and van der Plas (*J. Org. Chem.* 1987, 52, 71) followed by palladium-catalyzed coupling provides the desired 1,2,4-triazine.

Scheme 41

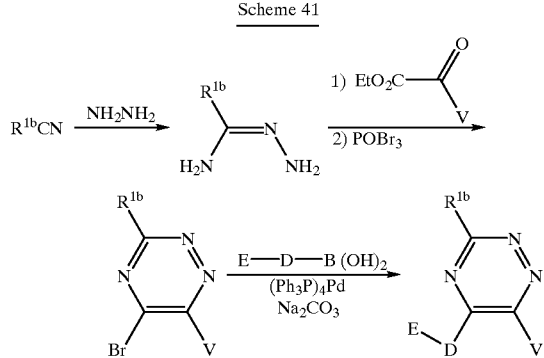

In Scheme 42, to achieve the opposite regioisomer the reaction scheme shown above is modify by the substituting a protected α-ketoester. This allows the most nucleophilic nitrogen to attack the ester functionality setting up the opposite regiochemistry. Deprotection and thermal cyclization gives the triazinone which is brominated as shown above. Palladium-catalyzed coupling provides the other desired 1,2,4-triazine.

Scheme 42

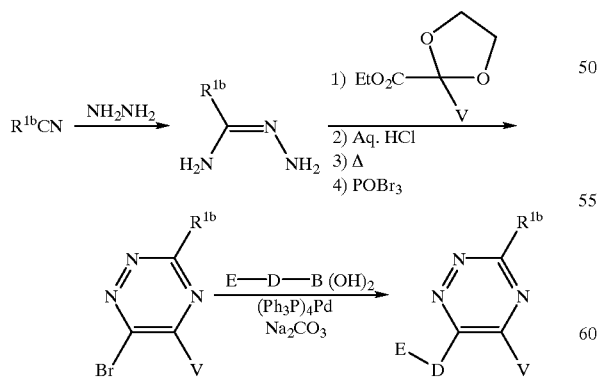

Scheme 43 describes the synthesis of compounds wherein M is a 1,2,3,4-tetrazine. Lithiation of a vinyl bromide, transmetallation with tin, palladium catalyzed carbonylation and hydrazone formation provides a diene for a subsequent Diels-Alder reaction as shown by Carboni and Lindsey (*J. Am. Chem. Soc.* 1959, 81, 4342). Reaction with dibenzyl azodicarboxylate followed by catalytic hydrogenation to debenzylate and decarboxylate should give after bromination the desired 1,2,3,4-tetrazine. Palladium-catalyzed coupling provides the desired substitution.

Scheme 43

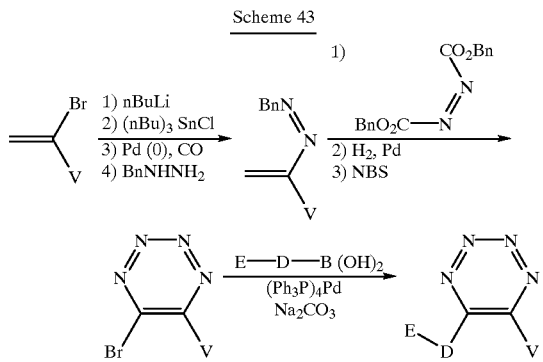

Preparation of Compounds of FORMULA I
Containing a Bicyclic Core

Schemes 44 and 45 illustrate the preparation of benzopyrazole and indole core intermediates useful for synthesizing compunds of Formula I. The starting pyrazole N-oxide in Scheme 44 can be obtained by a method outlined in *Chem. Ber.* (1926) 35–359. The pyrazole N-oxide can be reduced by any number of methods including triphenylphosphine in refluxing toluene followed by the hydrolysis of the nitrile substituent to a carboxylic acid with base to give the benzopyrazole intermediate which may be coupled in the usual way to give a compound of Formula I.

Scheme 44

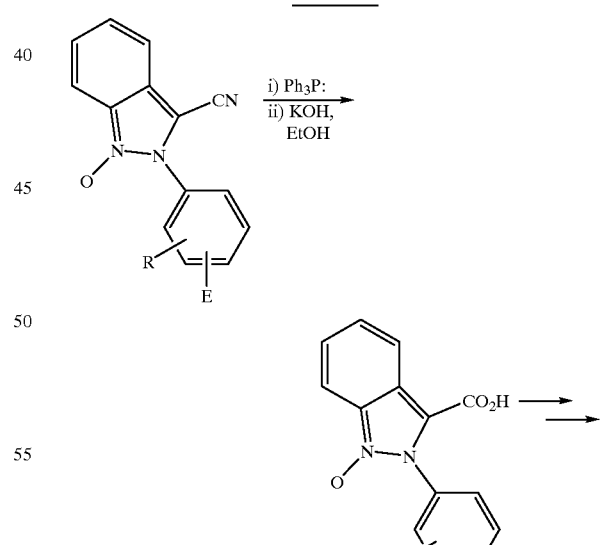

The starting indole in Scheme 45 may be obtained via the Fischer Indole Synthesis (*Org. Syn, Col.* Vol. III 725) from an appropriately substituted phenylhydrazine and acetophenone. Further elaboration using standard synthetic methods including the introduction of a 3-formyl group by treatment with POCl₃ in DMF, the optional protection of the indole NH with the SEM group (TMSCH2CH₂OCH2Cl, NaH, DMF) and oxidation of the aldehyde to a carboxylic acid which is now ready for transformation to compounds of Formula I.

Scheme 45

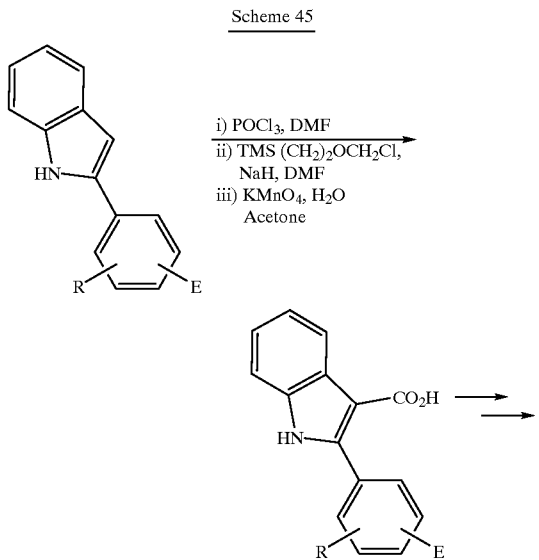

Preparation of Group A–B of FORMULA I

Compounds of this invention where B is either a carbocyclic or heterocyclic residue as defined in Formula 1 are coupled to A as shown generically and by specific example in Schemea 46 and 47, respectively. Either or both of A and B may be substituted with 0–2 $R^4$. W is defined as a suitable protected nitrogen, such as $NO_2$ or NHBOC; a protected sulfur, such as S-tBu or SMOM; or a methyl ester. Halogen-metal exchange of the bromine in bromo-B with n-butyl lithium, quenching with triisopropyl borate and acidic hydrolysis gives the required boronic acid, $B—B(OH)_2$. The W—A—Br subunit may be already linked to ring M before the Suzuki coupling reaction. Deprotection provides the complete subunit.

Scheme 46

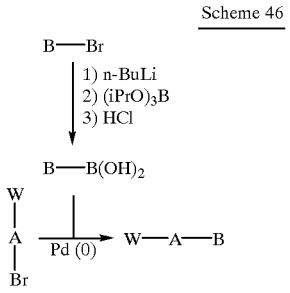

Scheme 47 describes a typical example of how the A-B subunit is prepared for attachment to ring M. 4-Bromoaniline is protected as Boc-derivative and the coupled to 2-(t-butylamino)sulfonylphenylboronic acid under Suzuki conditions. 2-(t-Butylamino) sulfonylphenylboronic acid is prepared by the method described by Rivero (*Bioorg. Med. Chem. Lett.* 1994, 189). Deprotection with TFA can provide the aminobiphen-4-yl compound. The aminobiphen-4-yl is then coupled to the core ring structures as described below.

Scheme 47

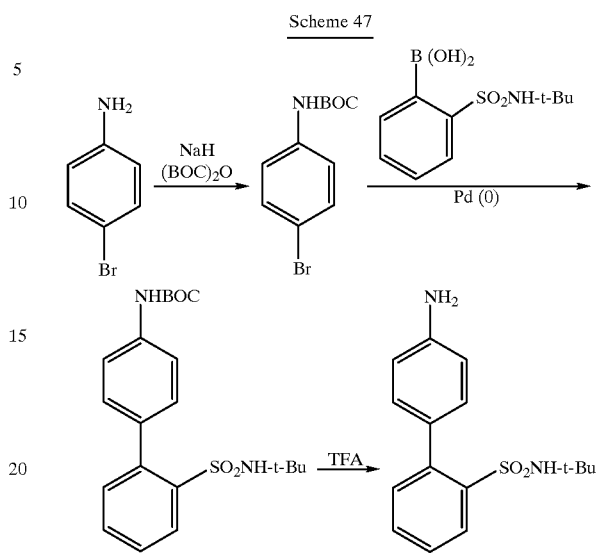

When B is defined as X—Y, the following description applies. Groups A and B are available either through commercial sources, known in the literature or readily synthesized by the adaptation of standard procedures known to practitioners skilled in the art of organic synthesis. the required reactive functional groups appended to analogs of A and B are also available either through commercial sources, known in the literature or readily synthesized by the adaptation of standard procedures known to practitioners skilled in the art of synthesis. In the tables that follow the chemistry required to effect the coupling of A to B is outlined.

TABLE A

Preparation of Amide Ester, Urea, Sulfonamide and Sulfamide Linkages Between A and B

| If A contains: | then the reactive substituent of Y is: | to give the following product A-X-Y: |
|---|---|---|
| A-NHR² as a substituent | ClC(O)-Y | A-NR²-C(O)-Y |
| a secondary NH as part of a ring or chain | ClC(O)-Y | A-C(O)-Y |
| A-OH as a substituent | ClC(O)-Y | A-O-C(O)-Y |
| A-NHR² as a substituent | ClC(O)-CR²R²ᵃ-Y | A-NR²-C(O)-CR²R²ᵃ-Y |
| a secondary NH as part of a ring or chain | ClC(O)-CR²R²ᵃ-Y | A-C(O)-CR²R²ᵃ-Y |
| A-OH as a substituent | ClC(O)-CR²R²ᵃ-Y | A-O-C(O)-CR²R²ᵃ-Y |
| A-NHR² as a substituent | ClC(O)-CNR²Y | A-NR²-C(O)-CNR²Y |
| a secondary NH as part of a ring or chain | ClC(O)-CNR²-Y | A-C(O)-CNR²Y |
| A-OH as a substituent | ClC(O)-CNR²-Y | A-O-C(O)-CNR²-Y |
| A-NHR² as a substituent | ClSO₂-Y | A-NR²-SO₂-Y |
| a secondary NH as part of a ring or chain | ClSO₂-Y | A-SO₂-Y |
| A-NHR² as a | ClSO₂-CR²R²ᵃ-Y | A-NR²-SO₂-CR²R²ᵃ-Y |

TABLE A-continued

Preparation of Amide Ester, Urea, Sulfonamide and Sulfamide Linkages Between A and B

| If A contains: | then the reactive substituent of Y is: | to give the following product A-X-Y: |
|---|---|---|
| substituent a secondary NH as part of a ring or chain | $ClSO_2$-$CR^2R^{2a}$-Y | A-$SO_2$-$CR^2R^{2a}$-Y |
| A-$NHR^2$ as a substituent | $ClSO_2$-$NR^2$-Y | A-$NR^2$-$SO_2$-$NR^2$-Y |
| a secondary NH as part of a ring or chain | $ClSO_2$-$NR^2$-Y | A-$SO_2$-$NR^2$-Y |
| A-C(O)Cl | HO-Y as a substituent | A-C(O)-O-Y |
| A-C(O)Cl | $NHR^2$-Y as a substituent | A-C(O)-$NR^2$-Y |
| A-C(O)Cl | a secondary NH as part of a ring or chain | A-C(O)-Y |
| A-$CR^2R^{2a}$C(O)Cl | HO-Y as a substituent | A-$CR^2R^{2a}$C(O)-O-Y |
| A-$CR^2R^{2a}$C(O)Cl | $NHR^2$-Y as a substituent | A-$CR^2R^{2a}$C(O)-$NR^2$Y |
| A-$CR^2R^{2a}$C(O)Cl | a secondary NH as part of a ring or chain | A-$CR^2R^{2a}$C(O)-Y |
| A-$SO_2$Cl | $NHR^2$-Y as a substituent | A-$SO_2$-$NR^2$-Y |
| A-$SO_2$Cl | a secondary NH as part of a ring or chain | A-$SO_2$-Y |
| A-$CR^2R^{2a}SO_2$Cl | $NHR^2$-Y as a substituent | A-$CR^2R^{2a}SO_2$-$NR^2$-Y |
| A-$CR^2R^{2a}SO_2$Cl | a secondary NH as part of a ring or chain | A-$CR^2R^{2a}SO_2$-Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of Ketone Linkages between A and B

| If A contains: | then the reactive substituent of Y is: | to give the following product A-X-Y: |
|---|---|---|
| A-C(O)Cl | BrMg-Y | A-C(O)-Y |
| A-$CR^2R^{2a}$C(O)Cl | BrMg-Y | A-$CR^2R^{2a}$C(O)-Y |
| A-C(O)Cl | BrMg$CR^2R^{2a}$-Y | A-C(O)$CR^2R^{2a}$-Y |
| A-$CR^2R^{2a}$C(O)Cl | BrMg$CR^2R^{2a}$-Y | A-$CR^2R^{2a}$C(O)$CR^2R^{2a}$-Y |

The coupling chemistry of table B can be carried out by a variety of methods. The Grignard reagent required for Y is prepared from a halogen analog of Y in dry ether, dimethoxyethane or tetrahydrofuran at 0° C. to the ref lux point of the solvent. This Grignard reagent can reacted directly under very controlled conditions, that is low temperature (−20° C. or lower) and with a large excess of acid chloride or with catalytic or stoichiometric copper bromide-dimethyl sulfide complex in dimethyl sulfide as a solvent or with a variant thereof. Other methods available include transforming the Grignard reagent. to the cadmium reagent and coupling according to the procedure of Carson and Prout (*Org. Syn. Col.* Vol. 3 601, 1955) or coupling mediated by Fe(acac)$_3$ according to Fiandanesse et al. (*Tet. Lett.,* 4805, 1984), or a coupling mediated by manganese(II) catalysis (*Cahiez and Laboue, Tet. Lett.,* 33(31), 4437, 1992).

TABLE C

Preparation of Ether and Thioether linkages between A and B

| If A contains: | then the reactive substituent of Y is: | to give the following product A-X-Y: |
|---|---|---|
| A-OH | Br-Y | A-O-Y |
| A-$CR^2R^{2a}$-OH | Br-Y | A-$CR^2R^{2a}$O-Y |
| A-OH | Br-$CR^2R^{2a}$-Y | A-OC$R^2R^{2a}$-Y |
| A-SH | Br-Y | A-S-Y |
| A-$CR^2R^{2a}$-SH | Br-Y | A-$CR^2R^{2a}$S-Y |
| A-SH | Br-$CR^2R^{2a}$-Y | A-SC$R^2R^{2a}$-Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at a temperature ranging from ambient to the reflux point of the solvent used.

TABLE D

Preparation of-SO-and-$SO_2$-linkages from thioether of Table C

| If the starting material is: | then it is oxidized with wet Alumina/Oxone to give: | then it is with m-chloroperbenzoic acid to give: |
|---|---|---|
| A-S-Y | A-S(O)-Y | A-$SO_2$-Y |
| A-$CR^2R^{2a}$S-Y | A-$CR^2R^{2a}$S(O)-Y | A-$CR^2R^{2a}SO_2$-Y |
| A-SC$R^2R^{2a}$-Y | A-S(O)$CR^2R^{2a}$-Y | A-$SO_2$$CR^2R^{2a}$-Y |

The thioethers of Table C serve as a convenient starting material for the preparation of the sulfoxide and sulfone analogs of Table D. A combination of wet alumina and Oxone can provide a reliable reagents for the oxidation of the thioether to the sulfoxide as shown by Greenhalgh (Syn. Lett., 235, 1992). The sulfone can be prepared according to the method of Satoh (Chem. Lett., 381, 1992) using m-chloroperbenzoic acid.

Other features of the invention will become apparent in the course of the following descriptions of exemplary embodiments which are given for illustration fo the invention and are not intended to be limiting thereof.

EXAMPLES

Abbreviations used in the Examples are defined as follows: "°C." for degrees Celsius, "d" for doublet, "dd" for doublet of doublets, "eq" for equivalent or equivalents, "ESMS" for electrospray mass spectroscopy, "H" for hydrogen or hydrogens, "h" for hour or hours, "g" for gram or grams, "m" for multiplet, "M" for molar, "mg" for milligram or milligrams, "MHz" for megahertz, "min" for minute or minutes, "mL" for milliliter or milliliters, "MS" for mass spectroscopy, "nmr" or "NMR" for nuclear magnetic resonance spectroscopy, "t" for triplet, "TLC" for thin layer chromatography, "BOPE" for benzotriazol-1-yloxy-tris(dimethylamino)phosphonium hexafluorophosphate, "DMAP" for dimethylaminopyridine, "DME" for dimethoxyethane, "EDAC" for 1-(3-dimethylaminopropyl)-3-ethylcarbodiimide hydrochloride, "LAH" for lithium aluminium hydride, "NBS" for N-bromosuccinimide, "PyBrop" for bromo-tris-pyrrolidino-phosphonium hexaflourophosphate, "TBAF" for tetrabutylammonium fluoride, "TBS-Cl" for t-butyldimethylsilyl chloride, and "TEA" for triethylamine.

Examples 1

3-Methyl-1-phenyl-1H-pyrazole-5-(N-(2'-aminosulfonyl-[1,1']-biphen-4-yl))carboxyamide

Ethyl 2-N-(methoxy)imino-4-oxopentanoate

A mixture of ethyl pentanoate-2,4-dione (24.5 g, 154.9 mmol) and methoxyamine hydrogen chloride (13.58 g, 162.6 mmol) in ethanol (100 mL) was allowed to stand over activated 3 Å molecular sieves (75 g) at ambient temperature for 18 Å. Following removal of the molecular sieves by filtration, dichloromethane (100 mL) was added and the reaction filtered. The resulting solution was evaporated and the residue applied to a silica gel column. The title compound was isolated in a homogenous form by elution with 5:1 hexane:ethyl acetate to give 9.09 g of product.

Ethyl 3-methyl-1-phenyl-1H-pyrazolecarboxylate

Ethyl 2-N-(methoxy)imino-4-oxcpentanoate (0.5 g, 2.67 mmol) and phenylhydrazine (0.58 g, 5.35 mmol) in acetic acid (10 mL) and 2-methoxyethanol (5 mL) were heated at 105° C. for 5 h. The reation was evaporated, dissolved in ethyl acetate and washed with 0.2N HCl then water. The solution was dried ($Na_2SO_4$) evaporated and the residue applied to a silica gel column. Elution with a gradient of 10:1 to 5:1 hexane:ethyl acetate gave 160 mg of ethyl 3-methyl-1-phenyl-1H-pyrazolecarboxylate; LRMS $(M+H)^+$ m/z: 231.

3-methyl-1-phenyl-1H-pyrazole-5-(N-(2'-N-t-butylaminosulfonyl-[1,1']-biphen-4-yl))carboxyamide To a 0° C. of 4-(2-N-t-butylaminosulfonyl)phenyl)aniline (0.22 g, 0.73 mmol) in dichloromethane (10 mL) was added a solution of trimethylaluminum (2.0 M in hexane, 5 eq, 1.75 mL). This mixture was stirred for 15 min then ethyl 3-methyl-1-phenyl-1H-pyrazolecarboxylate (0.16 g, 0.69 mmol) in dichloromethane (5 mL) was added. The reaction was allowed to warm to ambient temperature and stirred for 18 h. This mixture was carefully quenched with water, then diluted with ethyl acetate and the layers separated, dried and evaporated. The residue was applied to a silica gel column and the title compound isolated by gradient elution with mixture of 3:1 to 1:1 hexane:ethyl acetate. There was obtained 150 mg of 3-methyl-1-phenyl-1H-pyrazole-5-(N-(4-(2'-N-t-butylaminosulfonyl-[1,1']-biphen-4-yl)carboxyamide; HRMS $(M+H)^+$ calc. m/z: 489.196038, obs: 489.194346.

3-methyl-1-phenyl-1H-pyrazole-5-(N-(2'-aminosulfonyl-[1,1']-biphen-4-yl))carboxyamide A solution of 150 mg of 3-methyl-1-phenyl-1H-pyrazole-5-(N-(4-(2'-N-t-butylaminosulfonyl-[1,1']-biphen-4-yl) carboxyamide in trifluoroacetic acid (15 mL) was heated at reflux for 1 h. The reaction was evaporated, taken up in ethyl acetate and washed with 1 N sodium hydroxide solution. The organic solution was dried and evaporated to give 140 mg of product. Further purification of 3-methyl-1-phenyl-1H-pyrazole-5-(N-(4-(2'-aminosulfonyl-[1,1']-biphen-4-yl) carboxyamide was effected by hplc utilizing gradient elution with a mixture of water: acetonitrile with 0.05% trifluoroacetic acid on a reverse phase C18 (60 Å) column; HRMS $(M+H)^+$ calc. m/z: 433.133438, obs: 433.131005.

Example 2

3-Methyl-1-(2-methoxy)phenyl-1H-pyrazole-5-(N-(2'-aminosulfonyl-[1.1']-biphen-4-yl)carboxyamide This compound was prepared by the same methodology described for EXAMPLE 1 with 2-methoxyphenyl hydrazine .HCl substituted for phenyl hydrazine. There was obtained 3-methyl-1-(2-methoxy)phenyl-1H-pyrazole-5-(N-(2'-aminosulfonyl-[1,1']-biphen-4-yl)carboxyamide; HRMS $(M+H)^+$ calc. m/z: 463.144002, obs: 463.144162.

Example 3

3-Methyl-1-(3-methoxy)phenyl-1H-pyrazole-5-(N-(2'-aminosulfonyl-[1,1']-biphen-4-yl)carboxyamide This compound was prepared by the same methodology described for EXAMPLE 1 with -methoxyphenyl hydrazine.HCl substituted for phenyl hydrazine. There was obtained 3-methyl-1-(2-methoxy)phenyl-1H-pyrazole-5-(N-(2'-aminosulfonyl-[1,1']-biphen-4-yl)carboxyemide; HRMS $(M+H)^+$ calc. m/z: 463.144002, obs: 463.144301.

Example 4

3-Methyl-1-(4-methoxy)phenyl-1H-pyrazole-5-(N-(2'-aminosulfonyl-[1,1']-biphen-4-yl)carboxyamide This compound was prepared by the same methodology described for EXAMPLE 1 with 4-methoxyphenyl hydrazine.HCl substituted for phenyl hydrazine. There was obtained 3-methyl-1-(2-methoxy)phenyl-1H-pyrazole-5-(N-(2'-aminosulfonyl-[1,1']-biphen-4-yl)carboxyamide; HRMS $(M+H)^+$ calc. m/z: 463.144002, obs: 463.141980.

Example 5

3-Methyl-1-(2hydroxy)pheenyl-1H-pyrazole-5-(N-(2'-aminosulfonyl-[1,1']-biphen-4-yl)carboxyamide The product of EXAMPLE 2, 3-methyl-1-(2-methoxy) phenyl-1H-pyrazole-5-(N-(2'-aminosulfonyl-[1,1']-biphen-4-yl)carboxyamide (0.245 g, 0.53 mmol), in dichloromethane (20 mL) was cooled to 0° C. and a solution of borontribromide in dichloromethane (1.0 M, 6 equivalents, 3.2 mL) was added. The reaction was allowed to warm to ambient temperature and stirred for 18 h. The reaction was evaporated and the residue allpied to a small plug of silica gel and eluted with ethyl acetate. The ethyl acetate solution was dried and evaporated. This material was purified by hplc utilizing gradient elution with a mixture of water:acetonitrile with 0.05% trifluoroacetic acid on a reverse phase C18 (60 Å) column to give the title compound; HRMS $(M+H)^+$ calc. m/z: 449.128352, obs: 449.129006.

Example 6

3-Methyl-1-(3-hydroxy)-henyl-1H-pyrazole-5-(N-(2'-aminosulfonyl-[1,1']-biphen-4-yl)carboxyamide The product of EXAMPLE 3, 3-methyl-1-(3-methoxy) phenyl-1 H-pyrazole-5-(N-(2'-aminosulfonyl-[1,1']-biphen-4 -yl)carboxyamide was treated according to the procedure described for EXAMPLE 5 to give the title compound; HRMS $(M+H)^+$ calc. m/z: 449.128352, obs: 449.127620.

Example 7

3-Methyl-1-(4-hydroxy)phenyl-1H-pyrazole-5-(N-(2'-aminosulfonyl-[1,1']-biphen-4-yl)carboxyamide The product of EXAMPLE 4, 3-methyl-1-(4-methoxy) phenyl-1 H-pyrazole-5-(N-(2'-aminosulfonyl-[1,1']-biphen-4 -yl)carboxyamide was treated according to the procedure described for EXAMPLE 5 to give the title compound; HRMS $(M+H)^+$ calc. m/z: 449.128352, obs: 449.127304.

Example 8

3-Methyl-1-(4-methoxyphenyl)-1H-pyrazole-5-(N-(3-fluoro-(2'-aminosulfonyl-[1,1']1-biphen-4-yl) carboxyamide

3-Methyl-1-(4-methoxyphenyl)-1H-pyrazolecarboxylic acid

A mixture of ethyl 3-methyl-1-(4-methoxyphenyl)-1 H-pyrazolecarboxylate (0.01997 mol, 5.197 g) and potassium hydroxide (3.362 g, 3.0 eq.) in ethanol (70 mL) was stirred at ambient temperature for 5 h. The solvent was removed in vacuo and the residue was taken up in water. This was extracted with methylene chloride (3×) to remove unreacted starting material. The aqueous was made acidic (pH 3) by the dropwise addition of conc. HCl at 0° C. to give white precipitation of acid. The solid acid was obtained by filtration and pumped on for several hours to dry. This procedure gave 4.23 g of pure product (91%); mp: 161.8° C.

2-Fluoro-4-(2-aminosulfonylphenyl)aniline

A mixture of 2 -fluoro-4-bromoaniline (0.01 mol, 2.51 g), boronic acid (2.57 g, 1.0 eq.), sodium carbonate (3.18 g, 3.0 eq.), and tetrakis(triphenylphosphine) palladium(0) (0.23 g, 0.02 eq.) in tetrahydrofuran(100 mL) and water (50 mL) was stirred at ambient temperature for 30 min. while nitrogen gas was bubbling to remove oxygen. This reaction mixture was then refluxed for 18 h. The reaction mixture was filtered through celite to remove catalyst and washed with tetrahydrofuran(50 mL). The filtrate was evaporated in vacuo and the residue was taken up in water then extracted with ethyl acetate (3×); the ethyl acetate extracts were washed with brine, dried ($MgSO_4$), and evaporated. This residue was purified by flash chromatography on a silica gel column (150 g) eluted with 2.5:1 hexane:ethyl acetate to give 1.976 g of pure product (61 %)

3-Methyl-1-(4-methoxyphenyl)-1H-pyrazole-5-(N-(3-fluoro-4-(2'-aminosulfonyl-[1,1']-biphen-4-yl) carboxyamide To the solution of 3-methyl-1-(4-methoxyphenyl)-1H-pyrazolecarboxylic acid (0.001 mol, 0.232 g) in dry acetonitrile (10 mL) was added thionyl chloride (0.3 mL, 4.0 eq.). This reaction mixture was warmed up at 50° C. for 1 h then allowed to cool to ambient temperature and stirred for 1 h. The solvent and extra thionyl chloride were removed in vacuo and the residue was pumped on for several hours for further dry.

To this dried residue was added a mixture of 2-fluoro-4-((2 -N-t-butylsulfonamido)phenyl)aniline (0.322 g, 1.0 eq.) and triethyl amine (0.14 mL, 1.0 eq.; 2.0 eq. for HCl salt) in dry methylene chloride (10 mL). This reaction mixture was allowed to stir at ambient temperature for 2 h. The reaction mixture was evaporated and purified by flash chromatography on a silica gel column(50 g) eluted with 3:1 hexane:ethyl acetate to give 0.301 g of pure product with t-butyl sulfonamide(56%)

This product was treated with trifluoroacetic acid at 55 ° C. for 2 h for deprotection of sulfonamide to give 0.287 g of pure product(86%) after purification by reverse phase hplc; HRMS (M+H)+ calc. 481.134581, found 481.133650 for the title compound.

Example 9

3-Methyl-1-(4-methoxyphenyl)-1H-pyrazole-5-(N-(3-bromo-4-(2'-aminosulfonyl-[1,1']-biphen-4-yl) carboxyamide

2-Bromo-4-(2-aminosulfonylphenyl)aniline

This compound was prepared by the method described for 2-fluoro-4-(2 -aminosulfonylphenyl)aniline described in EXAMPLE 8 by starting with 2,4-dibromoaniline rather than 2-fluoro-4-bromoaniline.

3-Methyl-1-(4-methoxyphenyl)-1H-pyrazole-5-(N-(3-bromo-4-(2'-aminosulfonyl-[1,1']-biphen-4-yl) carboxyamide This compound was prepared by the same methods described for EXAMPLE 8 by coupling with 2-brorrio-4-((2 -N-t-butylsulfonamido)phenyl)aniline rather than 2-fluoro-4-((2 -N-t-butylsulfonamido)phenyl)aniline. The title compound was obtained as pure product after purification by reverse phase hplc; HRMS (M+H)+ calc. 541.054513, found 541.055340.

Example 10

3-Methyl-1-(4-methoxyphenyl)-1H-yrazole-5-(N-(3-iodo-(2'-aminosulfonyl-[1,1']-biphen-4-yl) carboxyamide

2-Iodo-4-(2-aminosulfonylphenyl)aniline

This compound was prepared by the method described for 2-fluoro-4-(2 -aminosulfonylphenyl)aniline described in EXAMPLE 8 by starting with 2-iodo-4-bromoaniline rather than 2-fluoro-4 -bromoaniline.

3-Methyl-1-(4-methoxyphenyl)-1H-pyrazole-5-(N-(3-iodo-(2'-aminosulfonyl-[1,1']-biphen-4-yl) carboxyamide This compound was prepared by the same methods described for EXAMPLE 8 by coupling with 2-iodo-4-((2-N-t-butylsulfonamido)phenyl)aniline rather than 2-fluoro,-4-((2 -N-t-butylsulfonamido)phenyl)aniline. The title compound was obtained as pure product after purification by reverse phase hplc; HRMS (M+H)+ calc. 589.040654, found 589.039223.

Example 11

3-Methyl-1-(4-methoxyphenyl)-1H-pyrazole-5-(N-(3-methyl-(2'-aminosulfonyl-[1,1']-biphen-4-yl) carboxyamide

2-Methyl-4-(2-aminosulfonylphenyl)aniline

This compound was prepared by the method described for 2-fluoro-4-(2 -aminosulfonylphenyl)aniline described in EXAMPLE 8 by starting with 2-methyl-4-bromoaniline rather than 2-fluoro-4-bromoaniline.

3-Methyl-1-(4-methoxyphenyl)-1H-pyrazole-5-(N-(3-methyl-(2'-aminosulfonyl-[1,1']-biphen-4-yl) carboxyamide This compound was prepared by the same methods described for EXAMPLE 8 by coupling with 2-methyl-4-((2 -N-t-butylsulfonamido)phenyl)aniline rather than 2-fluoro-4-((2 -N-t-butylsulfonamido)phenyl)aniline. The title compound was obtained as pure product after purification by reverse phase hplc; HRMS (M+H)+ calc. 477.159652, found 477.159337.

Example 12

3-Methyl-1-(4-methoxyphenyl)-1H-pyrazole-5-(N-(4 -N-carboxyldimethylamine)phenyl)carboxyamide

4-(N-Carboxyldimethylamine)aniline

A 2-fold excess of neat dimethylamine (ca. 0.73 g) was added to a 0° C. solution of p-nitrobenzoyl chloride (1.5 g, 8.1 mmol) in dichloromethane (50 mL). The reaction was then evaporated to dryness and the residue dissolved in ethyl acetate. This solution was washed with 1N hydrochloric acid solution and brine, then dried and evaporated to give 4-(N-carboxyldimethylamine)nitrobenzene.

This material was reduced under an atmosphere of hydrogen gas (50 psi) in methanol (100 mL) in the presence of 10% palladium on carbon catalyst (100 mg). After about 2 h, the reduction was complete; the reaction was purged with nitrogen gas and the catalyst removed by filtration through a pad of Celite. The solvent was evaporated to give the title compound.

3-Methyl-1-(4-methoxyphenyl)-1H-pyrazole-5-(N-(4-N-carboxyldimethylamine)phenyl)carboxyamide This compound was prepared by the same methods described for EXAMPLE 8 by coupling with 4-(N-carboxyldimethylamine)aniline rather than 2-fluoro-4-((2-N-t-butylsulfonamido)phenyl)aniline and then omitting the final the trifloroacetic acid deprotection step. The title compound was obtained as pure product after purification by reverse phase hplc; HRMS (M+H)$^+$ calc. 379.177016, found 379.176235.

Example 13

3-Methyl-1-(4-methoxyphenyl)-1H-pyrazole-5-(N-(4-N-pyrrolidinocarbonyl)-phenyl)carboxyamide

4-(N-Pyrrolidinocarbonyl)aniline

A 2-fold excess of neat pyrrolidine (1.15 g, 16.2 mmol) was added to a 0° C. solution of p-nitrobenzoyl chloride (1.5 g, 8.1 mmol) in dichloromethane (50 mL). The reaction was then evaporated to dryness and the residue dissolved in ehtyl acetate. This solution was washed with IN hydrochloric acid solution and brine, then dried and evaporated to give 4-(N-pyrrolidinocarbonyl)nitrobenzene. This material was reduced under an atmosphere of hydrogen gas (50 psi) in methanol (100 mL) in the presence of 10% palladium on carbon catalyst (100 mg). After about 2 h, the reduction was complete; the reaction was purged with nitrogen gas and the catalyst removed by filtration through a pad of Celite. The solvent was evaporated to give the title compound.

3-Methyl-1-(4-methoxyphenyl)-1H-pyrazole-5-(N-(4-N-pyrrolidinocarbonyl)phenyl)carboxyamide This compound was prepared by the same methods described for EXAMPLE 8 by coupling with 4-(N-pyrrolidinocarbonyl)aniline rather than 2 -fluoro-4-((2-N-t-butylsulfonamido)phenyl)aniline and then omitting the final the trifloroacetic acid deprotection step. The title compound was obtained as pure product after purification by reverse phase HPLC; HRMS (M+H)$^+$ calc. 404.184841, found 404.182119.

Example 14

3-Methyl-1-(4-methoxyphenyl)-1H-pyrazole-5-(N-(4-α-methyl-N-pyrrolidino)-phenyl)carboxyamide

4-(α-N-pyrrolidino)methyl aniline

To pyrrolidine (0.67 g, 0.79 mL, 9.4 mmol) in chloroform (50 mL) was added 4 -nitrobenzyl bromide (2.03 g, 9.4 mmol) and sodium carbonate (2 g). The reaction was heated at reflux for 2 h, then stirred at ambient temperature for 18 h. Water was added to the reaction mixture, then the layers were partitioned. The chloroform layer was dried and evaporated to give 1.55 g of N-alkylation product; LRMS (M+H)$^+$ m/z: 207.2.

Reduction of the nitro group on the material prepared above was effected by stirring this material with tin(II) chloride dihydrate (8.5 g, 37.6 mmol) in ethanol (50 mL) at ambient temperature for 18 h. The reaction was diluted with 1N sodium hydroxide solution and extracted with ethyl acetate (3×). The extracts were washed with brine, dried and evaporated to give 1.23 g of 4-(α-N-pyrrolidino)methyl aniline; LRMS (M+H)$^+$ m/z: 177.2.

3-Methyl-1-(4-methoxyphenyl)-1H-pyrazole-5-(N-(4-α-methyl-N-pyrrolidino)phenyl)carboxyamide A mixture of 3-Methyl-1-(4-methoxyphenyl)-1H-pyrazolecarboxylic acid (100 mg, 0.43 mmol), 4-(α-N-pyrrolidino)methyl aniline (76 mg, 0.43 mmol) in dimethylformamide (3 mL) was cooled to 0° C. N-Methylmorpholine (0.86 mmol, 87 mg, 0.1 mL) and HBTU (0.43 mmol, 163 mg) were added. The reaction was allowed to thaw to ambient temperature and stirred for 18 h. The reaction was diluted with 1N sodium hydroxide, then extracted with ethyl acetate. The extracts were washed with brine, dried and evaporated. This material was purified by hplc utilizing gradient elution with a mixture of water:acetonitrile with 0.05% trifluoroacetic acid on a reverse phase C18 (60 Å) column to give the title compound (70 mg); LRMS (M+H)$^+$ m/z: 391.2.

Example 15

3-Trifluoromethyl-1-(4-methoxyphenyl)-1H-pyrazole-5-(N-(2'-aminosulfonyl-[1,1']-biphen-4-yl)carboxyamide

3-Trifluoromethyl-5-methyl-1-(4-methoxyphenyl)-1H-pyrazole

A mixture of 1,1,1-trifluoro-2,4-pentanedione (0.02 mol, 2.4 ML) and 4-methoxyphenyl hydrazine.HCl (4.54 g, 1.3 eq.) in 2 -methoxyethanol (100 mL) and acetic acid (30 mL) was refluxed for 6 h. The reaction mixture was evaporated and purified by flash chromatography on a silica gel column (400 g) eluted with 4:1 hexane:ethyl acetate to give 4.5 g of pure product (88%)

3-Trifluoromethyl-5-hydroxymethyl-1-(4-methoxyphenyl)-1H-pyrazole

A mixture of 3-trifluoromethyl-5-methyl-1-($^4$-methoxyphenyl)-1H-pyrazole (0.01756 mol, 4.5 g), N-bromosuccinimide (3.439 g, 1.1 eq.), and AIBN (0.1 g) in carbon tetrachloride (100 mL) was refluxed for 18 h. The reaction mixture was filtered through celite to remove solid impurity and washed with carbon tetrachloride (100 mL). The filtrate was evaporated and purified by flash chromatography on a silica gel column (400 g) eluted with 4:1 hexane:ethyl acetate to give 3.826 g of pure product (65%).

This material was treated with calcium carbonate (2.637 g, 1.5 eq.) in dioxane (80 mL) and water (20 mL) at 55–60° C. for 18 h. The reaction mixture was evaporated and purified by flash chromatography on a silica gel column (400 g) eluted with 4:1 hexane:ethyl acetate to give 1.198 g of pure product (39%) Recrystallization from a mixture of benzene:hexane gave an analytically pu re sample; mp: 79.0° C.; CHNF: theory % C 52.95,% H 4.07, % N 10.29, % F 20.94; found % C 52.88; % H 3.98; % N 10.11; % F 20.62.

3-Trifluoromethyl-1-(4-methoxyphenyl)-1H-pyrazole-5-carboxylic acid

To the solution of 3-trifluoromethyl-5-hydroxymethyl-1-(4-methoxyphenyl)-1H-pyrazole (4.4007 mmol, 1.198 g) in acetonitrile (20 mL) and water (20 mL) was added sodium periodate (1.977, 2.1 eq.) and several crystals of ruthenium (III) chloride at 0° C. This reaction mixture was stirred at ambient temperature for 18 h. The reaction mixture was filtered through Celite to remove white solid impurity and the filter cake washed with 1:1 acetonitrile: water. The filtrate was evaporated in vacuo and the residue was taken up in water. The aqueous was made acidic (pH 3) by the dropwise addition of conc. HCl at 0° C. then extracted with ethyl acetate (3×); the ethyl acetate extracts were washed with brine, dried (MgSO$_4$), and evaporated to gave 1.13 g of pure product (90%).

3-Trifluoromethyl-1-(4-methoxyphenyl)-1H-pyrazole-5-(N-(2'-N-t-butylaminosulfonyl-[1,1']-biphen-4-yl)carboxyamide To 300 mg of 3-trifluoromethyl-1-(4-methoxyphenyl)-1H-pyrazole-5 -carboxylic acid (1.05 mmol) in dichloromethane (10 mL) at 0° C. was added a solution of oxalyl chloride in dichloromethane (2M, 1.5 equivilents, 1.58 mmol, 0.8 mL) and a drop of dimethylformamide. After 4 h the reaction was complete, the solvent was evaporated and the acid chloride carried on to the next reaction.

The material prepared above was dissolved in dichloromethane (20 mL) and then added over a period of 15–20 min to a 0° C. solution of 4-(2-N-t-butylaminosulfonyl) phenyl)aniline (1.2 equivilents, 1.25 mmol, 0.365 g), pyridine (10 equivilents, 12.5 mmol, 0.99 g, 1.0 mL) and N,N-dimethylaminopyridine (1.2 equivilents, 1.25 mmol, 0.155 g) in dichloromethane (20 mL). The reaction was maintained at 0° C. until thin layer chromatography indicated that all of the starting acid chloride was consumed. The reaction was evaporated, then the residue suspended in IN hydrochloric acid solution. The suspension was extracted with ethyl acetate; the extracts were washed with IN hydrochloric acid solution (2×) then dried and evaporated. There was obtained 660 mg of the desired product; LRMS (M+Na)$^+$ m/z: 594.5.

3-Trifluoromethyl-1-(4-methoxyphenyl)-1H-pyrazole-5-(N-(2'-aminosulfonyl-[1,1']-biphen-4-yl)carboxyamide 3-Trifluoromethyl-1-(4-methoxyphenyl)-1H-pyrazole-5-(N-(2'-N-t-butylaminosulfonyl-[1,1']-biphen-4-yl) carboxyamide (0.66 g) was dissolved in trifluoroacetic acid (20 mL) and heated at reflux for 30 min. The reaction was evaporated, then dissolved in ethyl acetate and washed with IN sodium hydroxide solution (2×) and brine. This solution was dried and evaporated to 0.48 g of crude product. This material was made analytically pure by first subjecting it to flash chromatography with a 200 g column of silica gel and elution with 2:1 hexane:ethyl acetate and finally recrystallizing the homogeneous chromatography product from chloroform. There was obtained 0.262 g of the title compound; mp: 237.3; CHNSF: theory % C 55.81, % H 3.718, % N 10.85, % S 6.218, % F 11.03; found % C 56.02, % H 3.77, % N 10.51, % S 5.84, % F 11.29.

Example 16

3-Trifluoromethyl-1-(4-methoxyphenyl)-1H-pyrazole-5-(N-(4-N-pyrrolidinocarbonyl)phenyl)carboxyamide

3-Trifluoromethyl-1-(4-methoxyphenyl)-1H-pyrazole-5-(N-(4-N-pyrrolidinocarbonyl)phenyl)carboxyamide 3-Trifluoromethyl-1 -(4-methoxyphenyl)-1H-pyrazole-5-carboxylic acid (500 mg) was dissolved in anhydrous CH$_2$Cl$_2$ (25 mL) with thionyl chloride (0.257 mL). This mixture was stirred at ambient temperature for 24 hours. The volatiles were removed under reduced pressure and the solution was dried under vacuum. 4-(N-Pyrrolidinocarbonyl)aniline (0.369 g) was dissolved in anhydrous CH$_2$Cl$_2$ 30 mL) and cooled to 0° C. Anhydrous pyridine (1.43 mL), and DMAP (0.259 g) was added and the mixture was stirred for 15 minutes. The prepared acid chloride was dissolved in anhydrous CH$_2$Cl$_2$ (5 mL) and was added dropwise to the reaction mixture. The reaction was warmed to ambient temperature and stirred overnight. The mixture was concentrated in vacuo. Purification was done on silica gel using ethyl acetate:hexanes (1:1) as the eluent yielding 325 mg (95% purity by HPLC). LRMS (M+H)$^+$=459 C$_{23}$H$_{21}$N$_4$O$_3$F$_3$. HRMS for C$_{23}$H$_{21}$N$_4$O$_3$F$_3$ (M+H)$^+$ calc. 458.156576, found 458.156478. $^1$H NMR (CDCl$_3$) δ1.85–1.99 (m, 4H), 3.41 (t, 2H, J=6.23 Hz), 3.63 (t, 2H, J=6.59 Hz), 3.85 (s, 3H), 6.99 (d, 2H, J=6.95 Hz), 7.31 (s, 1H), 7.31 (s, 4H), 7.42 (d, 2H, J=6.59 Hz), 8.42 (s, 1H).

Example 17

3-Trifluoromethyl-1-(4-methoxyphenyl)-1H-pyrazole-5-(N-(5-(2-methanesulfonyl)phenyl) pyridin-2-yl)carboxyamide

3-trifluoromethyl-1-(4-methoxyphenyl)-1H-pyrazole-5-(N-(5-(2-methanesulfonyl)phenyl) pyridin-2-yl)carboxyamide This material was prepared according to the methods described for EXAMPLE 15 with the exception that during the coupling step 2-amino-5-(2-N-t-butylaminosulfonyl) phenyl)pyridine was substituted for 4-(2-N-t-butylaminosulfonyl)phenyl)aniline. Purification by hplc utilizing gradient elution with a mixture of water:acetonitrile with 0.05% trifluoroacetic acid on a reverse phase C18 (60 Å) column gave a pure sample of the title compound; LRMS; (M+H)$^+$ m/z: 517, (M+Na)$^+$ m/z: 539.

Example 18

3-Trifluoromethyl-1-(4-methoxyphenyl)-1H-pyrazole-5-(N-(5-N-pyrrolidinocarbonyl)pyridin-2-yl)carboxyamide

2-Amino-5-(N-pyrrolidinocarbonyl)pyridine

A mixture of 2-aminonicotinic acid (2.26 g, 16.4 mmol) and pyrrolidine (1.16 g, 16.4 mmol) in dimethylformamide (20 mL) was cooled to 0° C. To the mixture was added N-methylmorpholine (3.31 g, 32.7 mmol) and HBTU (6.2 g, 16.4 mmol). The reaction was allowed to warm to ambient temperature and stirred 18 h. The reaction was diluted with 1N sodium hydroxide and extracted with ethyl acetate. The product was purified by flash chromatography using 10% methanol in chloroform as the eluent; 1.65 g of product was isolated; LRMS (M+H)$^+$ m/z: 192.

3-Trifluoromethyl-1-(4-methoxyphenyl)-1H-pyrazole-5-(N-(5-N-pyrrolidinocarbonyl)pyridin-2-yl)carboxyamide This material was prepared according to the methods described for EXAMPLE 15 with the exception that during the coupling step 2-amino-5-(N-pyrrolidinocarbonyl) pyridine was substituted for 4-(2-N-t-butylaminosulfonyl) phenyl)aniline. Purification by hplc utilizing gradient elution with a mixture of water:acetonitrile with 0.05% trifluoroacetic acid on a reverse phase C18 (60 Å) column gave a pure sample of the title compound; LRMS (M+H)$^+$ m/z: 460.2.

Example 19

3-Methyl-1-(4-methoxyphenyl)-1H-pyrazole-5-(N-(5-N-pyrrolidinocarbonyl)pyridin-2-yl) carboxyamide 3-Methyl-1-(4-methoxyphenyl)-1H-pyrazole-5-(N-(5-N-pyrrolidinocarbonyl)pyridin-2-yl) carboxyamide To a solution of 3-methyl-1-(4-methoxyphenyl)-1H-pyrazolecarboxylic acid (1.02 g, 4.4 mmol) in dichloromethane (20 mL) at 0° C. was added 4.4 mL of a 2M solution of oxalyl chloride in dichloromethane folLowed by a drop of dimethylformamide. After 2 h the solvent was removed and 1.12 g of acid chloride was obtained. This material carried on to the next step without further purification.

To 2-amino-5-(N-pyrrolidinocarbonyl)pyridine (0.4 g, 2.1 mmol) with triethylamine (0.3 g, 3.0 mmol) in dichloromethane (40 mL) was added a dichloromethane (10 mL) solution of the acid chloride prepared above (0.5 g, 2.0 mmol). The reaction was allowed to thaw to ambient temperature and evaporated. The product was isolated by flash chromatoigraphy with 10% chloroform in methanol. Purification by HPLC utilizing gradient elution with a mixture of water:acetonitrile with 0.05% trifluoroacetic acid on a reverse phase C18 (60 Å) column gave a pure s,ample of the title compound; HRMS (M+H)$^+$calc. m/z: 405.180090, obs: 405.180328.

Example 20

3-Methyl-1-(4-methoxyphenyl)-1H-pyrazole-5-(N-(5-(2-sulfonamido)phenyl)pyridin-2-yl) carboxyamide This compound was prepared by the methodology described for EXAMPLE 19 with the exception that in the coupling step 2-amino-5-(2-(N-t-butylsulfonamido)phenyl)pyridine was used in the place of 2-amino-5-(N-pyrrolidinocarbonyl)pyridine. The resulting product was stirred in trifluoroacetic acid (20 mL) for 18 h, whereupon the solvent was removed by distillation under reduced pressure. Purification of the crude product by hplc utilizing gradient elution with a mixture of water:acetonitrile with 0.05% trifluoroacetic acid on a reverse phase C18 (60 Å) column gave a pure sample of the title compound; HRMS (M+H)$^+$ calc. m/z: 464.139251, obs: 464.138485.

Example 21

3-Methyl-1-(4-methoxyphenyl)-1H-pyrazole-5-N-(4-(N-carboxyl-3-hydroxypyrrolidino)phenyl) carboxyamide 4-(N-Carboxyl-3-t-butyldimethylsilyloxypyrrolidino)aniline To 3-hydroxypyrrolidine hydrogen chloride (1.63 g, 14.9 mmol) and triethylamine (1.51 g, 14.9 mmol) in dichloromethane (50 mL) at 0° C., was added a solution of p-nitrobenzoyl chloride (2.5 g, 12.4 mmol) in dichloromethane (50 mL). The reaction was evaporated to dryness and the residue dissolved in ethyl acetate. This solution was washed with 1N hydrochloric acid solution and brine, then dried and evaporated to give 2.22 g of product; LRMS (M+H)$^+$ m/z: 237.

A tetrahydrofuran solution (75 mL) of the material prepared above (2.2 g, 9.4 mmol), t-butyldimethylsilyl chloride (1.54 g, 10.2 mmol) and imidazole (0.89 g, 13.0 mmol) was cooled to 0° C. and stirred for 72 h. The reaction mixture was filtered and evaporated. The residue was dissolved in ethyl acetate and washed with water and brine, dried and evaporated. Flash chromatography using 2:1 hexane:ethyl acetate gave 2.07 g of pure product; LRMS (M+H)$^+$ m/z: 351.

The material prepared above (2.07 g) was reduced under an atmosphere of hydrogen gas (50 psi) in methanol (100 mL) in the presence of 10% palladium on carbon catalyst (200 mg). After about 2 h, the reduction was complete; the reaction was purged with nitrogen gas and the catalyst removed by filtration through a pad of Celite. The solvent was evaporated to give 1.75 g of 4-(N-carboxyl-3-t-butyldimethylsilyloxypyrrolidino)aniline; LRMS (M+H)$^+$ m/z: 321.

3-Methyl-1-(4-methoxyphenyl)-1H-pyrazole-5-N-(4-(N-carboxyl-3-hydroxypyrrolidino)phenyl) carboxyamide This compound was prepared by the methodology described for EXAMPLE 19 with the exception that in the coupling step 4-(N-carboxyl-3-t-butyldimethylsilyloxypyrrolidino)aniline was used in the place of 2-amino-5-(N-pyrrolidinocarbonyl)pyridine. The t-butyldimethylsilyl protecting group was removed by treatment with 2 equivalents of tetrabutylammonium fluoride in tetrahydrofuran. The solvent was evaporated, the residue dissolved in ethyl acetate and washed with water. After drying and removal Cf the solvent, the crude product was purified by hplc utilizing gradient elution with a mixture of water:acetonitrile with 0.05% trifluoroacetic acid on a reverse phase C18 (60 Å) column gave a pure sample of the title compound;HRMS (M+H)$^+$ calc. m/z: 420.179756, obs: 420.175589.

Example 22

2-Amino-4-(4-methoxyphenyl)-5-[(2'-aminosulfonyl-[1,1']-biphen-4-yl)aminocarbonyl] thiazole 1-(4-Methoxyphenyl)-1'-(4-bromophenyl) aminocarbonyl acetone 4-Methoxyacetophenone (3.00 g, 19.97 mmol) was dissolved in 60 mL of THF followed by the addition of LDA (2.0 M in THF, 10.0 mL, 20 mmol) and stirred at room temperature for 1 hr. 4-bromophenylisocyanate (3.95 g, 19.97 mmol) was added and the reaction allowed to stir at room temperature overnight. The solution was acidified with 10% HCl and the solution diluted with 300 mL EtOAc. The solution was washed with brine (300 mL), dried over MgSO$_4$, filtered through a plug of silica gel and the volatiles removed in vacuum. The product was isolated by recrystallization from hot diethyl ether (3.08 g, 44%).

2-Amino-4-(4-methoxyphenyl)-5-(4-bromophenyl) thiazole 1-(4-Methoxyphenyl)-1'-(4-bromophenyl)aminocarbonyl acetone (3.08 g, 8.84 mmol) and hydroxy(tosyloxy) iodobenzene (3.46 g, 8.84 mmol) were combined in 100 mL of acetonitrile and refluxed for 45 min. followed by the addition of thiourea (0.673 g, 8.84 mmol) and refluxed for

2-Amino-4-(4-methoxyphenyl)-5-[(2'-tert-butylaminosulfonyl-[1,1']-biphen-4-yl)aminocarbonyl]thiazole 2-amino-4-(4-methoxyphenyl)-5-(4-bromophenyl) thiazole (1.68 g, 4.15 mmol), sodium carbonate (0.88 g, 8.31 mmol), tetrabutylammoniumbromide (0.134 g, 0.415 mmol) and 2-(tert-butylaminosulfonyl)phenyl boronic acid (1.50 g, 5.82 mmol) were combined in a solution containing 1:1:4 of benzene:acetonitrile:water and degassed with $N_2$ for 15 min. After the $N_2$ purge, tetrakistriphenylphosphine palladium (0) was added and the reaction mixture heated to reflux overnight. The solution was diluted with EtOAc, placed in a separatory funnel and washed with three, 150 mL portions of brine. The organics were dried over $MgSO_4$, filtered through a plug of silica gel and the volatiles removed in vacuum. The residue was dissolved in a minimal amount of hot $CHCl_3$, the product triturated with $Et_2O$ and isolated (1.59 g, 71.3%) by vacuum filtration. MS ($NH_3$-DCI) 537.2 $(M+H)^+$.

2-Amino-4-(4-methoxyphenyl)-5-[(2'-aminosulfonyl-[1,1']-biphen-4-yl)aminocarbonyl]thiazole 2-amino-4-(4-methoxyphenyl)-5-[(2'-tert-butylaminosulfonyl-[1,1']-biphen-4-yl)aminocarbonyl] thiazole (1.59 g, 2.96 mmol) was dissolved in 20 mL of TFA and heated to reflux for 1 hr. The volatiles were removed in vacuum and the title compound purified by preparative HPLC. MS ($NH_3$-DCI) 481.1 $(M+H)^+$.

Example 23

2-Bromo-4-(4-methoxyphenyl)-5-[(2'-aminosulfonyl-[1,1']-biphen-4-yl)aminocarbonyl]thiazole

Methyl-3-(methoxyphenyl)-3-oxopropionate

Bis-(trimethylsilyl)amine (158.2 mL, 0.750 mol) was dissolved in 150 mL of THF and cooled to –78° C. with the aid of a dry ice/acetone bath. N-butyl lithium (2.5 M in hexane, 300 mL, 0.750 mol) was introduced via cannula into the system and stirred at that temperature for 20 min. 4-methoxy acetophenone (51.20 g, 0.340 mol) was added via a solid addition funnel and stirred at –78° C. for 3 h. Dimethylcarbonate (87.0 mL, 1.02 mol) was added via cannula and the system allowed to stir overnight with warming to room temperature. The solution was acidified with 10% HCl, diluted with 1 liter of EtOAc and washed three times with 400 mL of 10% HCl. The organics were dried over $MgSO_4$, filtered through a silica gel plug and the volatiles removed in vacuum. The title compound was obtained as a viscous brown oil (65.09 g, 91.7%) MS ($NH_3$-DCI) 347.9 $(M+H)^+$.

2-Amino-4-(4-methoxyphenyl)-5-(carbomethoxy) thiazole

Methyl-3-(methoxyphenyl)-3-oxopropionate (33.34 g, 95.75 mmol) and hydroxy(tosyloxy)Ioclobenzene (37.55 g, 95.75 mmol) were combined in 350 mL of acetonitrile and refluxed for 45 min. followed by the addition of thiourea (7.29 g, 95.75 mmol) and refluxed for 2 h. The volatiles were removed in vacuum and the residue dissolved in 50/50 EtOAc/Hexane and passed through a plug of silica gel. Once the impurities eluted, the product was recovered by eluting with 100% EtOAC and removing the volatiles in vacuum. The title compound was obtained as a tan solid (38.52 g, 75%) MS ($NH_3$-DCI) 254.2 $(M+H)^+$.

2-Bromo-4-(4-methoxyphenyl)-5-(4-bromophenyl) thiazole

Cupric bromide (11.42 g, 51.17 mmol) and tert-butyl nitrite (6.93 mL, 58.16 mmol) were corbine in 75 mL of acetonitrile and heated to reflux until gas evolution stopped. 2-Amino-4-(4-methoxyphenyl)-5-(4-bromophenyl) thiazole (12.3 g, 46.55 mmol) was added to the acetonitrile solution and heated to reflux until gas evolution stopped. The solution was diluted with 300 mL of EtOAc and washed repeatedly with 250 mL of a saturated $Na_2CO_3$ solution. The organics were dried over $MgSO_4$, filtered through a plug of silica gel and the volatiles removed in vacuum. The residue was purified by preparative HPLC to yield the title compound as a brown solid, 8.95 g (57%) MS ($NH_3$-DCI) 328.0 $(M+H)^+$.

2-Bromo-4-(4-methoxyphenyl)-5-[(2'-tert-butylaminosulfonyl-[1,1']-biphen-4-yl)aminocarbonyl]thiazole To a solution of (2'-tert-butylaminosulfonyl-[1,1']-biphen-4-yl)amine (2.57 g, 8.47 mmol) in 50 mL of methylene chloride at 25° C. was added trimethylaluminum (12.7 mL of a 2.0 M solution in toluene, 25.41 mmol) dropwise. The resulting solution was allowed to stir until no more gas evolution was observed (~15 min.). To this solution was added 2-bromo-4-(4-methoxyphenyl)-5-(4-bromophenyl) thiazole (2.94 g, 9.31 mmol) and stirred at reflux for 2 h. The solution was quenched with sat. $NH_4Cl$, diluted with 200 mL of EtOAc and washed twice with 200 mL portions of brine. The organics, were dried over $MgSO_4$, filtered through a silica plug and the volatiles removed in vacuum to yield the title compounds as a golden solid (5.0 g, 98%) MS ($NH_3$-DCI) 600.3 $(M+H)^+$.

2-Bromo-4-(4-methoxyphenyl)-5-[(2'-aminosulfonyl-[1,1']-biphen-4-yl)aminocarbonyl]thiazole The trifluoroacetic acid deprotection employed in the last step of EXAMPLE 1 with 2-bromo-4-(4-methoxyphenyl)-5-[(2'-t-butylaminosulfonyl-[1,1']-biphen-4-yl) aminocarbonyl] thiazole (1.00 gm, 1.66 mmol), gave the title compound. It was isolated as a white solid by preparative HPLC, MS (ESI) 543.8 $(M+H)^+$.

Example 24

2-Chloro-4-(4-methoxyphenyl)-5-[(2'-aminosulfonyl-[1,1']-biphen-4-yl)aminocarbonyl]thiazole Employing methods similar to EXAMPLE 2 with the exception that $CuCl_2$ rather than $CuBr_2$ is used in the diazotization and halogenation of 2-amino-4-(4-methoxyphenyl)-5-(4-bromophenyl) thiazole to give the corresponding 2-chloro-4-(4-methoxyphenyl)-5-(4-bromophenyl)thiazole. The final product, 2-chloro-4-(4-methoxyphenyl)-5-[(2'-aminosulfonyl-[1,1']-biphen-4-yl) aminocarbonyl]thiazole, was isolated as a white solid by preparative HPLC; MS ($NH_3$-DCI) 500.3 $(M+H)^+$.

Example 25

2-Chloro-4-(4phenoxy)-5-[(2'-aminosulfonyl-[1,1']-biphen-4-yl)aminocarbonyl]thiazole

2-Chloro-4-(4-phenoxy)-5-[(2'-aminosulfonyl-[1,1']-biphen-4-yl)aminocarbonyl]thiazole 2-chloro-4-(4-methoxyphenyl)-5-[(2'-aminosulfonyl-[1,1']-biphen-4-yl)aminocarbonyl]thiazole (0.40 g, 0.8 mmol)

was dissolved in 5 mL CH$_2$Cl$_2$ and cooled to 0° C. followed by the addition of BCl$_3$ (1.0 M solution in CH$_2$Cl$_2$, 4.8 mL, 4.8 mmol) and allowed to stir 72 h. at room temperature. The solution was quenched with 10% HCl and the volatiles removed in vacuum. The title compound was purified by preparative HPLC, MS (NH3-DCI) 485.9 (M+H)$^+$.

Example 26

2-Methoxy-4-(4-methoxyphenyl)-5-[(2'-aminosulfonyl-[1,1']-biphen-4-yl)aminocarbonyl] thiazole

2-Methoxy-4-(4-methoxyphenyl)-5-[(2'-aminosulfonyl-[1,1']-biphen-4-yl)aminocarbonyl] thiazole 2-chloro-4-(4-methoxyphenyl)-5-[(2'-aminosulfonyl-[1,1']-biphen-4 -yl)aminocarbonyl]thiazole (0.120 g, 0.240 mmol) and sodium methoxide (0.10 g, 2.0 mmol) were dissolved in 20 mL of methanol and heated to reflux; the reaction was monitored by TLC. The title compound was isolated as a white solid by preparative HPLC MS (ESI) 518.0 (M+Na)$^+$.

Example 27

2-Thiomethyl-4-(4-methoxyphenyl)-5-[(2'-aminosulfonyl-[1,1']-biphen-4-yl)aminocarbonyl] thiazole

2-Thiomethyl-4-(4-methoxyphenyl)-5-[(2'-aminosulfonyl-[1,1']-biphen-4-yl)aminocarbonyl] thiazole 2-chloro-4-(4-methoxyphenyl)-5-[(2'-aminosulfonyl-[1,1']-biphen-4-yl)aminocarbonyl]thiazole (0.700 g, 1.4 mmol) and sodium thiomethoxide (0.490 g, 7.0 mmol) were refluxed in 50 mL of THF and the reaction monitored by TLC (~4 h). The volatiles were removed in vacuum and the title compound purified by preparative HPLC, MS, (ESI) 534.0 (M+H)$^+$.

Examples 28 and 29

2-Methylsulfoxide-4-(4-methoxyphenyl)-5-[(2'-aminosulfonyl-[1,1']-biphen-4-yl)aminocarbonyl] thiazole and 2-methylsulfone-4-(4-methoxyphenyl)-5-[(2'-aminosulfonyl-[1,1']-biphen-4-yl) aminocarbonyl]thiazole 2-Thiomethyl-4-(4-methoxyphenyl)-5-[(2'-aminosulfonyl-[1,1']-biphen-4-yl)aminocarbonyl]thiazole (0.54 g, 1.05 mmol) and Oxone® (1.94 g, 3.16 mmol) were dissolved in 300 mL of a 50/50 methanol/water solution and stirred at room temperature for 72 hr. The solution was diluted with 400 mL of EtOAc and washed with three, 200 mL portions of brine. The organics were dried over MgSO$_4$, filtered through a silica gel plug, the volatiles removed in vacuum and the residue purified by preparative HPLC. Both EXAMPLE 28 and 29 were recovered from the HPLC purification.

2-Methylsulfoxide-4-(4-methoxyphenyl)-5-[(2'-aminosulfonyl-[1,1']-biphen-4-yl)aminocarbonyl]thiazole MS (ESI) 527.9 (M+H)$^+$.

2-Methylsulfone-4-(4-methoxyphenyl)-5-[(2'-aminosulfonyl-[1,1']-biphen-4-yl)aminocarbonyl]thiazole MS (ESI) 543.9 (M+H)$^+$.

Example 30

2-Cyano-4-(4-methoxyphenyl)-5-[(2'-aminosulfonyl-[1,1']-biphen-4-yl)aminocarbonyl]thiazole

2-Cyano-4-(4-methoxyphenyl)-5-[(2'-aminosulfonyl-[1,1']-biphen-4-yl)aminocarbonyl]thiazole 2-methylsulfone-4-(4-methoxyphenyl)-5-[(2'-aminosulfonyl-[1,1']-biphen-4-yl)aminocarbonyl]thiazole (0.500 g, 0.920 mmol) and sodium cyanide (0.225 g, 4.60 mmol) were combined in 35 mL of DMF and stirred at room temperature overnight followed by heating for several hours at 70° C. The solution was dissolved in 300 mL of EtOAc and washed with three, 200 mL portions of brine, dried over MgSO$_4$, filtered through a plug of silica gel and the volatiles removed in vacuum. The title compound was isolated as a white solid by preparative HPLC MS (ESI) 490.9 (M+H)$^+$.

Example 31

2-N,N-Dimethylamino-4-(4-methoxyphenyl)-5-[(2'-aminosulfonyl-[1,1']-biphen-4-yl)aminocarbonyl] thiazole

2-N,N-Dimethylamino-4-(4-methoxyphenyl)-5-[(2'-aminosulfonyl-[1,1']-biphen-4-yl)aminocarbonyl] thiazole 2-chloro-4-(4-methoxyphenyl)-5-[(2'-aminosulfonyl-[1,1']-biphen-4-yl)aminocarbonyl]thiazole (0.200 g, 0.4 mmol) and dimethyl amine (40% solution in water, 1.00 mL, 2.0 mmol) were stirred at room temperature in 50 mL of THF overnight. The volatiles were removed in vacuum and the title compound purified by preparative HPLC, MS (ESI) 509.0 (M+H)$^+$.

Example 32

2-(1-Pyrrole)-4-(4-methoxyohenyl)-5-[(2'-aminosulfonyl-[1,1']-biphen-4-yl)aminocarbonyl] thiazole

2-(1-pyrrole)-4-(4-methoxyphenyl)-5-[(2'-aminosulfonyl-[1,1']-biphen-4-yl)aminocarbonyl] thiazole 2-amino-4-(4-methoxyphenyl)-5-[(2'-aminosulfonyl-[1,1']-biphen-4-yl)aminocarbonyl]thiazole (0.050 g, 0.104 mmol) and 2,5-dimethoxy tetrahydrofuran (0.015 mL, 0.114 mmol) were refluxed in 20 mL of acetic acid for 1 hr. The volatiles were removed in vacuum and the title compound purified by preparative HPLC, MS (ESI) 531.0 (M+H)$^+$.

Example 33

3-(4-Methoxyphenyl)-5-[5-(2'-aminosulfonylphenyl-1-yl)pyridin-2-yl]aminocarbonyl-5-carbomethoxymethyl-isoxazoline

4-Methoxybenzaldehyde oxime

4-Methoxybenzaldehyde (10.0 g, 73.4 mmol) was dissolved in 200 mL of ethanol. A solution of hydroxyamine hydrochloride (6.38 g, 91.8 mmol) in 50 mL of H$_2$O was added followed by a solution of sodium acetate (12.1 g, 146.8 mmol) in 50 mL of H$_2$O. The mixture was stirred at room temperature under N$_2$ for 12 h. The ethanol was removed in vacuo and the aqueous mixture was extracted with EtOAc. The EtOAc solution was washed with brine, dried over MgSO$_4$, and concentrated to afford 12.8 g of light yellow oil. $^1$H NMR showed it was 80% pure (92% yield). This material was taken into the next step without further purification. (CDCl$_3$): δ2.15 (s, 1H); 3.83 (s, 3H); 6.92 (d, 2H); 7.50 (d, 2H); 8.10 (s, 1H).

3-(4-Methoxyphenyl)-5-carbomethoxy methyl-isoxazolin-5-ylcarboxylic acid

4-Methoxybenzaldehyde oxime (5.00 g, 33.1 mmol) and itaconic acid monomethyl ester (5.72 g, 39.7 mol) were added together with 200 mL of THF. To the above mixture was added bleach (84 mL of 0.67M aqueous solution) dropwise at room temperature. The reaction mixture was then stirred at RT under $N_2$ for 12 h. The THF was removed in vacuo. The aqueous mixture was acidified with aqueous HCl and extracted with EtOAc. The EtOAc solution was washed with brine, dried over $MgSO_4$, concentrated, and chromatographed with 10–30% MeOH in $CH_2Cl_2$ on silica gel to give 5.58 g of the desired product (58%). $^1H$ NMR (DMSC-d6): δ63.08 (m, 2H); 3.61 (s, 3H); 3.55–3.87 (m, 2H); 3.80 (s, 3H); 7.00 (d, 2H); 7.61 (d, 2H).

3-(4-Methoxyphenyl)-5-N-[2'-t-butylaminosulfonylphenyl-1-yl)pyridin-2-yl]aminocarbonyl-5-carbomethoxymethyl-isoxazoline 3-(4-Methoxyphenyl)-5-carbomethoxy methyl-isoxazolin-5-ylcarboxylic acid (1.89 g, 6.44 mmol) was refluxed with 100 mL of acetonitrile and 4.70 mL (64.4 mmol) of thionyl chloride for 1 h under $N_2$. The solvent was removed in vacuo. Residual thionyl chloride was removed by adding toluene and then evaporating to dryness. The resulting solid was dissolved in 100 mL of $CH_2Cl_2$ and 2-amino-5-[(2'-t-butylaminosulfonyl)phenyl]pyridine (1.57 g, 5.15 mmol) was added followed by N,N-dimethylpyridine (0.94 g, 7.73 mmol). The reaction mixture was stirred at room temperature and the reaction was completed in less than 30 min. The mixture was diluted with $CH_2Cl_2$ and the solution was washed with water and brine. It was dried over $MgSO_4$ and concentrated. The crude product mixture was chromatographed on silica gel eluted with methylene chloride/ethyl acetate (9:1) to give 2.55 g of the desired product (68%). MS (ES$^+$) 581.1, (M+H); 603.1, (M+Na).

3-(4-Methoxyphenyl)-5-N-[2'-aminosulfonylphenyl-1-yl)pyridin-2-yl]aminocarbonyl-5-carbomethoxymethyl-isoxazoline 3-(4-Methoxyphenyl)-5-N-[2'-t-butylaminosulfonylphenyl-1-yl)pyridin-2-yl] aminocarbonyl-5-carbomethoxymethyl-isoxazoline (1.26 g, 2.17 mmol) was dissolved in 15 mL of TFA and stirred at room temperature under $N_2$ for 22 h. The TFA was removed in vacuo, and the crude product was purified by chromatography (on silica gel eluted with ethyl acetate and 5% methanol in $CH_2Cl_2$) to give 1.lC g of the desired product (97%). MS (ES$^+$) 525.0, (M+H); 547.0, (M+Na).

Example 34

3-(4-Methoxyphenyl)-5-[5-(2'-aminosulfonylphenyl-1-yl)pyridin-2-yl]aminocarbonyl-5-carboxymethyl-isoxazoline 3-(4-Methoxyphenyl)-5-N-[2'-aminosulfonylphenyl-1-yl)pyridin-2-yl]aminocarbonyl-5-carbomethoxymethyl-isoxazoline (0.95 g, 1.78 mmol) was dissolved in 20 mL of THF. Aqueous LiOH (2.3 mL of 1M solution) was added. The mixture was stirred at room temperature under $N_2$ for 1.5 h. The THF was removed in vacuo, the residue was diluted with $H_2O$ and extracted with EtOAc. The aqueous mixture was then acidified with HCl and extratecd with EtOAc. The EtOAc solution was washed with brine, dried over $MgSO_4$, and concentrated to a light yellow foam (0.85 g, 94%). MS (ES$^+$) 511.0, (M+H); 533.0, (M+Na).

Example 35

3-(4-Methoxyphenyl)-5-[5-(2'-aminosulfonylphenyl-1-yl)pyridin-2-yl]aminocarbonyl-5-(N-carbomethoxymethyl)carboxamidomethyl-isoxazoline 3-(4-Methoxyphenyl)-5-[5-(2'-aminosulfonylphenyl-1-yl)pyridin-2-yl]aminocarbonyl-5-carboxymethyl-isoxazoline (0.20 g, 0.39 mmol) was dissolved in 20 mL of EtOAc and 5 mL of DMF. To it was added methyl glycine ester hydrochloride (49.0 mg, .039 mmol), TBTU (0.13 g, 0.39 mmol), and $Et_3N$ (0.16 mL, 1.17 mmol). The mixture was stirred st room temperature under $N_2$ for 22 h. It was diluted with $H_2O$ and extracted with EtOAc. The EtOAc solution was washed with brine, dried over $MgSO_4$, concentrated, and chromatographed with 5% MeOH in $CH_2Cl_2$ on silica gel to give 0.11 g of the desired product (49%). MS (ES$^+$) 582.0, (M+H); 604.0, (M+Na).

Example 36

3-(4-Methoxyphenyl)-5-[5-(2'-aminosulfonylphenyl-1-yl)pryidin-2-yl]aminocarbonyl-5-(1,2,4-triazol-1-yl)methyl-isoxazoline 3-(4-Methoxyphenyl)-5-(1,2,4-triazol-1-yl)methyl-isoxazolin-5-ylcarboxylic acid 1,2,4-Tetrazole(5.04 g, 73.0 mmol) and $K_2CO_3$ (11.23 g, 81.3 mmol) were added together with 100 mL of DMF. Methyl 2-(bromomethyl)acrylate (13.0 g, 72.6 mmol) was added. The mixture was stirred at room temperature under $N_2$ for 4 h. The mixture was poured into water and extracted with EtOAc. The combined organic solution was washed with brine, dried over $MgSO_4$, and then concentrated to give 8.38 g of methyl 2-(1,2,4-triazol-1-ylmethyl)acrylate.

4-Methoxybenzaldehyde oxime (1.63, g, 10.8 mmol) and methyl 2-(1,2,4-triazol-1-ylmethyl)acrylate.(1.50 g, 8.97 mol) were added together with 100 mL of $CH_2Cl_2$. To the above mixture was added bleach (23 mL of 0.67M aqueous solution) dropwise at room temperature. The reaction mixture was then stirred at RT under $N_2$ for 12 h. The mixture was diluted with $CH_2Cl_2$ and washed with water and brine, It was dried over $MgSO_4$, concentrated, and chromatographed with 30–100% EtOAc in $CH_2Cl_2$ on silica gel to give 1.81 g of the desired product (66%).

The above ester (1.81 g) was dissolved in 25 mL of THF, and aqueous LiOH (7.2 mL of 1M solution) was added. The mixture was stirred at room temperature under $N_2$ for 0.5 h. The THF was removed in vacuo. The aqueous mixture was diluted with $H_2O$ and extracted with EtOAc. The resulting aqueous solution was acidified and then extracted with EtOAc. The white precipitate formed was filtered and dried (1.30 g). $^1H$ NMR (DMSO-d6): δ3.75 (q, 2H); 3.78 (s, 3H); 4.74(q, 2H); 6.98 (d, 2H);7.53 (d, 2H); 7.92 (s, 1H); 8.51 (s, 1H); 13.75 (s, 1H).

3-(4-Methoxyphenyl)-5-N-[2'-t-butylaminosulfonylphenyl-1-yl)pyridin-2-yl] aminocarbonyl-5-(1,2,4-triazol-1-yl)methyl-isoxazoline 3-(4-Methoxyphenyl)-5-(1,2,4-triazol-1-yl)methyl-isoxazolin-5-ylcarboxylic acid (0.30 g, 1.03 mmol) was refluxed with 20 mL of acetonitrile and 0.75 mL (10.3 mmol) of thionyl chloride for 1 h under $N_2$. The solvent was removed in vacuo. Residual thionyl chloride was removed by adding toluene and then evaporating to dryness. The resulting solid was dissolved in 20 mL of $CH_2Cl_2$ and 2-amino-5-[(2'-t-butylaminosulfonyl)phenyl]pyridine (0.25 g, 0.82 mmol) was added followed by N,N-dimethylpyridine (0.15 g, 1.24 mmol). The reaction mixture was stirred at room temperature and the reaction was completed in less than 30 min. The mixture was diluted with $CH_2Cl_2$ and the solution was washed with water and brine. It was dried over $MgSO_4$ and concentrated. The crude product mixture was chromatographed on silica gel eluted with methylene chloride/ethyl acetate (30–100%) to give 0.31 g of the desired product (51%). MS (ES+) 590.2, (M+H); 612.1, (M+Na).

3-(4-Methoxyphenyl)-5-N-[2'-aminosulfonylphenyl-1-yl)pyridin-2-yl]aminocarbonyl-5-(1,2,4-triazol-1-yl)methyl-isoxazoline 3-(4-Methoxyphenyl)-5-N-[2'-t-butylaminosulfonylphenyl-1-yl)pyridin-2-yl] aminocarbonyl-5-(1,2,4-triazol-1-yl)methyl-isoxazoline (0.24 g, 0.41 mmol) was dissolved in 5 mL of TFA and stirred at room temperature under $N_2$ for 12 h. The TFA was removed in vacuo, and the crude product was purified by chromatography on silica gel eluted with ethyl acetate to give 0.19 g of the desired product (87%). MS (ES+) 534.0, (M+H) 556.0, (M+Na).

Example 37

1-(4-Methoxyphenyl)-5-[(2'-aminosulfonyl-[1,1']-biphen-4-yl)aminocarbonyl]tetrazole 1-(4-Methoxyphenyl)-5-Carboethoxy-tetrazole 4-Methoxyaniline (20.0 g, 0.16 mol) and triethylamine (26.3 mL, 0.19 mol) were dissolved in $CH_2Cl_2$ (200 mL). Ethyl oxalyl chloride (18.1 mL, 0.16 mol) was added dropwise. The mixture was stirred at room temperature under $N_2$ for 15 min. It was diluted with $CH_2Cl_2$ and washed with water and brine. the $CH_2Cl_2$ solution was dried over $MgSO_4$ and concentrated to a tan solid (34.7 g, 96%). MS ($DCI-NH_3$) 224, (M+H); 241, ($M+NH_4$).

The above amide (34.0 g, 0.15 mol) was refluxed for 20 h with a solution of triphenylphosphine (56.6 g, 0.22 mol) in 500 mL of $CCl_4$ (The solution was stirred at 0° C. for 15 min before the amide was added). The reaction mixture was cooled and hexane was added. The precipitate was filtered off. The filtrate was concentrated to a solid. It was then dissolved in 400 mL of $CH_3CN$ and $NaN_3$ (10.0 g, 0.15 mol) was added. The mixture was stirred at room temperature under $N_2$ for 12 h. The solvent was removed. The solid was dissolved in EtOAc and washed with water and brine. It was dried over $MgSO_4$ and concentrated, and chromatographed on silica gel(eluted with $CH_2Cl_2$) to give 27.7 g of the desired product (58%). MS($DCI-NH_3$) 249, (M+H), 266 $(M+NH_4)^+$.

1-(4-Methoxyphenyl)-5-[(2'-t-butylaminosulfonyl-[1,1']-biphen-4-yl)aminocarbonyl]tetrazole 2'-t-Butylaminosulfonyl-4-amino-[1,1']-biphen-4-yl (1.84 g, 6.04 mmol) was dissolved in 100 mL of anhydrous $CH_2Cl_2$, and trimethylaluminium (15.2 mL of 2.0 M solution in heptane) was added slowly. The mixture was stirred at room temperature under $N_2$ for 15 min, and 1-(4-methoxyphenyl)-5-Carboethoxy-tetrazole (1.50 g, 6.04 mmol) was added. The reaction mixture was stirred at room temperature under $N_2$ for 18 h. The reaction was quenched carefully with 0.1N aqueous HCl. It was diluted with $CH_2Cl_2$ and washed with water and brine. The organic solution was then dried over $MgSO_4$, concentrated, and chromtographed on silica gel (10% EtOAc/$CH_2Cl_2$) to give 1.20 g of the desired product(39%) MS(ESI) 507.0 $(M+H)^+$.

1-(4-Methoxyphenyl)-5-[(2'-aminosulfonyl-[1,1']-biphen-4-yl)aminocarbonyl]tetrazole 1-(4-Methoxyphenyl)-5-[(2'-t-butylaminosulfonyl-[1,1']-biphen-4-yl)aminocarbonyl]tetrazole (1.20 g, 2.37 mmol) was dissolved in 10 mL of TFA. The mixture was refluxed under $N_2$ for h. The TFA was removed in vacuo. The crude mixture was purified by reversed phase HPLC to give 0.12 g of the desired product (11%). MS(ESI) 451.0 $(M+H)^+$.

Example 38

3-Methyl-1-(4-methoxy-3-chloro)phenyl-1H-pyrazole-5-(N-(2'-aminosulfonyl-[1,1']-biphen-4-yl) carboxyamide This compound was prepared by the same methodology described for EXAMPLE 1 with 4-methoxy-3-chlorophenyl hydrazine • HCl substituted for phenyl hydrazine. There was obtained 3-methyl-1-(4-trifluoromethyl)phenyl-1H-pyrazole-5-(N-(4-(2'-aminosulfonyl-[1,1']-biphen-4-yl) carboxyamide; HRMS $(M+H)^+$ calc. m/z: 497.1050, obs: 497.1045.

Example 39

3-Methyl-1-(4-trifluoromethoxy)phenyl-1H-pryrazole-5-(N-(2'-aminosulfonyl-[1,1']-biphen-4-yl) carboxyamide This compound was prepared by the same methodology described for EXAMPLE 1 with 4-trifluoromethoxyphenyl hydrazine • HCl substituted for phenyl hydrazine. There was obtained 3-methyl-1-(4-trifluoromethyl)phenyl-1H-pyrazole-5-(N-(2'-aminosulfonyl-[1,1']-biphen-4-yl) carboxyamide; HRMS $(M+H)^+$ calc. m/z: 517.1170, obs: 517.1176.

Example 40

1-(3-Bromophenyl)-3-methyl-1H-pyrazole-5-[(2'-aminosulfonyl-[1,1']-biphen-4-yl)carboxyamide This compound was prepared by the same methodology described for EXAMPLE 1 with 3-bromophenyl hydrazine • HCl substituted for phenyl hydrazine. There was obtained 1-(3-bromophenyl)-3-methyl-1H-pyrazole-5-[(2'-aminosulfonyl-[1,1']-biphen-4-yl)carboxyamide; HRMS $(M+H)^+$ calc. 511.043949; found: 511.043295.

Example 41

1-(3-Iodophenyl)-3-methyl-1H-pyrazole-5-[(2'-aminosulfonyl-[1,1']-biphen-4-yl)carboxyamide This compound was prepared by the same methodology described for EXAMPLE 1 with 3-iodophenyl hydrazine • HCl substituted for phenyl hydrazine. There was obtained 1-(3-iodophenyl)-3-methyl-1H-pyrazole-5-[(2'-aminosulfonyl-[1,1']-biphen-4 -yl)carboxyamide; HRMS $(M+H)^+$ calc. 559.030090; found: 559.027878.

Example 42

1-(3,4-Methylenedioxanephenyl)-3-methyl-1H-pyrazole-5-[(2'-aminosulfonyl-[1,1'-biphen-4-yl) carboxyamide This compound was prepared by the same methodology described for EXAMPLE 1 with 3,4-methylenedioxanephenyl hydrazine • HCl substituted for phenyl hydrazine. There was obtained 1-(3,4-methylenedioxanephenyl)-3-methyl-1H-pyrazole-5-[(2'-aminosulfonyl-[1,1']-biphen-4-yl)carboxyamide; HRMS $(M+H)^+$ calc. 477.123267; found: 477.124553.

Example 43

1-(4-Methoxyphenyl)-3-hydroxylmethylene-1H-pyrazole-5-(4'-pryrrolidinocarbonyl)anilide

1-(4-Methoxyphenyl)-3-hydroxylmethylene-1H-pyrazole-5-ethylcarboxylate

To a solution of 1-(4-methoxyphenyl)-3-methyl-1H-pyrazole-5-ethylcarboxylate (1.58 g, 7.1 mmol) in $CCl_4$ (250 mL) was added NBS (1.5 g, 8.5 mmol) and benzoyl peroxide (73 mg, 4% mmol), and the mixture was degassed and then filled with nitrogen. After the mixture was refluxed for 18 hours under nitrogen, it was cooled to room temperature, diluted with $CH_2Cl_2$ (100 mL), washed with 10% NaOH (20 mL×3), water (20 mL×3), and brine (10 mL×2), and dried over $MgSO_4$. Filtration and concentration gave a crude bromide (2.4 g). To a solution of the crude bromide in aqueous DMSO (75%, 40 mL) was added $Cu_2O$ (1.5 g, 10.5 mmol), and the mixture was stirred at 60° C. for 2 hours. The mixture was filtered to remove excess $Cu_2O$, aend the filtrate was extracted with ethyl ether. The ether layer was washed with brine (10 mL×5) and dried over $MgSO_4$. Filtration and concentration, followed by purification by flash chromatography with $EtOAc$-$CH_2Cl_2$ (1 to 1) gave 1-(4-methoxyphenyl)-3-hydroxylmethylene-1H-pyrazole-5-ethylcarboxylate (1.5 g, 81%). LRMS $(M+H)^+$ m/z: 277.

1-(4-Methoxyphenyl)-3-hydroxylmethylene-1H-pyrazole-5-(4'-pyrrolidincarbonyl)anilide To a solution of 4-(4'-pyrrolidinoncarbonyl)aniline (390 mg, 2.05 mmol) in $CH_2Cl_2$ (20 mL) was added $AlMe_3$ (2M in hexanes, 3 mmol) at 0° C. After the mixture was stirred at room temperature for 15 minutes, to it was added a solution of 1-(4-methoxyphenyl)-3-hydroxylmethylene-1H-pyrazole-5-ethylcarboxylate (560 mg, 2.05 mmol) in $CH_2Cl_2$ (5 mL), and the resulting mixture was stirred overnight. The mixture was quenched with water (5 mL), and filtered through a pad of Celite to remove $Al(OH)_3$. The filtrate was washed with water and brine, and dried over $MgSO_4$. Filtration, concentration, and purification by flash chromatography with $EtOAc$-$CH_2Cl_2$ gave 1-(4-methoxyphenyl)-3-hydroxylmethylene-1H-pyrazole-5-(4'-pyrrolidinocarbonyl)anilide (570 mg, 67% yield). ESMS $(M+Na)^+$ m/z: 443. HRMS $(M+H)^+$ calc. m/z: 420.1798, obs: 420.1771.

Example 44

1-(4-Methoxyphenyl)-3-formaldehyde-1H-pyrazole-5-(4'-pyrrolidinocarbonyl)anilide To a solution of 1-(4-methoxyphenyl)-3-hydroxylmethylene-1H-pyrazole-5-(4'-pyrrolidinocarbonyl)anilide (140 mg, 0.33 mmol) in THF (20 mL) was added $MnO_2$ (435 mg, 15 eq.), and the resulting mixture was refluxed for 12 hours. The mixture was filtrated to remove excess $MnO_2$, and the filtrate was concentrated to give 1-(4-methoxyphenyl)-3-formaldehyde-1H-pyrazole-5-(4'-pyrrolidinocarbonyl)anilide as a solid in almost quantitative yield. LRMS $(M+H)^+$ m/z: 419.

Example 45

1-(4-Methoxyphenyl)-5-(4'-pyrrolidinocarbonyl)anilide-3-pyrazolecarboxylic acid To a solution of $AgNO_3$ (34 mg, 0.2 mmol) in $H_2O$ (0.5 mL) was added NaOH (16 mg, 0.4 mmol), and then was added a solution of 1-(4-methoxyphenyl)-3-formaldehyde-1H-pyrazole-5-(4'-pyrrolidinocarbonyl)anilide (42 mg, 0.1 mmol) in MeOH (0.5 mL) at 0° C. After the resulting mixture was stirred at room temperature for 30 minutes, the mixture was carefully acidified with conc. HCl (35 μL) to pH~2, and concentrated to give a residue, which was purified by flash chromatography to give 1-(4-methoxyphenyl)-5-(4'-pyrrolidinocarbonyl)anilide-3-pyrazolecarboxylic acid (25 mg, 58%). ESMS $(M+Na)^+$ m/z: 456.9.

Example 46

1-(4-Methoxyphenyl)-3-methylcarboxylate-1H-pyrazole-5-(4'-pyrrolidinocarbonyl)anilide To a solution of 1-(4-methoxyphenyl)-3-formaldehyde-1H-pyrazole-5-(4'-pyrrolidinocarbonyl)anilide (42 mg, 0.1 mmol) in MeOH (1 mL) was added KCN (7.8 mg, 0.12 mmol), HOAc (7.2 mg, 0.12 mmol) and $MnO_2$ (120 mg, 0.83 mmol), and the resulting mixture was stirred ar r.t. for 12 hours. The mixture was diluted with EtOAc (50 mL), washed with water (10 mL×3) and brine, and dried over $MgSO_4$. The solution was filtrated, concentrated, and purified by flash chromatography with EtOAc gave 1-(4-methoxyphenyl)-3-methylcarboxylate-1H-pyrazole-5-(4'-pyrrolidinocarbonyl)anilide (38 mg, 85% yield). ESMS $(M+Na)^+$ m/z: 471.

Example 47

1-(4'-Chlorophenyl)-3-methyl-1H-pyrazole-5-[(2'-aminosulfonyl-[1,1']-biphen-4-yl)carboxyamide This compound was prepared by the same methodology described for EXAMPLE 1 with 4-chlorophenyl hydrazine • HCl substituted for phenyl hydrazine. There was obtained 1-(4'-chlorophenyl)-3-methyl-1H-pyrazole-5-[(2'-aminosulfonyl-[1,1']-biphen-4-yl)carboxyamide; HRMS, $(M+H)^+$: calc. 467.094465; found 467.093532.

Example 48

1-(4'-Chlorophenyl)-3-methyl-1H-pyrazole-5-[(2'-aminosulfonyl-[1-pyridyl-1'-phenyl]-4-yl)carboxyamide This compound was prepared by the same methodology described for EXAMPLE 8 with 4-chlorophenyl hydrazine • HCl substituted for phenyl hydrazine and 2-amino-5-(2-N-t-butylaminosulfonylphenyl)pyridine was used in the coupling step. There was obtained the title compound; HRMS $(M+H)^+$: calc. 468.089714; found 468.088873.

Example 49

1-(3',4'-Dichlorophenyl)-3-methyl-1H-pyrazole-5-[(2'-aminosulfonyl-[1,1']-biphen-4-yl)carboxyamide This compound was prepared by the same methodology described for EXAMPLE 1 with 3,4-dichlorophenyl hydrazine • HCl substituted for phenyl hydrazine. There was obtained the title compound; HRMS $(M+H)^+$: calc. 501.055493; found 501.053920.

Example 50

1-(3'-Chlorophenyl)-3-methyl-1H-pyrazole-5-[(2'-aminosulfonyl-[1,1']-biphen-4-yl)carboxyamide This compound was prepared by the same methodology described for EXAMPLE 1 with 3-chlorophenyl hydrazine

• HCl substituted for phenyl hydrazine. There was obtained the title compound; HRMS (M+H)+: calc. 467.094465; found 467.091517.

Example 51

2-Amino-4-phenyl-5-[(2'-aminosulfonyl-[1,1'-biphen-4-yl)aminocarbonyl]thiazole

2-Amino-4-phenyl-5-carboethoxythiazole

To a solution of ethyl 3-phenyl-3-oxopropionate (5.0 g, 26.0 mmol) in 100 mL of acetonitrile was added hydroxy (tosyloxy)iodobenzene (11.2 g, 28.6 mmol). The resulting suspension was stirred at 65° C. for 1 h at which time the reaction was a homogeneous solution. Thiourea (2.2 g, 28.6 mmol) was added and stirring was continued at 65° C. for 2 h. The mixture was cooled and concentrated, and the residue was taken up in ethyl acetate, washed with saturated aq $Na_2CO_3$ and brine, dried ($MgSO_4$) and concentrated. The residue was triturated with ethyl ether to afford 4.9 g (70%) of the title compound as a yellow solid. $^1$H NMR (CDCl3) d 7.65 (m, 2H), 7.39 (m, 3H), 5.98 (broad s, 2H), 4.18 (q, 2H), 1.22 (t, 3H).

2-Amino-4-phenyl-5-[(2'-tert-butylaminosulfonyl-[1,1']-biphen-4-yl)aminocarbonyl]thiazole To a solution of (2'-tert-butylaminosulfonyl-[1,1']-biphen-4-yl)amine (0.68 g, 2.22 mmol) in 15 mL of methylene chloride at 25° C. was added trimethylaluminum (3.3 mL of a 2.0 M solution in toluene, 6.68 mmol) dropwise. The resulting solution was allowed to stir until no more gas evolution was observed (~15 min). To this solution was added 2-amino-4-phenyl-5-carboethoxythiazole (0.30 g, 1.11 mmol) in 5 mL of methylene chloride. The resulting solution was stirred at 40° C. for 16 h and then was cooled to 25° C. and quenched by the addition of saturated aq $NH_4Cl$. After diluting with ethyl acetate, the organic layer was washed with 10% aq HCl, saturated aq $NaHCO_3$ and brine, dried ($MgSO_4$) and concentrated in vacuo. The residue was purified by flash chromatography (elution with 1:1 hexanes/ethyl acetate) to afford 0.3 g (54%) of the title compound as a solid. MS (ESI) 507.1 (M+H)+.

2-Amino-4-phenyl-5-[(2'-aminosulfonyl-[1,1']-biphen-4-yl)aminocarbonyl]thiazole

A solution of 2-amino-4-phenyl-5-[(2'-tert-butylaminosulfonyl-[1,1']-biphen-4-yl)aminocarbonyl]thiazole (80 mg, 0.16 mmol) in 3 mL of trifluoroacetic acid was stirred at reflux for 20 min and then was cooled to ambient temperature and concentrated in vacuo. The residue was purified by prep HPLC (C18 reverse phase column, elution with a $H_2O/CH_3CN$ gradient with 0.5% TFA) and lyophilized to afford 50 mg (71%) of the title compound as a white powder. MS (ESI) 451.0 (M+H)+.

Example 52

2-Chloro-4-phenyl-5-[(2'-aminosulfonyl-[1,1']-biphen-4-yl)aminocarbonyl]thiazole 2-Chloro-4-phenyl-5-[(2'-tert-butylaminosulfonyl-[1,1']-biphen-4-yl)aminocarbonyl]thiazole To a solution of copper (II) chloride (54 mg, 0.4 mmol) in 5 mL of acetonitrile was added tert-butyl nitrite (42 mg, 0.4 mmol). The mixture was warmed to 80° C. and then there was added 2-amino-4-phenyl-5-[(2'-tert-butylaminosulfonyl-[1,1']-biphen-4-yl)aminocarbonyl]thiazole (200 mg, 0.4 mmol). Stirring at 80° C. was continued for 1 h, at which time gas evolution had ceased. The reaction was cooled to ambient temperature, diluted with ethyl acetate, washed with 10% aq HCl, saturated aq $NaHCO_3$ and brine, dried ($MgSO_4$) and concentrated to afford 0.2 g (95%) of the title compound which was used without purification. MS (ESI) 526.1/528.0 (M+H)+.

2-Chloro-4-phenyl-5-[(2'-aminosulfonyl-[1,1']-biphen-4-yl)aminocarbonyl]thiazole A solution of 2-chloro-4-phenyl-5-[(2'-tert-butylaminosulfonyl-[1,1']-biphen-4-yl)aminocarbonyl]thiazole (100 mg, 0.19 mmol) in 5 mL of trifluoroacetic acid was stirred at reflux for 20 min and then was cooled to ambient temperature and concentrated in vacuo. The residue was purified by prep HPLC (C18 reverse phase column, elution with a $H_2O/CH_3CN$ gradient with 0.5% TFA) and lyophilized to afford 50 mg (56%) of the title compound as a white powder. MS (ESI) 469.9/471.9 (M+H)+.

Example 53

2-Amino-4-[3-(bromo)-4-(fluoro)-phenyl]-5-[(2'-aminosulfonyl-[1,1']-biphen-4-yl)aminocarbonyl]thiazole Methyl 3-[3-(bromo)-4-(fluoro)-phenyl]-3-oxopropionate To a suspension of sodium hydride (1.1 g of 60% suspension in mineral oil, hexane-washed, 27.6 mmol) in 50 mL of tetrahydrofuran was added dimethyl carbonate (2.3 mL, 27.6 inmol) and 3'-bromo-4'-fluoroacetophenone (3.0 g, 13.8 mmol). The resulting suspension was stirred at 65° C. for 1 h and then was cooled to room temperature. The reaction mixture was diluted with ethyl acetate and washed with water and brine, dried ($MgSO_4$) and concentrated in vacuo. The residue was purified by flash chromatography (elution with 3:1 hexane/ethyl acetate) to afford 1.0 g (26%) of the title compound. $^1$H NMR (CDCl$_3$) (data for keto tautomer) δ8.15 (dd, 1H), 7.87 (m, 1H), 7.2 (m, 1H), 3.95 (s, 2H), 3.73 (s, 3H).

2-Amino-4-[3-(bromo)-4-(fluoro)-phenyl]-5-carbomethoxythiazole

Following the procedure described in EXAMPLE 51, methyl 3-[3-(bromo)-4-(fluoro)-phenyl]-3-oxopropionate (1.0 g, 3.66 mmol) was converted into 0.6 g (50%) of the title compound. $^1$H NMR (CDCl$_3$) δ7.97 (m, 1H), 7.90 (broad s, 2H), 7.68 (m, 2H), 3.61 (s, 3H).

2-Amino-4-[3-(bromo)-4-(fluoro)-phenyl]-5-[2'-aminosulfonyl-[1,1']-biphen-4-yl)aminocarbonyl]thiazole Following the procedures described in EXAMPLE 51, 2-amino-4-[3-(bromo)-4-(fluoro)-phenyl]-5-carbomethoxythiazole (0.25 g, 0.75 mmol) was converted into the title compound as a white powder following HPLC purification. $^1$H NMR (CDCl$_3$) δ9.95 (s, 1H), 7.98 (d, 1H), 7.94 (dd, 1H), 7.65–7.55 (m, 3H), 7.50 (d, 2H), 7.36 (m 1H), 7.30–7.25 (m, 3H), 7.18 (s, 2H). MS (ESI) 546.9/548.8 (M+H)+.

Example 54

2-Amino-4-[4-fluorophenyl]-5-[(2'-aminosulfonyl-1,1']-biphen-4-yl)aminocarbonyl]thiazole Following the procedures described in EXAMPLE 51, 4'-fluoroacetophenone was converted into the title compound, 2-amino-4-[4-fluorophenyl]-5-[2'-aminosulfonyl-[1,1']-biphen-4-yl)aminocarbonyl]thiazole. $^1$H NMR (CDCl$_3$) δ(9.82 (s, 1H), 7.98 (d, 1H), 7.65–7.60 (m, 2H), 7.58–7.52 (m, 4H), 7.25 (m,3H), 7.20–7.13 (m, 4H). MS (ESI) 468.9 (M+H)+.

Example 55

2-Amino-4-[3-bromophenyl]-5-[(2'-aminosulfonyl-[1,1']-biphen-4-yl)aminocarbonyl]thiazole Following the procedures described in EXAMPLE 51, 3'-bromoacetophenone was converted into the title compound, 2-amino-4-[3-bromophenyl]-5-[2'-aminosulfonyl-[1,1']-biphen-4-yl)aminocarbonyl]thiazole. $^1$H NMR (CDCl$_3$) δ(9.95 (s, 1H), 7.98 (d, 1H), 7.81 (s, 1H), 7.60–7.45 (m, 6H), 7.30–7.22 (m,4H), 7.18 (broad s, 2H), 5.4 (broad s, 2H). MS (ESI) 528.8/530.8 (M+H)+.

Example 56

2-Chloro-4-[3-bromophenyl]-5-[(2'-aminosulfonyl-[1,1']-biphen-4-yl)aminocarbonyl]thiazole Following the procedures described in EXAMPLE 52, 2-amino-4-[3-bromophenyl]-5-[2'tert-butyl-aminosulfonyl-[1,1']-biphen-4-yl)aminocarbonyl]thiazole was converted into the title compound, 2-chloro-4-[3-bromophenyl]-5-[2'-aminosulfonyl-[1,1']-biphen-4-yl)aminocarbonyl]thiazole. MS (ESI) 547.9/549.8 (M+H)+.

Example 57

N-(2'-Aminosulfonyl-[1,1']-biphen-4-yl)-1-(4-methoxyphenyl)-3-(methylthio)pyrazole-5-carboxamide Ethyl N-(4-methoxyphenyl)glycine To a solution of 15.00 g (122 mmol) of p-anisidine in 100 mL of DMF under N$_2$ was added 23.50 g (141 mmol) of ethyl bromoacetate and 14.95 g (141 mmol) anhydrous sodium carbonate. The mixture was heated to 70° C. for 16 hours and then cooled to room temperature. Water (500 mL) was added and the mixture stirred vigorously until a precipitate formed. The solid was collected and washed with 100 mL water, then dried in vacuo to give 19.59 g (88%) of the desired compound as a grey solid. $^1$H NMR (CDCl$_3$) δ6.81 (d, J=8.8, 2H); 6.579 (d, J=8.8, 2H); 4.24 (q, J=7.0, 2H); 4.10 (s, 1H); 3.86 (s, 2H); 3.75 (s, 3H); 1.28 (t, J=7.0, 3H).

N-(4-Methoxyphenyl)glycine

To a solution of 19.59 g (108 mmol) of ethyl N-(4-methoxyphenyl)glycine in 100 mL of THF under N$_2$ was added 5.44 g (130 mmol) of lithium hydroxide monohydrate in 25 mL water. After 15 hours, the mixture was reduced to ½ the original volume in vacuo and then acidified with concentrated hydrochloric acid to ph 3 and a precipitate formed. The solid was collected and washed with 100 mL water, then dried in vacuo to give 9.92 g (51%) of the desired compound as a off-white solid. $^1$H NMR (CDCl$_3$): δ6.68 (d, J=8.8, 2H); 6.49 (d, J=8.8, 2H); 3.73 (s, 2H); 3.64 (s, 3H); 2.49 (br s, 2H).

N-(4-Methoxyphenyl)-N-nitrosoglycine

Sodium nitrite (3.97 g, 57.5 mmol) in 10 mL of water was added to a suspension of N-(4-methoxyphenyl)glycine (9.92 g, 54.7 mmol) in 50 mL of water under N$_2$. This was allowed to stir at room temperature until solution clarified, about 6 hours. The solution was acidified with concentrated hydrochloric acid to pH 3 and a precipitate formed. The solid was collected and washed with 50 mL water, then dried in vacuo to give 11.50 g (100%) of the desired compound as a white solid. $^1$H NMR (CDCl$_3$): δ7.17 (d, J=8.8, 2H); 6.70 (d, J=8.8, 2H); 4.30 (s, 2H), 3.56 (s, 3H), 2.29 (br s, 1H).

1-(4-Methoxyphenyl)-4-oxy-1,2,3-oxadiazole

N-(4-methoxyphenyl)-N-nitrosoglycine (11.50 g, 54.7 mmol) was dissolved in 100 mL of acetic anhydride and heated to 70° C. for 14 hours. The reaction mixture was cooled and then poured into 300 mL of ice-water. After stirring for 30 minutes to decompose the excess acetic anhydride, the reaction mixture was filtered to provide 10.50 g (100%) of a clear, thick oil. $^1$H NMR (CDCl$_3$): δ7.65 (d, J=9.2, 2H), 7.08 (d, J=9.2, 2H), 6.63 (s, 1H), 3.91 (s, 3H). MS (NH$_3$-CI) m/z 193.3 (M+H)$^+$.

1-(3-Cyanophenyl)-4-oxy-5-methylthio-1,2,3-oxadiazole 1-(4-methoxyphenyl)-4-oxy-1,2,3-oxadiazole (2.03 g, 10.6 mmol) was dissolved in 26 mL of dry DMSO and cooled to 0° C. Acetyl chloride (1.66 g, 21.1 mmol) was added very slowly via syringe below the surface of the liquid under N$_2$. The reaction mixture was allowed to stir at room temperature for 14 hours. The reaction mixture was diluted with 100 mL Et$_2$O and washed twice with 25 mL saturated aqueous NaHCO$_3$ then three times with 25 mL water to remove the DMSO. The organic extract was dried with MgSO$_4$ and concentrated in vacuo to give 1.83 g of a red solid which was used without further purification. MS (NH$_3$-CI) m/z 239.2 (M+H)$^+$.

Methyl 1-(4-methoxyphenyl)-3-methylthio-pyrazole-5-carboxylate

The crude 1-(4-methoxyphenyl)-4-oxy-5-methylthio-1,2, 3-oxadiazole (1.83 g, 7.68 mmol) and methyl propriolate (6.45 g, 76.8 mmol) were dissolved in 10 mL of CH$_2$Cl$_2$ and the quartz reaction vessel purged with N$_2$. The reaction mixture was irradiated in a Rayonet RPR-100 photochemical reactor for 14 hours. The crude product was concentrated in vacuo and then chromatographed with 20% EtOAc/hexanes on silica to provide 1.06 g (49%) of a yellow solid. $^1$H NMR (CDCl$_3$): δ7.33 (d, J=8.8, 2H); 6.95 (d, J=8.8, 2H); 6.89 (s, 1H); 3.85 (s, 3H); 3.78 (s, 3H); 2.55 (s, 3H). MS (NH$_3$-CI) m/z 279.2 (M+H)$^+$.

N-(2'-t-Butylaminosulfonyl-[1,1']-biphen-4-yl)-1-(4-methoxyphenyl)-3-methylthio-pyrazole-5-carboxamide Trimethyl aluminum (1.4 mL, 2.0 M in heptane, 2.8 mmol) was added to 2'-t-butylaminosulfonyl-4-amino-[1,1'] biphen-4-yl (215 mg, 0.71 mmol) in CH$_2$Cl$_2$ (5 mL,). After stirring at room temp under N$_2$ for 75 minutes, a solution of methyl 1-(4-methoxyphenyl)-3-methylthio-pyrazole-5-carboxylate (197 mg, 0.71 mmol) in CH$_2$Cl$_2$ (2 mL) was added and the resulting solution stirred 70 hours. The reaction was quenched carefully by dropwise addition of 1M HCl, diluted with H$_2$O, and extracted into CH$_2$Cl$_2$. The organic layer was dried over Na$_2$SO$_4$, filtered, and evaporated. The crude product was chromatographed on silica gel (30–40% EtOAc/hexanes) to yield the desired product (357 mg, 92%). $^1$H NMR (CDCl$_3$): δ8.14 (d, 1H, J=7.7), 7.50 (m, 9H), 7.27 (m, 1H), 7.01 (d, 2H, J=8.8), 6.83 (s, 1H), 3.87 (s, 3H), 3.57 (s, 1H), 2.59 (s, 3H), 1.01 (s, 9H)

N-(2'-Aminosulfonyl-[1,1']-biphen-4-yl)-1-(4-methoxyphenyl)-3-methylthio-pyrazole-5-carboxamide N-(2'-t-butylaminosulfonyl-[1,1']biphen-4-yl)-1-(4-methoxyphenyl)-3-methylthio-pyrazole-5-carboxamide (328 mg, 0.60 mmol) was stirred in TFA (5 mL) for 17 hours. The solvent was evaporated and the crude product chromatographed on silica gel (50% EtOAc/hexanes) to yield a yellow solid (267 mg, 91%). $^1$H NMR (CDCl$_3$): δ10.62 (s, 1H), 7.98 (dd, 1H, J=7.7, J'=1.5), 7.62 (d, 2H, J=8.8), 7.55 (m, 2H), 7.30 (m, 5H), 7.22 (s, 2H), 6.98 (m, 3H), 3.76 (s, 3H), 2.51 (s, 3H).

Example 58

1-(4-Methoxyphenyl)-3-(methylsulfonyl)-N-(5-(2'-methylsulfonylphenyl)pyrimid-2-yl)pyrazole-5-carboxamide 2-Methylthiophenylboronic acid 2-Bromothioanisole (29.0 g, 143 mmol) was dissolved in dry THF (400 mL) and cooled to −75° C. n-BuLi (62.0 mL, 2.5 M in hexane, 155 mmol) was added over 50 minutes. After stirring 25 minutes, triisopropyl borate (46 mL, 199 mmol) was added over 35 minutes. The cold bath was removed and the reaction was stirred at room temp for 16 hours. The resulting solution was cooled in an ice bathours, and 6 M HCl (100 mL) was added. This mixture was stirred at room temp 5 hours and concentrated to about half of the original volume. The concentrated solution was partitioned between Et$_2$O and water. The organic layer was extracted with 2 M NaOH, which was subsequently reacidified with 6 M HCl and extracted several times back into Et$_2$O. These Et$_2$O washes were dried over Na$_2$SO$_4$, filtered, and evaporated to yield a beige solid (20.4 g, 85%). $^1$H NMR (CDCl$_3$): δ8.01 (dd, 1H, J=7.3, J'=1.4), 7.53 (dd, 1H, J=7.7, J'=1.1), 7.43 (td, 1H, J=7.3, J'=1.8), 7.34 (td, 1H, J=7.3, J'=1.5), 6.22 (s, 2H), 2.50 (s, 3H).

2-[Bis(tert-butoxycarbonyl)amino]-5-bromopyrimidine

Sodium hydride (5.06 g, 60% 127 mmol) was added in 2 portions to 2-amino-5-bromopyrimidine (10.0 g, 57 mmol) in dry THF (500 mL) at 0° C. After stirring 30 minutes, di-t-butyl dicarbonate (27.6 g, 126 mmol) was added. The resulting mixture was refluxed 17 hours, quenched carefully with water, and concentrated. The concentrated mixture was diluted with EtOAc and extracted with water. The combined aqueous layers were extracted with EtOAc. All of the organic layers were combined, dried over Na$_2$SO$_4$, filtered, and evaporated. The crude product was chromatographed on silica gel (10–15% EtOAc/hexanes) to yield the desired product (15.48 g, 72%). $^1$H NMR (CDCl$_3$): δ8.78 (s, 2H), 1.47 (s, 18H).

2-[Bis(tert-butoxycarbonyl)amino]-5-(2'-methylthiophenyl) pyrimidine

2-[Bis(tert-butoxycarbonyl)amino]-5-bromopyrimidine (2.00 g, 5.3 mmol) was dissolved in benzene (130 mL). 2-methylthiophenylboronic acid (2.24 g, 13.3 mmol), aq. sodium carbonate (13 mL, 2.0 M, 26 mmol), tetrabutyl ammonium bromide (86 mg, 0.26 mmol), and bis(triphenylphosphine)palladium(II)chloride (190 mg, 0.27 mmol) were added, and the resulting mixture was first purged with vacuum and argon, then refluxed 17 hours. The cooled mixture was diluted with EtOAc and water. The layers were separated, and the organic was dried over Na$_2$SO$_4$, filtered, and evaporated. The crude product was chromatographed on silica gel (50% EtOAc/hexanes), evaporated, and chromatographed a second time on silica gel (30–50% EtOAc/hexanes) to yield the desired product (2.13 g, 96%). $^1$H NMR (CDCl$_3$): δ8.81 (s, 2H), 7.41 (m, 2H), 7.25 (m, 2H), 2.39 (s, 3H), 1.49 (s, 18H).

2-[Bis(tert-butoxycarbonyl)amino]-5-(2'-methylsulfonylphenyl) pyrimidine

2-[Bis(tert-butoxycarbonyl)amino]-5-(2'-methylthiophenyl)pyrimidine (2.13 g, 5.1 mmol) was dissolved in MeOH (20 mL) and cooled to 0° C. In a separate beaker, a solution of Oxone (5.49 g) was generated by dilution to 27 mL with water. A portion of this solution (17 mL, 5.6 mmol) was removed and adjusted to pH 4.2 with sat. Na$_3$PO$_4$ solution (4.7 mL). This mixture was added to the reaction and stirred 23 hours at room temp. The resulting mixture was diluted with water and extracted with CHCl$_3$. The organics were combined, washed with water and brine, dried over Na$_2$SO$_4$, filtered, and evaporated. The crude product was chromatographed on silica gel (50–100% EtOAc/hexanes) to yield the sulfone (1.28 g, 56%). $^1$H NMR (CDCl$_3$): δ8.81 (s, 2H), 8.28 (dd, 1H, J=7.6, J'=1.4), 7.72 (m, 2H), 7.39 (dd, 1H, J=7.3, J'=1.4), 2.76 (s, 3H), 1.50 (s, 18H).

2-Amino-5-(2'-methylsulfonylphenyl)pyrimidine hydrochloride

2-[Bis(tert-butoxycarbonyl)amino]-5-(2'-methylsulfonylphenyl) pyrimidine (1.28 g, 2.8 mmol) was suspended in HCl/dioxane (10 mL, 4.0 M) and stirred 20 hours at room temp. The resulting mixture was triturated with Et$_2$O and filtered to yield a white solid (772 mg, 95%). $^1$H NMR (CDCl$_3$+ few drops MeOD): δ8.53 (s, 2H), 8.22 (dd, 1H, J=7.7, J'=1.8), 7.77 (m, 2H), 7.40 (dd, 1H, J=7.4, J'=1.5), 2.94 (s, 3H).

Methyl 1-(4-methoxyphenyl)-3-methylsulfonyl-pyrazole-5-carboxylate

M-CPBA (1.18 g, 57–86%, minutes. 3.9 mmol) was added to methyl 1-(4-methoxyphenyl)-3-methylthio-pyrazole-5-carboxylate (434 mg, 1.6 mmol) in CH$_2$Cl$_2$ (40 mL) and stirred at room temperature for 24 hours. Additional m-CPBA (600 mg, 57–86%, minutes. 1.9 mmol) was added and stirred 2.5 days. The reaction was extracted with saturated Na$_2$SO$_3$ and saturated NaHCO$_3$. The organic layer was dried over Na$_2$SO$_4$, filtered, and evaporated. The crude product was chromatographed on silica gel (40% EtOAc/hexanes) to yield the desired product (416 mg, 86%). $^1$H NMR (CDCl$_3$): δ7.46 (s, 1H), 7.36 (d, 2H, J=8.8), 6.99 (d, 2H, J=8.8), 3.87 (s, 3H), 3.84 (s, 3H), 3.26 (s, 3H).

1-(4-Methoxyphenyl)-3-methylsulfonyl-pyrazole-5-carboxylic acid

A solution of lithium hydroxide (1.3 mL, 1.0 M, 1.3 mmol) was added to a suspension of methyl 1-(4-methoxyphenyl)- 3-methylsulfonyl-pyrazole-5-carboxylate (272 mg, 0.88 mmol) in MeOH (10 mL) and stirred at room temperature 17 hours. The resulting mixture was concentrated and partitioned between EtOAc and H$_2$O. The organic extracted was removed, and the aqueous extract was acidified with 1M HCl and extracted twice with EtOAc. The organic extracts from this extraction were combined, dried over Na$_2$SO$_4$, filtered, and evaporated to yield product (266 mg). $^1$H NMR (CDCl$_3$+ few drops MeOD): δ7.45 (s, 1H), 7.38 (d, 2H, J=9.2), 6.96 (d, 2H, J=9.2), 3.86 (s, 3H), 3.25 (s, 3H).

1-(4-Methoxyphenyl)-3-(methylsulfonyl)-N-(5-(2'-methylsulfonylphenyl)pyrimid-2-yl)pyrazole-5-carboxamide Oxalyl chloride (120 μl, 1.4 mmol) and dry DMF (2 drops) were added at room temperature to 1-(4-methoxyphenyl)-3-methylsulfonyl-pyrazole-5-carboxylic acid (262 mg, 0.88 mmol) in dry CH$_2$Cl$_2$ (5 mL) and stirred 2 hours under N$_2$. The resulting solution was evaporated and placed briefly under high vacuum before redissolving in CH$_2$Cl$_2$ (2 mL). This solution was added over a few minutes to a mixture of 2-amino-5-(2'-methylsulfonylphenyl)pyrimidine hydrochloride (253 mg, 0.89 mmol) and 4-dimethylaminopyridine (270 mg, 2.2 mmol) in CH$_2$Cl$_2$ (3 mL). The resulting solution was stirred at room temperature under N$_2$ for 23 hours, diluted with CH$_2$Cl$_2$, extracted with H$_2$O, dried over Na$_2$SO$_4$, filtered, and evaporated. The crude product was chromatographed on silica gel (75–100% EtOAc/hexanes) to yield an impure white solid, which was taken up in toluene and filtered to yield clean product (191 mg, 41%). $^1$H NMR (CDCl$_3$): δ8.65 (s, 2H), 8.62 (s, 1H), 8.24 (d, 1H, J=7.0), 7.71 (m, 2H), 7.47 (d, 2H, J=8.8), 7.39 (s, 1H), 7.33 (d, 1H, J=6.6), 6.98 (d, 2H, J=8.8), 3.85 (s, 3H), 3.30 (s, 3H), 2.80 (s, 3H).

Example 59

N-(2'-Aminosulfonyl-[1,1']-biphen-4-yl)-1-(4-methoxyphenyl)-3-(methylsulfonyl)-1H-pyrazole-5-carboxamide N-(2'-t-Butylaminosulfonyl-[1,1']-biphen-4-yl)-1-(4-methoxyphenyl)-3-(methylsulfonyl)-1H-pyrazole-5-carboxamide Trimethyl aluminum (930 μl, 2.0 M in heptane, 1.86 mmol) was added to 2'-t-butylaminosulfonyl-4-amino-[1,1']biphen-4-yl (142 mg, 0.47 mmol) in CH$_2$Cl$_2$ (5 mL). After stirring at room temperature under N$_2$ for 60 minutes, a solution of methyl 1-(4-methoxyphenyl)-3-methylsulfonyl-pyrazole-5-carboxylate (145 mg, 0.47 mmol) in CH$_2$Cl$_2$ (2 mL) was added and the resulting solution stirred for 51 hours. The reaction was quenched carefully by dropwise addition of 0.1 M HCl, diluted with H$_2$O, and extracted twice into CH$_2$Cl$_2$. The organic layer was dried over Na$_2$SO$_4$, filtered, and evaporated to yield the desired product (277 mg, 100%). $^1$H NMR (CDCl$_3$): δ8.21 (bs, 1H), 8.16 (dd, 1H, J=7.6, J'=1.1), 7.57 (m, 3H), 7.46 (m, 5H), 7.39 (s, 1H), 7.27 (d, 1H, J=7.3), 6.99 (d, 2H, J=8.8), 3.86 (s, 3H), 3.31 (s, 3H), 1.03 (s, 9H).

N-(2'-Aminosulfonyl-[1,1']-biphen-4-yl)-1-(4-methoxyphenyl)-3-(methylsulfonyl)-1H-pyrazole-5-carboxamide N-(2'-t-butylamino-sulfonyl-[1,1']-biphen-4-yl)-1-(4-methoxyphenyl)-3-(methylsulfonyl)pyrazole-5-carboxamide (274 mg, 0.47 mmol) was stirred in TFA (5 mL) for 74 hours. The solvent was evaporated. The crude product was recrystallized from CHCl$_3$ to yield a white solid (236 mg, 95%). $^1$H NMR (CDCl$_3$ + few drops MeOD): δ8.13 (d, 1H, J=7.7), 7.67 (d, 2H, J=8.4), 7.59 (t, 1H, J=6.3), 7.46 (m, 6H), 7.32 (d, 1H, J=8.5), 7.00 (d, 2H, J=9.2), 3.86 (s, 3H), 3.31 (s, 3H).

Example 60

N-(4-Benzoylpyrrolidino)-1-(4-methoxhenyl)-3-(methylthio)-1H-pryazole-5-carboxamide 1-(4-Methoxyphenyl)-3-methylthio-1H-pyrazole-5-carboxylic acid A solution of lithium hydroxide (4.5 mL, 1.0 M, 4.5 mmol) was added to a suspension of methyl 1-(4-methoxyphenyl)-3-methylthio-1H-pyrazole-5-carboxylate (840 mg, 3.0 mmol) in MeOH (30 mL) and stirred at room temperatureerature for 21 hours. The resulting mixture was concentrated and partitioned between EtOAc and H$_2$O. The organic layer was removed, and the aqueous layer was acidified with 1M HCl and extracted twice with EtOAc. The combined organic extracts were dried over Na$_2$SO$_4$, filtered, and evaporated to yield clean product (784 mg, 98%). $^1$H NMR (CDCl$_3$): δ7.33 (d, 2H, J=8.4), 6.97 (s, 1H), 6.95 (d, 2H, J=8.4), 3.85 (s, 3H), 2.55 (s, 3H).

N-(4-Benzoylpyrrolidino)-1-(4-methoxyphenyl)-3-(methylthio)-1H-pyrazole-5-carboxamide Oxalyl chloride (140 μl, 1.6 mmol) and dry DMF (2 drops) were added at room temperature to 1-(4-methoxyphenyl)-3-methylthio-1H-pyrazole-5-carboxylic acid (275 mg, 1.0 mmol) in dry CH$_2$Cl$_2$ (8 mL) and stirred for 100 minutes under N$_2$. The resulting solution was evaporated and placed briefly under high vacuum before redissolving in CH$_2$Cl$_2$ (8 mL). (4-aminobenzoyl)pyrrolidine (198 mg, 1.0 mmol) was added, followed by 4-dimethylaminopyridine (190 mg, 1.6 mmol). The resulting mixture was stirred at room temperature for 17 hours, diluted with CH$_2$Cl$_2$, and extracted with H$_2$O. The aqueous extract was extracted with CH$_2$Cl$_2$, the combined organic extracts were extracted with brine. The organic layer was dried over Na$_2$SO$_4$, filtered, and evaporated. The crude product was chromatographed on silica gel (75–100% EtOAc/hexanes) to yield the desired product (464 mg, 100%). $^1$H NMR (CDCl$_3$): δ7.91 (bs, 1H), 7.44 (s, 4H), 7.39 (d, 2H, J=8.8), 6.97 (d, 2H, J=8.8), 6.83 (s, 1H), 3.84 (s, 3H), 3.62 (t, 2H, J=6.6), 3.42 (t, 2H, J=6.6), 2.57 (s, 3H), 1.91 (m, 4H).

Example 61

1-(4-Methoxyphenyl)-N-(5-(2'-methylsulfonylphenyl)pyrimid-2-yl)-3-(methylthio)-1H-pyrazole-5-carboxamide 1-(4-Methoxyphenyl)-N-(5-(2'-methylsulfonylphenyl)pyrimid-2-yl)-3-(methylthio)-1H-pyrazole-5-carboxamide Trimethyl aluminum (1.5 mL, 2.0 M in heptane, 3.0 mmol) was added to 2-amino-5-(2'-methylsulfonylphenyl)pyrimidine hydrochloride (208 mg, 0.73 mmol) in CH$_2$Cl$_2$ (5 mL). After stirring at room temperature under N$_2$ for 75 minutes, a solution of methyl 1-(4-methoxyphenyl)-3-methylthio-1H-pyrazole-5-carboxylate (203 mg, 0.73 mmol) in CH$_2$Cl$_2$ (2 mL) was added and the resulting solution stirred for 70 hours. The reaction was quenched carefully by dropwise addition of 1M HCl, diluted with 1M HCl, and extracted into CH$_2$Cl$_2$. The organic layer was dried over Na$_2$SO$_4$, filtered, and evaporated. The crude product was chromatographed on silica gel (50–100% EtOAc/hexanes) to yield the desired product (101 mg, 28%). This material was combined with 19 mg from another reaction and purified by preparative HPLC on a C-18 reversed-phase column (30–100% MeCN/H$_2$O/0.05% TFA) to yield a white powder (111 mg). $^1$H NMR (CDCl$_3$): δ8.67 (s, 2H), 8.24 (d, 1H, J=7.3), 7.71 (m, 2H), 7.44 (d, 2H, J=9.1), 7.33 (d, 1H, J=8.4), 6.96 (d, 2H, J=9.2), 6.86 (s, 1H), 3.84 (s, 3H), 2.79 (s, 3H), 2.59 (s, 3H).

Example 62

N-(4-Benzoylpyrrolidino)-1-(4-methoxyphenyl)-3-(methylsulfonyl)-1H-pyrazole-5-carboxamide N-(4-Benzoylpyrrolidino)-1-(4-methoxyphenyl)-3-(methylsulfonyl)-1H-pyrazole-5-carboxamide N-(4-benzoylpyrrolidino)-1-(4-methoxyphenyl)-3-(methylthio)-1H-pyrazole-5-carboxamide (200 mg, 0.46 mmol) was dissolved in MeOH (6 mL). A solution of Oxone (561 mg, 0.91 mmol) in H$_2$O (3 mL) was added, and the resulting mixture stirred at room temperature under Ar for 17 hours. The reaction was diluted with H$_2$O and extracted twice with CHCl$_3$. The combined organic extracts were dried over Na$_2$SO$_4$, filtered, and evaporated. The crude product was purified by preparative HPLC on a C-18 reversed-phase column (10–70% MeCN/H$_2$O/0.05% TFA) to yield a white powder (200 mg, 93%). $^1$H NMR (CDCl$_3$): δ8.98 (s, 1H), 7.52 (s, 1H), 7.39 (m, 6H), 6.95 (d, 2H, J=8.8), 3.84 (s, 3H), 3.65 (t, 2H, J=6.6 ), 3.41 (t, 2H, J=6.2 ), 3.28 (s, 3H), 1.93 (m, 4H).

Example 63

N-(2'-Aminosulfonyl-[1,1']-biphen-4-yl)-1-(4-methoxyphenyl)-3-(methoxymethyl)-1H-pyrazole-5-carboxamide Ethyl 3-(bromomethyl)-1-(4-methoxyphenyl)-1H-pyrazole-5-carboxylate and ethyl 3-(dibromomethyl)-1-(4-methoxyphenyl)-1H-pyrazole-5-carboxylate Ethyl 1-(4-methoxyphenyl)-3-methyl-1H-pyrazole-5-carboxylate (2.00 g, 7.83 mmol) was dissolved in 30 mL CCl$_4$ and N-bromosuccinimide (3.06 g, 17.2 mmol) and benzoylperoxide (0.02 g, 0.08 mmol) were added. The reaction mixture was heated for 48 hours then cooled to room temperature. The succinimide was filtered away and the solvent evaporated. The reaction mixture was chromatographed on silica (20% EtOAc/hexanes) to give the 0.94 g (36%) of the monobromide. $^1$H NMR (CDCl$_3$): δ7.34 (d, J=8.8, 2H); 7.06 (s, 1H); 6.96 (d, J=8.8, 2H); 4.53 (s, 2H); 4.24 (q, J=7.0, 2H); 3.85 (s, 3H); 1.27 (t, J=7.0, 3H) . The dibromide (0.34 g, 10%) was also isolated. $^1$H NMR (CDCl$_3$) δ7.34 (d, J=9.1, 2H); 7.31 (s, 1H); 6.96 (d, J=9.1, 2H); 6.73 (s, 1H); 4.26 (q, J=7.0, 2H); 3.85 (s, 3H); 1.29 (t, J=7.0, 3H).

1-(4-Methoxyphenyl)-3-(methoxymethyl)-1H-pyrazole-5-carboxylic acid

Ethyl 3-(bromomethyl)-1-(4-methoxyphenyl)-1H-pyrazole-5-carboxylate (0.50 g, 1.47 mmol) is dissolved in 12 mL of 0.5 M NaOMe in methanol and heated to reflux for 14 hours. The reaction mixture was cooled and reduced to 1/10 original volume. The reaction mixture was dissolved in 20 mL of water and extracted with EtOAc. The aqueous mixture was acidified with 1N HCl and extracted with EtOAc to give 0.236 g (61%) of desired product. A mixture of ethyl and methyl esters (~0.05 g) was found in the first EtOAc extract. $^1$H NMR (CDCl$_3$): δ7.32 (d, J=8.8, 2H); 7.11 (s, 1H); 6.94 (d, J=8.8, 2H); 4.54 (s, 2H); 3.85 (s, 3H); 3.44 (s, 3H).

N-(2'-t-Butylaminosulfonyl-[1,1]-biphen-4-yl)-1-(4-methoxyphenyl)-3-(methoxymethyl)-1H-pyrazole-5-carboxamide Oxalyl chloride (460 mg, 3.6 mmol) and dry DMF (2 drops) were added at room temperature to 1-(4-methoxyphenyl)-3-(methoxymethyl)-1H-pyrazole-5-carboxylic acid (236 mg, 0.90 mmol) in dry CH$_2$Cl$_2$ (5 mL) and stirred 2 hours under N$_2$. The resulting solution was evaporated and placed briefly under high vacuum before redissolving in CH$_2$Cl$_2$ (2 mL). This solution was added over a few minutes to a mixture of 2'-t-butylaminosulfonyl-4-amino-[1,1']-biphen-4-yl (288 mg, 0.945 mmol) in 5 mL of CH$_2$Cl$_2$. The resulting solution was stirred at room temperature under N$_2$ for 23 hours, diluted with CH$_2$Cl$_2$, extracted with H$_2$O, dried over Na$_2$SO$_4$, filtered, and evaporated. The crude product was chromatographed on silica gel (30% EtOAc/hexanes) to yield an white solid (110 mg, 22%). MS (ESI) m/z 571.0 (M+Na)$^+$.

N-(2'-Aminosulfonyl-[1,1']-biphen-4-yl)-1-(4-methoxyphenyl)-3-(methoxymethyl)-1H-pyrazole-5-carboxamide N-(2'-t-Butylaminosulfonyl-[1,1']-biphen-4-yl)-1-(4-methoxyphenyl)-3-(methoxymethyl)-1H-pyrazole-5-carboxamide (110 mg, 0.20 mmol) was dissolved in 5 mL TFA and stirred at room temperature for 16 hours. The solvent was removed and the product purified by preparative HPLC on a C-18 reversed-phase column (10–90% MeCN/H$_2$O/0.05% TFA) to yield a white powder (94 mg, 95%). $^1$H NMR (CDCl$_3$): δ8.15 (d, J=8.1, 1H); 7.73 (br s, 1H); 7.53 (m, 4H); 7.43 (m, 4H); 7.32 (d, J=7.3, 1H); 7.01 (s, 1H); 6.96 (d, J=9.2, 2H); 4.59 (s, 2H); 4.26 (br s, 2H); 3.86 (s, 3H); 3.49 (s, 3H). HRMS m/z 493.1546 (M+H)$^+$.

Example 64

N-(2'-Aminosulfonyl-[1,1']-biphen-4-yl)-1-(4-methoxyphenyl)-3-carbomethoxy-1H-pyrazole-5-carboxamide 3-formyl-1-(4-Methoxyphenyl)-1H-pyrazole-5-carboxylic acid Ethyl 3-(dibromomethyl)-1-(4-methoxyphenyl)-1H-pyrazole-5-carboxylate (0.34 g, 0.813 mmol) was dissolved in 2 mL THF and lithium hydroxide (34 mg, 0.816 mmol) was dissolved in 0.5 mL water and added to the methanolic solution. After stirring at room temperature for 16 hours the solvent was evaporated, the residue was dissolved in 10 mL of water, acidified with 1N HCl and extracted with EtOAc to give 66 mg (33%) of the desired product after evaporation. $^1$H NMR (CDCl$_3$): δ10.06 (s, 1H); 7.56 (s, 1H); 7.40 (d, J=9.1, 2H); 7.01 (d, J=9.1, 2H); 4.54 (s, 2H); 3.88 (s, 3H).

N-(2'-t-Butylaminosulfonyl-[1,1']-biphen-4-yl)-3-formyl-1-(4-methoxyphenyl)-1H-pyrazole-5-carboxamide Oxalyl chloride (20 mL) and dry DMF (2 drops) were added at room temperature to 3-formyl-1-(4-Methoxyrhenyl)-1H-pyrazole-5-carboxylic acid (66 mg, 0.25 mmol) in dry CH$_2$Cl$_2$ (2 mL) and stirred 2 hours under N$_2$. The resulting solution was evaporated and placed briefly under high vacuum before redissolving in CH$_2$Cl$_2$ (2 mL). This solution was added over a few minutes to a mixture of 2'-t-butylaminosulfonyl-4-amino-[1,1']biphen-4-yl (51 mg, 0.17 mmol) in 2 mL of CH$_2$Cl$_2$. The resulting solution was stirred at room temperature under N$_2$ for 23 hours, diluted with CH$_2$Cl$_2$, extracted with H$_2$O, dried over Na$_2$SO$_4$, filtered, and evaporated. The crude product was chromatographed on silica gel (30% EtOAc/hexanes) to yield an white solid (16.2 mg, 11%). $^1$H NMR (CDCl$_3$): δ10.09 (s, 1H); 8.16 (d, J=8.1, 1H); 7.77 (br s, 1H); 7.56 (m, 3H); 7.49 (m, 4H); 7.40 (m, 1H); 7.25 (m, 2H); 7.04 (d, J=8.8, 2H); 3.89 (s, 3H); 3.61 (br s, 1H); 1.02 (s, 9H).

N-(2'-t-Butylaminosulfonyl-[1,1']-biphen-4-yl)-3-carbomethoxy-1-(4-methoxyphenyl)-1H-pyrazole-5-carboxamide N-(2'-t-Butylaminosulfonyl-[1,1']-biphen-4-yl)-3-formyl-1-(4-methoxyphenyl)-1H-pyrazole-5-carboxamide (16.2 mg, 0.03 mmol), KCN (6.9 mg, 0.11 mmol), manganese dioxide, activated (100 mg), and acetic acid (1.7 μL, 0.03 mmol) was dissolved/suspended in 1 mL of methanol and stirred at room temperature for 24 hours. The reaction mixture was filtered through Celite and evaporated to 14 mg (82%) of the desired product. $^1$H NMR (CDCl$_3$): δ8.16 (d, J=8.1, 1H); 7.67 (br s, 1H); 7.53 (m, 3H); 7.48 (m, 4H); 7.27 (m, 2H); 7.02 (d, J=8.8, 2H); 3.99 (s, 3H); 3.87 (s, 3H); 1.02 (s, 9H).

N-(2'-Aminosulfonyl-[1,1']-biphen-4-yl)-3-carbomethoxy-1-(4-methoxyphenyl)-1H-pyrazole-5-carboxamide N-(2'-t-Butylaminosulfonyl-[1,1']-biphen-4-yl)-3-carbomethoxy-1-(4-methoxyphenyl)-1H-pyrazole-5-carboxamide (14 mg, 0.02 mmol) was dissolved in 2 mL TFA and stirred at room temperature for 16 hours. The solvent was removed and the product purified by preparative HPLC on a C-18 reversed-phase column (10–90% MeCN/H$_2$O/0.05% TFA) to yield a white powder (9 mg, 81%). $^1$H NMR (CDCl$_3$): δ8.16 (d, J=8.1, 1H); 7.67 (br s, 1H); 7.50 (m, 11H); 7.31 (d, J=7.0, 1H); 7.00 (d, J=8.8, 2H); 4.59 (s, 2H); 4.20 (br s, 2H); 3.99 (s, 3H); 3.87 (s, 3H). HRMS m/z 507.1260 (M+H)$^+$.

Example 65

N-(2'-Aminosulfonyl-[1,1']-biphen-4-yl)-1-(4-methoxyphenyl)-3-(methylsulfonylmethyl)-1H-pyrazole-5-carboxamide Ethyl 1-(4-methoxyphenyl)-3-(methylsulfonylmethyl)-1H-pyrazole-5-carboxylate Ethyl 3-(bromomethyl) -1(4-methoxyphenyl)-1H-pyrazole-5-carboxylate (0.4440 g, 1.31 mmol) is dissolved in 10 mL THF with potassium thiomethoxide (0.248 g, 2.88 mmol) and heated to reflux for 14 hours. The reaction mixture was cooled and reduced to ⅒ original volume. The reaction mixture was dissolved in 20 mL of water and extracted with EtOAc and air oxidized over 24 hours to give 0.358 g of a crude mixture. The product was purified by preparative HPLC on a C-18 reversed-phase column (10–90% MeCN/H$_2$O/0.05% TFA) to yield a white powder 47 mg (11%) of desired product. $^1$H NMR (CDCl$_3$): δ7.32 (d, J=8.8, 2H); 7.18 (s, 1H); 6.97 (d, J=8.8, 2H); 4.37 (s, 2H); 4.25 (q, J=7.1, 2H); 3.86 (s, 3H); 1.28 (t, J=7.1, 3H).

N-(2'-t-Butylaminosulfonyl-[1,1']-biphen-4-yl)-1-(4-methoxyphenyl)-3-(methylsulfonylmethyl)-1H-pyrazole-5-carboxamide Trimethyl aluminum (0.41 mL, 2.0 M in heptane, 0.83 mmol) was added to 2'-t-butylaminosulfonyl-4-amino-[1,1'] biphen-4-yl (50.6 mg, 0.166 mmol) in CH$_2$Cl$_2$ (5 mL). After stirring at room temp under N$_2$ 75 minutes, a solution of ethyl 1-(4-methoxyphenyl)-3-(methylsulfonylmethyl)-1H-pyrazole-5-carboxylate (47 mg, 0.139 mmol) in CH$_2$Cl$_2$ (2 mL) was added and the resulting solution stirred 70 hours. The reaction was quenched carefully by dropwise addition of 1M HCl, diluted with H$_2$O, and extracted into CH$_2$Cl$_2$. The organic layer was dried over Na$_2$SO$_4$, filtered, and evaporated. The crude product was purified by preparative HPLC on a C-18 reversed-phase column (10–90% MeCN/H$_2$O/0.05% TFA) to yield the desired product (80 mg, 100%). $^1$H NMR (CDCl$_3$): δ8.16 (d, J=8.1, 1H); 7.76 (br s, 1H); 7.49 (m, 8H); 7.27 (m, 1H); 7.08 (m, 1H); 7.01 (d, J=8.8, 2H); 4.41 (s, 2H); 3.87 (s, 3H); 2.96 (s, 3H); 1.02 (s, 9H).

N-(2'-Aminosulfonyl-[1,1']-biphen-4-yl)-1-(4-methoxyphenyl)-3-(methylsulfonylmethyl)-1H-pyrazole-5-carboxamide N-(2'-t-Butylaminosulfonyl-[1,1']-biphen-4-yl)-1-(4-methoxyphenyl)-3-(methylsulfonylmethyl)-1H-pyrazole-5-carboxamide (80 mg, 0.15 mmol) was dissolved in 2 mL TFA and stirred at room temperature for 16 hours. The solvent was removed and the product purified by preparative HPLC on a C-18 reversed-phase column (10–90% MeCN/H$_2$O/0.05% TFA) to yield a white powder (47 mg, 58%). $^1$H NMR (CDCl$_3$) δ8.16 (d, J=8.1, 1H) ; 8.06 (br s, 1H); 7.60 (m, 4H); 7.44 (m, 4H); 7.33 (m, 1H); 7.09 (br s, 1H); 7.01 (d, J=9.1, 2H); 4.43 (s, 2H); 4.38 (br s, 2H); 3.87 (s, 3H); 2.97 (s,3H). HRMS m/z 541.1137 (M+H)$^+$.

Example 66

3-Trifluoromethyl-1-(4-methoxyphenyl)-1H-pyrazole-5-(N-(5-(2-methanesulfonyl)phenyl) pyrimidin-2-yl)carboxyamide 3-Trifluoromethyl-1-(4-methoxyphenyl)-1H-pyrazole-5-(N-(5-(2-methanesulfonyl)phenyl) pyrimidin-2-yl)carboxyamide This material was prepared according to the methods described for EXAMPLE 15 with the exception that during the coupling step 2-amino-5-(2-methanesulfonyl)phenyl) pyrimidine was substituted for 4-(2-N-t-butylaminosulfonyl)phenyl)aniline. Purification by HPLC utilizing gradient elution with a mixture of water:acetonitrile with 0.05% trifluoroacetic acid on a reverse phase C18 (60 Å) column gave a pure sample of the title compound; HRMS (M+H)$^+$ calc. m/z: 518.110986, obs: 518.108715.

Example 67

3-Methyl-1-(4-methoxyphenyl)-1H-pyrazole-5-N-(4-(N-carboxyl-2-carbomethoxypyrrolidino)phenyl) carboxyamide N-(4-Nitrobenzoyl)-2-carbomethoxypyrrolidine To 2-carbomethoxypyrrolidine (d,l-proline methylester, 1.64 g, 12.7 mmol) with pyridine (10.1 g, 12.7 mmol) in CH$_2$Cl$_2$ (100 mL) at 0° C. was added 4-nitrobenzoyl chloride (2.36 g, 12.7 mmol) in CH$_2$Cl$_2$ (25 mL) dropwise. The reaction was allowed to warm to ambient temperature and stirred 18 h. The reaction was evaporated and applied to a silica gel flash column and eluted with a gradient of 2:1 Hexane:EtOAc to 1:2 Hexane:EtOAc. There was isolated 1.3 g of the title compound; LRMS (M+H)+ m/z=279.

N-(4-Aminobenzoyl)-2-carbomethoxypyrrolidine

N-(4-nitrobenzoyl)-2-carbomethoxypyrrolidine (0.54 g, 1.94 mmol) in MeOH (50 mL) with 10% Pd-C (0.10 g) was shaken under an atmosphere of $H_2$ gas (50 psi) for 4 h. The reaction was filtered through a plug of Celite® and evaporated to give 0.41 g of the aniline; LRMS (M+H)+ m/z=249.

3-Methyl-1-(4-methoxyphenyl)-1H-pyrazole-5-N-(4-(N-carboxyl-2-carbomethoxypyrrolidino)phenyl)carboxyamide This compound was prepared by the methodology described for EXAMPLE 19 with the exception that in the coupling step N-(4-aminobenzoyl)-2-carbomethoxypyrrolidine was used in the place of 2-amino-5-(N-pyrrolidinocarbonyl)pyridine. The solvent was evaporated, the residue dissolved in ethyl acetate and washed with water. After drying and removal of the solvent, the crude product was purified by HPLC utilizing gradient elution with a mixture of water:acetonitrile with 0.05% trifluoroacetic acid on a reverse phase C18 (60 Å) column gave a pure sample of the title compound; mp 46° C., HRMS (M+H)+ calc. m/z: 462.190320, obs: 462.188795.

Example 68

3-Methyl-1-(4-methoxyphenyl)-1H-pyrazole-5-N-(4-(N-carboxyl-3-aminolyrrolidino)phenyl)carboxyamide 3-Methyl-1-(4-methoxyphenyl)-1H-pyrazole-5-N-(4-(N-carboxyl-3-azidopyrrolidino)phenyl)carboxyamide To 3-methyl-1-(4-methoxyphenyl)-1H-pyrazole-5-N-(4-(N-carboxyl-3-hydroxypyrrolidino)phenyl)carboxyamide (prepared in EXAMPLE 21, 0.14 g, 0.33 mmol) with $Et_3N$ (0.05 g, 0.5 mmol) in $CH_2Cl_2$ was added methanesulfonyl chloride (0.057 g, 0.05 mmol). After 18 h the reaction was complete; it was evaporated, dissolved in EtOAc, washed with 1N HCl, dried and evaporated. There was obtained 0.21 g of the methanesulfonate; LRMS (M-$SO_2CH_3$)+ m/z=403.

The methanesulfonate prepared above (0.17 g, 0.35 mmol) and sodium azide (0.11 g, 1.76 mmol) in DMF (10 mL) was heated at 60° C. for 4 h. Brine was added to the cooled reaction mixture and the suspension was extracted with EtOAc (3×). The combined extracts were washed with water (5×), dried ($MgSO_4$), and evaporated to give 0.10 g of the azide; LRMS (M-$N_2$)+ m/z=418.

3-Methyl-1-(4-methoxyphenyl)-1H-pyrazole-5-N-(4-(N-carboxyl-3-aminopyrrolidino)phenyl)carboxyamide The azide from above (0.10 g, 0.22 mmol) in MeOH (20 mL) with 10% Pd—C was stirred under an atmosphere of $H_2$ gas (1 atm). After 2 h the reaction was purged with $N_2$, filtered through a pad of Celite®, and evaporated. The crude product was purified by HPLC utilizing gradient elution with a mixture of water:acetonitrile with 0.05% trifluoroacetic acid on a reverse phase C18 (60 Å) column gave a pure sample of the title compound; mp 133.4° C., HRMS (M+H)+ calc. m/z: 420.203565, obs: 420.203373.

Example 69

3-Methyl-1-(4-methoxyphenyl)-1H-pyrazole-5-N-(4-(N-carboxyl-3-methoxpyrrolidino)phenyl)carboxyamide 4-(N-carboxyl-3-methoxypyrrolidino)aniline To 3-hydroxypyrrolidine hydrogen chloride (1.63 g, 14.9 mmol) and triethylamine (1.51 g, 14.9 mmol) in dichloromethane (50 mL) at 0° C., was added a solution of p-nitrobenzoyl chloride (2.5 g, 12.4 mmol) in dichloromethane (50 mL). The reaction was evaporated to dryness and the residue dissolved in ethyl acetate. This solution was washed with 1N hydrochloric acid solution and brine, then dried and evaporated to give 2.22 g of product; LRMS (M+H)+ m/z: 237.

To a suspension of NaH (0.16 g of a 60% suspension in mineral oil, 6.89 mmol) in THF (30 mL) was added dropwise a solution of the hydroxy compound prepared above (0.65 g, 2.75 mmol) in THF (10 mL). The reaction was cooled to 0° C. and methyliodide (0.43 g, 3.03 mmol) was added. The reaction was stirred at ambient temperature for 24 h. The reaction was diluted with Et2O and washed with 0.5N $NH_4Cl$, and brine, then dried and evaporated to give the methyl ether (0.47 g); LRMS (M+H)+ m/z=251.

The methyl ether (0.42 g, 1.68 mmol) in MeOH (50 mL) with 10% Pd—C (0.05 g) was stirred under an atmosphere of $H_2$ gas (1 atm) for 3 h. The reaction was purged with $N_2$, filtered through a Celite® pad and evaporated to give 0.28 g of the aniline; LRMS (M+H)+m/z=221.

3-Methyl-1-(4-methoxyphenyl)-1H-pyrazole-5-N-(4-(N-carboxyl-3-methoxypyrrolidino)phenyl)carboxyamide This compound was prepared by the methodology described for EXAMPLE 19 with the exception that in the coupling step 4-(N-carboxyl-3-methoxypyrrolidino)aniline was used in the place of 2-amino-5-(N-pyrrolidinocarbonyl) pyridine. The solvent was evaporated, the residue dissolved in ethyl acetate and washed with water. After drying and removal of the solvent, the crude product was purified by HPLC utilizing gradient elution with a mixture of water:acetonitrile with 0.05% trifluoroacetic acid on a reverse phase C18 (60 Å) column gave a pure sample of the title compound; mp 40.2° C., HRMS (M+H)+ calc. m/z: 434.195406, obs: 434.194469.

Example 70

3-Trifluoromethyl-1-(4-methoxyphenyl)-1H-pyrazole-5-(N-(5-(2-aminosulfonyl)phenyl)pyridin-2-yl)carboxyamide 3-Trifluoromethyl-1-(4-methoxyphenyl)-1H-pyrazole-5-(N-(5-(2-aminosulfonyl)phenyl)pyridin-2-yl)carboxyamide This material was prepared according to the methods described for EXAMPLE 15 with the exception that during the coupling step 2-amino-5-(2-N-t-butylaminosulfonyl) phenyl)pyridine was substituted for 4-(2-N-t-butylaminosulfonyl)phenyl)aniline. The t-butylsulfonamide group was removed by heating the coupling product at reflux in TFA for 1 h, then removing the TFA by distillation in vacuo. Purification of the final product was by HPLC utilizing gradient elution with a mixture of water:acetonitrile with 0.05% trifluoroacetic acid on a reverse phase C18 (60

Å) column gave a pure sample of the title compound; HRMS (M+H)⁺ calc. m/z: 518.110986, obs: 518.112930.

Example 71

3-Trifluoromethyl-1-(4-methoxyphenyl)-1H-pyrazole-5-(N-(4-amidino)phenyl) carboxyamide·TFA 3-Trifluoromethyl-1-(4-methoxyphenyl)-1H-pyrazole-5-(N-(4-cyano)phenyl)carboxyamide To 3-trifluoromethyl-5-methyl-1-(4-methoxyphenyl)-1H-pyrazole (EXAMPLE 15, 0.6 g, 2.1 mmol) in $CH_2Cl_2$ (20 mL) at 0° C. was added oxalyl chloride in $CH_2Cl_2$ (2M solution, 1.6 mL, 3.15 mmol) followed by a few drops of DMF. The reaction was allowed to warm to ambient temperature and stirred 18 h. The reaction was evaporated and pumped on for several hours to remove the last traces of HCl. The acid chloride was combined with p-aminobenzonitrile (0.3 g, 2.52 mmol) and DMAP (0.77 g, 6.3 mmol) in $CH_2Cl_2$ (40 mL) and stirred at ambient temperature for 18 h. The reaction was evaporated and then partioned between 1N HCl and EtOAc. The EtOAc layer was dried and evaporated to give 0.79 g of crude product. Further purification was effected by MPLC with a column of 200 g of flash silica, eluting with 3:1 Hexane:EtOAc and collecting 25 mL fractions. The 0.45 g of the desired nitrile was obtained from fractions 30–65; mp 188.2, HRMS (M+H)⁺ calc. m/z: 386.099081, obs: 386.098101.

3-Trifluoromethyl-1-(4-methoxyphenyl)-1H-pyrazole-5-(N-(4-(0-methyl)formimino)phenyl) carboxyamide ·HCl A stream of anhydrous HCl gas was passed through a solution of 3-trifluoromethyl-1-(4-methoxyphenyl)-1H-pyrazole-5-(N-(4-cyano)phenyl)carboxyamide (225 mg, 0.58 mmol) in dry MeOAc (25 mL) and dry MeOH (5 mL) at 0° C. until saturation. After standing for 18 h at 10° C., the tightly stoppered flask was unsealed and the solvent was removed by distillation in vacuo. The residue was repeatedly evaporated with dry $Et_2O$, then pumped on for several hours to remove the last traces of HCl.

3-Trifluoromethyl-1-(4-methoxyphenyl)-1H-pyrazole-5-(N-(4-amidino)phenyl)carboxyamide · TFA The imidate (0.58 mmol) prepared above was dissolved in dry MeOH (10 mL) and $(NH_4)_2CO_3$ (0.32 g, 3.33 mmol) leas added. This mixture was stirred at ambient temperature for 18 h, then evaporated to dryness. Purification of the final product was by HPLC utilizing gradient elution with a mixture of water:acetonitrile with 0.05% trifluoroaceti( acid on a reverse phase C18 (60 Å) column gave a pure sample of the title compound; mp 232.5, HRMS (M+H)⁺ calc. m/z: 404.133435, obs: 404.132331.

Example 72

3-Trifluoromethyl-1-(4-methoxyphenyl)-1H-pyrazole-5-(N-(4-(N-pyrrolidino)formylimino) phenyl)carboxyamide · TFA 3-Trifluoromethyl-1-(4-methoxyphenyl)-1H-pyrazole-5-(N-(4-(N-pyrrolidino)formylimino) phenyl)carboxyamide · TFA 3-trifluoromethyl-1-(4-methoxyphenyl)-1H-pyrazole-5-(N-(4-(0-methyl)formimino)phenyl)carboxyamide•HCl (EXAMPLE 71, 0.58 mmol) prepared above was dissolved in dry MeOH (10 mL) and pyrrolidine (0.12 g, 1.74 mmol) was added. This mixture was stirred at ambient temperature for 18 h, then evaporated to dryness. Purification of the final product was by HPLC utilizing gradient elution with a mixture of water:acetonitrile with 0.05% trifluoroacetic acid on a reverse phase C18 (60 Å) column gave a pure sample of the title compound; mp 89.5, HRMS (M+H)⁺ calc. m/z: 458.180385, obs: 458.183032.

Example 73

3-Trifluoromethyl-5-(N-(2'-aminosulfonyl-[1,1']-biphen-4-yl))-1-(4-methoxyphenyl)pyrrolo[3,4-d] pyrazole-4,6-(1H, 5H)-dione 1,1,1-Trifluoroacetaldehyde-N-(4-methoxyphenyl) hydrazone A mixture of 1,1,1-trifluoroacetaldehyde ethyl hemiacetal (4.2 g, 34.17 mmol) and 4-methoxyphenylhydrazine · HCl (4.97 g, 28.48 mmol) in EtOH (100 mL) was brought to reflux, then cooled to ambient temperature when all of the components were dissolved. The reaction was evaporated to dryness to give 5.34 g of a black oil that was used in the next step without further purification; LRMS (M+H)⁺ m/z=219.2.

1,1,1-Trifluoroacetoyl bromide-N-(4-methoxyphenyl)hydrazone

To the black oil (0.87 g, 4 mmol) produced above in DMF (25 mL) at 0° C. was added N-bromosuccinimide (0.72 g, 4 mmol) portionwise. The reaction was complete in 2 h (TLC, 3:1 Hexane:EtOAc). The reaction was diluted with brine and extracted with EtOAc. The extracts were washed with brine (5×), dried ($MgSO_4$) and evaporated to give 0.69 g of product as a black oil. This material was used without further purification.

4-(2-N-t-Butylaminosulfonyl)phenyl) bromomaleimide

Bromomaleic anhydride (0.29 g, 1.65 mmol) was added to 4-(2-N-t-butylaminosulfonyl)phenyl)aniline (0.5 g, 1.65 mmol) in THF (10 mL). After 1 h the solution was cooled to 0° C. and N-methylmorpholine (0.2 g, 1.98 mmol) followed by isobutylchloroformate (0.27 g, 1.98 mmol) was added. The reaction was allowed to warm to ambient temperature and stirred 18 h. The reaction was evaporated, dissolved in EtOAc, washed with 1N HCl, dried and evaporated. The product was purified further by MPLC using a column of 200 g of flash silica and eluting with 3:1 hexane:EtOAc and 25 mL fractions collected. The desired product (0.39 g) was isolated from fractions 35–65; HRMS (M+H)⁺ calc. m/z: 462.024890, obs: 462.025783.

3-Trifluoromethyl-5-(N-(2'-N-t-butylaminosulfonyl-[1,1']-biphen-4-yl))-1-(4-methoxyphenyl)pyrrolo[3, 4-d]pyrazole-4,6-(1H, 5H)-dione A mixture of 1,1,1-trifluoroacetoyl bromide-N-(4-methoxyphenyl)hydrazone (0.68 g, 2.29 mmol) and 4-(2-N-t-butylaminosulfonyl)phenyl)bromomaleimide (0.2 g, 0.4 mmol) with $Et_3N$ (0.35 g, 3.45 mmol) in toluene were heated at reflux for 3 h. The reaction was diluted with EtOAc, washed with 1N HCl, dried ($MgSO_4$) and evaporated to give 0.35 g of crude product. The product was isolated using MPLC by eluting the crude material from a column of flash silica gel (200 g) with 3:1 hexane:EtOAc and collecting 25 mL fractions. Fractions 33–58 yielded 0.15 g of pure material; mp 196.1° C., HRMS (M+H)+ calc. m/z: 653. 165176, obs: 653.166000.

3-Trifluoromethyl-5-(N-(2'-aminosulfonyl-[1,1']-biphen-4-yl))-1-(4-methoxyphenyl)pyrrolo[3,4-d]pyrazole-4,6-(1H, 5H)-dione The product from above (0.15 g, 0.25 mmol) was heated at reflux in TFA for 1 h. The reaction was cooled and evaporated to give 0.14 g of crude material. The product was isolated using MPLC by eluting the crude material from a column of flash silica gel (200 g) with 2:1 hexane:EtOAc and collecting 25 mL fractions. Fractions 55–90 were combined and triturated with a small quantity of Et$_2$O. This process gave 0.06 g of pure material; mp 210.7° C., HRMS (M+H)+ calc. m/z: 543.095002, obs: 543.097942.

Example 74

3-Trifluoromethyl-1-(4-methoxyphenyl)-1H-pyrazole-5-carbomethoxy-(N-(2'-aminosulfonyl-[1,1']-biphen-4-yl))carboxyamide

And Example 75

3-Trifluoromethyl-1-(4-methoxyphenyl)-1H-pyrazole-5-hydoxymethyl-(N-(2'-aminosulfonyl-[1,1']-biphen-4-yl))carboxyamide Preparation of a mixture of 3-trifluoromethyl-1-(4-methoxyphenyl)-1H-pyrazole-5-carbomethoxy-(N-(2'-N-t-butylaminosulfonyl-[1,1']-biphen-4-yl))carboxyamide and 3-trifluoromethyl-1-(4-methoxyphenyl)-1H-pyrazole-5-hydoxymethyl-(N-(2'-N-t-butylaminosulfonyl-[1,1']-biphen-4-yl))carboxyamide 3-Trifluoromethyl-5-(N-(2'-N-t-butylaminosulfonyl-[1,1']-biphen-4-yl))-1-(4-methoxyphenyl)pyrrolo[3, 4-d] pyrazole-4,6-(1H, 5H)-dione (0.37 g, 0.62 mmol) in AcCN (30 mL) was added dropwise to a solution of NaBH4 (0.096 g, 2.48 mmol) in MeOH (20 mL) at 0° C. The reaction was complete in less than 1 h (TLC, 3:1 hexane:EtOAc). It was evaporated, dissolved in EtOAc and washed with 1N HCl. The organic layer was dried and evaporated to give a mixture of the title compounds (0.37 g). This mixture was separated by MPLC using a 400 g column of flash silica gel and eluting with 2:1 hexane:EtOAc; 25 mL fractions of eluent were collected.

From fractions 50–66, 3-trifluoromethyl-1-(4-methoxyphenyl)-1H-pyrazole-5-carbomethoxy-(N-(2'-N-t-butylaminosulfonyl-[1,1']-biphen-4-yl))carboxyamide (0.15 g) was isolated; HRMS (M+Na)+ calc. m/z: 653.165761, obs: 653.164400.

From fractions 69–100, 3-trifluoromethyl-1-(4-methoxyphenyl)-1H-pyrazole-5-hydoxymethyl-(N-(2'-N-t-butylaminosulfonyl-[1,1']-biphen-4-yl))carboxyamide (0.12 g) was isolated; HRMS (M+Na)+ calc. m/z: 625.170847, obs: 625.169900.

3-Trifluoromethyl-1-(4-methoxyphenyl)-1H-pyrazole-5-carbomethoxy-(N-(2'-aminosulfonyl-[1,1']-biphen-4-yl))carboxyamide The product from fractions 50–66 (0.15 g) was heated at reflux in TFA for 1 h. The reaction was cooled and evaporated to give 0.14 g of crude material. Purification of the final product was by HPLC utilizing gradient elution with a mixture of water:acetonitrile with 0.05% trifluoroacetic acid on a reverse phase C18 (60 Å) column gave a pure sample of Example 74; mp 233.3° C., HRMS (M+H)+ calc. m/z: 575.121216, obs: 575.120500.

3-Trifluoromethyl-1-(4-methoxyphenyl)-1H-pyrazole-5-hydroxymethyl-(N-(2 aminosulfonyl-[1, 1']-biphen-4-yl))carboxyamide The product from fractions 69–100 (0.12 g) was heated at reflux in TFA for 1 h. The reaction was cooled and evaporated to give 0.11 g of crude material. Purification of the final product was by HPLC utilizing gradient elution with a mixture of water:acetonitrile with 0.05% trifluoroacetic acid on a reverse phase C18 (60 Å) column gave a pure sample of Example 75; mp 115.4° C., HRMS (M+H)+ calc. m/z: 547.126302, obs: 547.124400.

Example 76

3-Trifluoromethyl-1-(4-methoxyphenyl)-1H-pyrazole-5-(N-2fluoro(4-(N-pyrrolidino)formylimino)phenyl)carboxyamide · TFA

3-Fluoro-4-nitrobenzamide

3-Fluoro-4-nitrobenzoic acid (5.0 g, 27 mmol) and SOCl$_2$ (6.42 g, 54 mmol) with a few drops of DMF in benzene (100 mL) was heated at reflux for 3 h. The reaction was evaporated to dryness, then evaporated several times with Et$_2$O to purify, yield 5.56 g.

The acid chloride prepared above was dissolved in EtOAc (50 mL) and added dropwise to a 0° C. biphasic mixture of EtOAc (150 mL) and conc. NH$_4$OH (100 mL). After 30 min, the layers were separated, the water layer saturated with NaCl and extracted with EtOAc. The combined organic extracts were dried and evaporated to give a 4.85 g of the benzamide; LRMS/ES−(M−H)−m/z=182.9.

3-Fluoro-4-aminobenzonitrile

To a 0° C. EtOAc (150 mL) solution of 3-fluoro-4-nitrobenzamide (4.85 g, 26.4 mmol) and Et$_3$N (5.34 g, 52.8 mmol) was added dropwise a CH$_2$Cl$_2$ (50 mL) solution of 1,1,1-trichloroacetyl chloride (5.28 g, 29.04 mmol). The reaction was complete in 2 h (TLC, 1:1 hexane:EtOAc), then it was washed with 1N HCl, dried (MgSO$_4$) and evaporated to give 4.1 g of the corresponding nitrile.

The 4-nitrobenzonitrile derivative prepared above (4.1 g, 24.7 mmol) in EtOH/water (80 mL/40 mL) was heated at reflux with iron powder (8.3 g, 148 mmol) and NH$_4$Cl (0.83 g, 15.3 mmol) for 2 h. The reaction was filtered and evaporated to dryness. The residue was dissolved in EtOAc, washed with brine and dried (MgSO$_4$) to give 2.68 g of product; LRMS (M+H)+ m/z=137.0. The product was purified further by MPLC on a 360 g column of flash silica gel and eluting with 3:1 hexane:EtOAc 25 mL fractions were collected. From fractions 128–195, 1.32 g of pure product was obtained.

3-Trifluoromethyl-1-(4-methoxyphenyl)-1H-pyrazole-5-(N-(2-fluoro-4-cyano)phenyl)carboxyamide To 3-trifluoromethyl-5-methyl-1-(4-methoxyphenyl)-1H-pyrazole (EXAMPLE 15, 1.13 g, 3.95 mmol) in CH$_2$Cl$_2$ (100 mL) at 0° C. was added oxalyl chloride in CH$_2$Cl$_2$ (2M solution, 2.96 mL, 5.93 mmol) followed by a few drops of DMF. The reaction was allowed to warm to ambient temperature and stirred 18 h. The reaction was evaporated and pumped on for several hours to remove the last traces of HCl.

The acid chloride was combined with 3-fluoro-4-aminobenzonitrile (0.59 g, 4.35 mmol) and DMAP (1.45 g, 11.85 mmol) in CH$_2$Cl$_2$ (100 mL) and stirred at ambient temperature for 18 h. The reaction was evaporated then partitioned between 1N HCl and EtOAc. The EtOAc layer was dried and evaporated to give 0.79 g of crude product. Further purification was effected by MPLC with a column of 360 g of flash silica, eluting with 4:1 Hexane:EtOAc and collecting 25 mL fractions. The 0.83 g of the desired nitrile was obtained from fractions 91–133; mp 160.6, LRMS (M+H)$^+$ m/z=405.0.

3-Trifluoromethyl-1-(4-methoxyphenyl)-1H-pyrazole-5-(N-(2-fluoro-4-(O-methyl)formimino)phenyl)carboxyamide · HCl A stream of anhydrous HCl gas was passed through a solution of 3-trifluoromethyl-1-(4-methoxyphenyl)-1H-pyrazole-5-(N-(4-cyano)phenyl)carboxyamide (0.83 g, 2.05 mmol) in dry MeOAc (50 mL) and dry MeOH (10 mL) at 0° C. until saturation. After standing for 18 h at 10° C., the tightly stoppered flask was unsealed and the solvent was removed by distillation in vacuo. The residue was then repeatedly evaporated with dry Et$_2$O, then pumped on for several hours to remove the last traces of HCl.

3-Trifluoromethyl-1-(4-methoxyphenyl)-1H-pyrazole-5-(N-(2-fluoro-4-(N-pyrrolidino)formylimino)phenyl)carboxyamide · TFA 3-Trifluoromethyl-1-(4-methoxyphenyl)-1H-pyrazole-5-(N-(2-fluoro-4-(O-methyl)formimino)phenyl)carboxyamide ·HCl (2.05 mmol) prepared above was dissolved in dry MeOH (15 mL) and pyrrolidine (0.44 g, 6.15 mmol) was added. This mixture was stirred at ambient temperature for 18 h, then evaporated to dryness. Purification of the final product was by HPLC utilizing gradient elution with a mixture of water:acetonitrile with 0.05% trifluoroacetic acid on a reverse phase C18 (60 Å) column gave a pure sample of the title compound; mp 61.8° C., HRMS (M+H)$^+$ calc. m/z: 476.170963, obs: 476.170693.

Example 77

3-Trifluoromethyl-1-(4-methoxyphenyl)-1H-pyrazole-5-(N-(4-(N-pyrrolidino)formyl-N-((2-propyl)methylcarbamoyl)imino)phenyl)carboxyamide 3-Trifluoromethyl-1-(4-methoxyphenyl)-1H-pyrazole-5-(N-(4-(N-pyrrolidino)formyl-N-((2-propyl)methylcarbamoyl)imino)phenyl)carboxyamide To 3-trifluoromethyl-1-(4-methoxyphenyl)-1H-pyrazole-5-(N-(4-(N-pyrrolidino)formylimino)phenyl)carboxyamide · TFA (EXAMPLE 72, (0.311 g) was added 1N NaOH (25 mL), a suspension formed which was extracted with CH$_2$Cl$_2$ (2×35 mL). The organic extracts were dried and evaporated to give 0.18 g (0.39 mmol) of the free base. The free base was re-dissolved in CH$_2$Cl$_2$ (20 mL) and cooled to 0° C., then Et$_3$N (0.08 g, 0.78 mmol) was added. To the cooled solution 4.4 mL (0.44 mmol) of a 0.1N solution of isobutylchloroformate (from 0.01 mol [1.3 mL] of neat isobutylchloroformate in 100 mL of CH$_2$Cl$_2$) was added dropwise and stirred at 0° C. for 2 h. The reaction was evaporated and partitioned between EtOAc and 1N HCl. The EtOAc layer was dried and evaporated to give 0.10 g of crude material. This was purified further by MPLC using a 200 g column of flash silica gel and eluting with 2:1 hexane:EtOAc. 25 mL fractions were collected and 0.056 g of pure product was isolated from fractions 40–80; mp 90.1° C., HRMS (M+H)$^+$ calc. m/z: 558.2345, obs: 558.2334.

Example 78

3-Trifluoromethyl-1-(4-methoxyphenyl)-1H-prazole-5-(N-(4-(N-pyrrolidino)formyl-N-(methanesulfamoyl)imino)phenyl)carboxyamide 3-Trifluoromethyl-1-(4-methoxyphenyl)-1H-pyrazole-5-(N-(4-(N-pyrrolidino)formyl-N-(methanesulfamoyl)imino)phenyl)carboxyamide To 3-trifluoromethyl-1-(4-methoxyphenyl)-1H-pyrazole-5-(N-(4-(N-pyrrolidino)formylimino)phenyl)carboxyamide · TFA (EXAMPLE 72, (0.332 g) was added 1N NaOH (25 mL), a suspension formed which was extracted with CH$_2$Cl$_2$ (2×35 mL). The organic extracts were dried and evaporated to give 0.18 g (0.39 mmol) of the free base. The free base was re-dissolved in CH$_2$Cl$_2$ (25 mL) and cooled to 0° C., then DMAP (0.095 g, 0.78 mmol) was added. To the cooled solution 4.2 mL (0.42 mmol) of a 0.1N solution of methanesulfonyl chloride (from 0.01 mol [0.78 mL] of neat methanesulfonyl chloride in 100 mL of CH$_2$Cl$_2$) was added dropwise and stirred at 0° C. for 48 h. The reaction was evaporated and partitioned between EtOAc and 1N HCl. The EtOAc layer was dried and evaporated to give 0.11 g of crude material. This was purified further by MPLC using a 200 g column of flash silica gel and eluting with 2:1 hexane:EtOAc. 25 mL fractions were collected and 0.050 g of pure product was isolated from fractions 81–130; mp 117.2° C., HRMS (M+Na)$^+$obs. m/z: 558.1381.

Example 79

3-Trifluoromethyl-1-(4-methoxypyhenyl)-1H-pyrazole-5-(N-((4-amidino)phenyl)methyl)carboxyamide · TFA α-Amino-4-cyanotoluene A mixture of 4-cyanobenzyl bromide (3 g, 15.3 mmol) and NaN$_3$ (1.99 g, 30.6 mmol) in DMF (20 mL) was stirred at ambient temperture for 18 h. The reaction was diluted with brine and extracted with EtOAc. The organic extracts were washed with brine (5×), dried (MgSO$_4$) and evaporated to give 1.87 g of the benzylic azide product.

The benzylic azide (1.87 g, 11.84 mmol) and SnCl$_2$·H$_2$O (7.25 g, 32.2 mmol) in MeOH (50 mL) was stirred at ambient temperature for 18 h. The solution was evaporated to dryness then the residue was dissolved in 1N NaOH and extracted with EtOAc. The EtOAc layer was washed with brine, dried and evaporated to give 0.83 g of α-amino-4-cyanotoluene.

3-Trifluoromethyl-1(4-methoxyphenyl)-1H-pyrazole-5-(N-((4-cyano)phenyl)methyl)carboxyamide To 3-trifluoromethyl-5-methyl-1-(4-methoxyphenyl)-1H-pyrazole (EXAMPLE 15, 0.4 g, 1.4 mmol) and N-methylmorpholine (0.156 g, 1.54 mmol) in CH$_2$Cl$_2$ (30 mL) at 0° C. was added isobutylchloroformate (0.21 g, 1.54 mmol). The reaction was stirred for 30 min at 0° C. and 0.203 g of α-amino-4-cyanotoluene (1.54 mmol) in CH$_2$Cl$_2$ (8 mL) was added. After 18 h the reaction was washed with 1N HCl and 1N NaOH, then dried and evaporated to give 0.54 g of crude material. Further purification was effected by MPLC with a column of 200 g of flash silica, eluting with 2:1 Hexane:EtOAc and collecting 25 mL fractions. The 0.32 g of the desired nitrile was obtained from fractions 61–120; mp 197.5, LRMS (M+H)$^+$ m/z=401.0.

3-Trifluoromethyl-1-(4-methoxyphenyl)-1H-pyrazole-5-(N-((2-fluoro-4-(O-methyl)formimino)phenyl)methyl)carboxyamide ·HCl A stream of anhydrous HCl gas was passed through a solution of 3-trifluoromethyl-1-(4-methoxyphenyl)-1H-pyrazole-5-(N-((4-cyano)phenyl)methyl)carboxyamide (0.32 g, 0.8 mmol) in dry MeOAc (25 mL) and dry MeOH (5 mL) at 0° C. until saturation. After standing for 18 h at 10° C., the tightly stoppered flask was unsealed and the solvent was removed by distillation in vacuo. The residue was then repeatedly evaporated with dry Et$_2$O, then pumped on for several hours to remove the last traces of HCl.

3-Trifluoromethyl-1-(4-methoxyphenyl)-1H-pyrazole-5-(N-((4-amidino)phenyl)methyl)carboxyamide · TFA The imidate (0.4 mmol) prepared above was dissolved in dry MeOH (15 mL) and (NH$_4$)$_2$CO$_3$ (0.192 g, 2.0 mmol) was added. This mixture was stirred at ambient temperature for 18 h, then evaporated to dryness. Purification of the final product was by HPLC utilizing gradient elution with a mixture of water:acetonitrile with 0.05% trifluoroacetic acid on a reverse phase C18 (60 Å) column gave a pure sample of the title compound; mp 131.4, HRMS (M+H)$^+$obs. m/z: 418.1478.

Example 80

3-Trifluoromethyl-1-(4-methoxyphenyl)-1H-pyrazole-5-(N-((4-(N-pyrrolidino)formylimino)phenyl)methyl)carboxyamide · TFA 3-Trifluoromethyl-1-(4-methoxyphenyl)-1H-pyrazole-5-(N-((4-(N-pyrrolidino)formylimino)phenyl)methyl)carboxyamide · TFA 3-trifluoromethyl-1-(4-methoxyphenyl)-1H-pyrazole-5-(N-((4-(O-methyl)formimino)phenyl)methyl)carboxyamide•HCl (EXAMPLE 79, 0.4 mmol) prepared above was dissolved in dry MeOH (15 mL) and pyrrolidine (0.09 g, 1.2 mmol) was added. This mixture was stirred at ambient temperature for 18 h, then evaporated to dryness. Purification of the final product was by HPLC utilizing gradient elution with a mixture of water:acetonitrile with 0.05% trifluoroacetic acid on a reverse phase C18 (60 Å) column gave a pure sample of the title compound; LRMS, (M+H)$^+$ m/z: 472.3.

Example 81

3-Trifluoromethyl-1-(4-methoxphenyl)-1H-pyrazole-5-(N-((1-benzyl)piperidin-4-yl)carboxyamide · TFA 3-Trifluoromethyl-1-(4-methoxyphenyl)-1H-pyrazole-5-(N-((1-benzyl)piperidin-4-yl)carboxyamide · TFA To 3-trifluoromethyl-5-methyl-1-(4-methoxyphenyl)-1H-pyrazole (EXAMPLE 15, 2.86 g, 10 mmol) and N-methyl morpholine (1.01 g, 10 mmol) in THF (50 mL) at 0° C. was added isobutylchloroformate (1.36 g, 10 mmol). The reaction was stirred for 30 min at 0° C. and 1.90 g of 1-benzyl-4-aminopiperidine (10 mmol) was added. After 18 h the reaction was evaporated to dryness and dissolved in 1N NaOH, then extracted with EtOAc. The EtOAc layer was washed with brine, then dried and evaporated to give 4.36 g of crude material. Recrystallization with n-butylchloride gave 1.16 g of product; mp 120.8° C.

A 0.10 g sample was dissolved in Et$_2$O and TFA added to form the TFA salt. Trituration with Et$_2$O and n-butylchloride gave 0.015 g of pure product; mp 175.6° C., HRMS (M+H)$^+$ calc. m/z: 459.200, obs: 459.1.99.

Example 82

3-Trifluoromethyl-1-(4-methoxyphenyl)-1H-pyrazole-5-(N-((1-pyridin-2-yl)methyl)piperidin-4-yl)carboxyamide · TFA 3-Trifluoromethyl-1-(4-methoxyphenyl)-1H-pyrazole-5-(N-(piperidin-4-yl)carboxyamide · HCl To a solution of 3-trifluoromethyl-1-(4-methoxyphenyl)-1H-pyrazole-5-(N-((benzyl)piperidin-4-yl)carboxyamide (EXAMPLE 81, 1.06 g, 2.31 mmol) in CH$_2$Cl$_2$ (40 mL) was added 1-chloroethylchloroformate (0.5 g, 3.5 mmol). The reaction was stirred for 2 h, then evaporated to dryness. The residue was dissolved in MeOH (50 mL) and heated at reflux for 1 h. The reaction was evaporated to give 0.8 g of product; LRMS (M+H)$^+$ m/z: 369.2.

3-Trifluoromethyl-1-(4-methoxyphenyl)-1H-pyrazole-5-(N-((1-(pyridin-2-yl)methyl)piperidin-4-yl)carboxyamide · TFA To 3-trifluoromethyl-1-(4-methoxyphenyl)-1H-pyrazole-5-(N-(piperidin-4-yl)carboxyamide · HCl (0.21 g) and K$_2$CO$_3$ (0.3 g) in AcOH (20 mL) was added 2-picolyl chloride (0.16 g). The reaction was stirred at ambient temperature for 18 h. The reaction was diluted with water and extracted with EtOAc (3×). The extracts were dried (MgSO$_4$) and evaporated to give 0.29 g of crude product. Purification of the final product was by HPLC utilizing gradient elution with a mixture of water:acetonitrile with 0.05% trifluoroacetic acid on a reverse phase C18 (60 Å) column gave a pure sample of the title compound; LRMS (M+H)$^+$ m/z: 460.3.

Example 83

3-Trifluoromethyl-1-(4-methoxyphenyl)-1H-pyrazole-5-(N-(4-(2-methylimidazo-1-yl))phenyl)carboxyamide · TFA 3-Trifluoromethyl-1-(4-methoxyphenyl)-1H-pyrazole-5-(N-(4-(2-methylimidazo-1-yl))phenyl)carboxyamide · TFA A mixture of 3-trifluoromethyl-5-methyl-1-(4-methoxyphenyl)-1H-pyrazole (EXAMPLE 15, 0.20 g, 0.7 mmol), BOP (0.44 g, 1 mmol), Et$_3$N (0.1 g, 1 mmol) and 1-(4-aminophenyl)-2-methylimidazole (0.17 g, 1 mmol) in DMF (20 mL) was heated at 50–55° C. for 1 h, then cooled to ambient temperature and stirred 18 h. The reaction was diluted with water and extracted with EtOAc. The EtOAc extracts were washed with water (5×), dried (MgSO$_4$) and evaporated. Purification of the final product was by HPLC utilizing gradient elution with a mixture of water:acetonitrile with 0.05% trifluoroacetic acid on a reverse phase C18 (60 Å) column gave a pure sample of the title compound; mp 103.7° C., HRMS (M+H)$^+$ m/z: 442.188.

Example 84

3-Methyl-(4-methoxy)phenyl-1H-pyrazole-5-(N-{4-(5-methyl-imidazol-1-yl}phenyl)carboxyamide And Example 85

3-Methyl-(4-methoxy)phenyl-1H-pyrazole-5-(N-{4-(4-methyl-imidazol-1-yl}phenyl)carboxyamide, N-(4-nitrophenyl)-5-methylimidazole A solution of p-nitrofluorobenzene (2 g, 14 mmol) in DMF (20 mL) was treated with potassium carbonate (8 g, 58 mmol) and 4-methylimidazole (1.2 g, 14 mmol). After refluxing for 18 h, the reaction mixture was cooled down and concentrated at reduced pressure. The residue was treated with water and the mixture was extracted with ethyl acetate and dried over magnesium sulphate. The organic layer was concentrated and the residue was purified by flash-chromatography (methanol/methylene chloride, 0.5:9.5) affording 1.8 g (62%) of p-nitro-4 (5)-methyl-imidazol-1-yl as 7:1 mixture of regioisomers.

N-(4-aminophenyl)-5-methylimidazole

Reduction in MeOH:TFA(9.5:0.5) with 0.1 eq. of Pd/C (10%) at 55 psi at ambient temperature over 20 h, followed by filtration over Celite afforded 1.4 g (93%)of p-amino-4 (5)-methyl-imidazol-1-yl.

Preparation of the mixture of 3-methyl-(4-methoxy)phenyl-1H-pyrazole-5-(N-{4-(5-methyl-imidazol-1-yl}phenyl)carboxyamide and 3-methyl-(4-methoxy)phenyl-1H-pyrazole-5-(N-{4-(4-methyl-imidazol-1-yl}phenyl)carboxyamide A solution of 3-methyl-1-(4-methoxyphenyl)-1H-pyrazolecarboxylic acid (200 mg, 0.8 mmol) in acetonitrile (5 mL) was treated with an excess of thionyl chloride. The resultant mixture was refluxed for 2 h, cooled down, concentrated, dissolved in methylene chloride (5 mL) and treated with DMAP (0.22 mg, 1.8 mmol) and N-(4-aminophenyl)-5-methyLimidazole (131 mg, 0.7 mmol). The reaction mixture was stirred at ambient temperature for 18 h. The residue was treated with water and the mixture was extracted with ethyl acetate and dried over magnesium sulphate. The organic layer was concentrated and the residue was purified by flash-chromatography (methanol/methylene chloride, 0.5:9.5) affording a mixture of 3-methyl-(4-methoxy)phenyl-1H-pyrazole-5-(N-{4-(5-methyl-imidazol-1-yl}phenyl)carboxyamide and 3-methyl-(4-methoxy)phenyl-1H-pyrazole-5-(N-{4-(4-methyl-imidazol-1-yl}phenyl)carboxyamide. The final products were purified by normal phase HPLC eluting with solvent A (hexane) and solvent B(ethanol) using 80% of A and 20% of B and eluting at 7.5 mL/min.

Example 84

3-methyl-(4-methoxy)phenyl-1H-pyrazole-5-(N-{4-(5-methyl-imidazol-1-yl}phenyl)carboxyamide $^1$H NMR (CDCl$_3$): 2.19 (s, 3H), 2.38 (s, 3H), 3.85 (s, 3H), 6.76 (s, 1H), 6.97 (m, 2H), 7.14 (m, 1H), 7.25 (m, 2H), 7.39 (m, 2H), 7.50 (s, 1H), 7.71 (m, 2H), 8.05 (s, 1H).

Example 85

3-methyl-(4-methoxy)phenyl-1H-pyrazole-5-(N-{4-(4-methyl-imidazol-1-yl}phenyl)carboxyamide $^1$H NMR (CDCl$_3$): 2.31 (s, 3H), 2.36 (s, 3H), 3.83 (s, 3H), 6.71 (s, 1H), 6.94 (m, 3H), 7.26 (m, 2H), 7.39 (m, 2H), 7.58 (m, 2H), 7.92 (s, 1H), 8.23 (s, 1H)

Example 86

3-Trifluoromethyl-(4-methoxy)phenyl-1H-pyrazole-5-(N-{4-(5-carbomethoxy-imidazol-1-yl}phenyl)carboxyamide Butyl glyoxyl(4-nitroanilino)imine A solution of p-nitroaniline (6.3 g, 53.4 mmol) in ethyl alcohol (50 mL) was treated with n-butyl gluoxylate (8 g, 53.8 mmol). After stirring at ambient temperature for 18 h, the reaction mixture was concentrated at reduced pressure. The residue was treated with water and the mixture was extracted with ethyl acetate and dried over magnesium sulphate. The organic layer was concentrated to afford the title compound in nearly quantitative yield, which was used without further purification.

4-Amino-(5-(carbomethoxy)imidazol-1-yl)benzene

To the solution of butyl glyoxyl (4-nitroanilino)imine (1.6 g, 6.9 mmol) in methyl alcohol (10 mL) was added potassium carbonate (1.9 g, 13.9 mmol) and tosylmethyl isocyanate (2.3 g, 11.8 mmol). The solution was stirred for 1 h at rt, then solvent was removed under reduced pressure. The residue was treated with the saturated sodium chloride solution and the mixture was extracted with methylene chloride. The organic extract was concentrated and triturated with methyl alcohol. The precipitate was collected and dried to afford an intermediate 4-nitro-(5-(carbomethoxy)imidazol-1-yl)benzene (1.5 g, 94%). MS (ES) m/z (rel. intensity), 249 (M+, 100).

Reduction to 4-amino-(5-(carbomethoxy)imidazol-1-yl)benzene was accomplished according to the procedure described in EXAMPLES 84 and 85; MS (ES) m/z (rel. intensity), 219 (M+, 100).

3-Trifluoromethyl-(4-methoxy)phenyl-1H-pyrazole-5-(N-{4-(5-carbomethoxy-imidazol-1-yl}phenyl)carboxyamide A solution of 4-amino-(5-(carbomethoxy)imidazol-1-yl)benzene (152 mg, 0.7 mmol) was coupled with 3-trifluoromethyl-(4-methoxy)phenyl-1H-pyrazole-5-carbonyl chloride (205 mg, 0.7 mmol) according to the procedure, described in EXAMPLES 84 and 85. Purification by flash chromatography (methanol/methylene chloride, 1:9) afforded 3-trifluoromethyl-(4-methoxy)phenyl-1H-pyrazole-5-(N-{4-(5-carbomethoxy-imidazol-1-yl}phenyl) carboxyamide, (70 mg, 20%); MS (ES) m/z (rel. intensity), 486 (M+, 100).

Example 87

3-Trifluoromethyl-(4-methoxy)phenyl-1H-pyrazole-5-(N-{4-(5-carboxy-imidazol-1-yl}phenyl)carboxyamide 3-Trifluoromethyl-(4-methoxy)phenyl-1H-pyrazole-5-(N-{4-(5-carboxy-imidazol-1-yl}phenyl)carboxyamide 3-Trifluoromethyl-(4-methoxy)phenyl-1H-pyrazole-5-(N-{4-(5-carbomethoxy-imidazol-1-yl}phenyl)carboxyamide (147 mg, 0.3 mmol) was suspended in 4:1 mixture of THF and water and treated with LIOH (37 mg, 0.9 mmol) in 0.5 mL of water. The reaction mixture was allowed to stir for 1 hr at ambient temperature, neutralized with 1N HCl, extracted with ethyl acetate, dried over MgSO$_4$ and concentrated to give the acid. The final product was purified by reverse phase HPLC on a Vydec® C-18 column eluting with solvent mixture A (water:TFA, 99.5:0.5) and solvent mixture B (acetonitrile:water:TFA, 90:9.5:0.5) using a gradient starting with A at 100% and changing to B at 100% over 60 min ; MS (ES) m/z (rel. intensity), 471.9 (M+, 100).

Example 88–90

The crude acid, 3-trifluoromethyl-(4-methoxy)phenyl-1H-pyrazole-5-(N-{4-(5-carboxy-imidazol-1-yl}phenyl) carboxyamide, was dissolved in acetonitrile, treated with excess thionyl chloride and refluxed over a period of 2 hr. The solvent was removed under reduced pressure. The coupling with the amines specified below was conducted according to the procedure described in EXAMPLES 84 and 85 to afford EXAMPLES 88–90. The final products were purified by reverse phase HPLC on a Vydec® C-18 column eluting with solvent mixture A (water:TFA, 99.5:0.5) and solvent mixture B (acetonitrile:water:TFA, 90:9.5:0.5) using a gradient starting with A at 100% and changing to B at 100% over 60 min to obtain EXAMPLES 88–90 as the trifluoroacetic acid salts.

Example 88

3-Trifluoromethyl-(4-methoxy)phenyl-1H-pyrazole-5-(N-{4-(5-N-methylcarbamide-imidazol-1-yl}phenyl)carboxyamide Prepared using an excess of N-methylamine·HCl; 1H NMR (CDCl$_3$): 2.89 (d, J=4.7 Hz, 3H), 6.13 (m, 1H), 6.98 (d, J=9.1 Hz, 3H), 7.15 (d, J=8.8 Hz, 2H), 7.37 (d, J=8.8 Hz, 2H), 7.48 (m, 3H), 7.59 (s, 1H), 8.79 (s, 1H).

Example 89

3-Trifluoromethyl-(4-methoxy)phenyl-1H-pyrazole-5-(N-{4-(5-carbamide-imidazol-1-yl}phenyl) carboxyamide Prepared by saturating the 0° C. CH$_2$Cl$_2$ solution of the acid chloride with NH$_3$ gas; MS (ES) m/z (rel. intensity), 468.9 (M+, 100)

Example 90

3-Trifluoromethyl-(4-methoxy)phenyl-1H-pyrazole-5-(N-{4-(5-methylsulfonylcarbamide-1-imidazole}phenyl)carboxyamide Prepared using methane sulfonamide as the amine component; MS (ES) m/z (rel. intensity), 546.9 (M+, 100)

Example 91

1-(4'-Methoxyphenyl)-3-hydroxylmethyl-1H-pyrazole-5-N-(4'-pyrrolidinocarbonyl)phenyl) carboxyamide 1-(4'-methoxyphenyl)-3-hydroxylmethyl-1H-pyrazole-5-ethylcarboxylate To a solution of 1-(4'-methoxyphenyl)-3-methyl-1H-pyrazole-5-ethylcarboxylate (1.58 g, 7.1 mmol) in CCl$_4$ (250 mL) was added NBS (1.5 g, 8.5 mmol) and benzoyl peroxide (73 mg, 4 mmol %). The mixture was degassed and filled with nitrogen, refluxed for 18 hours under nitrogen, and then cooled to room temperature. The mixture was diluted with CH$_2$Cl$_2$ (100 mL), washed with 10% NaOH (20 mL×3), water (20 mL×3), and brine (10 mL×2), and dried over MgSO$_4$. Filtration and concentration gave crude 1-(4'-methoxyphenyl)-3-bromomethyl-1H-pyrazole-5-ethylcarboxylate (2.4 g). To a solution of the crude in aqueous DMSO (75%, 40 mL) was added Cu$_2$O (1.5 g, 10.5 mmol), and the mixture was stirred at 60° C. for 2 hours. The mixture was filtered to remove excess Cu$_2$O, and the filtrate was extracted with ethyl ether. The ether layer was washed with brine (10 mL×5) and dried over MgSO$_4$. Filtration and concentration, followed by purification by silica gel column chromatography with EtOAc/CH$_2$Cl$_2$ (1 to 1) gave the title compound (1.5 g, 81% yield). ESMS (M+H)$^+$ m/z: 277.

1-(4'-Methoxyphenyl)-3-hydroxylmethyl-1H-pyrazole-5-N-(4'-pyrrolidinocarbonyl)phenyl) carboxyamide To a solution of 4-(pyrrolidinyl-one)aniline (390 mg, 2.05 mmol) in CH$_2$Cl$_2$ (20 mL) was added AlMe$_3$ (2M in hexane, 3 mmol) at 0° C. The mixture was stirred at room temperature for 15 minutes and a solution of 1-(4'-methoxyphenyl)-3-hydroxylmethylene-1H-pyrazole-5-ethylcarboxylate (560 mg, 2.05 mmol) in CH$_2$Cl$_2$ (5 mL) was added. The resulting mixture was stirred overnight, quenched with water (5 mL), and filtered through a pad of Celite to remove Al(OH)$_3$. The filtrate was washed with water and brine, and dried over MgSO$_4$. Filtration, concentration, and purification by silica gel column chromatography with gradient solvents (CH$_2$Cl$_2$ to EtOAc) gave the title compound (570 mg, 67% yield). ESMS (M+Na)$^+$ m/z: 443. HRMS (M+H)+ calc. m/z: 420.1798, obs: 420.1771.

Example 92

1-(4'-Methoxyphenyl)-3-formaldehyde-1H-pyrazole-5-N-(4'-(pyrrolidinocarbonyl)phenyl)carboxyamide To a solution of 1-(4-methoxyphenyl)-3-hydroxylmethyl-1H-pyrazole-5-N-((4'-pyrrolidinocarbonyl)phenyl) carboxyamide 6 (140 mg, 0.33 mmol) in THF (20 mL) was added MnO$_2$ (435 mg, 4.95 mmol), and the resulting mixture was refluxed for 12 hours. The mixture was filtered to remove excess MnO$_2$, and the filtrate was concentrated to give EXAMPLE 92 (138 mg, 100%) as a white solid. ESMS (M+H)$^+$ m/z: 419.

Example 93

1-(4'-Methoxyphenyl)-5-N-(4'-(pyrrolidinocarbonyl) anilide)-1H-pyrazol-3-yl-carboxylic acid 1-(4'-Methoxyphenyl)-5-N-(4'-(pyrrolidinocarbonyl) anilide)-1H-pyrazol-3-yl-carboxylic acid To a solution of AgNO$_3$ (34 mg, 0.2 mmol) in H$_2$O (0.5 mL) was added NaOH (16 mg, 0.4 mmol), and a solution of 1-(4'-methoxyphenyl)-3-formaldehyde-1H-pyrazole-5-N-((4'-pyrrolidinocarbonyl)phenyl)carboxyamide (EXAMPLE 92, 42 mg, 0.1 mmol) in MeOH (0.5 mL) at 0° C. After being stirred at room temperature for 30 minutes, the mixture was carefully acidified with conc. HCl (35 mL) to pH~2, and concentrated to give a residue, which was purified by silica gel column chromatography with gradient solvents (CH$_2$Cl$_2$ to EtOAc) to give the title compound (25 mg, 58%). ESMS (M+Na)$^+$ m/z: 456.9.

Example 94

1-(4'-Methoxyphenyl)-3-methylcarboxylate-1H-pyrazole-5-N-(4'-pyrrolidinocarbonyl)phenyl) carboxyamide 1-(4'-Methoxyphenyl)-3-methylcarboxylate-1H-pyrazole-5-N-(4'-pyrrolidinocarbonyl)phenyl) carboxyamide To a solution of 1-(4'-methoxyphenyl)-3-formaldehyde-1H-pyrazole-5-N-((4'-pyrrolidinocarbonyl)phenyl)

carboxyamide (EXAMPLE 92, 42 mg, 0.1 mmol) in MeOH (1 mL) was added KCN (7.8 mg, 0.12 mmol), HOAc (7.2 mg, 0.12 mmol) and MnO$_2$ (120 mg, 0.83 mmol), and the resulting mixture was stirred at room temperature for 12 hours. The mixture was diluted with EtOAc (50 mL), washed with water (10 mL×3) and brine, and dried over MgSO$_4$. The solution was filtered, concentrated, and purified by silica gel column chromatography with EtOAc to give the title compound (38 mg, 85% yield). ESMS (M+Na)$^+$ m/z: 471.

Example 95

1-(4'-Methoxyphenyl)-3-cyanomethyl-1H-pyrazole-5-N-(4'-pyrrolidinocarbonyl)phenyl)carboxyamide 1-(4'-Methoxyphenyl)-3-cyanomethyl-1H-pyrazole-5-N-(4'-pyrrolidinocarbonyl)phenyl)carboxyamide To a solution of 1-(4'-methoxyphenyl)-3-hydroxylmethyl-1H-pyrazole-5-N-((4'-pyrrolidinocarbonyl)phenyl) carboxyamide (120 mg, 0.29 mmol) in CH$_2$Cl$_2$ (15 mL) was added MsCl (48 mg, 0.43 mmol) and Et$_3$N (44 mg, 0.43 mmol). After being stirred at room temperature for 2 hours, the resulting mixture was concentrated. A solution of the residue in DMF (3 mL) was treated with NaCN (43 mg, 0.87 mmol) and stirred for 16 hours. To the reaction mixture was added EtOAc (50 mL) and water (5 mL), and the EtOAc layer was washed with brine (10 mL×5), dried over MgSO$_4$, concentrated, and purified on silica gel TLC plates eluted with EtOAc to give the title compound (57 mg, 46%). ESMS (M+Na)$^+$ m/z: 430.

Example 96

2-(1'-(4"-Methoxyphenyl)-5'-(4"-pyrrolidinocarbonyl)anilide-1H-pyrazol-3'-yl)acetic acid 2-(1'-(4"-Methoxyphenyl)-5'-(4"-pyrrolidinocarbonyl)anilide-1H-pyrazol-3'-yl)acetic acid To 1-(4'-methoxyphenyl)-3-cyanomethyl-1H-pyrazole-5-N-((4'-pyrrolidinocarbonyl)phenyl)carboxyamide (27 mg, 0.063 mmol) was added 6N HCl (1 mL), and the resulting mixture was stirred at 75° C. for 16 hours. The mixture was extracted with EtOAc and the organic layer was dried over MgSO$_4$, concentrated, and purified on silica gel TLC plates eluted with 20% MeOH in EtOAc to give the title compound (2 mg, 7%). MS(ES-)(M−H)$^+$m/z: 447.

Example 97

1-(4'-Methoxyphenyl)-3-bromomethyl-1H-pyrazole-5-N-(2'-aminosulfonyl-[1,1']-biphen-4-yl) carboxyamide 1-(4'-Methoxyphenyl)-3-hydroxylmethyl-1H-pyrazole-5-N-(2'-tert-butylaminosulfonyl-[1,1']-biphen-4-yl)carboxyamide To a solution of 4-(2'-tert-butylaminosulfonylphenyl) aniline (1.33 g, 4.3 mmol) in CH$_2$Cl$_2$ (40 mL) was added AlMe$_3$ (2M in hexane, 6.5 mmol) at 0° C. After the mixture was stirred at room temperature for 30 minutes, a solution of 1-(4'-methoxyphenyl)-3-hydroxylmethyl-1H-pyrazole-5-ethylcarboxylate (1.09 g, 3.95 mmol) in CH$_2$Cl$_2$ (5 mL) was added, and the resulting mixture was refluxed for 6 hours and quenched with water (5 mL). The mixture was filtered through a pad of Celite, and the filtrate was washed with water and brine, and dried over MgSO$_4$. Filtration, concentration, and purification by silica gel column chromatography with gradient solvents (CH$_2$Cl$_2$ to EtOAc to 10% MeOH/EtOAc) gave the title compound (1.8 g, 85%). ESMS (M+H)$^+$ m/z: 535.

1-(4'-Methoxyphenyl)-3-bromomethyl-1H-pyrazole-5-N-(2'-aminosulfonyl-[1,1']-biphen-4-yl) carboxyamide To a solution of 1-(4'-methoxyphenyl)-3-hydroxylmethyl-1H-pyrazole-5-N-(2'-tert-butylaminosulfonyl-[1,1']-biphen-4-yl)carboxyamide (880 mg, 2.49 mmol) in CH$_2$Cl$_2$ (100 mL) was added PBr$_3$ (675 mg, 2.49 mmol). The resulting mixture was stirred at room temperature for 2 hours and concentrated. The residue was treated with TFA (10 mL), refluxed for 2 hours, and then concentrated. The residue was dissolved in EtOAc (50 mL) and water (5 mL). The EtOAc layer was washed with brine (10 mL), dried over MgSO$_4$, concentrated, and purified by silica gel column chromatography with gradient solvents (hexane to EtOAc) to give the title compound (800 mg, 90%). ESMS (M+H)$^+$ m/z: 541/543.

Example 98

1-(4'-Methoxyphenyl)-3-aminomethyl-1H-pyrazole-5-N-(2'-aminosulfonyl-[1,1']-biphen-4-yl) carboxyamide 1-(4'-Methoxyphenyl)-3-aminomethyl-1H-pyrazole-5-N-(2'-aminosulfonyl-[1,1']-biphen-4-yl) carboxyamide To a solution of 1-(4'-methoxyphenyl)-3-bromomethyl-1H-pyrazole-5-N-(2'-aminosulfonyl-[1,1']-biphen-4-yl) carboxyamide (140 mg, 0.259 mmol) in a mixture solvents (EtOH/CH$_3$CN/H$_2$O=10:5:1, 20 mL) was added NaN$_3$ (50.5 mg, 0.776 mmol). After refluxing for 16 hours, the resulting solution was cooled to room temperature. A solution of SnCl$_2$·2H$_2$O (350 mg, 1.55 mmol) in MeOH (4 mL) was added to the above solution, and the resulting mixture was stirred at room temperature for 2 hours. The mixture was neutralized with 1N NaOH to pH 8–9, and extracted with EtOAc. The EtOAc layer was concentrated and purified on silica gel TLC plates eluted with 20% MeOH in CH$_2$Cl$_2$ to give the title compound (126 mg, ~100%). ESMS (M+H)$^+$ m/z: 478.1.

Example 99

1-(4'-Methoxyphenyl)-3-(N-methylsulfonylamino) methyl-1H-pyrazole-5-N-(2'-aminosulfonyl-[1,1']-biphen-4-yl)carboxyamide 1-(4'-Methoxyphenyl)-3-(N-methylsulfonylamino) methyl-1H-pyrazole-5-N-(2'-aminosulfonyl-[1,1']-biphen-4-yl)carboxyamide To a solution of 1-(4'-methoxyphenyl)-3-aminomethyl-1H-pyrazole-5-N-(2'-aminosulfonyl-[1,1']-biphen-4-yl) carboxyamide (15 mg, 0.031 mmol) in CH$_2$Cl$_2$ (1 mL) was added MsCl (3.6 mg, 0.035 mmol) and Et$_3$N (4.7 mg, 0.047 mmol). After stirring at room temperature for 2 hours, the resulting mixture was concentrated and purified on a silica gel TLC plate eluted with EtOAc-CH$_2$Cl$_2$ (1:1) to give the title compound (12 mg, 70%). HRMS (M+H)$^+$ calc. m/z: 556.1324, obs.: 556.1320.

Example 100

1-(4'-Methoxyphenyl)-3-(imidazol-1-yl)methyl-1H-pyrazole-5-N-(2'-aminosulfonyl-[1,1']-biphen-4-yl)carboxyamide 1-(4'-Methoxyphenyl)-3-(imidazol-1-yl)methyl-1H-pyrazole-5-N-(2'-aminosulfonyl-[1,1']-biphen-4-yl)carboxyamide To a solution of 1-(4'-methoxyphenyl)-3-bromomethyl-1H-pyrazole-5-N-(2'-aminosulfonyl-[1,1']-biphen-4-yl)carboxyamide (30 mg, 0.055 mmol) in $CH_2Cl_2$ (2 mL) was added imidazole (12 mg, 0.176 mg), and the resulting mixture was stirred at room temperature for 8 hours. The mixture was concentrated and purified on silica gel TLC plates eluted with $CH_2Cl_2$/EtOAc (1:3) to give the title compound. ESMS $(M+Na)^+$ m/z: 528.5.

Example 101

1-(4'-Methoxyphenyl)-3-hydroxylmethyl-1H-pyrazole-5-N-(2'-aminosulfonyl-[1,1']-biphen-4-yl)carboxyamide And Example 102

1-(4'-Methoxyphenyl)-3-trifluoroacetylhydroxylmethyl-1H-pyrazole-5-N-(2'-aminosulfonyl-[1,1']-biphen-4-yl)carboxyamide Preparation of a mixture of 1-(4'-methoxyphenyl)-3-hydroxylmethyl-1H-pyrazole-5-N-(2'-aminosulfonyl-[1,1']-biphen-4-yl)carboxyamide and 1-(4'-methoxyphenyl)-3-trifluoroacetylhydroxylmethyl-1H-pyrazole-5-N-(2'-aminosulfonyl-[1,1']-biphen-4-yl)carboxyamide To 1-(4'-methoxyphenyl)-3-hydroxylmethyl-1H-pyrazole-5-N-(2'-tert-butylaminosulfonyl-[1,1']-biphen-4-yl)carboxyamide (40 mg, 0.075 mmol) was added 25% TFA in $CH_2CH_2$ (6 mL), and the mixture was stirred at room temperature for 20 hours. The mixture was concentrated and purified by prep. HPLC to give Example 101: 1-(4'-methoxyphenyl)-3-hydroxylmethyl-1H-pyrazole-5-N-(2'-aminosulfonyl-[1,1']-biphenyl)carboxyamide (8 mg, 22%): ESMS $(M+H)^+$ m/z: 479; and EXAMPLE 102: 1-(4'-methoxyphenyl)-3-trifluoroacetylhydroxylmethyl-1H-pyrazole-5-N-(2'-aminosulfonyl-[1,1']-biphen-4-yl)carboxyamide (18 mg, 42%): ESMS $(M+H)^+$ m/z: 575.

Example 103

1-(4'-Methoxy-2'-methoxycarbonylphenyl)-3-trifluoromethyl-1H-pyrazole-5-N-(2'-methylsulfonyl-[1,1']-biphen-4-yl)carboxyamide 1N-(4'-methoxy-2'-methoxycarbonylphenyl)-3-trifluoromethyl-5-methylpyrazole To a solution of 2-bromo-5-methoxyphenyl methylcarboxylate (4.9 g, 20 mmol) in DMF (25 mL) was added 3-methyl-5-trifluoromethylimidazole (3.0 g, 20 mmol), CuBr (1 g, 7 mmol), and $K_2CO_3$ (2.76 g, 20 mmol). The mixture was stirred at 110° C. for 18 hours and diluted with EtOAc (150 mL). The mixture was filtered through a pad of Celite, and the filtrate was washed with water and brine (10 mL×5), and dried over $MgSO_4$. Filtration, concentration, and purification by silica gel column chromatography with hexane-$CH_2Cl_2$ (1:1) gave 1N-(4'-methoxy-2'-methoxycarbonylphenyl)-3-trifluoromethyl-5-methylpyrazole (3.17 g, 51%). ESMS $(M+H)^+$ m/z: 315.

1N-(4'-methoxy-2'-methoxycarbonylphenyl)-3-trifluoromethyl-1H-pyrazole-5-carboxylic acid To a solution of 1N-(4'-methoxy-2'-methoxycarbonylphenyl)-3-trifluoromethyl-5-methylpyrazole (2.54 g, 8.09 mmol) in $CCl_4$ (150 mL) was added NBS (2.88 g, 16.18 mmol), benzoyl peroxide (31 mg, 0.12 mmol), and AIBN (123 mg, 0.44 mmol), and the mixture was degassed and then filled with nitrogen. After refluxing under nitrogen for 24 hours, the mixture was cooled to 0° C. and filtered. The filtrate was concentrated to give a crude oil. To a solution of the crude oil in $CH_3CN$ (50 mL) and water (20 mL) was added $KMnO_4$ (1.8 g, 11.4 mmol). The mixture was stirred at 95° C. for 1.5 hours and cooled to room temperature. A solution of $Na_2SO_3$ (5 g in 15 mL of water) and $NaHCO_3$ (5.5 g in 30 mL of water) was added, and the resulting mixture was filtered through a pad of Celite. The filtrate was extracted with ether, and the aqueous layer was carefully acidified with conc. HCl to pH 2 and extracted with EtOAc. The EtOAc layer was washed with brine (10 mL) and dried over $MgSO_4$. Filtration and concentration gave pure 1N-(4'-methoxy-2'-methoxycarbonylphenyl)-3-trifluoromethyl-1H-pyrazole-5-carboxylic acid (1.2 g, 43.1%). ESMS $(M+H)^+$ m/z: 345.

1-(4'-Methoxy-2'-methoxycarbonylphenyl)-3-trifluoromethyl-1H-pyrazole-5-N-(2'-methylsulfonyl-[1,1']-biphen-4-yl)carboxyamide To a solution of 1N-(4'-methoxy-2'-methoxycarbonylphenyl)-3-trifluoromethyl-1H-pyrazole-5-carboxylic acid (344 mg, 1 mmol) in DMF (5 mL) was added PyBrop (559 mg, 1.2 mmol), and the mixture was stirred at room temperature for 30 minutes. After N,N-diisopropylethylamine (288 mg, 2.5 mmol) was added, the resulting mixture was stirred for 10 minutes, and then a solution of 4-(2'-methylsulfonylphenyl)aniline (265 mg, 1 mmol) was added. The resulting mixture was stirred at 90° C. for 16 hours, diluted with EtOAc (100 mL), washed with 1N HCl (20 mL×2), 10% $NaHCO_3$ (20 mL×2), water (10 mL), and brine (20 mL×4), dried over $MgSO_4$, and concentrated. The residue was dissolved in $CH_2Cl_2$ (20 mL) and treated with DOWAX(1 g) for 30 minutes. The mixture was filtered and the filtrate was purified by silica gel column chromatography with gradient solvents ($CH_2Cl_2$ to EtOAc) to give the title compound (430 mg, 73%). ESMS $(M+H)^+$ m/z: 592.

Example 104

1-(4'-Methoxy-2'-hydroxycarbonylphenyl)-3-trifluoromethyl-1H-pyrazole-5-N-(2'-methylsulfonyl-[1,1']-biphen-4-yl)carboxyamide To a solution of 1-(4'-methoxy-2'-methoxycarbonylphenyl)-3-trifluoromethyl-1H-pyrazole-5-N-(2'-methylsulfonyl-[1,1']-biphen-4-yl)carboxyamide (290 mg, 0.49 mmol) in MeOH (10 mL) was added aqueous NaOH (0.39 g in 5 mL of water), and the mixture was stirred at room temperature for 16 hours. After extracting with ether, the resulting aqueous solution was carefully acidified with conc. HCl to pH 2 and extracted with EtOAc. The EtOAc layer was dried over $MgSO_4$, concentrated, and purified by silica gel column chromatography with EtOAc to give the title compound (110 mg, 50%) as a white solid. ESMS $(M+H)^+$ m/z: 578.

Example 105

1-(4'-Methoxy-2'-methoxycarbonylphenyl)-3-trifluoromethyl-1H-pyrazole-5-N-(2'-aminosulfonyl-[1,1']-biphen-4-yl)carboxyamide

To a solution of 1N-(4'-methoxy-2'-methoxycarbonylphenyl)-3-trifluoromethyl-1H-pyrazole-5-carboxylic acid (344 mg, 1 mmol) in DMF (5 mL) was added PyBrop (559 mg, 1.2 mmol), and the mixture was stirred at room temperature for 30 minutes. N,N-diisopropylethylamine (288 mg, 2.5 mmol) was added and the resulting mixture was stirred for 10 minutes, and then a solution of 4-(2'-tert-butylaminosulfonylphenyl)aniline hydrochloride salt (358 mg, 1 mmol) was added. The resulting mixture was stirred at 90° C. for 16 hours and quenched with EtOAc (100 mL). The mixture was washed with 1N HCl (20 mL×2), 10% NaHCO$_3$ (20 mL×2), water (10 mL), and brine (20 mL×4), dried over MgSO$_4$, and concentrated. The residue was dissolved in CH$_2$Cl$_2$ (20 mL) and treated with DOWEX (1 g) for 30 minutes, and filtered. The filtrate was purified by silica gel column chromatography with gradient solvents (CH$_2$Cl$_2$ to EtOAc) to give 1-(4'-methoxy-2'-methoxycarbonylphenyl)-3-trifluoromethyl-1H-pyrazole-5-N-(2'-tert-butylaminosulfonyl-[1,1']-biphen-4-yl)carboxyamide (550 mg, 85%). ESMS (M+H)$^+$ m/z: 649.

To 1-(4'-methoxy-2'-methoxycarbonylphenyl)-3-trifluoromethyl-1H-pyrazole-5-N-(2'-tert-butylaminosulfonyl-[1,1']-biphen-4-yl)carboxyamide (200 mg) was added TFA (5 mL), and the resulting solution was refluxed for 2 hours. The mixture was concentrated and purified on silica gel TLC plates eluted with 10% EtOAc in CH$_2$Cl$_2$ to give the title compound (160 mg, 87%). ESMS (M+H)$^+$ m/z: 593.

Example 106

1-(4'-Methoxy-2'-hydroxycarbonylphenyl)-3-trifluoromethyl-1H-pyrazole-5-N-(2'-tert-butylaminosulfonyl-[1,1'-biphenyl)carboxyamide

To a solution of 1-(4'-methoxy-2'-methoxycarbonylphenyl)-3-trifluoromethyl-1H-pyrazole-5-N-(2'-tert-butylaminosulfonyl-[1,1']-biphen-4-yl)carboxyamide (350 mg, 0.54 mmol) in MeOH (5 mL) was added aqueous NaOH (90 mg in 5 mL of water), and the mixture was stirred at room temperature for 16 hours. After extracting with ether, the resulting aqueous solution was carefully acidified with conc. HCl to pH 2 and extracted with EtOAc. The EtOAc layer was dried over MgSO$_4$, concentrated, and purified by silica gel column chromatography with EtOAc to give the title compound (210 mg, 61.3%) as a white solid. ESMS (M+H)$^+$ m/z: 635.

Example 107

1-(4'-Methoxy-2'-hydroxycarbonylphenyl)-3-trifluoromethyl-1H-pyrazole-5-N-(2'-aminosulfonyl-[1,1']-biphen-4-yl)carboxyamide

To 1-(4'-methoxy-2'-hydroxycarbonylphenyl)-3-trifluoromethyl-1H-pyrazole-5-N-(2'-tert-butylaminosulfonylphenyl)-phenyl)carboxyamide (210 mg, 0.33 mmol) was added TFA (5 mL), and the resulting solution was refluxed for 1 hour. The mixture was concentrated and purified on silica gel TLC plates eluted with 10% MeOH in EtOAc to give the title compound (190 mg, 99%). ESMS (M+H)$^+$ m/z: 579.

Example 108

1-(4'-Methoxy-2'-hydroxylmethylphenyl)-3-trifluoromethyl-1H-pyrazole-5-N-(2'-aminosulfonyl-[1,1']-biphen-4-yl)carboxyamide

To a solution of 1-(4'-methoxy-2'-hydroxycarbonylphenyl)-3-trifluoromethyl-1H-pyrazole-5-N-(2'-aminosulfonylphenyl)-phenyl)carboxyamide (210 mg, 0.36 mmol) in THF (5 mL) at 0° C. was added N,N-diisopropylethylamine (62 mg, 0.54 mmol) and isopropylchloroformate (freshly distilled, 46 mg, 0.38 mmol), and the resulting mixture was stirred at room temperature for 1.5 hours. NaBH$_4$ (30 mg, 0.79 mmol) was added and the mixture was stirred for 1 hour. The reaction was quenched with 1 N HCl and stirred for 30 minutes. The mixture was diluted with EtOAc and the organic layer was washed with water and brine, dried over Na$_2$SO$_4$, and purified on silica gel TLC plates eluted with EtOAc to give the title compound (75 mg, 37%). ESMS (M+Na)$^+$ m/z: 586.9.

Example 109 to 115

1N-(4'-Methoxyphenyl)-3-methylpyrazol-5-yl)ethylcarboxylate

To a solution of 4-methoxyphenylhydrazine (8.65 g, 50 mmol) in HOAc (300 mL) at 80° C. was added oxime (ethyl 2-N-(methoxy)imino-4-oxopentanoate (see Example 1), 6 g, 32 mmol), and the mixture was refluxed for 18 hours and concentrated. The residue was dissolved in EtOAc (300 mL), washed with 10% NaOH (100 mL), water (100 mL×2), and brine (20 mL×2), dried over MgSO$_4$, concentrated, and purified by silica gel column chromatography with CH$_2$Cl$_2$ to give partially purified product, which was recrystalized in hexane to give the title compound (10.5 g, 80%). ESMS (M+H)$^+$ m/z: 261.

1N-(4'-Methoxyphenyl)-3-methylpyrazol-5-yl)carboxylic acid

A solution of 1N-(4'-methoxyphenyl)-3-methylpyrazol-5-yl)ethylcarboxylate (5.9 g, 22.7 mmol) in THF (50 mL) was treated with 1N NaOH (50 mL) at room temperature for 24 hours. The aqueous layer of the mixture was carefully acidified with conc. HCl to pH 2 and extracted with EtOAc. The EtOAc layer was dried, concentrated, and purified by silica gel column chromatography with gradient solvents (CH$_2$Cl$_2$ to EtOAc) to give the title compound (3.7 g, 66.3%). ESMS (M−H)$^+$ m/z: 245.

Preparation of a Examples 109–115 via a library

To a solution of 1N-(4'-methoxyphenyl)-3-methylpyrazol-5-yl)carboxylic acid (450 mg, 1.94 mmol) in CH$_3$CN (30 mL) was added SOCl$_2$ (1.4 g, 11.6 mmol). The resulting mixture was refluxed for 1.5 hours and then concentrated. A solution of the residue in THF (38 mL) was divided into portions and added to solutions of anilines or amines (0.1 mmol/sample/well) and DMAP (12.4 mg/well) in THF (1 mL/well) in a 96 well polyfiltronics filter plate. The 96 well polyfiltronics filter plate containing the reaction mixtures was shaken at room temperature for 2 days. To each solution/well was added a suspension of DOWEX (0.2 g) in CH$_2$Cl$_2$ (0.4 mL) and the resulting mixtures were shaken for one hour. The mixtures were filtered and the filtrates were carefully collected and dried under vacuum to give the library.

Example 109

1-(4'-Methoxphenyl)-3-methyl-1H-pyrazole-5-N-(4'-sec-butyl)phenyl)carboxyamide

ESMS (M+H)$^+$ m/z: 404.

Example 110

1-(4'-Methoxyphenyl)-3-methyl-1H-pyrazole-5-N-(4'-(3"-methyl-3"-pyrazolin-5"-one-2"-yl)phenyl)carboxyamide ESMS (M+H)$^+$ m/z: 364.

Example 111

1-(4'-Methoxyphenyl)-3-methyl-1H-pyrazole-5-N-(4'-(6"-methylbenzothiazol-2"-yl)phenyl)carboxyamide ESMS (M+H)$^+$m/z: 455.

Example 112

1-(4'-Methoxyphenyl)-3-methyl-1H-pyrazole-5-N-(3', 4'-dibromophenyl)carboxyamide ESMS (M+H)$^+$ m/z: 364.

Example 113

1-(4'-Methoxyphenyl)-3-methyl-1H-pyrazole-5-N-(4'-n-butyl)phenyl)carboxyamide

ESMS (M+H)$^+$ m/z: 464.

Example 114

1-(4'-Methoxyphenyl)-3-methyl-1H-pyrazole-5-N-(4'-(4"-methylpiperidino)phenyl)carboxyamide ESMS (M+H)$^+$ m/z: 405.

Example 115

1-(4'-Methoxyphenyl)-3-methyl-1H-pyrazole-5-N-(4'-(2"-methylimidazol-1-yl)phenyl)carboxyamide ESMS (M+H)$^+$ m/z: 388.

Example 116

3-Trifluoromethyl-1-(4-methoxyphenyl)-1H-pyrazole-5-(N-(4-carboxy(N-methylimidazo-2-yl)phenyl)carboxyamide Part A. To 4-nitro-1-(2'-N-methylimidazoyl)benzene (0.58 g, 2.51 mmol), prepared from 4-nitrobenzoyl chloride and 1-methylimidazole by the method of Regel, E. et al., Liebigs Ann. Chem. (1977) 145, was added ethanol (50 mL), trifluoroacetic acid (1 mL) and 10% palladium on carbon (60 mg). The mixture was hydrogenated on the Parr at 40 psi for 0.5 h. The reaction mixture was filtered and concentrated. The recovered aniline salt was dissolved in water and extracted with ether. The aqueous layer was made basic with 1N NaOH, extracted with ethyl acetate and dried (MgSO$_4$) and evaporated to give 0.35 g (70%) of the aniline. MS (AP+) 202.1 (M+H)$^+$.

Part B. To 1-(4-methoxyphenyl)-3-trifluoromethyl-1H-pyrazole-5-carboxylic acid (0.25 g, 0.87 mmol) in CH$_2$Cl$_2$ (15 mL) was added oxalyl chloride (0.1 mL, 1.14 mmol) and several drops of DMF. The reaction was stirred for 24 h, then concentrated. The aniline from Part A (0.175 g, 0.87 mmol), DMAP (0.27 g, 2.2 mmol), and fresh CH$_2$Cl$_2$ (20 mL) were added to the acid chloride and the reaction was stirred for 24 h. The mixture was concentrated and the residue was dissolved in EtOAc (10 mL) and TFA (0.1 mL), concentrated and purified by reverse phase HPLC and lyophilized to afford the title compound 60 mg (11%); $^1$H NMR (DMSO-d6) δ 10.97 (s, 1H), 8.30 (d, j=8.80 Hz, 2H), 7.80 (d, j=8.80 Hz, 2H), 7.63 (d, j=10.2 Hz, 2H), 7.48 (d, j=9.20 Hz, 2H), 7.22 (s, 1H), 7.07 (d, j=8.80 Hz, 2H), 3.98 (s, 3H), 3.82 (s, 3H) ppm; HRMS (M+H)$^+$C$_{23}$H$_{19}$F$_3$N$_5$O$_3$ 470.1443.

Example 117

3-Trifluoromethyl-1-(4-methoxyphenyl)-1H-pyrazole-5-(N-(4-hydroxymethyl(2-(imidazol-2-yl)phenyl)))carboxyamide

And Example 118

3-Trifluoromethyl-1-(4-methoxyphenyl)-1H-pyrazole-5-(N-(4-hydroxymethyl(2-(1-benzyl-imidazol-2-yl)phenyl)))carboxyamide

And Example 119

1-(4-Methoxyphenyl)-3-trifluoromethyl-1H-pyrazole-5-(N-(4-(2-carboxy(imidazol-2-yl)phenyl)))carboxyamide Part A: To 4-nitro-1-(2'-N-benzylimidazoyl)benzene (0.47 g, 1.53 mmol), prepared from 4-nitrobenzoyl chloride and 1-benzylimidazole by the method of Regel, E. et al., Liebigs Ann. Chem. (1977) 145, was added EtOAc (15 mL) and stannous chloride (0.86 g, 3.80 mmol). The reaction was heated to reflux for 2 h then stirred at rt for 18 h. An additional 0.3 g of stannous chloride was added and the reaction stirred 3 h. The reaction was cooled to 0° C., quenched with 6M NaOH, and extracted with EtOAc and dried (Na$_2$SO$_4$) to afford 0.4 g (95%) orange solid. MS (M+H)$^+$278.2 (AP+).

Part B: The benzyl compound from part A (0.229 g, 0.4 mmol) was hydrogenated on the Parr in EtOH (30 mL) and TFA (0.5 mL) with 30 mg 10% Pd/C at 40psi for 0.5 h. The reaction was filtered, concentrated and purified via reverse phase HPLC to afford the above mentioned titled compounds, respectively.

Example 117

5.3 mg (2.2%) $^1$H NMR(DMSO-d6)δ: 10.75 (s, 1H), 7.66 (d, j=8.40 Hz, 2H), 7.55 (m+d, j=6.60 Hz, 3H), 7.45 (d, j=9.10 Hz, 2H), 7.40 (d, j=8.40 Hz, 2H), 7.05 (d, j=8.80 Hz, 2H), 6.55 (brd s, 2H), 6.00 (d, j=4.0 Hz, 1H), 3.81 (3H,s) ppm. HRMS for (M+H)$^+$C$_{22}$H$_{19}$F$_3$N$_5$O$_3$ 458.1437,

Example 118

73mg (25%) $^1$H NMR (DMSO-d6)δ: 10.76 (s, 1H), 7.69 (s, 1H), 7.64 (d, j=1.90 Hz, 1H), 7.63 (d, j=8.80 Hz, 2H), 7.55 (s, 1H), 7.34 (d, j=5.80 Hz, 2H), 7.32 m, 5H), 7.19 (brd, 1H), 7.10 (dd, j=2.20, 5.80 Hz, 2H), 7.06 (d, j=9.20 Hz, 2H), 6.24 (s, 1H), 5.38 (d, j=3.70 Hz, 2H), 3.81 (s, 3H) ppm; HRMS (M+H)$^+$for C$_{29}$H$_{25}$F$_3$N$_5$O$_3$ 548.1923,

Example 119

15 mg (6.2%) $^1$H NMR (DMSO-d6)δ: 10.99 (s, 1H), 8.56 (d, j=8.50 Hz, 2H), 7.84 (d, j=8.80 Hz, 2H), 7.64 (s, 1H), 7.48 (d, j=8.80 Hz, 2H), 7.41 (s, 2H), 7.31 (m, 1H), 7.07 (m+d, j=8.80 Hz, 3H), 3.82 (s, 3H) ppm; HRMS (M+H)+for C22H17F3N5O3 456.1271.

Example 120

3-Trifluoromethyl-1-(4-methoxyphenyl)-1H-pyrazole-5-(N-(4-(N-(4-methoxyphenyl)amino-(2-thiazolyl)methyl)phenyl)))carboxyamide

And Example 121

1-(4-Methoxyphenyl)-3-trifluoromethyl-1H-pyrazole-5-(N-(4-(2-carboxy-(4,5-dihyrothiazol-2-yl)phenyl)))carboxyamide Part A: p-Aminobenzaldehyde (135 mg, 1.11 mmol), and TEA (0.155 mL, 1.11 mmol) were added to 3-trifluoromethyl-1-(4-methoxyphenyl)-1H-pyrazole-5-carboxylic acid chloride (0.34 g, 1.11 mmol) in $CH_2Cl_2$ (10 mL). The reaction was stirred for 18 h, then concentrated. Purification by chromatography on silica gel using 2:1 hexanes/EtOAc as eluent to give 0.16 g (37%) pale yellow solid. MS (ESI)(M–H)$^+$388.1.

3-Trifluoromethyl-1-(4-methoxyphenyl)-1H-pyrazole-5-(N-(4-(N-(4-methoxyphenyl)amino-(2-thiazolyl)methyl)phenyl)))carboxyamide Part B: To thiazole (0.1 mL, 1.43 mmol) in THF(6 mL) cooled to –40° C. was added n-BuLi (0.6 mL, 1.43 mmol) and stirred for 1.5 h. To the aldehyde from part A (0.14 g, 0.36 mmol) in benzene (10 mL) and MeOH (5 mL) was added 4A molecular sieves and p-anisidine (44 mg, 0.36 mmol) and the mixture was heated to reflux for 15 minutes. The mixture was filtered and concentrated to give the imine. To the imine in THF (5 mL) at –78° C. was added the thiazole anion by cannula. The reaction was stirred at 0° C. for 0.5 h then quenched with 1M $KHSO_4$ (0.4 mL). The product was extracted with EtOAc and dried ($MgSO_4$). Purification by chromatography on silica gel using 1:2 Hexanes/EtOAc afforded 0.113 g (54%) of the title compound; MS (M–H)$^+$578.1; $^1$H NMR ($CDCl_3$)δ: 7.74 (d, j=3.30 Hz, 1H), 7.50 (d, j=15.4 Hz, 2H), 7.41 (brd s, 5H), 7.27 (d, j=3.30 Hz, 1H), 7.12 (s, 1H), 7.01 (d, j=9.20 Hz, 2H), 6.74 (d, j=8.80 Hz, 2H), 6.59 (d, j=8.80 Hz, 2H), 5.71 (d, j=3.60 Hz, 1H), 4.56 (d, j=3.60 Hz, 1H), 3.85 (s, 3H), 3.71 (s, 3H) ppm.

1-(4-Methoxyphenyl)-3-trifluoromethyl-1H-pyrazole-5-(N-(4-(2-carboxy-(4,5-dihyrothiazol-2-yl)phenyl)))carboxyamide Part C: To the product from part B (98 mg, 0.17 mmol) in acetonitrile (10 mL)at 0° C. was added cerric ammonium nitrate (0.185 g, 0.34 mmol) in water (10 mL). The reaction was stirred for 10 minutes, then concentrated. The residue was dissolved in EtOAc and washed with aqueous sodium bisulfite and dried ($MgSO_4$). The product was purified by silica gel chromatography, reverse phase HPLC and lyophilized to afford the title compound (10 mg, 12%). $^1$H NMR ($CDCl_3$)δ: 8.54 (d, j=8.80 Hz, 2H), 8.09 (d, j=2.90 Hz, 1H), 7.73 (d, j=3.30 Hz, 1H), 7.66 (s, 1H), 7.59 (d, j=8.80 Hz, 2H), 7.48 (d, j=8.80 Hz, 2H), 7.19 (s, 1H), 7.05 (d, j=9.20 Hz, 2H), 3.88 (s, 3H) ppm; MS (M+H)$^+$473.2 (AP+).

Example 122

1-(4-Methoxyphenyl)-3-trifluoromethyl-1H-pyrazole-5-N-4-(2-(4', 5'-dihydro-1'H-imidazol-2'yl)phenyl)carboxyamide

And Example 123

1-(4-Methoxyphenyl)-3-trifluoromethyl-1H-pyrazole-5-N-(4-(N-2'-aminoethylenecarboxyamide)phenyl)carboxyamide To trimethylaluminum (1.2 mL, 2M in heptane), cooled to 0° C. was added ethylenediamine (57 mg, 0.95 mmol) and the mixture was stirred for 15 minutes. A suspension of ethyl-3-trifluoromethyl-1-(4-methoxyphenyl)-1H-pyrazole-5-(N-(4-carboxyphenyl)carboxyamide previously prepared (0.2 g, 0.47 mmol) in toluene (10 mL) was added. The reaction was heated to 50° C. for a total of 9 h and room temperature for 18 h. The reaction was quenched with ice water, filtered and concentrated. The aqueous layer was extracted with $CH_2Cl_2$ which was then extracted with 1N HCl. The acid layer was basified and extracted with EtOAc and dried ($MgSO_4$). Purification by reverse phase HPLC and freeze drying afforded 56 mg (22%)of the imidazoline (EXAMPLE 122) and 7 mg (3%) of the ring open amide (EXAMPLE 123).

Example 122

For the imidazoline: $^1$H NMR (DMSO-d6)δ: 11.10 (s, 1H), 10.40 (s, 1H), 7.91 (d, j=3.60 Hz, 4H), 7.64 (s, 1H), 7.48 (d, j=8.80 Hz, 2H), 7.07 (d, j=9.20 Hz, 2H), 3.99 (s, 4H), 3.82 (s, 3H) ppm; MS (ESI) 430.2 (M+H)$^+$.

Example 123

For the amide: $^1$H NMR (DMSO-d6)δ: 10.88 (s, 1H), 8.59 (t, j=5.50 Hz, 1H), 7.87 (d, j=8.80 Hz, 2H), 7.79 (m, 2H), 7.75 (d, j=8.80 Hz, 2H), 7.61 (s, 1H), 7.47 (d, j=9.2 Hz, 2H), 7.06 (d, j=8.80 Hz, 2H), 3.82 (s, 3H), 3.51 (q, j=5.50 Hz, 2H), 2.98 (q, j=5.90 Hz, 2H) ppm; MS (ESI) 448.2 (M+H)$^+$.

Example 124

1-(4-Methoxyphenyl)-3-trifluoromethyl-1H-pyrazole-5-[4-(1,4,5,6-tetrahydro-pyrimid-2-yl)-phenyl]carboxyamide Ethyl-3-trifluoromethyl-1-(4-methoxyphenyl)-1H-pyrazole-5-(N-(4-carboxyphenyl)carboxyamide (0.2 g, 0.48 mmol) and 1,3-diaminopropane (70 mg, 0.95 mmol) were coupled as described above. Purification by reverse phase HPLC and freeze drying afforded 20 mg (7.5%). $^1$H NMR (DMSO-d6)δ: 11.0 (s, 1H) , 10.3 (s, 1H), 7.86 (d, j=8.80 Hz, 2H), 7.72 (d, j=8.80 Hz, 2H), 7.63 (s, 1H), 7.48 (d, j=9.20 Hz, 2H), 7.06 (d, j=9.20 Hz, 2H), 3.82 (s, 3H), 3.40 (m, 4H), 1.96 (t, 2H); HRMS for $C_{22}H_{21}F_3N_5O_2$ fnd 444.1646.

Example 125

1-(4-Methoxyphenyl)-3-trifluoromethyl-1H-pyrazole-5-[4-(N-methyl-4,5,6-trihydro-pyrimid-2-yl)-phenyl]carboxyamide Ethyl-3-trifluoromethyl-1-(4-methoxyphenyl)-1H-pyrazole-5-(N-(4-carboxyphenyl)carboxyamide (0.2 g, 0.48 mmol) and N-methyl-1, 3-propanediamine (0.1 mL, 0.95 mmol) were coupled as described above. Purification by reverse phase HPLC and freeze drying afforded 58 mg (21%). $^1$H NMR (DMSO-d6) δ: 9.70 (s, 1H), 7.85 (d, j=8.80 Hz, 2H), 7.62 (d, j=9.20 Hz, 2H), 7.55 (s, 1H), 7.47 (d, j=9.20 Hz, 2H), 7.07 (d, j=9.20 Hz, 2H), 3.82 (s, 3H), 3.57 (t, j=5.50 Hz, 2H), 3.39 (m, 2H), 2.97 (s, 3H), 2.05 (t, j=5.50 Hz, 2H) ppm.

Example 126

1-(4-Methoxyphenyl)-3-trifluoromethyl-1H-pyrazole-5-N-1-(2-fluoro-4-imadazolinephenyl)carboxyamide Part A: To 3-fluoro-4-nitrobenzoic acid (2.81 g, 15 mmol) in $CH_2Cl_2$ (75 mL) was was added oxalyl chloride (1.72 mL, 19.7 mmol) and several drops of DMF. The reaction was stirred 6 h, stripped and ethanol (20 mL) was added. After 18 h the ethanol was removed and EtOAc (30 mL) and stannous chloride (13.7 g, 61 mmol) were added. The reaction was heated to reflux for 2 h, cooled and quenched with sat'd $NaHCO_3$. Extraction with EtOAc and drying ($MgSO_4$) afforded 2.7 g (97%) of the aniline.

Part B: To 1-(4-methoxyphenyl)-3-trifluoromethyl-1H-pyrazole-5-carboxylic acid (0.21 g, 0.73 mmol) in $CH_2Cl_2$ (15 mL) was added oxalyl chloride (0.08 mL, 0.95 mmol) and several drops of DMF. The reaction was stirred for 24 h, then concentrated. The acid chloride, DMAP (0.27 g, 2.20 mmol), and the aniline from Part A (134 mg, 0.73 mmol) were combined in fresh $CH_2Cl_2$ and stirred 18 h. The reaction mixture was washed with 1N HCl, sat'd $NaHCO_3$, brine and dried ($MgSO_4$). Purification by chromatography on silica gel using 1:1 hexanes/EtOAc as eluent afforded 254 mg (79.6%). $^1H$ NMR ($CDCl_3$) δ: 8.44 (t, j=8.10 Hz, 1H), 7.89 (d, j=3.30 Hz, 1H), 7.84 (d, j=9.60 Hz, 1H), 7.77 (dd, j=11.40, 1.50 Hz, 1H), 7.46 (d, j=9.10 Hz, 2H), 7.20 (s, 1H), 7.04 (d, j=8.80 Hz, 2H), 4.39 (q, j=7.0 Hz, 2H), 3.88 (s, 3H), 1.41 (t, j=6.90 Hz, 3H) ppm.

Part C: To trimethylaluminum (0.57 mL, 2M in heptane), cooled to 0° C. was added ethylenediamine (27.6 mg, 0.46 mmol) and the mixture was stirred for 15 min. A suspension of ethyl-3-trifluoromethyl-1-(4-methoxyphenyl)-1H-pyrazole-5-(N-(4-carboxy-2-fluorophenyl)carboxyamide (0.1 g, 0.23 mmol) in toluene (10 mL) was added. The reaction was heated to 50° C. for 18 h and then, was quenched with ice water, filtered and concentrated. The aqueous layer was extracted with $CH_2Cl_2$ which was then extracted with 1N HCl. The acid layer was basified and extracted with EtOAc and dried ($MgSO_4$). Purification by reverse phase HPLC and lyophilization afforded 26 mg (20%). $^1H$ NMR (DMSO-d6) δ10.90 (s, 1H), 10.55 (s, 1H), 8.10 (t, j=8.06 Hz, H), 7.93 (dd, j=11.0, 1.5 Hz, 1H), 7.80 (d, j=8.79 Hz, 1H), 7.64 (s, 1H), 7.47 (d, j=9.15 Hz, 2H), 7.06 (d, j=8.80 Hz, 2H), 4.01 (s, 4H), 3.81 (s, 3H) ppm; HRMS for $C_{21}H_{18}F_4O_2N_5$ found 488.1393.

Example 127

1-(4-Methoxyphenyl)-3-trifluoromethyl-1H-pyrazole-5-N-1-(2-fluoro-4-N-methylimadazolinephenyl)carboxyamide N-Methylethylenediamine (52 mg, 0.71 mmol) and ethyl-3-trifluoromethyl-1-(4-methoxyphenyl)-1H-pyrazole-5-(N-(4-carboxy-2-fluorophenyl)carboxyamide (150 mg, 0.35 mmol) were coupled by the same procedure as the previous example. Purification by reverse phase HPLC and lyophilization afforded 54 mg (27%). $^1H$ NMR (DMSO-d6) δ: 10.90 (s, 1H), 8.03 (t, j=8.10 Hz, 1H), 7.74 (dd, j=11.0, 1.5 Hz, 1H), 7.63 (s, 1H), 7.56 (d, j=9.90 Hz, 1H), 7.47 (d, j=8.80 Hz, 2H), 7.05 (d, j=8.80 Hz, 2H), 4.06 (m, 2H), 3.95 (m, 2H), 3.80 (s, 3H), 3.08 (s, 3H) ppm; MS (ESI) 462.3 $(M+H)^+$; Analysis calc'd for $C_{22}H_{19}F_4N_5O_2$ (TFA)1.4 ($H_2O$)C:46.61 H:3.53 N:10.96, found C:46.68 H:3.29 N:10.91.

Example 128

1-(4-Methoxyphenyl)-3-trifluoromethyl-1H-pyrazole-5-N-[4-(4, 5-dihydro-1-N-methyl-imidazo-2-yl)-phenyl]carboxyamide And Example 129

1-(4-Methoxyphenyl)-3-trifluoromethyl-1H-pyrazole-5-N-[4-carbonxylguanidine)phenyl] carboxyamide Part A: To a dichloromethane solution (50 mL) of N-4'-methoxyphenyl-3-trifluromethyl-pyrazole-5-carboxylic acid (2 g, 6.99 mmol) was added oxalyl chloride (1.36 g, 10.48 mmol) and a few drops of DMF. The reaction mixture was stirred at room temperature for 3 h then evaporated to a pale yellow solid and redissolved in dichloromethane (50 mL). To this solution was then added methyl-4-amino-benzoate (1 g, 6.99 mmol) and DMAP (2.1 g, 17.47 mmol). The reaction mixture was stirred at room temperature overnight, quenched with dil HCl (50 mL) and extracted organics with ethylacetate (2×100 mL), dried ($MgSO_4$) and evaporated to a yellow solid. Purification of the crude coupled product via flash silica gel chromatography (hexane:ethylacetate 7:3) afforded desired coupled precursor as colorless crystals (1.9 g). LRMS (ESI) m/z 420.0 (100). $^1HNMR(CDCl_3)$: δ8.019 (d, J=8.8, 2H); 7.617 (s, 1H); 7.480 (m, 4H); 7.158 (s, 1H); 7.03 (d, J=8.8, 2H); 3.90 (s, 3H); 3.87 (s, 3H) ppm.

1-(4-Methoxyphenyl)-3-trifluoromethyl-1H-pyrazole-5-N-[4-(4, 5-dihydro-1-N-methyl-imidazo-2-yl)phenyl]carboxyamide Part B: The product from part A (0.2 g, 0.048 mmol) in dichloromethane (50 mL) was subjected to treatment with $N_1$-methylethylenediamine (0.071 g, 0.099 mmcl) followed by trimethylaluminum (1.23 mL, 2.45 mmol). The reaction mixture was stirred at room temperature overnight then quenched with dil HCl (5 mL). The product was concentrated in vacuo and purified via preparation HPLC (acetonitrile/water, 2% TFA). Lyophilization afforded colorless crystals (0.167 g) of the desired product. LRMS (ESI) m/z 444.2 (100). HRMS: $(M+H)^+$ calc. 444.1647, found 444.1644. $^1HNMR(DMSO-d_6)$: δ11.07 (s, 1H); 10.12 (s, 1H); 7.88 (d, J=8.8, 2H); 7.71 (d, J=8.8, 2H); 7.63 (s, 1H); 7.47 (m, 2H): 7.06 (m, 2H): 4.05 (m, 2H): 3.89 (m, 2H); 3.82 (s, 3H): 3.09 (s, 3H) ppm.

1-(4-Methoxyphenyl)-3-trifluoromethyl-1H-pyrazole-5-N-[4-carbonylguanidine)phenyl] carboxyamide Part C: The product from part A (150 mg, 0.358 mmol) was subjected to the standard Weinreb methodology described above with guanidine hydrochloride (103 mg, 1.074 mmol) and trimethylaluminum (103 mg, 1.432 mmol) in dichloromethane (10 mL). The mixture was stirred at ambient temperature for 18 h and quenched with 1N hydrochloric acid (5 mL). The slurry was then basified (pH 9, sat. sodium bicarbonate). The organics were extracted with dichloromethane (3×100 mL) and dried ($Na_2SO_4$). Evaporation of the solvent followed by purification via reverse phase Prep HPLC and lyophilization then afforded the desired acylguanidyl compound as colorless crystals. LRMS (ESI) m/z 447.2 (100); HRMS $(M+H)^+$447.1392 (calc.), 447.1391 (obs); $^1HNMR(DMSO)$ δ: 11.20 (s, 1H); 11.00 (s, 1H); 8.33 (brd, 4H); 7.98 (d, J=8.79, 2H); 7.88 (d, J=8.79, 2H); 7.64 (s, 1H): 7.48 (d, J=8.79, 2H); 7.07 (d, J=9.16, 2H); 3.82 (s, 3H) ppm.

Example 130

1-(4-Methoxyphenyl)-3-trifluoromethyl-1H-pyrazole-5-N-[4-(pyrimidin-2-yl)phenyl] carboxyamide Part A: Standard Suzuki coupling of the 4-trifluoromethylphenylboronic acid (0.88 g, 3.77 mmol) and 2-bromopyrimidine (0.5 g, 3.144 mmol) afforded the coupled product (0.47 g). LRMS(ESI) m/z 268.1 (100); $^1HNMR(CDCl_3)$ δ: 8.82 (d, J=5.1, 2H): 8.52 (d, J=8.8, 2H): 7.96 (brd, 1H): 7.73 (d, J=8.8, 2H); 7.23 (t, J=4.8, 1H) ppm; Hydrolysis of this compound with 1N NaOH/EtOH (1:1, 10 mL for 18 h, followed by purification using flash chromatography (4:1/Hexanes:Ethyl acetate) afforded the desired anilinopyrimidyl precursor (0.24 g). LRMS(NH$_3$-CI) m/z 172.2 (100); $^1$HNMR (CDCl$_3$) δ: 8.73 (d, J=5.1, 2H); 8.28 (m, 2H); 7.06 (t, J=5.1, 1H); 6.76 (m, 2H); 3.94 (brd, 2H) ppm.

1-(4-Methoxyphenyl)-3-trifluoromethyl-1H-pyrazole-5-N-[4-(pyrimidin-2-yl)phenyl]carboxyamide Part B: Standard DMAP (0.23 g, 1.92 mmol) coupling of the compound obtained in part A (0.13 g, 0.77 mmol) with trifluoromethylpyrazole acid chloride (0.22 g, 0.77 mmol of carboxylic acid) obtained previously afforded the desired coupled product which was purified via silica gel flash chromatography (hexane/ethyl acetate, 1:1) to afford the titled compound as colorless crystals (0.14 g).LRMS(ESI) m/z 440.1 (100); HRMS (M+H)$^+$440.1334 (calc.) 440.1333 (obs); $^1$HNMR(DMSO-D6) δ: 10.89 (s, 1H): 8.88 (d, J=4.8, 2H): 8.39 (d, J=8.8, 2H): 7.82 (d, J=8.4, 2H): 7.61 (s, 1H): 7.48 (d, J=8.8, 2H): 7.43 (t, J=4.7, 1H): 7.07 (d, J=9.2, 2H): 3.82 (s, 3H) ppm.

Example 131

2-(Carboxyamide)-4-[(4-methoxy)phenyl]-5-[(2'-aminosulfonyl-[1,1']-biphen-4-yl)carboxyamide]thiazole 2-Bromo-4-[(4-methoxy)phenyl]-5-(methoxycarbonyl)thiazole A mixture of copper (II) bromide (11.43 g, 51.2 mmol) and tert-butylnitrite (6.0 g, 58.2 mmol) in 200 mL of acetonitrile was stirred at 80° C. until gas evolution stopped (about 30 min). To this solution was added 2-amino-4-[(4-methoxy)phenyl]-5-(methoxycarbonyl)thiazole (12.3 g, 46.55 mmol) in 100 mL of acetonitrile. The solution was stirred at 80° C. until gas evolution stopped (about 1 h). The mixture was cooled, diluted with saturated aq Na$_2$CO$_3$ and then was filtered through a pad of celite. The filtrate was diluted with ethyl acetate and the organic layer was washed with saturated aq Na$_2$CO$_3$, dried (MgSO$_4$) and concentrated to afford 8.95 g (59%) of the title compound, which was used without purification. LRMS (ES+): 328 (M+H)$^+$.

2-Bromo-4-[(4-methoxy)phenyl]thiazole-5-carboxylic acid

To a solution of 2-bromo-4-[(4-methoxy)phenyl]-5-(methoxycarbonyl)th-azole (6.24 g, 19.74 mmol) in 20 mL of methanol and 20 mL of water was added lithium hydroxide monohydrate (0.91 g, 21.7 mmol). The mixture was stirred at ambient temperature for 1 h, whereupon additional lithium hydroxide monohydrate (0.91 g, 21.7 mmol) was added. After stirring an additional hour, the volatiles were removed in vacuo and the residue was quenched with 10% aq HCl. The mixture was extracted with ethyl acetate and the organics were washed with brine, dried (MgSO$_4$) and concentrated. The residue was recrystallized from chloroform/hexane to afford 2.2 g (37%) of the title compound as a white solid. LRMS (ES-): 303 (M-H)$^-$.

2-tert-Butylcarboxyamide-4-[(4-methoxy)phenyl]thiazole-5-carboxylic acid

To a solution of 2-bromo-4-[(4-methoxy)phenyl]thiazole-5-carboxylic acid (2.0 g, 6.36 mmol) in 70 mL of tetrahydrofuran at −78° C. was added tert-butyllithium (12.3 mL of a 1.7 M solution in hexanes, 21.0 mmol) dropwise. The reaction was stirred for 15 min and then tert-butylisocyanate was added dropwise. The cooling bath was removed and the reaction was allowed to stir with warming to room temperature for 18 h. The reaction was quenched with 10% aq HCl and then was diluted with ethyl acetate. The organic layer was washed with brine, dried (MgSO$_4$) and concentrated to afford 0.9 g (43%) of the title compound, which was used without purification. LRMS (ES-): 332.9 (M-H)$^-$.

2-(tert-Butylcarboxyamide)-4-[(4-methoxy)phenyl]-5-[(2'-(tert-butylamino)sulfonyl-[1,1']-biphen-4-yl)carboxyamide]thiazole To a solution of 2-(tert-butylamino)carbonyl-4-((4-methoxy)phenyl]thiazole-5-carboxylic acid (0.50 g, 1.49 mmol) in 10 mL of methylene chloride was added oxalyl chloride (0.16 mL, 1.86 mmol) and three drops of dimethylformamide. The reaction was allowed to stir at ambient temperature for 4 h and then the volatiles were removed in vacuo. The residue was dissolved in 10 mL of methylene chloride and then there was added 4-dimethylaminopyridine (0.36 g, 2.99 mmol). This mixture was stirred at ambient temperature for 15 min and then there was added 2'-(tert-butylamino)sulfonyl-[1,1']-biphen-4-ylamine (0.38 g, 1.24 mmol). The reaction was allowed to stir for 24 h. The reaction mixture was diluted with ethyl acetate, washed sequentially with 10% aq HCl, saturated aq NaHCO$_3$ and brine, dried (MgSO$_4$) and concentrated to afford 0.69 g (75%) of the title compound which was used without purification. LRMS (ES+): 643.4 (M+Na)$^+$.

2-(tert-Butylcarboxyamide)-4-[(4-methoxy)phenyl]-5-[(2'aminosulfonyl-[1,1']-biphen-4-yl)carboxyamide]thiazole A solution of 2-(tert-butylcarboxyamide)-4-[(4-methoxy)phenyl]-5-[(2'-(tert-butylamino)sulfonyl-[1,1']-biphen-4-yl)carboxyamide]thiazole (0.69 g, 1.11 mmol) in 5 mL of trifluoroacetic acid was stirred at 80° C. for 1 h and then cooled and concentrated in vacuo. The residue was purified by prep HPLC (C18 reverse phase column, elution with a H$_2$O/CH$_3$CN gradient with 0.5% TFA) and lyophilized to afford 0.34 g (53%) of the title compound as a white powder. LRMS (ES+): 565.1 (M+H)$^+$.

2-(Carboxyamide)-4-[(4-methoxy)phenyl]-5-[(2'-aminosulfonyl-[1,1']-biphen-4-yl)carboxyamide]thiazole A solution of 2-(tert-butylcarboxyamide) -4-[(4-methoxy)phenyl]-5-[(2'-aminosulfonyl-[1,1']-biphen-4-yl)carboxyamide]thiazole (70 mg, 0.10 mmol) in 20 mL of trifluoroacetic acid was stirred at 80° C. for 24 h. The reaction was cooled and concentrated in vacuo. The residue was purified by prep HPLC (C18 reverse phase column, elution with a H$_2$O/CH$_3$CN gradient with 0.5% TFA) and lyophilized to afford 20 mg (32%) of the title compound as a white powder. LRMS (ES+): 508.8 (M+H)$^+$.

Example 132

2-(2-Methoxyethylamine)-4-[(4-methoxy)phenyl]-5-[(2'-aminosulfonyl-[1,1'-biphen-4-yl)carboxyamide]thiazole To a solution of 2-bromo-4-[(4-methoxy)phenyl]-5-[(2'-aminosulfonyl-[1,1']-biphen-4-yl)carboxyamide]thiazole (25 mg, 0.046 mmol) in 3 mL of acetonitrile was added 2-methoxyethylamine (0.04 mL, 0.46 mmol). The resulting solution was stirred at 60° C. for 18 h and then was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 10 mg (41%) of the title compound as a white powder. LRMS (ES+): 538.9 (M+H)$^+$.

Example 133

2-(3-Hydroxypropylamino)-4-[(4-methoxy)-phenyl]-5-[(2'-aminosulfonyl-[1,1']-biphen-4-yl)carboxyamide]thiazole To a solution of 2-bromo-4-[(4-methoxy)phenyl]-5-[(2'-aminosulfonyl-[1,1']-biphen-4-yl)carboxyamide]thiazole (50 mg, 0.092 mmol) in 3 mL of acetonitrile was added 3-hydroxypropylamine (0.5 mL, 5.5 mmol). The resulting solution was stirred at 60° C. for 18 h and then was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 19 mg (37%) of the title compound as a white powder. LRMS (ES+): 538.9 (M+H)$^+$.

Example 134

2-(2-Cyanoethylamino)-4-[(4-methoxy)phenyl]-5-[(2'-aminosulfonyl-[1,1']-biphen-4-yl)carboxyamide]thiazole To a solution of 2-bromo-4-[(4-methoxy)phenyl]-5-[(2'-aminosulfonyl -[1,1']-biphen-4-yl)carboxyamide]thiazole (80 mg, 0.15 mmol) in 3 mL of acetonitrile was added 3-aminopropionitrile (0.11 mL, 1.5 mmol) The resulting solution was stirred at 60° C. for 48 h and then was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 35 mg (41%) of the title compound as a white powder. LRMS (ES+): 534.2 (M+H)$^+$.

Example 135

2-(3-Methoxypronpylamino)-4-[(4-methoxy)phenyl]-5-[(2'-aminosulfonyl-[1,1']-biphen-4-yl)carboxyamide]thiazole To a solution of 2-bromo-4-[(4-methoxy)phenyl]-5-[(2'-aminosulfonyl-[1,1']-biphen-4-yl)carboxyamide]thiazole (80 mg, 0.15 mmol) in 3 mL of acetonitrile was added 3-methoxypropylamine (0.15 mL, 1.5 mmol). The resulting solution was stirred at 60° C. for 18 h and then was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 25 mg (31%) of the title compound as a white powder. LRMS (ES+): 552.8 (M+H)$^+$.

Example 136

2-(N-β-Alanyl)-4-[(4-methoxy)-phenyl]-5-[(2'-aminosulfonyl-[1,1']-biphen -4-yl)carboxyamide]thiazole 2-(2-(methoxycarbonyl)ethylamino)-4-[(4-methoxy)phenyl]-5-[(2'-aminosulfonyl-[1,1']-biphen-4-yl)carboxyamide]thiazole. To a solution of 2-bromo-4-[(4-methoxy)phenyl]-5-[(2'-aminosulfonyl-[1,1']-biphen-4-yl)carboxyamide]thiazole (80 mg, 0.15 mmol) in 3 mL of acetonitrile was added methyl 3-aminopropionate hydrochloride (0.20 g, 1.5 mmol) and N,N-diisopropylethylamine (0.26 mL, 1.5 mmol). The resulting solution was stirred at 60° C. for 48 h and then was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 45 mg (55%) of the title compound as a white powder. LRMS (ES+): 567.2 (M+H)$^+$.

2-(N-β-alanyl)-4-[(4-methoxy)phenyl]-5-[(2'-aminosulfonyl-[1,1']-biphen-4-yl)carboxyamide]thiazole To a solution of 2-(2-(methoxycarbonyl)ethylamino) -4-[(4-methoxy)phenyl]-5-[(2'-aminosulfonyl-[1,1']-biphen-4-yl)carboxyamide]thiazole (38 mg, 0.066 mmol) in 2 mL of tetrahydrofuran and 2 mL of water was added lithium hydroxide monohydrate (5 mg, 0.13 mmol). The resulting solution was stirred at ambient temperature for 18 h and then was concentrated in vacuo. The residue was purified by prep HPLC (C18 reverse phase column, elution with a H$_2$O/CH$_3$CN gradient with 0.5% TFA) and lyophilized to afford 32 mg (88%) of the title compound as a white powder. LRMS (ES–): 665.0 (M–H+TFA)$^-$.

Example 137

2-(Isopropylamino)-4-[(4-methoxy)phenyl]-5-[(2'-aminosulfonyl-[1,1']-biphen-4-yl)carboxyamide]thiazole To a solution of 2-bromo-4-[(4-methoxy)phenyl]-5-[(2'-aminosulfonyl-[1,1']-biphen-4-yl)carboxyamide]thiazole (80 mg, 0.15 mmol) in 3 mL of acetonitrile was added isopropylamine (0.13 mL, 1.5 mmol). The resulting solution was stirred at 60° C. for 72 h and then was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 28 mg (37%) of the title compound as a white powder. LRMS (ES+): 523.1 (M+H)$^+$.

Example 138

2-(1, 3-Dihydroxy-2-propylamino)-4-[(4-methoxy)phenyl]-5-[(2'-aminosulfonyl-[1,1']-biphen-4-yl)carboxyamide]thiazole To a solution of 2-bromo-4-[(4-methoxy)phenyl]-5-[(2'-aminosulfonyl-[1,1']-biphen-4-yl)carboxyamide]thiazole (80 mg, 0.15 mmol) in 3 mL of acetonitrile was added 1, 3-dihydroxy-2 -aminopropane (0.13 g, 1.5 mmol). The resulting solution was stirred at 60° C. for 72 h and then at 75° C. for an additional 24 h. The reaction mixture was cooled, filtered through a small pad of silica gel and concentrated in vacuo. The residue was purified by prep HPLC (C18 reverse phase column, elution with a H$_2$O/CH$_3$CN gradient with 0.5% TFA) and lyophilized to afford 30 mg (37%) of the title compound as a white powder. LRMS (ES+): 555.1 (M+H)$^+$.

Example 139

2-[(Methoxycarbonyl)methylamino]-4-[(4-methoxy)phenyl]-5-[(2'-aminosulfonyl-[1,1']-biphen-4-yl)carboxyamide]thiazole To a solution of 2-bromo-4-[(4-methoxy)phenyl]-5-[(2'-aminosulfonyl-[1,1']-biphen-4-yl)carboxyamide]thiazole (80 mg, 0.15 mmol) in 3 mL of acetonitrile was added glycine methyl ester hydrochloride (0.18 g, 1.5 mmol) and N,N-diisopropylethylamine (0.26 mL, 1.5 mmol). The resulting solution was stirred at 60° C. for 72 h and then at 75° C. for an additional 24 h. The reaction mixture was cooled, filtered through a small pad of silica gel and concentrated in vacuo. The residue was purified by prep HPLC (C18 reverse phase column, elution with a $H_2O/CH_3CN$ gradient with 0.5% TFA) and lyophilized to afford 40 mg (49%) of the title compound as a white powder. LRMS (ES+): 553.0 (M+H)$^+$.

Example 140

2-(N-Glycyl)-4-[(4-methoxy)phenyl]-5-[(2'-aminosulfonyl-[1,1']-biphen -4-yl)carboxyamide] thiazole To a solution of 2-(2-(methoxycarbonyl)methylamino)-4-[(4-methoxy)phenyl ]-5-[(2'-aminosulfonyl-[1,1']-biphen-4-yl)carboxyamide]thiazole (27 mg, 0.049 mmol) in 2 mL of tetrahydrofuran and 2 mL of water was added lithium hydroxide monohydrate (4 mg, 0.098 mmol). The resulting solution was stirred at ambient temperature for 18 h and then was concentrated in vacuo. The residue was purified by prep HPLC (C18 reverse phase column, elution with a $H_2O/CH_3CN$ gradient with 0.5% TFA) and lyophilized to afford 16 mg (61%) of the title compound as a white powder. LRMS (ES–): 536.8 (M–H)$^-$.

Example 141

1-[(4-Methoxy)phenyl]-3-(ethoxycarbonyl)-1H-pyrazole-5-[(4-(N-pyrrolidinocarbonyl) phenyl) carboxyamide 1-[(4-methoxy)phenyl]-3,5-dimethylpyrazole To a solution of 4-methoxyphenylhydrazine hydrochloride (118.7 g, 0.68 mol) in 300 mL of glacial acetic acid was added 2, 4-pentanedione (68.0 g, 0.68 mol). The resulting solution was stirred at 100° C. for 18 h and then was cooled and concentrated in vacuo. The residue was dissolved in ethyl acetate, filtered through a pad of silica gel and concentrated to afford 131 g (95%) of the title compound, which was used without purification. LRMS ($NH_4$-CI): 203.3 (M+H)$^+$.

1-[(4-methoxy)phenyl]pyrazole-3,5-dicarboxylic acid

To a suspension of 1-[(4-methoxy)phenyl]-3, 5-dimethylpyrazole (131 g, 0.65 mol) in 400 mL of water was added potassium permanganate (410 g, 2.6 mol). This mixture was heated to 70° C. and was stirred for 1 h. The reaction was filtered and the filter cake was washed with hot water. The filtrate was acidified with HCl and then was extracted twice with ethyl acetate. The combined organics were washed with brine, dried (MgSO$_4$) and concentrated. The residue was triturated with chloroform and filtered to afford 39.7 g (23%) of the title compound. LRMS (ES–): 260.9 (M–H)$^-$.

Dimethyl 1-[(4-methoxy)phenyl]pyrazole-3,5-dicarboxylate

A solution of 1-[(4-methoxy)phenyl]pyrazole-3, 5-dicarboxylic acid (39.7 g, 0.15 mol) in 300 mL of anhydrous methanol was cooled to 0° C. and then anhydrous HCl was bubbled through the solution for 15 minutes through a gas dispersion tube. The flask was tightly stoppered and the reaction was allowed to stir at ambient temperature for 24 h. The volatiles were removed in vacuo. The residue was dissolved in ethyl acetate, filtered through a pad of silica gel and concentrated in vacuo to afford 32.8 g (74%) of the title compound which was used without purification. LRMS ($NH_4$ -CI): 291.2 (M+H)$^+$.

1-[(4-methoxy)phenyl]-5-(methoxycarbonyl) pyrazole-3-carboxylic acid

To a solution of dimethyl 1-[(4-methoxy)phenyl] pyrazole-3, 5-dicarboxylate (32.7 g, 110 mmol) in 50 mL of dioxane and 100 mL of water was added concentrated sulfuric acid (1.50 mL, 28.2 mmol). The resulting solution was stirred at 100° C. for 18 h and then cooled to room temperature. The reaction was made basic with potassium carbonate and then extracted with ether to remove unreacted diester. The aqueous layer was acidified with HCl and was extracted twice with ethyl acetate. The combined organics were washed with brine, dried (MgSO$_4$) and concentrated to afford 19.2 g (63%) of the title compound along with 5.0 g (15%) of unreacted starting material. The title compound was used without further purification. LRMS (ES–): 274.9 (M–H)$^-$.

1-[(4-methoxy)phenyl]-3-(ethoxycarbonyl)-5-(methoxycarbonyl)pyrazole

A solution of 1-[(4-methoxy)phenyl]-5-(methoxycarbonyl)pyrazole -3-carboxylic acid (7.50 g, 27.1 mmol) in 50 mL of thionyl chloride was stirred at 80° C. for 1 h. The volatiles were then removed and the residue was azeotroped with 20 mL of toluene and dried in vacuo. The residue was dissolved in 100 mL of tetrahydrofuran and then there was added diisopropylethylamine (11.8 mL, 67.9 mmol) and absolute ethanol (3.2 mL, 54.3 mmol). The reaction mixture was allowed to stir at ambient temperature for 24 h. The volatiles were removed and the residue was dissolved in ethyl acetate. This solution was filtered through a pad of silica gel and was concentrated in vacuo to afford 3.7 g (45%) of the title compound which was used without purification. LRMS (DCI): 305.1 (M+H)$^+$.

1-[(4-methoxy)phenyl]-3-(ethoxycarbonyl)pyrazole-5-carboxylic acid

To a solution 1-[(4-methoxy)phenyl]-3-(ethoxycarbonyl)-5-(methoxycarbonyl)pyrazole (4.0 g, 13.2 mmol) in 40 mL of tetrahydrofuran and 20 mL of water was added an aqueous solution of lithium hydroxide monohydrate (0.55 g, 13.2 mmol). The reaction was allowed to stir at ambient temperature for 1 h. The tetrahydrofuran was removed in vacuo and the aqueous was extracted with ether to remove unreacted diester. The aqueous layer was acidified with HCl and extracted with ethyl acetate. The organics were washed with brine, dried (MgSO$_4$) and concentrated to afford 3.2 g (84%) of the title compound, which was used without further purification. LRMS (ES–): 289.0 (M–H)$^-$.

1-[(4-methoxy)phenyl]-3-(ethoxycarbonyl)-1H-pyrazole-5-[(4-(N-pyrrolidinocarbonyl)phenyl) carboxyamide A solution of 1-[(4-methoxy)phenyl]-3-(ethoxycarbonyl) pyrazole-5-carboxylic acid (3.2 g, 11.1 mmol) in 20 mL of thionyl chloride was stirred at 80° C. for 1 h. The volatiles were then removed and the residue was azeotroped with 20 mL of toluene and dried in vacuo. The residue was dissolved in 50 mL of methylene chloride and then there was added triethylamine (4.6 mL, 33.3 mmol) and 4-(N- pyrrolidinocarbonyl)aniline (3.2 mL, 54.3 mmol). The reaction mixture was allowed to stir at ambient temperature for 4 h. The volatiles were removed and the residue was dissolved in ethyl acetate, washed sequentially with 10% aq HCl and brine, dried (MgSO$_4$), filtered through a short pad of silica gel and concentrated to afford 2.5 g (50%) of the title compound. A small portion was further purified by prep HPLC (C18 reverse phase column, elution with a H$_2$O/CH$_3$CN gradient with 0.5% TFA) and lyophilized to afford the title compound as a white powder. LRMS (ES+): 463.1 (M+H)$^+$.

Example 142

1-[(4-Methoxy)phenyl]-3-(carboxyamide)-1H-pyrazole-5-[(4-(N-pyrrolidinocarbonyl)phenyl) carboxyamide 1-[(4-methoxy)phenyl]-1H-pyrazole-5-[(4-(N-pyrrolidinocarbonyl)phenyl) carboxyamide-3-carboxylic acid To a solution 1-[(4-methoxy)phenyl]-3-(ethoxycarbonyl)-1H-pyrazole-5-[(4-(N-pyrrolidinocarbonyl)phenyl) carboxyamide (2.05 g, 4.43 mmol) in 10 mL of THF and 10 mL of water was added potassium hydroxide (0.32 g, 5.76 mmol). The resulting solution was stirred at ambient temperature for 18. The THF was removed in vacuo and the aqueous was extracted with ether to remove unreacted ester. The aqueous layer was acidified with HCl and extracted with ethyl acetate. The organics were washed with brine, dried (MgSO$_4$) and concentrated to afford 1.1 g (57%) of the title compound, which was used without further purification. LRMS (ES−): 433.0 (M−H)$^-$.

1-[(4-methoxy)phenyl]-3-(carboxyamide)-1H-pyrazole-5-[(4-(N-pyrrolidinocarbonyl) phenyl) carboxyamide To a solution of 1-[(4 -methoxy)phenyl]-1H-pyrazole-5-[(4-(N-pyrrolidinocarbonyl) phenyl)carboxyamide-3-carboxylic acid (117 mg, 0.27 mmol) in 10 mL of 1:1 THF/CH$_3$CN was added triethylamine (0.056 mL, 0.40 mmol) and iso-butyl chloroformate (0.038 mL, 0.30 mmol). After stirring at ambient temperature for 30 min, there was added methanolic ammonia solution (1.34 mL of a 2.0 M solution of ammonia in methanol, 2.7 mmol). The reaction was stirred for 1 h and then the volatiles were removed. The residue was purified by prep HPLC (C18 reverse phase column, elution with a H$_2$O/CH$_3$CN gradient with 0.5% TFA) and lyophilized to afford 50 mg (43%) of the title compound as a white powder. LRMS (ES+): 434.1 (M+H)$^+$.

Example 143

1-[(4-Methoxy)phenyl]-3-[(2-hydroxyethyl) carboxyamide]-1H-pyrazole -5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (110 mg, 0.25 mmol) in 5 mL of acetonitrile was added triethylamine (0.053 mL, 0.38 mmol) and iso-butyl chloroformate (0.036 mL, 0.28 mmol). After stirring at ambient temperature for 30 min, there was added ethanolamine (0.06 mL, 1.01 mmol). The reaction was stirred for 1 h and then the volatiles were removed. The residue was purified by prep HPLC (C18 reverse phase column, elution with a H$_2$O/CH$_3$CN gradient with 0.5% TFA) and lyophilized to afford 80 mg (67%) of the title compound as a white powder. LRMS (ES+): 478.0 (M+H)$^+$.

Example 144

1-[(4-Methoxy)-phenyl)-1H-pyrazole-5-[(4-(N-pyrrolidinocarbonyl) phenyl)carboxyamide-3-hydroxamic acid To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.064 mL, 0.46 mmol) and iso-butyl chloroformate (0.030 mL, 0.23 mmol). After stirring at ambient temperature for 30 min, there was added hydroxylamine hydrochloride (16 mg, 0.23 mmol). The reaction was stirred for 1 h and then the volatiles were removed. The residue was purified by prep HPLC (C18 reverse phase column, elution with a H$_2$O/CH$_3$CN gradient with 0.5% TFA) and lyophilized to afford 28 mg (27%) of the title compound as a white powder. LRMS (ES−): 562.1 (M−H+TFA)$^-$.

Example 145

1-(4-Methoxy)phenyl]-3-[phenylcarboxyamide]-1H-pyrazole-5-[(4-(N-pyrrolidinocarbonyl) phenyl) carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.064 mL, 0.46 mmol) and iso-butyl chloroformate (0.030 mL, 0.23 mmol). After stirring at ambient temperature for 30 min, there was added aniline (0.02 mL, 0.23 mmol). The reaction was stirred for 1 h and then the volatiles were removed. The residue was purified by prep HPLC (C18 reverse phase column, elution with a H$_2$O/CH$_3$CN gradient with 0.5% TFA) and lyophilized to afford 22 mg (19%) of the title compound as a white powder. LRMS (ES+): 510.2 (M+H)$^+$.

Example 146

1-[(4-Methoxy)phenyl-3-[(3-hydroxypropyl) carboxyamide]-1H-pyrazole -5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.064 mL, 0.46 mmol) and iso-butyl chloroformate (0.030 mL, 0.23 mmol). After stirring at ambient temperature for 30 min, there was added 3-hydroxypropylamine (0.02 mL, 0.23 mmol). The reaction was stirred for 1 h and then the volatiles were removed. The residue was purified by prep HPLC (C18 reverse phase column, elution with a H$_2$O/CH$_3$CN gradient with 0.5% TFA) and lyophilized to afford 38 mg (30%) of the title compound as a white powder. LRMS (ES+): 492.3 (M+H)$^+$.

Example 147

1-[(4-Methoxy)phenyl]-3-[methylcarboxyamide]-1H-pyrazole-5-[(4-(N-pyrrolidinocarbonyl) phenyl) carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added methylamine hydrochloride (23 mg, 0.35 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 15 mg (15%) of the title compound as a white powder. LRMS (ES+): 448.2 $(M+H)^+$.

Example 148

1-[(4-Methoxy)phenyl]-3-[(benzyl)carboxyamide]-1H-pyrazole-5-[(4-(N-pyrrolidinocarbonyl) phenyl) carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added benzylamine hydrochloride (49 mg, 0.35 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 19 mg (16%) of the title compound as a white powder. LRMS (ES+): 524.2 $(M+H)^+$.

Example 149

1-[(4-Methoxy)phenyl]-3-[(dimethyl)carboxyamide]-1H-pyrazole-5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added aqueous dimethylamine (0.040 mL of a 40% aqueous solution, 0.80 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 20 mg (19%) of the title compound as a white powder. LRMS (ES+): 462.2 $(M+H)^+$.

Example 150

1-[(4-Methoxy)phenyl]-3-[(Phenylethyl)carboxyamide]-1H-pyrazole-5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added phenethylamine (0.043 mL, 0.80 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 15 mg (12%) of the title compound as a white powder. LRMS (ES+): 538.2 $(M+H)^+$.

Example 151

1-[(4-Methoxy)phenyl]-3-[(2-hydroxyphenyl)carboxyamide]-1H-pyrazole -5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added 2-hydroxyaniline (75 mg, 0.69 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 10 mg (8%) of the title compound as a white powder. LRMS (ES+): 526.1 $(M+H)^+$.

Example 152

1-[(4-Methoxy)phenyl]-3-[(3-hydroxyphenyl)carboxyamide]-1H-pyrazole -5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added 3-hydroxyaniline (75 mg, 0.69 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 12 mg (10%) of the title compound as a white powder. LRMS (ES+): 526.2 $(M+H)^+$.

Example 153

1-[(4-Methoxy)phenyl-3-[(4-hydroxyphenyl)carboxyamide]-1H-pyrazole -5-[(4-(N-pyrrolidinocarbonyl)phenyl)carboxyamide To a solution of 1-[(4-methoxy)phenyl]-1H-pyrazole-5-[(4-(N-pyrrolidinocarbonyl) phenyl)carboxyamide-3-carboxylic acid (100 mg, 0.23 mmol) in 5 mL of acetonitrile was added triethylamine (0.096 mL, 0.69 mmol) and iso-butyl chloroformate (0.033 mL, 0.25 mmol). After stirring at ambient temperature for 30 min, there was added 4-hydroxyaniline (75 mg, 0.69 mmol). The reaction was stirred for 1 h and then the volatiles were removed. The residue was purified by prep HPLC (C18 reverse phase column, elution with a $H_2O/CH_3CN$ gradient with 0.5% TFA) and lyophilized to afford 12 mg (10%) of the title compound as a white powder. LRMS (ES+): 548.1 $(M+Na)^+$.

Example 154

1-[(4-Methoxy)phenyl]-3-[(methoxycarbonyl)amino]-1H-pyrazole-5-[(2'-aminosulfonyl-[1,1']-biphen-4-yl)carboxyamide 1-[(4-Methoxy)phenyl]-3-[(methoxycarbonyl)amino]-5-(methoxycarbonyl)pyrazole.

To a solution of 1-[(4-methoxy)phenyl]-5-(methoxycarbonyl)pyrazole-3-carboxylic acid (3.0 g, 10.9 mmol) in 50 mL of acetone at 0° C. was added triethylamine (1.66 mL, 11.9 mmol) followed by iso-butyl chloroformate (1.14 mL, 11.9 mmol). The resulting was stirred for 30 min whereupon an aqueous solution of sodium azide (2.82 g, 43.4 mmol) was added. The reaction was stirred at 0° C. for 1 h. The reaction was then diluted with ethyl acetate and washed with brine. The organics were dried ($MgSO_4$) and concentrated in vacuo. The residue was dissolved in 50 mL of toluene and stirred at 100° C. for 1 h. The volatiles were removed in vacuo and the residue was dissolved in methanolic sodium methoxide (5 mL of a 25% solution of sodium methoxide in methanol, 21 mmol) and stirred at ambient temperature for 2 h. The reaction was diluted with ethyl acetate, washed with water and brine, dried ($MgSO_4$) and concentrated in vacuo. The residue was purified by flash chromatography (elution with 1:1 hexanes/ethyl acetate) to afford 1.1 g (33%) of the title compound as a solid. LRMS (DCI): 306.3 (M+H)+.

1-[(4-Methoxy)phenyl]-3-[(methoxycarbonyl)amino]-1H-pyrazole-5-[(2'-tert-butylaminosulfonyl-[1,1']-biphen-4-yl)carboxyamide To a solution of (2'-tert-butylaminosulfonyl-[1,1']-biphen-4-yl)amine (0.90 g, 2.95 mmol) in 20 mL of methylene chloride at ambient temperature was added trimethylaluminum (8.85 mL of a 2.0 M solution in toluene, 17.68 mmol) dropwise. The resulting solution was allowed to stir until no more gas evolution was observed (~15 min). To this solution was added 1-[(4-methoxy)phenyl]-3-(methoxycarbonylamino) -5-(methoxycarbonyl)pyrazole (0.90 g, 2.95 mmol) in 10 mL of methylene chloride. The resulting solution was stirred at 40° C. for 16 h and then was cooled to ambient temperature and quenched by the addition of saturated aq $NH_4Cl$. After diluting with ethyl acetate, the organic layer was washed with 10% aq HCl, saturated aq $NaHCO_3$ and brine, dried ($MgSO_4$), filtered through a pad of silica gel and concentrated in vacuo. The solid residue was recrystallized from hexanes/ethyl acetate to afford 1.4 g (82%) of the title compound. LRMS (ES+): 577.9 (M+H)+.

1-[(4-Methoxy)phenyl]-3-[(methoxycarbonyl)amino]-1H-pyrazole-5-[(2'-aminosulfonyl-[1,1']-biphen-4-yl)carboxyamide A solution of 1-[(4-methoxy)phenyl]-3-[(methoxycarbonyl)amino]-1H-pyrazole-5-[(2'-tert-butylaminosulfonyl-[1,1']-biphen-4-yl)carboxyamide (0.40 g, 0.69 mmol) in 5 mL of trifluoroacetic acid was stirred at reflux for 20 min and then was cooled to ambient temperature and concentrated in vacuo. The residue was purified by prep HPLC (C18 reverse phase column, elution with a $H_2O/CH_3CN$ gradient with 0.5% TFA) and lyophilized to afford 200 mg (56%) of the title compound as a white powder. LRMS (ES+): 521.8 (M+H)+.

Example 155

1-[(4-Methoxy)phenyl]-3-amino-1H-pyrazole-5-[(2'-aminosulfonyl-[1,1']-biphen-4-yl)carboxyamide To a solution of 1-[(4-methoxy)phenyl]-3-[(methoxycarbonyl)amino]-1H-pyrazole-5-[(2'-aminosulfonyl-[1,1']-biphen-4-yl)carboxyamide (0.22 g, 0.42 mmol) in 10 mL of 1:1 water/methanol was added potassium hydroxide (2.0 g, 35 mmol). The resulting mixture was stirred at 70° C. for 4 h and then was cooled to ambient temperature and was acidified with aq HCl. The reaction mixture was diluted with ethyl acetate and the organics were washed with brine, dried ($MgSO_4$) and concentrated in vacuo. The residue was purified by prep HPLC (C18 reverse phase column, elution with a $H_2O/CH_3CN$ gradient with 0.5% TFA) and lyophilized to afford 75 mg (38%) of the title compound as a white powder. LRMS (ES+): 463.8 (M+H)+.

Example 156

1-[(4-Methoxy)phenyl]-3-[(methoxycarbonyl)methylamino]-1H-pyrazole -5-[(2'-aminosulfonyl-[1,1']-biphen-4-yl)carboxyamide To a solution of 1-[(4-methoxy)phenyl]-3-amino-1H-pyrazole-5-[(2'-tert-butylaminosulfonyl-[1,1']-biphen-4-yl)carboxyamide (1.0 g, 1.92 mmol) in 10 mL of DMF was added sodium bicarbonate (0.24 g, 2.88 mmol) and methyl bromoacetate (0.22 mL, 2.30 mmol) The resulting mixture was stirred at 85° C. for 16 h. The reaction was not complete so additional portions of sodium bicarbonate (0.48 g, 5.76 mmol) and methyl bromoacetate (0.22 mL, 2.30 mmol) were added and the reaction was stirred at 95° C. for 6 h longer. The reaction was cooled to ambient temperature and was diluted with ethyl acetate. The organics were washed with brine, dried ($MgSO_4$) and concentrated in vacuo. The residue was dissolved in 5 mL of trifluoroacetic acid and was stirred at reflux for 20 min and then was cooled to ambient temperature and concentrated in vacuo. The residue was purified by prep HPLC (C18 reverse phase column, elution with a $H_2O/CH_3CN$ gradient with 0.5% TFA) and lyophilized to afford 450 mg (44%) of the title compound as a white powder. LRMS (ES+): 536.0 (M+H)+.

Example 157

1-[(4-Methoxy)phenyl]-3-[(2-hydroxy)ethylamino]-1H-pyrazole-5-[(2'-aminosulfonyl-[1,1']-biphen-4-yl)carboxyamide 1-[(4-Methoxy)phenyl]-3-[N-glycyl]-1H-pyrazole-5-[(2'-aminosulfonyl -[1,1']-biphen-4-yl)carboxyamide To a solution of 1-[(4-methoxy)phenyl]-3-[(methoxycarbonyl)methylamino]-1H -pyrazole-5-[(2'-aminosulfonyl-[1,1']-biphen-4-yl)carboxyamide (0.40 g, 0.75 mmol) in 10 mL of 1:1 methanol/water was added lithium hydroxide monohydrate (0.13 g, 2.98 mmol). The resulting mixture was stirred at ambient temperature for 16 h. The reaction was acidified with aq HCl and was diluted with ethyl acetate. The organics were washed with brine, dried ($MgSO_4$) and concentrated in vacuo. The residue was purified by prep HPLC (C18 reverse phase column, elution with a $H_2O/CH_3CN$ gradient with 0.5% TFA) and lyophilized to afford 200 mg (51%) of the title compound as a white powder. LRMS (ES+): 522.0 (M+H)+.

1-[(4-Methoxy)phenyl]-3-[(2-hydroxy)ethylamino]-1H-pyrazole-5-[(2'-aminosulfonyl-[1,1']-biphen-4-yl)carboxyamide To a solution of 1-[(4-methoxy)phenyl]-3-[N-glycyl]-1H-pyrazole-5-[(2'-aminosulfonyl-[1,1']-biphen-4-yl) carboxyamide (0.14 g, 0.27 mmol) in tetrahydrofuran at −20° C. was added triethylamine (0.038 mL, 0.27 mmol) and ethyl chloroformate (0.026 mL, 0.27 mmol). This mixture was stirred for 30 min and then there was added sodium borohydride (20 mg, 0.54 mmol) in a minimal amount of water. The reaction mixture was stirred with slow warming to room temperature for 1 h and then was quenched with 10% aq HCl. After diluting with ethyl acetate, the organics were washed with brine, dried ($MgSO_4$) and concentrated in vacuo. The residue was purified by prep HPLC (C18 reverse phase column, elution with a $H_2O/CH_3CN$ gradient with 0.5% TFA) and lyophilized to afford 35 mg (26%) of the title compound as a white powder. LRMS (ES+): 507.9 (M+H)+.

Example 158

1-[(4-Methoxy)phenyl]-3-[E-2-(methoxycarbonyl)ethenyl]-1H -pyrazole-5-[(2'-aminosulfonyl-[1,1']-biphen-4-yl)carboxyamide 1-[(4-Methoxy)phenyl]-3-(hydroxymethyl)-1H-pyrazole-5-(methoxycarbonyl)pyrazole To a solution of 1-[(4-methoxy)phenyl]-1H-pyrazole-5-(methoxycarbonyl)pyrazole-3-carboxylic acid (2.4 g, 8.69 mmol) in 50 mL of tetrahydrofuran at −20° C. was added triethylamine (1.21 mL, 8.69 mmol) and ethyl chloroformate (0.83 mL, 8.69 mmol). This mixture was stirred for 30 min and then there was added sodium borohydride (0.66 g, 17.4 mmol) in a minimal amount of water. The reaction mixture was stirred with slow warming to room temperature for 1 h and then was quenched with 10% aq HCl. After diluting with ethyl acetate, the organics were washed with brine, dried (MgSO$_4$) and concentrated in vacuo. The residue was purified by flash chromatography (elution with 3:2 ethyl acetate/hexane) to afford 1.4 g (61%) of the title compound. LRMS (DCI): 263.3 (M+H)+.

1-[(4-Methoxy)phenyl]-3-(hydroxymethyl)-1H-pyrazole-5-[(2'-tert-butylaminosulfonyl -[1,1']-biphen-4-yl)carboxyamide To a solution of (2'-tert-butylaminosulfonyl-[1,1']-biphen-4-yl)amine (1.44 g, 4.73 mmol) in 40 mL of methylene chloride at ambient temperature was added trimethylaluminum (14.2 mL of a 2.0 M solution in toluene, 28.4 mmol) dropwise. The resulting solution was allowed to stir until no more gas evolution was observed (~15 min). To this solution was added 1-[(4-methoxy)phenyl]-3-(hydroxymethyl) -5-(methoxycarbonyl)pyrazole (1.24 g, 4.73 mmol) in 10 mL of methylene chloride. The resulting solution was stirred at 40° C. for 16 h and then was cooled to ambient temperature and quenched by the addition of saturated aq NH$_4$Cl. After diluting with ethyl acetate, the organic layer was washed with 10% aq HCl, saturated aq NaHCO$_3$ and brine, dried (MgSO$_4$), filtered through a pad of silica gel and concentrated in vacuo. The solid residue was recrystallized from hexanes/ethyl acetate to afford 1.7 g (68%) of the title compound. LRMS (ES+): 557.1 (M+Na)$^+$.

1-[(4-Methoxy)phenyl]-3-(carboxaldehyde)-1H-pyrazole-5-[(2'-tert-butylaminosulfonyl -[1,1']-biphen-4-yl)carboxyamide To a solution of oxalyl chloride (0.33 mL, 3.81 mmol) in 20 mL of methylene chloride at−78° C. was added dimethyl sulfoxide (0.54 mL, 7.63 mmol). This mixture was stirred for 15 minutes and then 1-[(4-methoxy)phenyl]-3-(hydroxymethyl)-1H-pyrazole-5-[(2'-tert-butylaminosulfonyl -[1,1']-biphen-4-yl)carboxyamide (1.70 g, 3.18 mmol) was added in 10 mL of methylene chloride. The reaction was allowed to stir while slowly warming to room temperature over 2 h. Triethylamine (2.21 mL, 15.90 mmol) was added and the reaction was stirred at room temperature for 30 min. The reaction was diluted with ethyl acetate and the organic layer was washed with 10% HCl, sat'd aq NaHCO$_3$ and brine, dried (MgSO$_4$), filtered through a pad of silica gel and concentrated in vacuo to afford 1.3 g (76%) of the title compound which was sufficiently pure to be used without purification. LRMS (ES+): 533.2 (M+H)$^+$.

1-[(4-Methoxy)phenyl]-3-[E-2-(methoxycarbonyl) ethenyl]-1H-pyrazole -5-[(2'-tert-butylaminosulfonyl-[1,1']-biphen-4-yl)carboxyamide To a solution of 1-[(4-methoxy)phenyl]-3-(carboxaldehyde) -1H-pyrazole-5-[(2'-tert-butylaminosulfonyl-[1,1']-biphen-4-yl)carboxyamide (1.30 g, 2.44 mmol) in 30 mL of methylene chloride was added methyl (triphenylphosphoranylidene)acetate (0.98 g, 2.92 mmol). The mixture was allowed to stir at ambient temperature for 18 h. The volatiles were removed in vacuo and the residue was purified by flash chromatography (elution with 1:1 ethyl acetate/hexane) to afford 1.2 g (83%) of the title compound. LRMS (ES+): 589.1 (M+H)$^+$.

1-[(4-Methoxy)phenyl]-3-[E-2-(methoxycarbonyl) ethenyl]-1H-pyrazole -5-[(2'-aminosulfonyl-[1,1']-biphen-4-yl)carboxyamide A solution of 1-[(4-methoxy)phenyl]-3-[E-2-(methoxycarbonyl)ethenyl]-1H-pyrazole-5-[(2'-tert-butylaminosulfonyl -[1,1']-biphen-4-yl)carboxyamide (1.2 g, 2.04 mmol) in 10 mL of trifluoroacetic acid was stirred at reflux for 20 min and then was cooled to ambient temperature and concentrated in vacuo. The residue was purified by prep HPLC (C18 reverse phase column, elution with a H$_2$O/CH$_3$CN gradient with 0.5% TFA) and lyophilized to afford 1.0 g (90%) of the title compound as a white powder. LRMS (ES+): 533.0 (M+H)$^+$.

Example 159

1-[(4-Methoxy)phenyl]-3-[2-(methoxycarbonyl) ethyl]-1H-pyrazole-5-[(2'-aminosulfonyl -[1,1']-biphen-4-yl)carboxyamide To a solution of 1-[(4-methoxy)phenyl]-3-[E-2-(methoxycarbonyl) ethenyl]-1H-pyrazole-5-[(2'-aminosulfonyl-[1,1']-biphen-4-yl) carboxyamide (35 mg, 0.065 mmol) in 20 mL of absolute ethanol at ambient temperature was added 10% palladium on carbon catalyst (3.5 mg). This mixture was stirred under 1 atm of hydrogen gas for 3 h and then was filtered through a pad of celite and concentrated in vacuo. The residue was purified by prep HPLC (C18 reverse phase column, elution with a H$_2$O/CH$_3$CN gradient with 0.5% TFA) and lyophilized to afford 15 mg (42%) of the title compound as a white powder. LRMS (ES+): 534.9 (M+H)$^+$.

Example 160

1-[(4-Methoxy)phenyl]-3-[E-2-(carboxy)ethenyl]-1H-pyrazole-5-[(2'-aminosulfonyl -[1,1']-biphen-4-yl)carboxyamide To a solution of 1-[(4-methoxy)phenyl]-3-[E-2-(methoxycarbonyl)ethenyl]-1H-pyrazole-5-[(2'-aminosulfonyl-[1,1']-biphen -4-yl)carboxyiamide (1.2 g, 2.25 mmol) in 20 mL of 1:1 methanol/water at ambient temperature was lithium hydroxide monohydrate (0.19 g, 4.5 mmol). This mixture was stirred for 3 h and then was acidified with aq HCl and diluted with ethyl acetate. The organics were washed with brine, dried (MgSO$_4$) and concentrated in vacuo. The residue was purified by prep HPLC (C18 reverse phase column, elution with a H$_2$O/CH$_3$CN gradient with 0.5% TFA) and lyophilized to afford 1.0 g (83%) of the title compound as a white powder. LRMS (ES-): 516.8 (M-H)$^-$.

Example 161

1-[(4-Methoxy)phenyl]-3-[2-(carboxy)ethyl]-1H-pyrazole-5-[(2'-aminosulfonyl -[1,1']-biphen-4-yl) carboxyamide To a solution of 1-1[(4-methoxy)phenyl]-3-[E-2-(carboxy)ethenyl]-1H -pyrazole-5-[(2'-aminosulfonyl-[1,1']-biphen-4-yl)carboxyamide (40 mg, 0.077 mmol) in 20 mL of absolute ethanol at ambient temperature was added 10% palladium on carbon catalyst (20 mg). This mixture was stirred under 1 atm of hydrogen gas for 3 h and then was filtered through a pad of celite and concentrated in vacuo. The residue was purified by prep HPLC (C18 reverse phase column, elution with a H$_2$O/CH$_3$CN gradient with 0.5% TFA) and lyophilized to afford 10 mg (25%) of the title compound as a white powder. LRMS (ES+): 520.9 (M+H)$^+$.

Example 162

1-[(4-Methoxy)-phenyl]-3-[E-2-(carboxyamide) ethenyl]-1H-pyrazole-5-[(2'-aminosulfonyl-[1,1']-biphen-4-yl)carboxyamide

To a solution of 1-[(4-methoxy)phenyl]-3-[E-2-(carboxy) ethenyl]-1H-pyrazole-5-[(2'-aminosulfonyl-[1,1']-biphen-4-yl)carboxyamide (140 mg, 0.27 mmol) in 10 mL of acetonitrile was added triethylamine (0.11 mL, 0.81 mmol) and iso-butyl chloroformate (0.039 mL, 0.30 mmol). After stirring at ambient temperature for 30 min, there was added methanolic ammonia solution (0.27 mL of a 2.0 M solution of ammonia in methanol, 0.54 mmol). The reaction was stirred for 16 h and then the volatiles were removed. The residue was purified by prep HPLC (C18 reverse phase column, elelution with a $H_2O/CH_3CN$ gradient with 0.5% TFA) and lyophilized to afford 35 mg (25%) of the title compound as a white powder. LRMS (ES+): 517.9 $(M+H)^+$.

Example 163

1-[(4-Methoxy)phenyl]-3-[E-2-(hydroxymethyl) ethenyl]-1H-pyrazole -5-[(2'-aminosulfonyl-[1,1']-biphen-4-yl)carboxyamide

To a solution of 1-[(4-methoxy)phenyl]-3-[E-2-(carboxy) ethenyl]-1H-pyrazole-5-[(2'-aminosulfonyl-[1,1']-biphen-4-yl)carboxyamide (1.0 g, 1.93 mmol) in 20 mL of tetrahydrofuran at -20° C. was added triethylamine (0.27 mL, 1.93 mmol) and iso-butyl chloroformate (0.25 mL, 1.93 mmol). This mixture was stirred for 30 min and then there was added sodium borohydride (0.22 g, 5.78 mmol) in a minimal amount of water. The reaction mixture was stirred with slow warming to room temperature for 1 h and then was quenched with 10% aq HCl. After diluting with ethyl acetate, the organics were washed with brine, dried (MgSO4) and concentrated in vacuo. The residue was purified by prep HPLC (C18 reverse phase column, elution with a $H_2O/CH_3CN$ gradient with 0.5% TFA) and lyophilized to afford 0.5 g (52%) of the title compound as a white powder. LRMS (ES+): 504.9 $(M+H)^+$.

Example 164

1-[(4-Methoxy)phenyl]-3-(3-hydroxypropyl)-1H-pyrazole-5-[(2'-aminosulfonyl -[1,1']-biphen-4-yl)carboxyamide

And Example 165

1-[(4-Methoxy)phenyl-3-propyl-1H-pyrazole-5-[(2'-aminosulfonyl -[1,1']-biphen-4-yl)carboxyamide

To a solution of 1-[(4-methoxy)phenyl]-3-[E-2-(hydroxymethyl)ethenyl]-1H-pyrazole-5-[(2'-aminosulfonyl-[1,1']-biphen-4-yl) carboxyamide (40 mg, 0.08 mmol) in 20 mL methanol at ambient temperature was added 10% palladium on carbon catalyst (4 mg). This mixture was stirred under 1 atm of hydrogen gas for 3 h and then was filtered through a pad of celite and concentrated in vacuo. The residue was purified by prep HPLC (C18 reverse phase column, elution with a $H_2O/CH_3CN$ gradient with 0.5% TFA) and lyophilized to afford 15 mg (38%) of EXAMPLE 164 as a white powder. LRMS (ES+) 506.9 $(M+H)^+$. There was also obtained 8 mg (20%) of EXAMPLE 165 as a white powder. LRMS (ES+): 490.9 $(M+H)^+$.

Example 166

1-[(4-Methoxy)phenyl]-3-(trifluoromethyl)-4-cyano-1H-pyrazole-5-[(2'-methylsulfonyl-3-fluoro-[1,1']-biphen-4-yl)carboxyamide

1-[(4-Methoxy)phenyl]-3-(trifluoromethyl)-4-cyano-1H-pyrazole-5-(2-furyl)pyrazole

To a solution of 2-furoylacetonitrile (0.91 g, 6.73 mmol) in 20 mL of absolute ethanol was added sodium ethoxide (2.5 mL of a 21% weight solution in ethanol, 6.73 mmol) followed by 2, 2, 2-trifluoroacetoyl bromide-N-(4-methoxyphenyl)hydrazone (2.0 g, 6.73 mmol). This mixture was stirred at ambient temperature for 4 h. The volatiles were removed in vacuo and the residue was dissolved in ethyl acetate, washed with water and brine, dried (MgSO4) and concentrated. The residue was purified by recrystallization from hexane/ethyl acetate to afford 1.1 g (49%) of the title compound.

1-[(4-Methoxy)phenyl]-3-(trifluoromethyl)-4-cyano-pyrazole-5-carboxylic acid

To a solution of 1-[(4-methoxy)phenyl]-3-(trifluoromethyl) -4-cyano-5-(2-furyl)pyrazole (0.68 g, 2.04 mmol) in 4:4:6 carbon tetrachloride/acetonitrile/water was added sodium periodate (1.96 g, 9.2 mmol) and ruthenium (III) chloride monohydrate (42 mg, 0.20 mmol). The resulting biphasic reaction was stirred vigorously at ambient temperature for 24 h. The reaction was quenched with 10% aq HCl and diluted with ethyl acetate. The organics were washed with brine, dried (MgSO4), filtered through a pad of Celite and concentrated. The residue was dissolved in 1:1 hexanes/ethyl acetate and extracted with sat'd aq $Na_2CO_3$ (2 times). The combined aqueous extracts were acidified and extracted with ethyl acetate. The ethyl acetate extracts were washed with brine, dried (MgSO4) and concentrated to afford 0.42 g (67%) of the title compound as a solid. LRMS (ES-): 310.0 $(M-H)^-$.

1-[(4-Methoxy)phenyl]-3-(trifluoromethyl)-4-cyano-1H-pyrazole-5-[(2'-methylsulfonyl-3-fluoro-[1,1']-biphen-4-yl)carboxyamide

To a solution of 1-[(4-methoxy)phenyl]-3-(trifluoromethyl)-4-cyano-pyrazole -5-carboxylic acid (0.41 g, 1.32 mmol) in 20 mL of methylene chloride was added oxalyl chloride (0.17 mL, 1.98 mmol) and 2 drops of dimethylformamide. The reaction was stirred at ambient temperature for 6 h and then the volatiles were removed in vacuo. The residue was dissolved in 20 mL of methylene chloride and then there was added 4-dimethylaminopyridine (0.48 g, 3.96 mmol). The reaction was stirred for 10 min and then there was added (2'-methylsulfonyl-3-fluoro-[1,1']-biphen-4-yl)amine hydrochloride (0.47 g, 1.45 mmol). The resulting mixture was allowed to stir at ambient temperature for 16 h. The reaction was diluted with ethyl acetate and the organics were washed with 10% aq HCl, sat'd aq $NaHCO_3$ and brine, dried (MgSO4), filtered through a pad of silica gel and concentrated to afford 0.6 g (81%) of the title compound as a tan solid. LRMS (ES+): 581.3 $(M+Na)^+$.

Example 167

1-[(4-Methoxy)phenyl-3-(trifluoromethyl)-4-(amidino)-1H-pyrazole -5-[(2'-methylsulfonyl-3-fluoro-[1,1']-biphen-4-yl)carboxyamide

And Example 168

1-[(4-Methoxy)phenyl]-3-(trifluoromethyl)-4-(N-hydroxyamidino)-1H-pyrazole -5-[(2'-methylsulfonyl-3-fluoro-[1,1']-biphen-4-yl) carboxyamide

To a solution of 1-[(4-methoxy)phenyl]-3-(trifluoromethyl)-4-cyano -1H-pyrazole-5-[(2'-methylsulfonyl-3-fluoro-[1,1']-biphen-4-yl)carboxyamide (100 mg, 0.18 mmol) in 5 mL of absolute ethanol was added hydroxylamine hydrochloride (38 mg, 0.54 mmol) and sodium carbonate (29 mg, 0.27 mmol). This mixture was stirred at 80° C. for 16 h. The reaction was diluted with water and ethyl acetate. The organics were washed with brine, dried (MgSO$_4$) and concentrated to a solid. The residue was dissolved in 10 mL of absolute ethanol and then there was added cyclohexene (1 mL), 20% palladium hydroxide on carbon (50 mg) and acetic acid (0.02 mL, 0.36 mmol). The resulting mixture was stirred at 80° C. for 6 h. The reaction was allowed to cool and was filtered through a pad of celite and concentrated in vacuo. The residue was purified by prep HPLC (C18 reverse phase column, elution with a H$_2$O/CH$_3$CN gradient with 0.5% TFA) and lyophilized to afford 20 mg (16%) of EXAMPLE 167 as a white powder. LRMS (ES+): 576.2 (M+H)$^+$. There was also obtained 15 mg (12%) of EXAMPLE 168 as a white powder. LRMS (ES+): 592.2 (M+H)$^+$.

Example 169

1-[(4-Methoxy)phenpyl]-3-(trifluoromethyl)-4-(ethoxycarbonyl)-1H-pyrazole -5-[(2'-methylsulfonyl-3-fluoro-[1,1']-biphen-4-yl) carboxyamide 1-[(4-Methoxy)phenyl]-3-(trifluoromethyl)-4-(ethoxycarbonyl)-5-(2-furyl)pyrazole To a solution of ethyl 3-(2-furyl)-3-ketopropionate (2.45 g, 13.4 mmol) in 20 mL of absolute ethanol was added sodium ethoxide (4.6 mL of a 21% weight solution in ethanol, 12.2 mmol) followed by 2, 2, 2-trifluoroacetoyl bromide -N-(4-methoxyphenyl)hydrazone (1.82 g, 6.1 mmol). This mixture was stirred at ambient temperature for 4 h. The volatiles were removed in vacuo and the residue was dissolved in ethyl acetate, washed with water and brine, dried (MgSO$_4$) and concentrated. The residue was purified by recrystallization from hexane/ethyl acetate to afford 1.4 g (61%) of the title compound. LRMS (ES+): 381.2 (M+H)$^+$.

1-[(4-Methoxy)phenyl]-3-(trifluoromethyl)-4-(ethoxycarbonyl)-pyrazole -5-carboxylic acid To a solution of 1-[(4-methoxy)phenyl]-3-(trifluoromethyl)-4-(ethoxycarbonyl)-5-(2-furyl)pyrazole (1.0 g, 2.63 mmol) in 4:4:6 carbon tetrachloride/acetonitrile/water was added sodium periodate (2.5 g, 11.8 mmol) and ruthenium (III) chloride monohydrate (11 mg, 0.05 mmol). The resulting biphasic reaction was stirred vigorously at ambient temperature for 24 h. The reaction was quenched with 10% aq HCl and diluted with ethyl acetate. The organics were washed with brine, dried (MgSO$_4$), filtered through a pad of Celite and concentrated. The residue was dissolved in 1:1 hexanes/ethyl acetate and extracted with sat'd aq Na$_2$CO$_3$ (2 times). The combined aqueous extracts were acidified and extracted with ethyl acetate. The ethyl acetate extracts were washed with brine, dried (MgSO$_4$) and concentrated to afford 0.5 g (53%) of the title compound as a solid. LRMS (ES-): 357.0 (M-H)$^-$.

1-[(4-Methoxy)phenyl]-3-(trifluoromethyl)-4-(ethoxycarbonyl)-1H-pyrazole -5-[(2'-methylsulfonyl-3-fluoro-[1,1']-biphen-4-yl) carboxyamide To a solution of 1-[(4-methoxy)phenyl]-3-(trifluoromethyl) -4-(ethoxycarbonyl)-pyrazole-5-carboxylic acid (0.5 g, 1.4 mmol) in 10 mL of methylene chloride was added oxalyl chloride (0.18 mL, 2.1 mmol) and 2 drops of dimethylformamide. The reaction was stirred at ambient temperature for 6 h and then the volatiles were removed in vacuo. The residue was dissolved in 20 mL of methylene chloride and then there was added 4-dimethylaminopyridine (0.51 g, 4.2 mmol). The reaction was stirred for 10 min and then there was added (2'-methylsulfonyl-3-fluoro -[1,1']-biphen-4-yl)amine hydrochloride (0.42 g, 1.4 mmol). The resulting mixture was allowed to stir at ambient temperature for 16 h. The reaction was diluted with ethyl acetate and the organics were washed with 10% aq HCl, sat'd aq NaHCO$_3$ and brine, dried (MgSO$_4$), filtered through a pad of silica gel and concentrated to afford 0.6 g (70%) of the compound of EXAMPLE 169 as a solid. A portion was purified by prep HPLC (C18 reverse phase column, elution with a H$_2$O/CH$_3$CN gradient with 0.5% TFA) and lyophilized to afford the title compound as a white powder. LRMS (ES+): 628.1 (M+Na)$^+$.

Example 170

1-[(4-Methoxy)phenyl]-3-(trifluoromethyl)-1H-pyrazole-5-[(2'-methylsulfonyl -3-fluoro-[1,1']-biphen-4-yl)carboxyamide-4-carboxylic acid To a solution of 1-[(4-methoxy)phenyl]-3-(trifluoromethyl)-4 -(ethoxycarbonyl)-1H-pyrazole-5-[(2'-methylsulfonyl-3-fluoro-[1,1']-biphen-4-yl)carboxyamide (0.30 g, 0.49 mmol) in 10 mL of 1:1 methanol/water was added potassium hydroxide (55 mg, 0.98 mmol). The reaction was stirred at 60° C. for 2 h and then was cooled to room temperature and acidified with 10% aq HCl. The mixture was diluted with ethyl acetate, washed with brine, dried (MgSO$_4$) and concentrated. The residue was purified by prep HPLC (C18 reverse phase column, elution with a H$_2$O/CH$_3$CN gradient with 0.5% TFA) and lyophilized to afford 150 mg (53%) of the title compound as a white powder. LRMS (ES-): 576.2 (M-H)$^-$.

TABLE 1

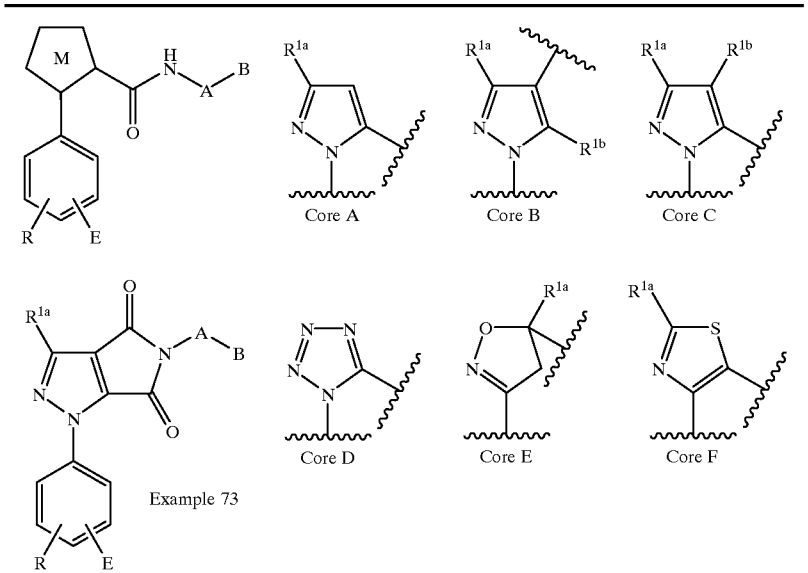

| Ex | R,E | M | $R^{1a}$ | A-B |
|---|---|---|---|---|
| 1 | — | Core-A | $CH_3$ | 2'-$H_2NSO_2$-biphen-4-yl |
| 2 | 2-$CH_3O$ | Core-A | $CH_3$ | 2'-$H_2NSO_2$-biphen-4-yl |
| 3 | 3-$CH_3O$ | Core-A | $CH_3$ | 2'-$H_2NSO_2$-biphen-4-yl |
| 4 | 4-$CH_3O$ | Core-A | $CH_3$ | 2'-$H_2NSO_2$-biphen-4-yl |
| 5 | 2-HO | Core-A | $CH_3$ | 2'-$H_2NSO_2$-biphen-4-yl |
| 6 | 3-HO | Core-A | $CH_3$ | 2'-$H_2NSO_2$-biphen-4-yl |
| 7 | 4-HO | Core-A | $CH_3$ | 2'-$H_2NSO_2$-biphen-4-yl |
| 8 | 4-$CH_3O$ | Core-A | $CH_3$ | 2'-$H_2NSO_2$-3-F-biphen-4-yl |
| 9 | 4-$CH_3O$ | Core-A | $CH_3$ | 2'-$H_2NSO_2$-3-Br-biphen-4-yl |
| 10 | 4-$CH_3O$ | Core-A | $CH_3$ | 2'-$H_2NSO_2$-3-I-biphen-4-yl |
| 11 | 4-$CH_3O$ | Core-A | $CH_3$ | 2'-$H_2NSO_2$-3-methylbiphen-4-yl |
| 12 | 4-$CH_3O$ | Core-A | $CH_3$ | 4-$(CH_3)_2NC(O))C_6H_4$ |
| 13 | 4-$CH_3O$ | Core-A | $CH_3$ | 4-(N-pyrrolidinocarbonyl)$C_6H_4$ |
| 14 | 4-$CH_3O$ | Core-A | $CH_3$ | 4-(N-pyrrolidinomethyl)$C_6H_4$ |
| 15 | 4-$CH_3O$ | Core-A | $CF_3$ | 2'-$H_2NSO_2$-biphen-4-yl |
| 16 | 4-$CH_3O$ | Core-A | $CF_3$ | 4-(N-pyrrolidinocarbonyl)$C_6H_4$ |
| 17 | 4-$CH_3O$ | Core-A | $CF_3$ | 5-(2'-$CH_3SO_2$-$C_6H_4$)pyrid-2-yl |
| 18 | 4-$CH_3O$ | Core-A | $CF_3$ | 5-(N-pyrrolidinocarbonyl)pyrid-2-yl |
| 19 | 4-$CH_3O$ | Core-A | $CH_3$ | 5-(N-pyrrolidinocarbonyl)pyrid-2-yl |
| 20 | 4-$CH_3O$ | Core-A | $CH_3$ | 5-(2'-$H_2NSO_2$-$C_6H_4$)pyrid-2-yl |
| 21 | 4-$CH_3O$ | Core-A | $CH_3$ | 4-(3'-HO-N-pyrrolidinocarbonyl)$C_6H_4$ |
| 22 | 4-$CH_3O$ | Core-F | $NH_2$ | 2'-$H_2NSO_2$-biphen-4-yl |
| 23 | 4-$CH_3O$ | Core-F | Br | 2'-$H_2NSO_2$-biphen-4-yl |
| 24 | 4-$CH_3O$ | Core-F | Cl | 2'-$H_2NSO_2$-biphen-4-yl |
| 25 | 4-HO | Core-F | Cl | 2'-$H_2NSO_2$-biphen-4-yl |
| 26 | 4-$CH_3O$ | Core-F | $CH_3O$ | 2'-$H_2NSO_2$-biphen-4-yl |
| 27 | 4-$CH_3O$ | Core-F | $CH_3S$ | 2'-$H_2NSO_2$-biphen-4-yl |
| 28 | 4-$CH_3O$ | Core-F | $CH_3S(O)$ | 2'-$H_2NSO_2$-biphen-4-yl |
| 29 | 4-$CH_3O$ | Core-F | $CH_3SO_2$ | 2'-$H_2NSO_2$-biphen-4-yl |
| 30 | 4-$CH_3O$ | Core-F | —CN | 2'-$H_2NSO_2$-biphen-4-yl |
| 31 | 4-$CH_3O$ | Core-F | $(CH_3)_2N$ | 2'-$H_2NSO_2$-biphen-4-yl |
| 32 | 4-$CH_3O$ | Core-F | pyrrol-1-yl | 2'-$H_2NSO_2$-biphen-4-yl |
| 33 | 4-$CH_3O$ | Core-E | $CH_2CO_2H_3$ | 5-(2'-$H_2NSO_2$-$C_6H_4$)pyrid-2-yl |
| 34 | 4-$CH_3O$ | Core-E | $CH_2CO_2H$ | 5-(2'-$H_2NSO_2$-$C_6H_4$)pyrid-2-yl |
| 35 | 4-$CH_3O$ | Core-E | (a) | 5-(2'-$H_2NSO_2$-$C_6H_4$)pyrid-2-yl |
| 36 | 4-$CH_3O$ | Core-E | (b) | 5-(2'-$H_2NSO_2$-$C_6H_4$)pyrid-2-yl |
| 37 | 4-$CH_3O$ | Core-D | — | 2'-$H_2NSO_2$-biphen-4-yl |
| 38 | 4-$CH_3O$ 3-Cl | Core-A | $CH_3$ | 2'-$H_2NSO_2$-biphen-4-yl |
| 39 | 4-$CF_3O$ | Core-A | $CH_3$ | 2'-$H_2NSO_2$-biphen-4-yl |
| 40 | 3-Br | Core-A | $CH_3$ | 2'-$H_2NSO_2$-biphen-4-yl |
| 41 | 3-I | Core-A | $CH_3$ | 2'-$H_2NSO_2$-biphen-4-yl |
| 42 | 3,4-$OCH_2O$ | Core-A | $CH_3$ | 2'-$H_2NSO_2$-biphen-4-yl |
| 43 | 4-$CH_3O$ | Core-A | $CH_2OH$ | 4-(N-pyrrolidinocarbonyl)$C_6H_4$ |
| 44 | 4-$CH_3O$ | Core-A | CHO | 4-(N-pyrrolidinocarbonyl)$C_6H_4$ |
| 45 | 4-$CH_3O$ | Core-A | $CO_2H$ | 4-(N-pyrrolidinocarbonyl)$C_6H_4$ |
| 46 | 4-$CH_3O$ | Core-A | $CO_2CH_3$ | 4-(N-pyrrolidinocarbonyl)$C_6H_4$ |

TABLE 1-continued

| | | | | |
|---|---|---|---|---|
| 47 | 4-Cl | Core-A | CH$_3$ | 2'-H$_2$NSO$_2$-biphen-4-yl |
| 48 | 4-Cl | Core-A | CH$_3$ | 5-(2'-H$_2$NSO$_2$—C$_6$H$_4$)pyrid-2-yl |
| 49 | 3,4-diCl | Core-A | CH$_3$ | 2'-H$_2$NSO$_2$-biphen-4-yl |
| 50 | 3-Cl | Core-A | CH$_3$ | 2'-H$_2$NSO$_2$-biphen-4-yl |
| 51 | — | Core-F | NH$_2$ | 2'-H$_2$NSO$_2$-biphen-4-yl |
| 52 | — | Core-F | Cl | 2'-H$_2$NSO$_2$-biphen-4-yl |
| 53 | 3-Br 4-F | Core-F | NH$_2$ | 2'-H$_2$NSO$_2$-biphen-4-yl |
| 54 | 4-F | Core-F | NH$_2$ | 2'-H$_2$NSO$_2$-biphen-4-yl |
| 55 | 3-Br | Core-F | NH$_2$ | 2'-H$_2$NSO$_2$-biphen-4-yl |
| 56 | 3-Br | Core-F | Cl | 2'-H$_2$NSO$_2$-biphen-4-yl |
| 57 | 4-CH$_3$O | Core-A | CH$_3$S | 2'-H$_2$NSO$_2$-biphen-4-yl |
| 58 | 4-CH$_3$O | Core-A | CH$_3$SO$_2$ | 5-(2'-CH$_3$CO$_2$—C$_6$H$_4$)pyrimid-2-yl |
| 59 | 4-CH$_3$O | Core-A | CH$_3$SO$_2$ | 2'-H$_2$NSO$_2$-biphen-4-yl |
| 60 | 4-CH$_3$O | Core-A | CH$_3$S | 4-(N-pyrrolidinocarbonyl)C$_6$H$_4$ |
| 61 | 4-CH$_3$O | Core-A | CH$_3$S | 2'-CH$_3$SO$_2$-biphen-4-yl |
| 62 | 4-CH$_3$O | Core-A | CH$_3$SO$_2$ | 4-(N-pyrrolidionocarbonyl)C$_6$H$_4$ |
| 63 | 4-CH$_3$O | Core-A | CH$_3$OCH$_2$ | 2'-H$_2$NSO$_2$-biphen-4-yl |
| 64 | 4-CH$_3$O | Core-A | CH$_3$OC(O) | 2'-H$_2$NSO$_2$-biphen-4-yl |
| 65 | 4-CH$_3$O | Core-A | CH$_3$SO$_2$CH$_2$ | 2'-H$_2$NSO$_2$-biphen-4-yl |
| 66 | 4-CH$_3$O | Core-A | CF$_3$ | 5-(2'-CH$_3$SO$_2$—C$_6$H$_4$)pyrimid-2-yl |
| 67 | 4-CH$_3$O | Core-A | CH$_3$ | 4-(2'-CH$_3$CO$_2$-pyrrolidinocarbonyl)C$_6$H$_4$ |
| 68 | 4-CH$_3$O | Core-A | CF$_3$ | 4-(3'-H$_2$N-pyrrolidinocarbonyl)C$_6$H$_4$ |
| 69 | 4-CH$_3$O | Core-A | CH$_3$ | 4- (3'-CH$_3$O-pyrrolidinocarbonyl)C$_6$H$_4$ |
| 70 | 4-CH$_3$O | Core-A | CF$_3$ | 5-(2'-H$_2$NSO$_2$—C$_6$H$_4$)pyrid-2-yl |
| 71 | 4-CH$_3$O | Core-A | CF$_3$ | 4-amidinophenyl |
| 72 | 4-CH$_3$O | Core-A | CF$_3$ | 4-(N-pyrrolidino-C(=NH))C$_6$H$_4$ |
| 73 | 4-CH$_3$O | — | CF$_3$ | 2'-H$_2$NSO$_2$-biphen-4-yl |
| 74 | 4-CH$_3$O | Core-B | 3-CF$_3$, 5-CO$_2$CH$_3$ | 2'-H$_2$NSO$_2$-biphen-4-yl |
| 75 | 4-CH$_3$O | Core-B | 3-CF$_3$, 5-(CH$_2$)$_2$OH | 2'-H$_2$NSO$_2$-biphen-4-yl |
| 76 | 4-CH$_3$O | Core-A | CF$_3$ | 4-(N-pyrrolidino-C(=NH))C$_6$H$_4$ |
| 77 | 4-CH$_3$O | Core-A | CF$_3$ | 4-(N-pyrrolidino-C(=NCO$_2$-i-butyl))C$_6$H$_4$ |
| 78 | 4-CH$_3$O | Core-A | CF$_3$ | 4-(N-pyrrolidino-C(=N)SO$_2$CH$_3$)C$_6$H$_4$ |
| 79 | 4-CH$_3$O | Core-A | CF$_3$ | 4-amidinophenylmethyl |
| 80 | 4-CH$_3$O | Core-A | CF$_3$ | 4-(N-pyrrolidino-C(=NH$_2$))C$_6$H$_4$—CH$_2$— |
| 81 | 4-CH$_3$O | Core-A | CF$_3$ | N-benzyl-piperidin-4-yl |
| 82 | 4-CH$_3$O | Core-A | CF$_3$ | N-(pyrid-2-lymethyl)piperidin-4-yl |
| 83 | 4-CH$_3$O | Core-A | CF$_3$ | 4-(2'-methylimidazolyl)C$_6$H$_4$ |
| 84 | 4-CH$_3$O | Core-A | CH$_3$ | 4-(5'-methylimidazolyl)C$_6$H$_4$ |
| 85 | 4-CH$_3$O | Core-A | CH$_3$ | 4-(4'-methylimidazolyl)C$_6$H$_4$ |
| 86 | 4-CH$_3$O | Core-A | CF$_3$ | 4-(5'-CH$_3$C(O)-imidazolyl)C$_6$H$_4$ |
| 87 | 4-CH$_3$O | Core-A | CF$_3$ | 4-(5'-carboxylmidazolyl)C$_6$H$_4$ |
| 88 | 4-CH$_3$O | Core-A | CF$_3$ | 4-(5'-CH$_3$NHC(O)-imidazolyl)C$_6$H$_4$ |
| 89 | 4-CH$_3$O | Core-A | CF$_3$ | 4-(5'-H$_2$NC(O)-imidazolyl)C$_6$H$_4$ |
| 90 | 4-CH$_3$O | Core-A | CF$_3$ | 4-(5'-CH$_3$NHC(O)-imidazolyl)C$_6$H$_4$ |
| 91 | 4-CH$_3$O | Core-A | CH$_2$OH | 4-(N-pyrrolidinocarbonyl)C$_6$H$_4$ |
| 92 | 4-CH$_3$O | Core-A | CHO | 4-(N-pyrrolidinocarbonyl)C$_6$H$_4$ |
| 93 | 4-CH$_3$O | Core-A | CO$_2$H | 4-(N-pyrrolidinocarbonyl)C$_6$H$_4$ |
| 94 | 4-CH$_3$O | Core-A | CO$_2$CH$_3$ | 4-(N-pyrrolidinocarbonyl)C$_6$H$_4$ |
| 95 | 4-CH$_3$O | Core-A | CH$_2$CN | 4-(N-pyrrolidinocarbonyl)C$_6$H$_4$ |
| 96 | 4-CH$_3$O | Core-A | CH$_2$CO$_2$H | 4-(N-pyrrolidinocarbonyl)C$_6$H$_4$ |
| 97 | 4-CH$_3$O | Core-A | CH$_2$Br | 2'-H$_2$NSO$_2$-biphen-4-yl |
| 98 | 4-CH$_3$O | Core-A | CH$_2$NH$_2$ | 2'-H$_2$NSO$_2$-biphen-4-yl |
| 99 | 4-CH$_3$O | Core-A | CH$_2$NH$_2$—SO$_2$CH$_3$ | 2'-H$_2$NSO$_2$-biphen-4-yl |
| 100 | 4-CH$_3$O | Core-A | CH$_2$-imidazole | 2'-H$_2$NSO$_2$-biphen-4-yl |
| 101 | 4-CH$_3$O | Core-A | CH$_2$OH | 2'-H$_2$NSO$_2$-biphen-4-yl |
| 102 | 4-CH$_3$O | Core-A | CH$_2$—OC(O)CF$_3$ | 2'-H$_2$NSO$_2$-biphen-4-yl |
| 103 | 4-CH$_3$O 2-CO$_2$Me | Core-A | CF$_3$ | 2'-CH$_3$SO$_2$-biphen-4-yl |
| 104 | 4-CH$_3$O 2-CO$_2$H | Core-A | CF$_3$ | 2'-CH$_3$SO$_2$-biphen-4-yl |
| 105 | 4-CH$_3$O 2-CO$_2$CH$_3$ | Core-A | CF$_3$ | 2'-H$_2$NSO$_2$-biphen-4-yl |
| 106 | 4-CH$_3$O 2-CO$_2$H | Core-A | CF$_3$ | 2'-t-Bu-HNSO$_2$-biphen-4-yl |
| 107 | 4-CH$_3$O 2-CO$_2$H | Core-A | CF$_3$ | 2'-H$_2$NSO$_2$-biphen-4-yl |
| 108 | 4-CH$_3$O 2-CH$_2$OH | Core-A | CF$_3$ | 2'-H$_2$NSO$_2$-biphen-4-yl |
| 109 | 4-CH$_3$O | Core-A | CH$_3$ | 4-sec-butyl-phenyl |
| 110 | 4-CH$_3$O | Core-A | CH$_3$ | 4-(3'-methyl-3'-pyrazolin-5'-on-2'-yl)C$_6$H$_4$ |
| 111 | 4-CH$_3$O | Core-A | CH$_3$ | 4-(6'methylbenzothiazol-2'-yl)C$_6$H$_4$ |

TABLE 1-continued

| | | | | |
|---|---|---|---|---|
| 112 | 4-CH$_3$O | Core-A | CH$_3$ | 3,4-dibromophenyl |
| 113 | 4-CH$_3$O | Core-A | CH$_3$ | 4-butylphenyl |
| 114 | 4-CH$_3$O | Core-A | CH$_3$ | 4-(4-methylpiperidinyl)C$_6$H$_4$ |
| 115 | 4-CH$_3$O | Core-A | CH$_3$ | 4-(2'-methylimidazolyl)C$_6$H$_4$ |
| 116 | 4-CH$_3$O | Core-A | CF$_3$ | 4-(N-methylimidazol-2-yl-carbonyl)C$_6$H$_4$ |
| 117 | 4-CH$_3$O | Core-A | CF$_3$ | 4-(imidazol-2-yl-hydroxylnethyl)C$_6$H$_4$ |
| 118 | 4-CH$_3$O | Core-A | CF$_3$ | 4-(N-benzylimidazol-2-yl-hydroxymethyl)C$_6$H$_4$ |
| 119 | 4-CH$_3$O | Core-A | CF$_3$ | 4-(imidazol-2-yl-carbonyl)C$_6$H$_4$ |
| 120 | 4-CH$_3$O | Core-A | CF$_3$ | [(thiazol-2-yl)(4'-CH$_3$OC$_6$H$_4$—NH)CH$_2$]C$_6$H$_4$ |
| 121 | 4-CH$_3$O | Core-A | CF$_3$ | 4-(2'thiazolin-2'-yl-carbonyl)C$_6$H$_4$ |
| 122 | 4-CH$_3$O | Core-A | CF$_3$ | 4-(2'-imidazolin-2'yl)C$_6$H$_4$ |
| 123 | 4-CH$_3$O | Core-A | CF$_3$ | 4-(H$_2$N(CH$_2$)$_2$NHC(O))C$_6$H$_4$ |
| 124 | 4-CH$_3$O | Core-A | CF$_3$ | 4-(1',4',5',6'-tetrahydropyrimid-2-yl)C$_6$H$_4$ |
| 125 | 4-CH$_3$O | Core-A | CF$_3$ | 4-(N-methyl-1',4',5',6'-tetrahydropyrimid-2-yl)C$_6$H$_4$ |
| 126 | 4-CH$_3$O | Core-A | CF$_3$ | 4-(1',4',5',6'-tetrahydropyrimid-2-yl)-2-F—C$_6$H$_4$ |
| 127 | 4-CH$_3$O | Core-A | CF$_3$ | 4-(N—CH$_3$-4'-imidazolin-2'yl)-2-F—C$_6$H$_4$ |
| 128 | 4-CH$_3$O | Core-A | CF$_3$ | 4-(N—CH$_3$-4'-imidazolin-2'-yl)C$_6$H$_4$ |
| 129 | 4-CH$_3$O | Core-A | CF$_3$ | 4-(guanidino-carbonyl)C$_6$H$_4$ |
| 130 | 4-CH$_3$O | Core-A | CF$_3$ | 4-(pyrimid-2-yl)phenyl |
| 131 | 4-CH$_3$O | Core-F | C(O)NH$_2$ | 2'-H$_2$NSO$_2$-biphen-4-yl |
| 132 | 4-CH$_3$O | Core-F | NH(CH$_2$)$_2$—OCH$_3$ | 2'-H$_2$NSO$_2$-biphen-4-yl |
| 133 | 4-CH$_3$O | Core-F | NH(CH$_2$)$_3$—OH | 2'-H$_2$NSO$_2$-biphen-4-yl |
| 134 | 4-CH$_3$O | Core-F | NH(CH$_2$)$_2$—CN | 2'-H$_2$NSO$_2$-biphen-4-yl |
| 135 | 4-CH$_3$O | Core-F | NH(CH$_2$)$_3$—OCH$_3$ | 2'-H$_2$NSO$_2$-biphen-4-yl |
| 136 | 4-CH$_3$O | Core-F | NH(CH$_2$)$_2$—CO$_2$H | 2'-H$_2$NSO$_2$-biphen-4-yl |
| 137 | 4-CH$_3$O | Core-F | NH-i-Pr | 2'-H$_2$NSO$_2$-biphen-4-yl |
| 138 | 4-CH$_3$O | Core-F | NHCH(CH$_2$OH)$_2$ | 2'-H$_2$NSO$_2$-biphen-4-yl |
| 139 | 4-CH$_3$O | Core-F | NHCH$_2$CO$_2$CH$_3$ | 2'-H$_2$NSO$_2$-biphen-4-yl |
| 140 | 4-CH$_3$O | Core-F | NHCH$_2$CO$_2$H | 2'-H$_2$NSO$_2$-biphen-4-yl |
| 141 | 4-CH$_3$O | Core-A | CO$_2$C$_2$H$_5$ | 4-(N-pyrrolidinocarbonyl)C$_6$H$_4$ |
| 142 | 4-CH$_3$O | Core-A | CONH$_2$ | 4-(N-pyrrolidinocarbonyl)C$_6$H$_4$ |
| 143 | 4-CH$_3$O | Core-A | C(O)NH—(CH$_2$)$_2$OH | 4-(N-pyrrolidinocarbonyl)C$_6$H$_4$ |
| 144 | 4-CH$_3$O | Core-A | CONHOH | 4-(N-pyrrolidinocarbonyl)C$_6$H$_4$ |
| 145 | 4-CH$_3$O | Core-A | CONHC$_6$H$_5$ | 4-(N-pyrrolidinocarbonyl)C$_6$H$_4$ |
| 146 | 4-CH$_3$O | Core-A | CONH(CH$_2$)$_3$OH | 4-(N-pyrrolidinocarbonyl)C$_6$H$_4$ |
| 147 | 4-CH$_3$O | Core-A | CONHCH$_3$ | 4-(N-pyrrolidinocarbonyl)C$_6$H$_4$ |
| 148 | 4-CH$_3$O | Core-A | CONHCH$_2$C$_6$H$_5$ | 4-(N-pyrrolidinocarbonyl)C$_6$H$_4$ |
| 149 | 4-CH$_3$O | Core-A | CON(CH$_3$)$_2$ | 4-(N-pyrrolidinocarbonyl)C$_6$H$_4$ |
| 150 | 4-CH$_3$O | Core-A | CONH(CH$_2$)$_2$—C$_6$H$_5$ | 4-(N-pyrrolidinocarbonyl)C$_6$H$_4$ |
| 151 | 4-CH$_3$O | Core-A | CONH-2-OH—C$_6$H$_4$ | 4-(N-pyrrolidinocarbonyl)C$_6$H$_4$ |
| 152 | 4-CH$_3$O | Core-A | CONH-3-OH—C$_6$H$_4$ | 4-(N-pyrrolidinocarbonyl)C$_6$H$_4$ |
| 153 | 4-CH$_3$O | Core-A | CONH-4-OH—C$_6$H$_4$ | 4-(N-pyrrolidinocarbonyl)C$_6$H$_4$ |
| 154 | 4-CH$_3$O | Core-A | NHCO$_2$CH$_3$ | 2'-H$_2$NSO$_2$-biphen-4-yl |
| 155 | 4-CH$_3$O | Core-A | NH$_2$ | 2'-H$_2$NSO$_2$-biphen-4-yl |
| 156 | 4-CH$_3$O | Core-A | NHCH$_2$CO$_2$CH$_3$ | 2'-H$_2$NSO$_2$-biphen-4-yl |
| 157 | 4-CH$_3$O | Core-A | NH(CH$_2$)$_2$OH | 2'-H$_2$NSO$_2$-biphen-4-yl |
| 158 | 4-CH$_3$O | Core-A | CH=CHCO$_2$CH$_3$ | 2'-H$_2$NSO$_2$-biphen-4-yl |
| 159 | 4-CH$_3$O | Core-A | CH$_2$CH$_2$CO$_2$CH$_3$ | 2'-H$_2$NSO$_2$-biphen-4-yl |
| 160 | 4-CH$_3$O | Core-A | CH=CHCO$_2$H | 2'-H$_2$NSO$_2$-biphen-4-yl |
| 161 | 4-CH$_3$O | Core-A | CH$_2$CH$_2$CO$_2$H | 2'-H$_2$NSO$_2$-biphen-4-yl |
| 162 | 4-CH$_3$O | Core-A | CH=CHCONH$_2$ | 2'-H$_2$NSO$_2$-biphen-4-yl |
| 163 | 4-CH$_3$O | Core-A | CH=CHCH$_2$OH | 2'-H$_2$NSO$_2$-biphen-4-yl |
| 164 | 4-CH$_3$O | Core-A | (CH$_2$)$_3$OH | 2'-H$_2$NSO$_2$-biphen-4-yl |
| 165 | 4-CH$_3$O | Core-A | (CH$_2$)$_2$CH$_3$ | 2'-H$_2$NSO$_2$-biphen-4-yl |
| 166 | 4-CH$_3$O | Core-C | 3-CF$_3$, 4-CN | 2'-CH$_3$SO$_2$-3-F-biphen-4-yl |
| 167 | 4-CH$_3$O | Core-C | 3-CF$_3$, 4-amidino | 2'-CH$_3$SO$_2$-3-F-biphen-4-yl |
| 168 | 4-CH$_3$O | Core-C | 3-CF$_3$, 4-amidino-OH | 2'-CH$_3$SO$_2$-3-F-biphen-4-yl |
| 169 | 4-CH$_3$O | Core-C | 3-CF$_3$, 4-CO$_2$C$_2$H$_5$ | 2'-CH$_3$SO$_2$-3-F-biphen-4-yl |
| 170 | 4-CH$_3$O | Core-C | 3-CF$_3$, 4-CO$_2$H | 2'-CH$_3$SO$_2$-3-F-biphen-4-yl |

TABLE 1-continued (a) -CH$_2$C(O)NHCH$_2$CO$_2$CH$_3$
(b) -(1,2,4-triazol-1-yl)CH$_2$
(c)

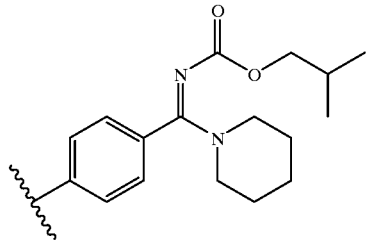

The following tables contain representative examples of the present invention. Each entry in each table is intended to be paired with each formulae at the start of the table. For example, example 1 in Table 2 is intended to be paired with each of formulae $a_1$–$f_9$.

TABLE 2

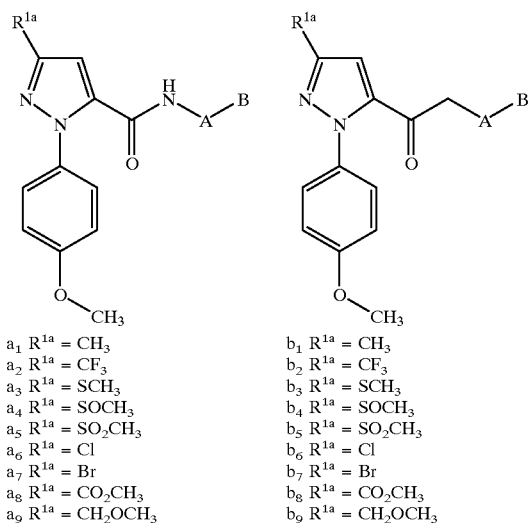

| | |
|---|---|
| $a_1$ $R^{1a}$ = CH$_3$ | $b_1$ $R^{1a}$ = CH$_3$ |
| $a_2$ $R^{1a}$ = CF$_3$ | $b_2$ $R^{1a}$ = CF$_3$ |
| $a_3$ $R^{1a}$ = SCH$_3$ | $b_3$ $R^{1a}$ = SCH$_3$ |
| $a_4$ $R^{1a}$ = SOCH$_3$ | $b_4$ $R^{1a}$ = SOCH$_3$ |
| $a_5$ $R^{1a}$ = SO$_2$CH$_3$ | $b_5$ $R^{1a}$ = SO$_2$CH$_3$ |
| $a_6$ $R^{1a}$ = Cl | $b_6$ $R^{1a}$ = Cl |
| $a_7$ $R^{1a}$ = Br | $b_7$ $R^{1a}$ = Br |
| $a_8$ $R^{1a}$ = CO$_2$CH$_3$ | $b_8$ $R^{1a}$ = CO$_2$CH$_3$ |
| $a_9$ $R^{1a}$ = CH$_2$OCH$_3$ | $b_9$ $R^{1a}$ = CH$_2$OCH$_3$ |

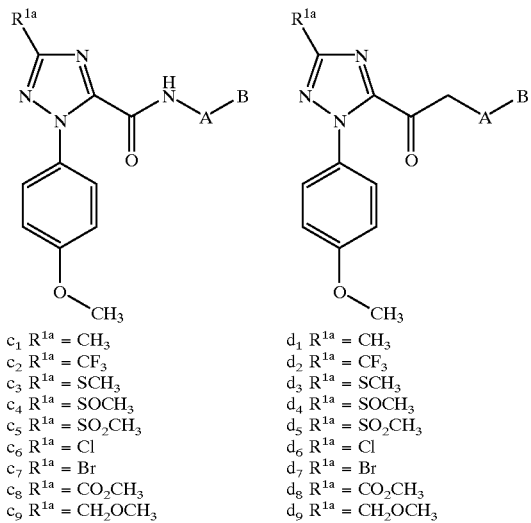

| | |
|---|---|
| $c_1$ $R^{1a}$ = CH$_3$ | $d_1$ $R^{1a}$ = CH$_3$ |
| $c_2$ $R^{1a}$ = CF$_3$ | $d_2$ $R^{1a}$ = CF$_3$ |
| $c_3$ $R^{1a}$ = SCH$_3$ | $d_3$ $R^{1a}$ = SCH$_3$ |
| $c_4$ $R^{1a}$ = SOCH$_3$ | $d_4$ $R^{1a}$ = SOCH$_3$ |
| $c_5$ $R^{1a}$ = SO$_2$CH$_3$ | $d_5$ $R^{1a}$ = SO$_2$CH$_3$ |
| $c_6$ $R^{1a}$ = Cl | $d_6$ $R^{1a}$ = Cl |
| $c_7$ $R^{1a}$ = Br | $d_7$ $R^{1a}$ = Br |
| $c_8$ $R^{1a}$ = CO$_2$CH$_3$ | $d_8$ $R^{1a}$ = CO$_2$CH$_3$ |
| $c_9$ $R^{1a}$ = CH$_2$OCH$_3$ | $d_9$ $R^{1a}$ = CH$_2$OCH$_3$ |

TABLE 2-continued

| | |
|---|---|
| $e_1$ $R^{1a}$ = CH$_3$ | $f_1$ $R^{1a}$ = CH$_3$ |
| $e_2$ $R^{1a}$ = CF$_3$ | $f_2$ $R^{1a}$ = CF$_3$ |
| $e_3$ $R^{1a}$ = SCH$_3$ | $f_3$ $R^{1a}$ = SCH$_3$ |
| $e_4$ $R^{1a}$ = SOCH$_3$ | $f_4$ $R^{1a}$ = SOCH$_3$ |
| $e_5$ $R^{1a}$ = SO$_2$CH$_3$ | $f_5$ $R^{1a}$ = SO$_2$CH$_3$ |
| $e_6$ $R^{1a}$ = Cl | $f_6$ $R^{1a}$ = Cl |
| $e_7$ $R^{1a}$ = Br | $f_7$ $R^{1a}$ = Br |
| $e_8$ $R^{1a}$ = CO$_2$CH$_3$ | $f_8$ $R^{1a}$ = CO$_2$CH$_3$ |
| $e_9$ $R^{1a}$ = CH$_2$OCH$_3$ | $f_9$ $R^{1a}$ = CH$_2$OCH$_3$ |

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | 2-pyridyl | 2-(aminosulfonyl)phenyl |
| 9 | 2-pyridyl | 2-(methylaminosulfonyl)phenyl |
| 10 | 2-pyridyl | 1-pyrrolidinocarbonyl |
| 11 | 2-pyridyl | 2-(methylsulfonyl)phenyl |
| 12 | 2-pyridyl | 4-morpholino |
| 13 | 2-pyridyl | 2-(1'-CF$_3$-tetrazol-2-yl)phenyl |
| 14 | 2-pyridyl | 4-morpholinocarbonyl |
| 15 | 3-pyridyl | 2-(aminosulfonyl)phenyl |
| 16 | 3-pyridyl | 2-(methylaminosulfonyl)phenyl |
| 17 | 3-pyridyl | 1-pyrrolidinocarbonyl |
| 18 | 3-pyridyl | 2-(methylsulfonyl)phenyl |
| 19 | 3-pyridyl | 4-morpholino |
| 20 | 3-pyridyl | 2-(1'-CF$_3$-tetrazol-2-yl)phenyl |
| 21 | 3-pyridyl | 4-morpholinocarbonyl |
| 22 | 2-pyrimidyl | 2-(aminosulfonyl)phenyl |
| 23 | 2-pyrimidyl | 2-(methylaminosulfonyl)phenyl |
| 24 | 2-pyrimidyl | 1-pyrrolidinocarbonyl |
| 25 | 2-pyrimidyl | 2-(methylsulfonyl)phenyl |
| 26 | 2-pyrimidyl | 4-morpholino |
| 27 | 2-pyrimidyl | 2-(1'-CF$_3$-tetrazol-2-yl)phenyl |
| 28 | 2-pyrimidyl | 4-morpholinocarbonyl |
| 29 | 5-pyrimidyl | 2-(aminosulfonyl)phenyl |
| 30 | 5-pyrimidyl | 2-(methylaminosulfonyl)phenyl |

TABLE 2-continued

| | | |
|---|---|---|
| 31 | 5-pyrimidyl | 1-pyrrolidinocarbonyl |
| 32 | 5-pyrimidyl | 2-(methylsulfonyl)phenyl |
| 33 | 5-pyrimidyl | 4-morpholino |
| 34 | 5-pyrimidyl | 2-(1'-CF$_3$-tetrazol-2-yl)phenyl |
| 35 | 5-pyrimidyl | 4-morpholinocarbonyl |
| 36 | 2-Cl-phenyl | 2-(aminosulfonyl)phenyl |
| 37 | 2-Cl-phenyl | 2-(methylaminosulfonyl)phenyl |
| 38 | 2-Cl-phenyl | 1-pyrrolidinocarbonyl |
| 39 | 2-Cl-phenyl | 2-(methylsulfonyl)phenyl |
| 40 | 2-Cl-phenyl | 4-morpholino |
| 41 | 2-Cl-phenyl | 2-(1'-CF$_3$-tetrazol-2-yl)phenyl |
| 42 | 2-Cl-phenyl | 4-morpholinocarbonyl |
| 43 | 2-F-phenyl | 2-(aminosulfonyl)phenyl |
| 44 | 2-F-phenyl | 2-(methylaminosulfonyl)phenyl |
| 45 | 2-F-phenyl | 1-pyrrolidinocarbonyl |
| 46 | 2-F-phenyl | 2-(methylsulfonyl)phenyl |
| 47 | 2-F-phenyl | 4-morpholino |
| 48 | 2-F-phenyl | 2-(1'-CF$_3$-tetrazol-2-yl)phenyl |
| 49 | 2-F-phenyl | 4-morpholinocarbonyl |
| 50 | 2,5-diF-phenyl | 2-(aminosulfonyl)phenyl |
| 51 | 2,5-diF-phenyl | 2-(methylaminosulfonyl)phenyl |
| 52 | 2,5-diF-phenyl | 1-pyrrolidinocarbonyl |
| 53 | 2,5-diF-phenyl | 2-(methylsulfonyl)phenyl |
| 54 | 2,5-diF-phenyl | 4-morpholino |
| 55 | 2,5-diF-phenyl | 2-(1'-CF$_3$-tetrazol-2-yl)phenyl |
| 56 | 2,5-diF-phenyl | 4-morpholinocarbonyl |
| 57 | phenyl | 2-(N-pyrrolidinyl-methyl)phenyl |
| 58 | phenyl | 2-(N-piperidinyl-methyl)phenyl |
| 59 | phenyl | 2-(N-morpholino-methyl)phenyl |
| 60 | phenyl | 2-(N,N'-methylmorpholinium-methyl)phenyl |
| 61 | phenyl | 2-(N-pyridinium-methyl)phenyl |
| 62 | phenyl | 2-(N-4-(N,N'-dimethylamino)-pyridinium-methyl)phenyl |
| 63 | phenyl | 2-(N-azatanyl-methyl)phenyl |
| 64 | phenyl | 2-(N-azetidinyl-methyl)phenyl |
| 65 | phenyl | 2-(N-piperazinyl-methyl)phenyl |
| 66 | phenyl | 2-(N,N'-BOC-piperazinyl-methyl)phenyl |
| 67 | phenyl | 2-(N-imidazolyl-methyl)phenyl |
| 68 | phenyl | 2-(N-methoxy-N-methylamino-methyl)phenyl |
| 69 | phenyl | 2-(N-pyridonyl-methyl)phenyl |
| 70 | phenyl | 2-(N-(N',N'-dimethylhylhydrazinyl-methyl)phenyl |
| 71 | phenyl | 2-(amidinyl)phenyl |
| 72 | phenyl | 2-(N-guanidinyl)phenyl |
| 73 | phenyl | 2-(imidazolyl)phenyl |
| 74 | phenyl | 2-(imidazolidinyl)phenyl |
| 75 | phenyl | 2-(2-imidazolidinyl-sulfonyl)phenyl |
| 76 | phenyl | 2-(2-pyrrolidinyl)phenyl |
| 77 | phenyl | 2-(2-piperidinyl)phenyl |
| 78 | phenyl | 2-(amidinyl-methyl)phenyl |
| 79 | phenyl | 2-(2-imidazolidinyl-methyl)phenyl |
| 80 | phenyl | 2-(N-(2-aminoimidazolyl)-methyl)phenyl |
| 81 | phenyl | 2-dimethylaminoimidazol-1-yl |
| 82 | phenyl | 2-(3-aminophenyl) |
| 83 | phenyl | 2-(3-pyrrolidinylcarbonyl) |
| 84 | phenyl | 2-glycinoyl |
| 85 | phenyl | 2-(imidazol-1-ylacetyl) |
| 86 | 2-pyridyl | 2-(N-pyrrolidinyl-methyl)phenyl |
| 87 | 2-pyridyl | 2-(N-piperidinyl-methyl)phenyl |
| 88 | 2-pyridyl | 2-(N-morpholino-methyl)phenyl |
| 89 | 2-pyridyl | 2-(N,N'-methylmorpholinium-methyl)phenyl |
| 90 | 2-pyridyl | 2-(N-pyridinium-methyl)phenyl |
| 91 | 2-pyridyl | 2-(N-4-(N,N'-dimethylamino)-pyridinium-methyl)phenyl |
| 92 | 2-pyridyl | 2-(N-azatanyl-methyl)phenyl |
| 93 | 2-pyridyl | 2-(N-azetidinyl-methyl)phenyl |
| 94 | 2-pyridyl | 2-(N-piperazinyl-methyl)phenyl |
| 95 | 2-pyridyl | 2-(N,N'-BOC-piperazinyl-methyl)phenyl |
| 96 | 2-pyridyl | 2-(N-imidazolyl-methyl)phenyl |
| 97 | 2-pyridyl | 2-(N-methoxy-N-methylamino-methyl)phenyl |
| 98 | 2-pyridyl | 2-(N-pyridonyl-methyl)phenyl |
| 99 | 2-pyridyl | 2-(N-(N',N'-dimethylhydrazinyl-methyl)phenyl |
| 100 | 2-pyridyl | 2-(amidinyl)phenyl |
| 101 | 2-pyridyl | 2-(N-guanidinyl)phenyl |
| 102 | 2-pyridyl | 2-(imidazolyl)phenyl |
| 103 | 2-pyridyl | 2-(imidazolidinyl)phenyl |
| 104 | 2-pyridyl | 2-(2-imidazolidinyl-sulfonyl)phenyl |
| 105 | 2-pyridyl | 2-(2-pyrrolidinyl)phenyl |
| 106 | 2-pyridyl | 2-(2-piperidinyl)phenyl |
| 107 | 2-pyridyl | 2-(amidinyl-methyl)phenyl |
| 108 | 2-pyridyl | 2-(2-imidazolidinyl-methyl)phenyl |
| 109 | 2-pyridyl | 2-(N-(2-aminoimidazolyl)-methyl)phenyl |
| 110 | 2-pyridyl | 2-dimethylaminoimidazol-1-yl |
| 111 | 2-pyridyl | 2-(3-aminophenyl) |
| 112 | 2-pyridyl | 2-(3-pyrrolidinylcarbonyl) |
| 113 | 2-pyridyl | 2-glycinoyl |
| 114 | 2-pyridyl | 2-(imidazol-1-ylacetyl) |
| 115 | 3-pyridyl | 2-(N-pyrrolidinyl-methyl)phenyl |
| 116 | 3-pyridyl | 2-(N-piperidinyl-methyl)phenyl |
| 117 | 3-pyridyl | 2-(N-morpholino-methyl)phenyl |
| 118 | 3-pyridyl | 2-(N,N'-methylmorpholinium-methyl)phenyl |
| 119 | 3-pyridyl | 2-(N-pyridinium-methyl)phenyl |
| 120 | 3-pyridyl | 2-(N-4-(N,N'-dimethylamino)-pyridinium-methyl)phenyl |
| 121 | 3-pyridyl | 2-(N-azatanyl-methyl)phenyl |
| 122 | 3-pyridyl | 2-(N-azetidinyl-methyl)phenyl |
| 123 | 3-pyridyl | 2-(N-piperazinyl-methyl)phenyl |
| 124 | 3-pyridyl | 2-(N,N'-BOC-piperazinyl-methyl)phenyl |
| 125 | 3-pyridyl | 2-(N-imidazolyl-methyl)phenyl |
| 126 | 3-pyridyl | 2-(N-methoxy-N-methylamino-methyl)phenyl |
| 127 | 3-pyridyl | 2-(N-pyridonyl-methyl)phenyl |
| 128 | 3-pyridyl | 2-(N-(N',N'-dimethylhydrazinyl-methyl)phenyl |
| 129 | 3-pyridyl | 2-(amidinyl)phenyl |
| 130 | 3-pyridyl | 2-(N-guanidinyl)phenyl |
| 131 | 3-pyridyl | 2-(imidazolyl)phenyl |
| 132 | 3-pyridyl | 2-(imidazolidinyl)phenyl |
| 133 | 3-pyridyl | 2-(2-imidazolidinyl-sulfonyl)phenyl |
| 134 | 3-pyridyl | 2-(2-pyrrolidinyl)phenyl |
| 135 | 3-pyridyl | 2-(2-piperidinyl)phenyl |
| 136 | 3-pyridyl | 2-(amidinyl-methyl)phenyl |
| 137 | 3-pyridyl | 2-(2-imidazolidinyl-methyl)phenyl |
| 138 | 3-pyridyl | 2-(N-(2-aminoimidazolyl)-methyl)phenyl |
| 139 | 3-pyridyl | 2-dimethylaminoimidazol-1-yl |
| 140 | 3-pyridyl | 2-(3-aminophenyl) |
| 141 | 3-pyridyl | 2-(3-pyrrolidinylcarbonyl) |
| 142 | 3-pyridyl | 2-glycinoyl |
| 143 | 3-pyridyl | 2-(imidazol-1-ylacetyl) |
| 144 | 2-pyrimidyl | 2-(N-pyrrolidinyl-methyl)phenyl |
| 145 | 2-pyrimidyl | 2-(N-piperidinyl-methyl)phenyl |
| 146 | 2-pyrimidyl | 2-(N-morpholino-methyl)phenyl |
| 147 | 2-pyrimidyl | 2-(N,N'-methylmorpholinium-methyl)phenyl |
| 148 | 2-pyrimidyl | 2-(N-pyridinium-methyl)phenyl |
| 149 | 2-pyrimidyl | 2-(N-4-(N,N'-dimethylamino)-pyridinium-methyl)phenyl |
| 150 | 2-pyrimidyl | 2-(N-azatanyl-methyl)phenyl |
| 151 | 2-pyrimidyl | 2-(N-azetidinyl-methyl)phenyl |
| 152 | 2-pyrimidyl | 2-(N-piperazinyl-methyl)phenyl |
| 153 | 2-pyrimidyl | 2-(N,N'-BOC-piperazinyl-methyl)phenyl |
| 154 | 2-pyrimidyl | 2-(N-imidazolyl-methyl)phenyl |
| 155 | 2-pyrimidyl | 2-(N-methoxy-N-methylamino-methyl)phenyl |
| 156 | 2-pyrimidyl | 2-(N-pyridonyl-methyl)phenyl |
| 157 | 2-pyrimidyl | 2-(N-(N',N'-dimethylhydrazinyl-methyl)phenyl |
| 158 | 2-pyrimidyl | 2-(amidinyl)phenyl |
| 159 | 2-pyrimidyl | 2-(N-guanidinyl)phenyl |
| 160 | 2-pyrimidyl | 2-(imidazolyl)phenyl |
| 161 | 2-pyrimidyl | 2-(imidazolidinyl)phenyl |
| 162 | 2-pyrimidyl | 2-(2-imidazolidinyl-sulfonyl)phenyl |
| 163 | 2-pyrimidyl | 2-(2-pyrrolidinyl)phenyl |
| 164 | 2-pyrimidyl | 2-(2-piperidinyl)phenyl |
| 165 | 2-pyrimidyl | 2-(amidinyl-methyl)phenyl |
| 166 | 2-pyrimidyl | 2-(2-imidazolidinyl-methyl)phenyl |
| 167 | 2-pyrimidyl | 2-(N-(2-aminoimidazolyl)-methyl)phenyl |
| 168 | 2-pyrimidyl | 2-dimethylaminoimidazol-1-yl |
| 169 | 2-pyrimidyl | 2-(3-aminophenyl) |
| 170 | 2-pyrimidyl | 2-(3-pyrrolidinylcarbonyl) |
| 171 | 2-pyrimidyl | 2-glycinoyl |
| 172 | 2-pyrimidyl | 2-(imidazol-1-ylacetyl) |
| 173 | 2-Cl-phenyl | 2-(N-pyrrolidinyl-methyl)phenyl |
| 174 | 2-Cl-phenyl | 2-(N-piperidinyl-methyl)phenyl |
| 175 | 2-Cl-phenyl | 2-(N-morpholino-methyl)phenyl |
| 176 | 2-Cl-phenyl | 2-(N,N'-methylmorpholinium-methyl)phenyl |
| 177 | 2-Cl-phenyl | 2-(N-pyridinium-methyl)phenyl |
| 178 | 2-Cl-phenyl | 2-(N-4-(N,N'-dimethylamino)-pyridinium-methyl)phenyl |
| 179 | 2-Cl-phenyl | 2-(N-azatanyl-methyl)phenyl |

TABLE 2-continued

| | | |
|---|---|---|
| 180 | 2-Cl-phenyl | 2-(N-azetidinyl-methyl)phenyl |
| 181 | 2-Cl-phenyl | 2-(N-piperazinyl-methyl)phenyl |
| 182 | 2-Cl-phenyl | 2-(N,N'-BOC-piperazinyl-methyl)phenyl |
| 183 | 2-Cl-phenyl | 2-(N-imidazolyl-methyl)phenyl |
| 184 | 2-Cl-phenyl | 2-(N-methoxy-N-methylamino-methyl)phenyl |
| 185 | 2-Cl-phenyl | 2-(N-pyridonyl-methyl)phenyl |
| 186 | 2-Cl-phenyl | 2-(N-(N',N'-dimethylhydrazinyl-methyl)phenyl |
| 187 | 2-Cl-phenyl | 2-(amidinyl)phenyl |
| 188 | 2-Cl-phenyl | 2-(N-guanidinyl)phenyl |
| 189 | 2-Cl-phenyl | 2-(imidazolyl)phenyl |
| 190 | 2-Cl-phenyl | 2-(imidazolidinyl)phenyl |
| 191 | 2-Cl-phenyl | 2-(2-imidazolidinyl-sulfonyl)phenyl |
| 192 | 2-Cl-phenyl | 2-(2-pyrrolidinyl)phenyl |
| 193 | 2-Cl-phenyl | 2-(2-piperidinyl)phenyl |
| 194 | 2-Cl-phenyl | 2-(amidinyl-methyl)phenyl |
| 195 | 2-Cl-phenyl | 2-(2-imidazolidinyl-methyl)phenyl |
| 196 | 2-Cl-phenyl | 2-(N-(2-aminoimidazolyl)-methyl)phenyl |
| 197 | 2-Cl-phenyl | 2-dimethylaminoimidazol-1-yl |
| 198 | 2-Cl-phenyl | 2-(3-aminophenyl) |
| 199 | 2-Cl-phenyl | 2-(3-pyrrolidinylcarbonyl) |
| 200 | 2-Cl-phenyl | 2-glycinoyl |
| 201 | 2-Cl-phenyl | 2-(imidazol-1-ylacetyl) |
| 202 | 2-F-phenyl | 2-(N-pyrrolidinyl-methyl)phenyl |
| 203 | 2-F-phenyl | 2-(N-piperidinyl-methyl)phenyl |
| 204 | 2-F-phenyl | 2-(N-morpholino-methyl)phenyl |
| 205 | 2-F-phenyl | 2-(N,N-methylmorpholinium-methyl)phenyl |
| 206 | 2-F-phenyl | 2-(N-pyridinium-methyl)phenyl |
| 207 | 2-F-phenyl | 2-(N-4-(N,N'-dimethylamino)-pyridinium-methyl)phenyl |
| 208 | 2-F-phenyl | 2-(N-azatanyl-methyl)phenyl |
| 209 | 2-F-phenyl | 2-(N-azetidinyl-methyl)phenyl |
| 210 | 2-F-phenyl | 2-(N-piperazinyl-methyl)phenyl |
| 211 | 2-F-phenyl | 2-(N,N'-BOC-piperazinyl-methyl)phenyl |
| 212 | 2-F-phenyl | 2-(N-imidazolyl-methyl)phenyl |
| 213 | 2-F-phenyl | 2-(N-methoxy-N-methylamino-methyl)phenyl |
| 214 | 2-F-phenyl | 2-(N-pyridonyl-methyl)phenyl |
| 215 | 2-F-phenyl | 2-(N-(N',N'-dimethylhydrazinyl-methyl)phenyl |
| 216 | 2-F-phenyl | 2-(amidinyl)phenyl |
| 217 | 2-F-phenyl | 2-(N-guanidinyl)phenyl |
| 218 | 2-F-phenyl | 2-(imidazolyl)phenyl |
| 219 | 2-F-phenyl | 2-(imidazolidinyl)phenyl |
| 220 | 2-F-phenyl | 2-(2-imidazolidinyl-sulfonyl)phenyl |
| 221 | 2-F-phenyl | 2-(2-pyrrolidinyl)phenyl |
| 222 | 2-F-phenyl | 2-(2-piperidinyl)phenyl |
| 223 | 2-F-phenyl | 2-(amidinyl-methyl)phenyl |
| 224 | 2-F-phenyl | 2-(2-imidazolidinyl-methyl)phenyl |
| 225 | 2-F-phenyl | 2-(N-(2-aminoimidazolyl)-methyl)phenyl |
| 226 | 2-F-phenyl | 2-dimethylaminoimidazol-1-yl |
| 227 | 2-F-phenyl | 2-(3-aminophenyl) |
| 228 | 2-F-phenyl | 2-(3-pyrrolidinylcarbonyl) |
| 229 | 2-F-phenyl | 2-glycinoyl |
| 230 | 2-F-phenyl | 2-(imidazol-1-ylacetyl) |
| 231 | 2,5-diF-phenyl | 2-(N-pyrrolidinyl-methyl)phenyl |
| 232 | 2,5-diF-phenyl | 2-(N-piperidinyl-methyl)phenyl |
| 233 | 2,5-diF-phenyl | 2-(N-morpholino-methyl)phenyl |
| 234 | 2,5-diF-phenyl | 2-(N,N'-methylmorpholinium-methyl)phenyl |
| 235 | 2,5-diF-phenyl | 2-(N-pyridinium-methyl)phenyl |
| 236 | 2,5-diF-phenyl | 2-(N-4-(N,N'-dimethylamino)-pyridinium-methyl)phenyl |
| 237 | 2,5-diF-phenyl | 2-(N-azatanyl-methyl)phenyl |
| 238 | 2,5-diF-phenyl | 2-(N-azetidinyl-methyl)phenyl |
| 239 | 2,5-diF-phenyl | 2-(N-piperazinyl-methyl)phenyl |
| 240 | 2,5-diF-phenyl | 2-(N,N'-BOC-piperazinyl-methyl)phenyl |
| 241 | 2,5-diF-phenyl | 2-(N-imidazolyl-methyl)phenyl |
| 242 | 2,5-diF-phenyl | 2-(N-methoxy-N-methylamino-methyl)phenyl |
| 243 | 2,5-diF-phenyl | 2-(N-pyridonyl-methyl)phenyl |
| 244 | 2,5-diF-phenyl | 2-(N-(N',N'-dimethylhydrazinyl methyl)phenyl |
| 245 | 2,5-diF-phenyl | 2-(amidinyl)phenyl |
| 246 | 2,5-diF-phenyl | 2-(N-guanidinyl)phenyl |
| 247 | 2,5-diF-phenyl | 2-(imidazolyl)phenyl |

TABLE 2-continued

| | | |
|---|---|---|
| 248 | 2,5-diF-phenyl | 2-(imidazolidinyl)phenyl |
| 249 | 2,5-diF-phenyl | 2-(2-imidazolidinyl-sulfonyl)phenyl |
| 250 | 2,5-diF-phenyl | 2-(2-pyrrolidinyl)phenyl |
| 251 | 2,5-diF-phenyl | 2-(2-piperidinyl)phenyl |
| 252 | 2,5-diF-phenyl | 2-(amidinyl-methyl)phenyl |
| 253 | 2,5-diF-phenyl | 2-(2-imidazolidinyl-methyl)phenyl |
| 254 | 2,5-diF-phenyl | 2-(N-(2-aminoimidazolyl)-methyl)phenyl |
| 255 | 2,5-diF-phenyl | 2-dimethylaminoimidazol-1-yl |
| 256 | 2,5-diF-phenyl | 2-(3-aminophenyl) |
| 257 | 2,5-diF-phenyl | 2-(3-pyrrolidinylcarbonyl) |
| 258 | 2,5-diF-phenyl | 2-glycinoyl |
| 259 | 2,5-diF-phenyl | 2-(imidazol-1-ylacetyl) |

TABLE 3

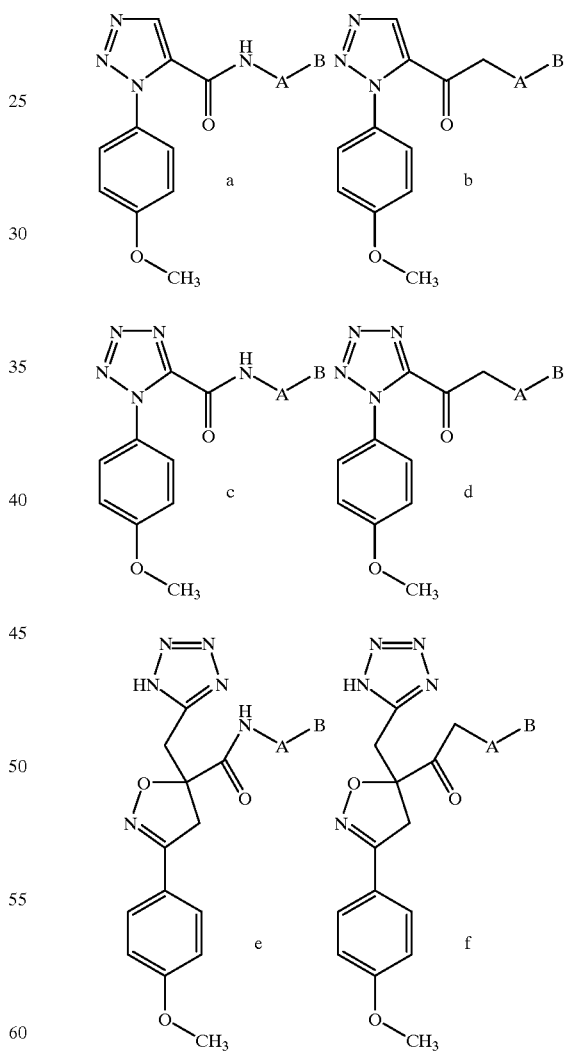

TABLE 3-continued

[Structures g, h, i, j shown with Ex # A B column headers]

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | 2-pyridyl | 2-(aminosulfonyl)phenyl |
| 9 | 2-pyridyl | 2-(methylaminosulfonyl)phenyl |
| 10 | 2-pyridyl | 1-pyrrolidinocarbonyl |
| 11 | 2-pyridyl | 2-(methylsulfonyl)phenyl |
| 12 | 2-pyridyl | 4-morpholino |
| 13 | 2-pyridyl | 2-(1'-CF$_3$-tetrazol-2-yl)phenyl |
| 14 | 2-pyridyl | 4-morpholinocarbonyl |
| 15 | 3-pyridyl | 2-(aminosulfonyl)phenyl |
| 16 | 3-pyridyl | 2-(methylaminosulfonyl)phenyl |
| 17 | 3-pyridyl | 1-pyrrolidinocarbonyl |
| 18 | 3-pyridyl | 2-(methylsulfonyl)phenyl |
| 19 | 3-pyridyl | 4-morpholino |
| 20 | 3-pyridyl | 2-(1'-CF$_3$-tetrazol-2-yl)phenyl |
| 21 | 3-pyridyl | 4-morpholinocarbonyl |
| 22 | 2-pyrimidyl | 2-(aminosulfonyl)phenyl |
| 23 | 2-pyrimidyl | 2-(methylaminosulfonyl)phenyl |
| 24 | 2-pyrimidyl | 1-pyrrolidinocarbonyl |
| 25 | 2-pyrimidyl | 2-(methylsulfonyl)phenyl |
| 26 | 2-pyrimidyl | 4-morpholino |
| 27 | 2-pyrimidyl | 2-(1'-CF$_3$-tetrazol-2-yl)phenyl |
| 28 | 2-pyrimidyl | 4-morpholinocarbonyl |
| 29 | 5-pyrimidyl | 2-(aminosulfonyl)phenyl |
| 30 | 5-pyrimidyl | 2-(methylaminosulfonyl)phenyl |
| 31 | 5-pyrimidyl | 1-pyrrolidinocarbonyl |
| 32 | 5-pyrimidyl | 2-(methylsulfonyl)phenyl |
| 33 | 5-pyrimidyl | 4-morpholino |
| 34 | 5-pyrimidyl | 2-(1'-CF$_3$-tetrazol-2-yl)phenyl |
| 35 | 5-pyrimidyl | 4-morpholinocarbonyl |
| 36 | 2-Cl-phenyl | 2-(aminosulfonyl)phenyl |
| 37 | 2-Cl-phenyl | 2-(methylaminosulfonyl)phenyl |
| 38 | 2-Cl-phenyl | 1-pyrrolidinocarbonyl |
| 39 | 2-Cl-phenyl | 2-(methylsulfonyl)phenyl |
| 40 | 2-Cl-phenyl | 4-morpholino |
| 41 | 2-Cl-phenyl | 2-(1'-CF$_3$-tetrazol-2-yl)phenyl |
| 42 | 2-Cl-phenyl | 4-morpholinocarbonyl |
| 43 | 2-F-phenyl | 2-(aminosulfonyl)phenyl |
| 44 | 2-F-phenyl | 2-(methylaminosulfonyl)phenyl |
| 45 | 2-F-phenyl | 1-pyrrolidinocarbonyl |
| 46 | 2-F-phenyl | 2-(methylsulfonyl)phenyl |
| 47 | 2-F-phenyl | 4-morpholino |
| 48 | 2-F-phenyl | 2-(1'-CF$_3$-tetrazol-2-yl)phenyl |
| 49 | 2-F-phenyl | 4-morpholinocarbonyl |
| 50 | 2,5-diF-phenyl | 2-(aminosulfonyl)phenyl |
| 51 | 2,5-diF-phenyl | 2-(methylaminosulfonyl)phenyl |
| 52 | 2,5-diF-phenyl | 1-pyrrolidinocarbonyl |
| 53 | 2,5-diF-phenyl | 2-(methylsulfonyl)phenyl |
| 54 | 2,5-diF-phenyl | 4-morpholino |
| 55 | 2,5-diF-phenyl | 2-(1'-CF$_3$-tetrazol-2-yl)phenyl |
| 56 | 2,5-diF-phenyl | 4-morpholinocarbonyl |
| 57 | phenyl | 2-(N-pyrrolidinyl-methyl)phenyl |
| 58 | phenyl | 2-(N-piperidinyl-methyl)phenyl |
| 59 | phenyl | 2-(N-morpholino-methyl)phenyl |
| 60 | phenyl | 2-(N,N'-methylmorpholinium-methyl)phenyl |
| 61 | phenyl | 2-(N-pyridinium-methyl)phenyl |
| 62 | phenyl | 2-(N-4-(N,N'-dimethylamino)-pyridinium-methyl)phenyl |
| 63 | phenyl | 2-(N-azatanyl-methyl)phenyl |
| 64 | phenyl | 2-(N-azetidinyl-methyl)phenyl |
| 65 | phenyl | 2-(N-piperazinyl-methyl)phenyl |
| 66 | phenyl | 2-(N,N'-BOC-piperazinyl-methyl)phenyl |
| 67 | phenyl | 2-(N-imidazolyl-methyl)phenyl |
| 68 | phenyl | 2-(N-methoxy-N-methylamino-methyl)phenyl |
| 69 | phenyl | 2-(N-pyridonyl-methyl)phenyl |
| 70 | phenyl | 2-(N-(N',N'-dimethylhylhydrazinyl-methyl)phenyl |
| 71 | phenyl | 2-(amidinyl)phenyl |
| 72 | phenyl | 2-(N-guanidinyl)phenyl |
| 73 | phenyl | 2-(imidazolyl)phenyl |
| 74 | phenyl | 2-(imidazolidinyl)phenyl |
| 75 | phenyl | 2-(2-imidazolidinyl-sulfonyl)phenyl |
| 76 | phenyl | 2-(2-pyrrolidinyl)phenyl |
| 77 | phenyl | 2-(2-piperidinyl)phenyl |
| 78 | phenyl | 2-(amidinyl-methyl)phenyl |
| 79 | phenyl | 2-(2-imidazolidinyl-methyl)phenyl |
| 80 | phenyl | 2-(N-(2-aminoimidazolyl)-methyl)phenyl |
| 81 | phenyl | 2-dimethylaminoimidazol-1-yl |
| 82 | phenyl | 2-(3-aminophenyl) |
| 83 | phenyl | 2-(3-pyrrolidinylcarbonyl) |
| 84 | phenyl | 2-glycinoyl |
| 85 | phenyl | 2-(imidazol-1-ylacetyl) |
| 86 | 2-pyridyl | 2-(N-pyrrolidinyl-methyl)phenyl |
| 87 | 2-pyridyl | 2-(N-piperidinyl-methyl)phenyl |
| 88 | 2-pyridyl | 2-(N-morpholino-methyl)phenyl |
| 89 | 2-pyridyl | 2-(N,N'-methylmorpholinium-methyl)phenyl |
| 90 | 2-pyridyl | 2-(N-pyridinium-methyl)phenyl |
| 91 | 2-pyridyl | 2-(N-4-(N,N'-dimethylamino)-pyridinium-methyl)phenyl |
| 92 | 2-pyridyl | 2-(N-azatanyl-methyl)phenyl |
| 93 | 2-pyridyl | 2-(N-azetidinyl-methyl)phenyl |
| 94 | 2-pyridyl | 2-(N-piperazinyl-methyl)phenyl |
| 95 | 2-pyridyl | 2-(N,N'-BOC-piperazinyl-methyl)phenyl |
| 96 | 2-pyridyl | 2-(N-imidazolyl-methyl)phenyl |
| 97 | 2-pyridyl | 2-(N-methoxy-N-methylamino-methyl)phenyl |
| 98 | 2-pyridyl | 2-(N-pyridonyl-methyl)phenyl |
| 99 | 2-pyridyl | 2-(N-(N',N'-dimethylhydrazinyl-methyl)phenyl |
| 100 | 2-pyridyl | 2-(amidinyl)phenyl |
| 101 | 2-pyridyl | 2-(N-guanidinyl)phenyl |
| 102 | 2-pyridyl | 2-(imidazolyl)phenyl |
| 103 | 2-pyridyl | 2-(imidazolidinyl)phenyl |
| 104 | 2-pyridyl | 2-(2-imidazolidinyl-sulfonyl)phenyl |
| 105 | 2-pyridyl | 2-(2-pyrrolidinyl)phenyl |
| 106 | 2-pyridyl | 2-(2-piperidinyl)phenyl |
| 107 | 2-pyridyl | 2-(amidinyl-methyl)phenyl |
| 108 | 2-pyridyl | 2-(2-imidazolidinyl-methyl)phenyl |
| 109 | 2-pyridyl | 2-(N-(2-aminoimidazolyl)-methyl)phenyl |
| 110 | 2-pyridyl | 2-dimethylaminoimidazol-1-yl |
| 111 | 2-pyridyl | 2-(3-aminophenyl) |
| 112 | 2-pyridyl | 2-(3-pyrrolidinylcarbonyl) |
| 113 | 2-pyridyl | 2-glycinoyl |
| 114 | 2-pyridyl | 2-(imidazol-1-ylacetyl) |
| 115 | 3-pyridyl | 2-(N-pyrrolidinyl-methyl)phenyl |
| 116 | 3-pyridyl | 2-(N-piperidinyl-methyl)phenyl |
| 117 | 3-pyridyl | 2-(N-morpholino-methyl)phenyl |
| 118 | 3-pyridyl | 2-(N,N'-methylmorpholinium-methyl)phenyl |

TABLE 3-continued

| | | |
|---|---|---|
| 119 | 3-pyridyl | 2-(N-pyridinium-methyl)phenyl |
| 120 | 3-pyridyl | 2-(N-4-(N,N'-dimethylamino)-pyridinium-methyl)phenyl |
| 121 | 3-pyridyl | 2-(N-azatanyl-methyl)phenyl |
| 122 | 3-pyridyl | 2-(N-azetidinyl-methyl)phenyl |
| 123 | 3-pyridyl | 2-(N-piperazinyl-methyl)phenyl |
| 124 | 3-pyridyl | 2-(N,N'-BOC-piperazinyl-methyl)phenyl |
| 125 | 3-pyridyl | 2-(N-imidazolyl-methyl)phenyl |
| 126 | 3-pyridyl | 2-(N-methoxy-N-methylamino-methyl)phenyl |
| 127 | 3-pyridyl | 2-(N-pyridonyl-methyl)phenyl |
| 128 | 3-pyridyl | 2-(N-(N',N'-dimethylhydrazinyl-methyl)phenyl |
| 129 | 3-pyridyl | 2-(amidinyl)phenyl |
| 130 | 3-pyridyl | 2-(N-guanidinyl)phenyl |
| 131 | 3-pyridyl | 2-(imidazolyl)phenyl |
| 132 | 3-pyridyl | 2-(imidazolidinyl)phenyl |
| 133 | 3-pyridyl | 2-(2-imidazolidinyl-sulfonyl)phenyl |
| 134 | 3-pyridyl | 2-(2-pyrrolidinyl)phenyl |
| 135 | 3-pyridyl | 2-(2-piperidinyl)phenyl |
| 136 | 3-pyridyl | 2-(amidinyl-methyl)phenyl |
| 137 | 3-pyridyl | 2-(2-imidazolidinyl-methyl)phenyl |
| 138 | 3-pyridyl | 2-(N-(2-aminoimidazolyl)-methyl)phenyl |
| 139 | 3-pyridyl | 2-dimethylaminoimidazol-1-yl |
| 140 | 3-pyridyl | 2-(3-aminophenyl) |
| 141 | 3-pyridyl | 2-(3-pyrrolidinylcarbonyl) |
| 142 | 3-pyridyl | 2-glycinoyl |
| 143 | 3-pyridyl | 2-(imidazol-1-ylacetyl) |
| 144 | 2-pyrimidyl | 2-(N-pyrrolidinyl-methyl)phenyl |
| 145 | 2-pyrimidyl | 2-(N-piperidinyl-methyl)phenyl |
| 146 | 2-pyrimidyl | 2-(N-morpholino-methyl)phenyl |
| 147 | 2-pyrimidyl | 2-(N,N'-methylmorpholinium-methyl)phenyl |
| 148 | 2-pyrimidyl | 2-(N-pyridinium-methyl)phenyl |
| 149 | 2-pyrimidyl | 2-(N-4-(N,N'-dimethylamino)-pyridinium-methyl)phenyl |
| 150 | 2-pyrimidyl | 2-(N-azatanyl-methyl)phenyl |
| 151 | 2-pyrimidyl | 2-(N-azetidinyl-methyl)phenyl |
| 152 | 2-pyrimidyl | 2-(N-piperazinyl-methyl)phenyl |
| 153 | 2-pyrimidyl | 2-(N,N'-BOC-piperazinyl-methyl)phenyl |
| 154 | 2-pyrimidyl | 2-(N-imidazolyl-methyl)phenyl |
| 155 | 2-pyrimidyl | 2-(N-methoxy-N-methylamino-methyl)phenyl |
| 156 | 2-pyrimidyl | 2-(N-pyridonyl-methyl)phenyl |
| 157 | 2-pyrimidyl | 2-(N-(N',N'-dimethylhydrazinyl-methyl)phenyl |
| 158 | 2-pyrimidyl | 2-(amidinyl)phenyl |
| 159 | 2-pyrimidyl | 2-(N-guanidinyl)phenyl |
| 160 | 2-pyrimidyl | 2-(imidazolyl)phenyl |
| 161 | 2-pyrimidyl | 2-(imidazolidinyl)phenyl |
| 162 | 2-pyrimidyl | 2-(2-imidazolidinyl-sulfonyl)phenyl |
| 163 | 2-pyrimidyl | 2-(2-pyrrolidinyl)phenyl |
| 164 | 2-pyrimidyl | 2-(2-piperidinyl)phenyl |
| 165 | 2-pyrimidyl | 2-(amidinyl-methyl)phenyl |
| 166 | 2-pyrimidyl | 2-(2-imidazolidinyl-methyl)phenyl |
| 167 | 2-pyrimidyl | 2-(N-(2-aminoimidazolyl)-methyl)phenyl |
| 168 | 2-pyrimidyl | 2-dimethylaminoimidazol-1-yl |
| 169 | 2-pyrimidyl | 2-(3-aminophenyl) |
| 170 | 2-pyrimidyl | 2-(3-pyrrolidinylcarbonyl) |
| 171 | 2-pyrimidyl | 2-glycinoyl |
| 172 | 2-pyrimidyl | 2-(imidazol-1-ylacetyl) |
| 173 | 2-Cl-phenyl | 2-(N-pyrrolidinyl-methyl)phenyl |
| 174 | 2-Cl-phenyl | 2-(N-piperidinyl-methyl)phenyl |
| 175 | 2-Cl-phenyl | 2-(N-morpholino-methyl)phenyl |
| 176 | 2-Cl-phenyl | 2-(N,N'-methylmorpholinium-methyl)phenyl |
| 177 | 2-Cl-phenyl | 2-(N-pyridinium-methyl)phenyl |
| 178 | 2-Cl-phenyl | 2-(N-4-(N,N'-dimethylamino)-pyridinium-methyl)phenyl |
| 179 | 2-Cl-phenyl | 2-(N-azatanyl-methyl)phenyl |
| 180 | 2-Cl-phenyl | 2-(N-azetidinyl-methyl)phenyl |
| 181 | 2-Cl-phenyl | 2-(N-piperazinyl-methyl)phenyl |
| 182 | 2-Cl-phenyl | 2-(N,N'-BOC-piperazinyl-methyl)phenyl |
| 183 | 2-Cl-phenyl | 2-(N-imidazolyl-methyl)phenyl |
| 184 | 2-Cl-phenyl | 2-(N-methoxy-N-methylamino-methyl)phenyl |
| 185 | 2-Cl-phenyl | 2-(N-pyridonyl-methyl)phenyl |
| 186 | 2-Cl-phenyl | 2-(N-(N',N'-dimethylhydrazinyl-methyl)phenyl |
| 187 | 2-Cl-phenyl | 2-(amidinyl)phenyl |
| 188 | 2-Cl-phenyl | 2-(N-guanidinyl)phenyl |
| 189 | 2-Cl-phenyl | 2-(imidazolyl)phenyl |
| 190 | 2-Cl-phenyl | 2-(imidazolidinyl)phenyl |
| 191 | 2-Cl-phenyl | 2-(2-imidazolidinyl-sulfonyl)phenyl |
| 192 | 2-Cl-phenyl | 2-(2-pyrrolidinyl)phenyl |
| 193 | 2-Cl-phenyl | 2-(2-piperidinyl)phenyl |
| 194 | 2-Cl-phenyl | 2-(amidinyl-methyl)phenyl |
| 195 | 2-Cl-phenyl | 2-(2-imidazolidinyl-methyl)phenyl |
| 196 | 2-Cl-phenyl | 2-(N-(2-aminoimidazolyl)-methyl)phenyl |
| 197 | 2-Cl-phenyl | 2-dimethylaminoimidazol-1-yl |
| 198 | 2-Cl-phenyl | 2-(3-aminophenyl) |
| 199 | 2-Cl-phenyl | 2-(3-pyrrolidinylcarbonyl) |
| 200 | 2-Cl-phenyl | 2-glycinoyl |
| 201 | 2-Cl-phenyl | 2-(imidazol-1-ylacetyl) |
| 202 | 2-F-phenyl | 2-(N-pyrrolidinyl-methyl)phenyl |
| 203 | 2-F-phenyl | 2-(N-piperidinyl-methyl)phenyl |
| 204 | 2-F-phenyl | 2-(N-morpholino-methyl)phenyl |
| 205 | 2-F-phenyl | 2-(N,N'-methylmorpholinium-methyl)phenyl |
| 206 | 2-F-phenyl | 2-(N-pyridinium-methyl)phenyl |
| 207 | 2-F-phenyl | 2-(N-4-(N,N'-dimethylamino)-pyridinium-methyl)phenyl |
| 208 | 2-F-phenyl | 2-(N-azatanyl-methyl)phenyl |
| 209 | 2-F-phenyl | 2-(N-azetidinyl-methyl)phenyl |
| 210 | 2-F-phenyl | 2-(N-piperazinyl-methyl)phenyl |
| 211 | 2-F-phenyl | 2-(N,N'-BOC-piperazinyl-methyl)phenyl |
| 212 | 2-F-phenyl | 2-(N-imidazolyl-methyl)phenyl |
| 213 | 2-F-phenyl | 2-(N-methoxy-N-methylamino-methyl)phenyl |
| 214 | 2-F-phenyl | 2-(N-pyridonyl-methyl)phenyl |
| 215 | 2-F-phenyl | 2-(N-(N',N'-dimethylhydrazinyl-methyl)phenyl |
| 216 | 2-F-phenyl | 2-(amidinyl)phenyl |
| 217 | 2-F-phenyl | 2-(N-guanidinyl)phenyl |
| 218 | 2-F-phenyl | 2-(imidazolyl)phenyl |
| 219 | 2-F-phenyl | 2-(imidazolidinyl)phenyl |
| 220 | 2-F-phenyl | 2-(2-imidazolidinyl-sulfonyl)phenyl |
| 221 | 2-F-phenyl | 2-(2-pyrrolidinyl)phenyl |
| 222 | 2-F-phenyl | 2-(2-piperidinyl)phenyl |
| 223 | 2-F-phenyl | 2-(amidinyl-methyl)phenyl |
| 224 | 2-F-phenyl | 2-(2-imidazolidinyl-methyl)phenyl |
| 225 | 2-F-phenyl | 2-(N-(2-aminoimidazolyl)-methyl)phenyl |
| 226 | 2-F-phenyl | 2-dimethylaminoimidazol-1-yl |
| 227 | 2-F-phenyl | 2-(3-aminophenyl) |
| 228 | 2-F-phenyl | 2-(3-pyrrolidinylcarbonyl) |
| 229 | 2-F-phenyl | 2-glycinoyl |
| 230 | 2-F-phenyl | 2-(imidazol-1-ylacetyl) |
| 231 | 2,5-diF-phenyl | 2-(N-pyrrolidinyl-methyl)phenyl |
| 232 | 2,5-diF-phenyl | 2-(N-piperidinyl-methyl)phenyl |
| 233 | 2,5-diF-phenyl | 2-(N-morpholino-methyl)phenyl |
| 234 | 2,5-diF-phenyl | 2-(N,N'-methylmorpholinium-methyl)phenyl |
| 235 | 2,5-diF-phenyl | 2-(N-pyridinium-methyl)phenyl |
| 236 | 2,5-diF-phenyl | 2-(N-4-(N,N'-dimethylamino)-pyridinium-methyl)phenyl |
| 237 | 2,5-diF-phenyl | 2-(N-azatanyl-methyl)phenyl |
| 238 | 2,5-diF-phenyl | 2-(N-azetidinyl-methyl)phenyl |
| 239 | 2,5-diF-phenyl | 2-(N-piperazinyl-methyl)phenyl |
| 240 | 2,5-diF-phenyl | 2-(N,N'-BOC-piperazinyl-methyl)phenyl |
| 241 | 2,5-diF-phenyl | 2-(N-imidazolyl-methyl)phenyl |
| 242 | 2,5-diF-phenyl | 2-(N-methoxy-N-methylamino-methyl)phenyl |
| 243 | 2,5-diF-phenyl | 2-(N-pyridonyl-methyl)phenyl |
| 244 | 2,5-diF-phenyl | 2-(N-(N',N'-dimethylhydrazinyl-methyl)phenyl |
| 245 | 2,5-diF-phenyl | 2-(amidinyl)phenyl |
| 246 | 2,5-diF-phenyl | 2-(N-guanidinyl)phenyl |
| 247 | 2,5-diF-phenyl | 2-(imidazolyl)phenyl |
| 248 | 2,5-diF-phenyl | 2-(imidazolidinyl)phenyl |
| 249 | 2,5-diF-phenyl | 2-(2-imidazolidinyl-sulfonyl)phenyl |
| 250 | 2,5-diF-phenyl | 2-(2-pyrrolidinyl)phenyl |
| 251 | 2,5-diF-phenyl | 2-(2-piperidinyl)phenyl |
| 252 | 2,5-diF-phenyl | 2-(amidinyl-methyl)phenyl |
| 253 | 2,5-diF-phenyl | 2-(2-imidazolidinyl-methyl)phenyl |
| 254 | 2,5-diF-phenyl | 2-(N-(2-aminoimidazolyl)-methyl)phenyl |
| 255 | 2,5-diF-phenyl | 2-dimethylaminoimidazol-1-yl |
| 256 | 2,5-diF-phenyl | 2-(3-aminophenyl) |
| 257 | 2,5-diF-phenyl | 2-(3-pyrrolidinylcarbonyl) |
| 258 | 2,5-diF-phenyl | 2-glycinoyl |
| 259 | 2,5-diF-phenyl | 2-(imidazol-1-ylacetyl) |

TABLE 4

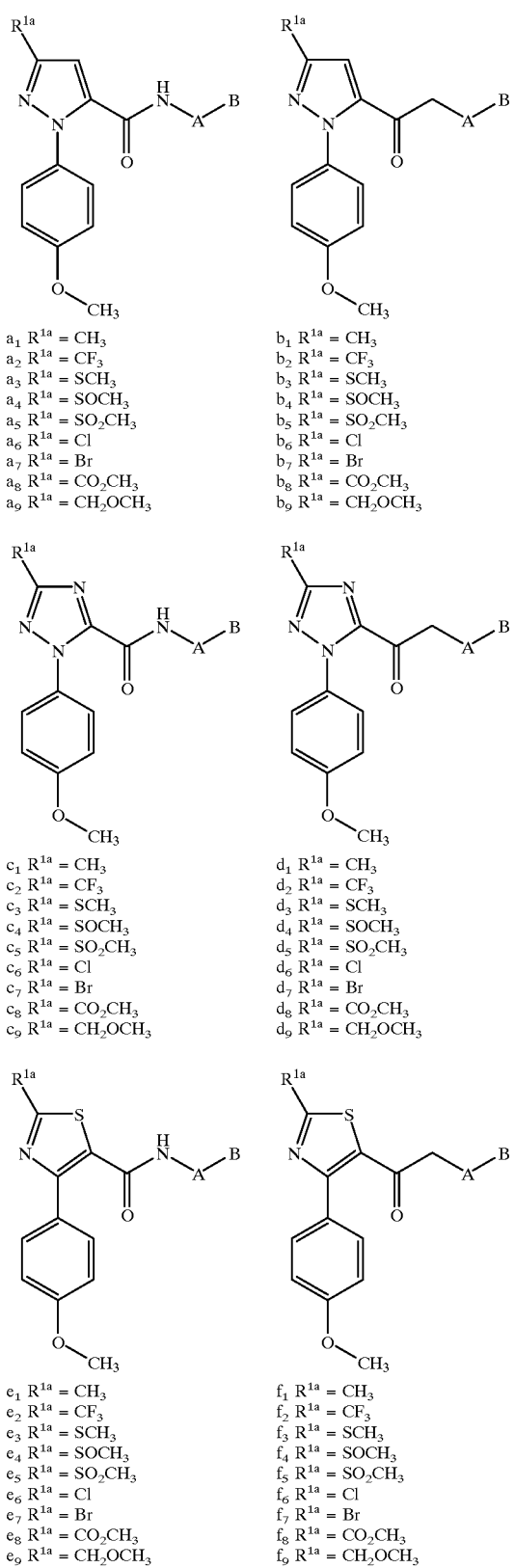

| Ex # | A | B |

TABLE 4-continued

| | | |
|---|---|---|
| 1 | phenyl | 2-((Me)₂N-methyl)phenyl |
| 2 | phenyl | 2-((Me)NH-methyl)phenyl |
| 3 | phenyl | 2-(H₂N-methyl)phenyl |
| 4 | phenyl | 2-HOCH₂-phenyl |
| 5 | 2-F-phenyl | 2-((Me)₂N-methyl)phenyl |
| 6 | 2-F-phenyl | 2-((Me)NH-methyl)phenyl |
| 7 | 2-F-phenyl | 2-(H₂N-methyl)phenyl |
| 8 | 2-F-phenyl | 2-HOCH₂-phenyl |
| 9 | phenyl | 2-methylimidazol-1-yl |
| 10 | phenyl | 2-ethylimidazol-1-yl |
| 11 | phenyl | 2-((Me)₂N-methyl)imidazol-1-yl |
| 12 | phenyl | 2-CH₃SO₂-imidazol-1-yl |
| 13 | phenyl | 2-CH₃OCH₂-imidazol-1-yl |
| 14 | 2 -F-phenyl | 2-methylimidazol-1-yl |
| 15 | 2-F-phenyl | 2-ethylimidazol-1-yl |
| 16 | 2-F-phenyl | 2-((Me)₂N-methyl)imidazol-1-yl |
| 17 | 2-F-phenyl | 2-CH₃SO₂-imidazol-1-yl |
| 18 | 2-F-phenyl | 2-CH₃OCH₂-imidazol-1-yl |
| 19 | 2-Cl-phenyl | 2-methylimidazol-1-yl |
| 20 | 2-Cl-phenyl | 2-ethylimidazol-1-yl |
| 21 | 2-Cl-phenyl | 2-((Me)₂N-methyl)imidazol-1-yl |
| 22 | 2-Cl-phenyl | 2-CH₃SO₂-imidazol-1-yl |
| 23 | 2-Cl-phenyl | 2-CH₃OCH₂-imidazol-1-yl |
| 24 | 2-(Me)₂N-phenyl | 2-methylimidazol-1-yl |
| 25 | 2-(Me)₂N-phenyl | 2-ethylimidazol-1-yl |
| 26 | 2-(Me)₂N-phenyl | 2-((Me)₂N-methyl)imidazol-1-yl |
| 27 | 2-(Me)₂N-phenyl | 2-CH₃SO₂-imidazol-1-yl |
| 28 | 2-(Me)₂N-phenyl | 2-CH₃OCH₂-imidazol-1-yl |
| 29 | phenyl | N-methylimidazol-2-yl |
| 30 | phenyl | 4-methylimidazol-5-yl |
| 31 | phenyl | 5-CF₃-pyrazol-1-yl |
| 32 | 2-F-phenyl | N-methylimidazol-2-yl |
| 33 | 2-F-phenyl | 4-methylimidazol-5-yl |
| 34 | 2-F-phenyl | 5-CF₃-pyrazol-1-yl |
| 35 | phenyl | guanidino |
| 36 | phenyl | 2-thiazolin-2-ylamine |
| 37 | phenyl | N-methyl-2-imidazolin-2-yl |
| 38 | phenyl | N-methyl-1,4,5,6-tetrahydropyrimid-2-yl |
| 39 | phenyl | N-methylimidazol-2-ylthiol |
| 40 | phenyl | t-butoxycarbonylamine |
| 41 | phenyl | (N-pyrrolidino)formylimino |
| 42 | phenyl | (N-pyrrolidino)formyl-N-methanesulfamoyl)imino |
| 43 | 2-F-phenyl | guanidino |
| 44 | 2-F-phenyl | 2-thiazolin-2-ylamine |
| 45 | 2-F-phenyl | N-methyl-2-imidazolin-2-yl |
| 46 | 2-F-phenyl | N-methyl-1,4,5,6-tetrahydropyrimid-2-yl |
| 47 | 2-F-phenyl | N-methylimidazol-2-ylthio |
| 48 | 2-F-phenyl | t-butoxycarbonylamine |
| 49 | 2-F-phenyl | (N-pyrrolidino)formylimino |
| 50 | 2-F-phenyl | (N-pyrrolidino)formyl-N-methanesulfamoyl)imino |
| 51 | 2-CH₃O-phenyl | (N-pyrrolidino)formylimino |
| 52 | 2-CH₃O-phenyl | (N-pyrrolidino)formyl-N-(methanesulfamoyl)imino |

TABLE 5

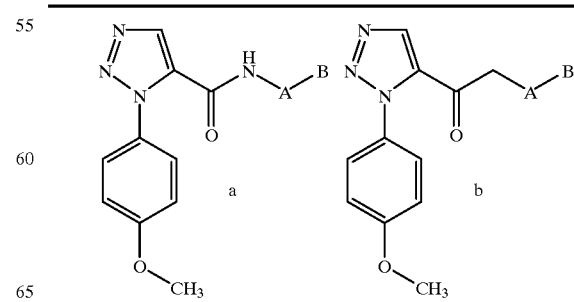

TABLE 5-continued

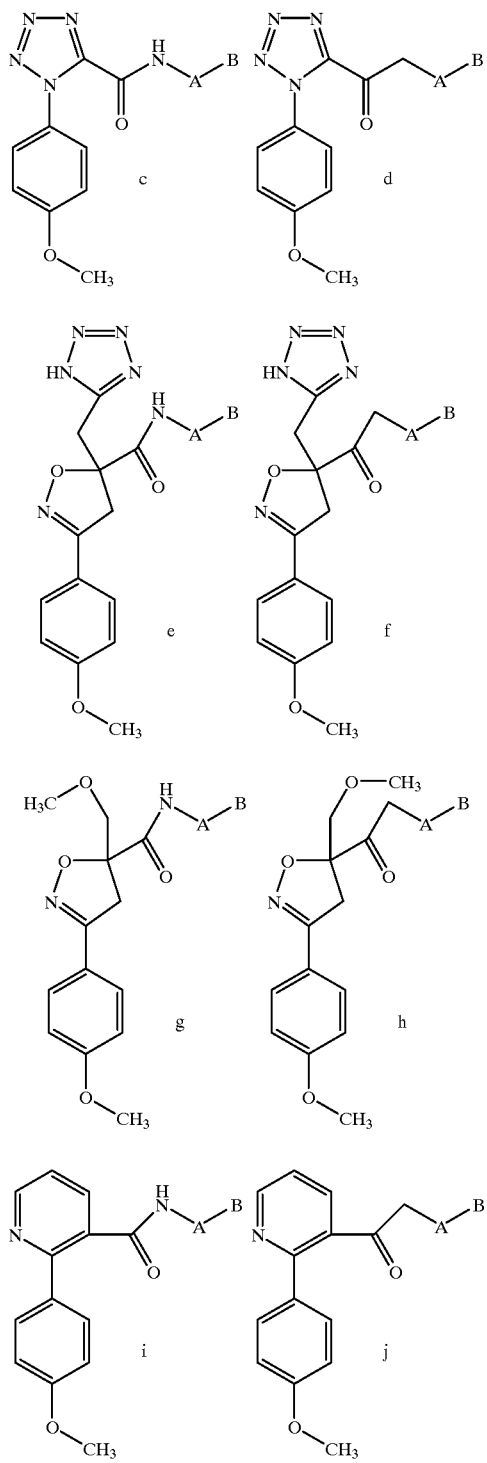

| Ex # | A | B |
|---|---|---|
| 1 | phenyl | 2-((Me)$_2$N-methyl)phenyl |
| 2 | phenyl | 2-((Me)NH-methyl)phenyl |
| 3 | phenyl | 2-(H$_2$N-methyl)phenyl |
| 4 | phenyl | 2-HOCH$_2$-phenyl |
| 5 | 2-F-phenyl | 2-((Me)$_2$N-methyl)phenyl |
| 6 | 2-F-phenyl | 2-((Me)NH-methyl)phenyl |
| 7 | 2-F-phenyl | 2-(H$_2$N-methyl)phenyl |
| 8 | 2-F-phenyl | 2-HOCH$_2$-phenyl |
| 9 | phenyl | 2-methylimidazol-1-yl |
| 10 | phenyl | 2-ethylimidazol-1-yl |
| 11 | phenyl | 2-((Me)$_2$N-methyl)imidazol-1-yl |
| 12 | phenyl | 2-CH$_3$SO$_2$-imidazol-1-yl |
| 13 | phenyl | 2-CH$_3$OCH$_2$-imidazol-1-yl |
| 14 | 2-F-phenyl | 2-methylimidazol-1-yl |
| 15 | 2-F-phenyl | 2-ethylimidazol-1-yl |
| 16 | 2-F-phenyl | 2-((Me)$_2$N-methyl)imidazol-1-yl |
| 17 | 2-F-phenyl | 2-CH$_3$SO$_2$-imidazol-1-yl |
| 18 | 2-F-phenyl | 2-CH$_3$OCH$_2$-imidazol-1-yl |
| 19 | 2-Cl-phenyl | 2-methylimidazol-1-yl |
| 20 | 2-Cl-phenyl | 2-ethylimidazol-1-yl |
| 21 | 2-Cl-phenyl | 2-((Me)$_2$N-methyl)imidazol-1-yl |
| 22 | 2-Cl-phenyl | 2-CH$_3$SO$_2$-imidazol-1-yl |
| 23 | 2-Cl-phenyl | 2-CH$_3$OCH$_2$-imidazol-1-yl |
| 24 | 2-(Me)$_2$N-phenyl | 2-methylimidazol-1-yl |
| 25 | 2-(Me)$_2$N-phenyl | 2-ethylimidazol-1-yl |
| 26 | 2-(Me)$_2$N-phenyl | 2-((Me)$_2$N-methyl)imidazol-1-yl |
| 27 | 2-(Me)$_2$N-phenyl | 2-CH$_3$SO$_2$-imidazol-1-yl |
| 28 | 2-(Me)$_2$N-phenyl | 2-CH$_3$OCH$_2$-imidazol-1-yl |
| 29 | phenyl | N-methylimidazol-2-yl |
| 30 | phenyl | 4-methylimidazol-5-yl |
| 31 | phenyl | 5-CF$_3$-pyrazol-1-yl |
| 32 | 2-F-phenyl | N-methylimidazol-2-yl |
| 33 | 2-F-phenyl | 4-methylimidazol-5-yl |
| 34 | 2-F-phenyl | 5-CF$_3$-pyrazol-1-yl |
| 35 | phenyl | guanidino |
| 36 | phenyl | 2-thiazolin-2-ylamine |
| 37 | phenyl | N-methyl-2-imidazolin-2-yl |
| 38 | phenyl | N-methyl-1,4,5,6-tetrahydropyrimid-2-yl |
| 39 | phenyl | N-methylimidazol-2-ylthiol |
| 40 | phenyl | t-butoxycarbonylamine |
| 41 | phenyl | (N-pyrrolidino)formylimino |
| 42 | phenyl | (N-pyrrolidino)formyl-N-methanesulfamoyl)imino |
| 43 | 2-F-phenyl | guanidino |
| 44 | 2-F-phenyl | 2-thiazolin-2-ylamine |
| 45 | 2-F-phenyl | N-methyl-2-imidazolin-2-yl |
| 46 | 2-F-phenyl | N-methyl-1,4,5,6-tetrahydropyrimid-2-yl |
| 47 | 2-F-phenyl | N-methylimidazol-2-ylthio |
| 48 | 2-F-phenyl | t-butoxycarbonylamine |
| 49 | 2-F-phenyl | (N-pyrrolidino)formylimino |
| 50 | 2-F-phenyl | (N-pyrrolidino)formyl-N-methanesulfamoyl)imino |
| 51 | 2-CH$_3$O-phenyl | (N-pyrrolidino)formylimino |
| 52 | 2-CH$_3$O-phenyl | (N-pyrrolidino)formyl-N-(methanesulfamoyl)imino |

TABLE 6

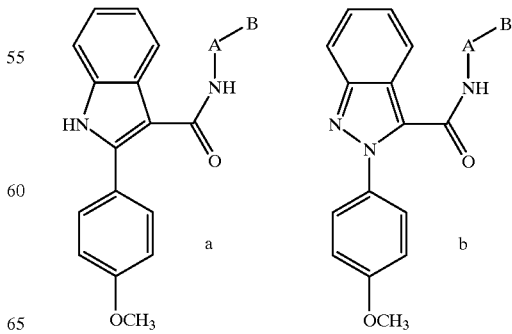

TABLE 6-continued

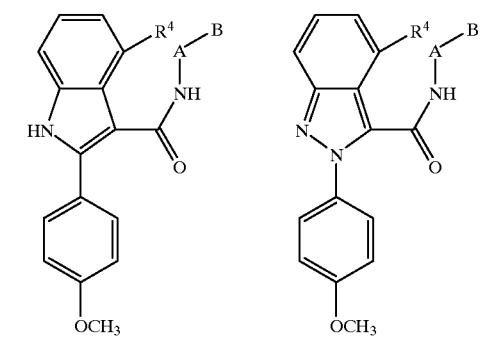

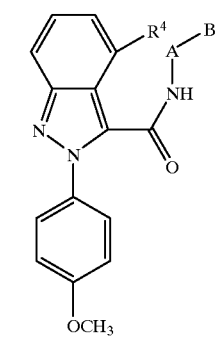

c₁ R⁴ = OCH₃
c₂ R⁴ = CO₂CH₃
c₃ R⁴ = CH₂OCH₃
c₄ R⁴ = CH₃
c₅ R⁴ = CF₃
c₆ R⁴ = Cl
c₇ R⁴ = F d₁ R⁴ = OCH₃
d₂ R⁴ = CO₂CH₃
d₃ R⁴ = CH₂OCH₃
d₄ R⁴ = CH₃
d₅ R⁴ = CF₃
d₆ R⁴ = Cl
d₇ R⁴ = F

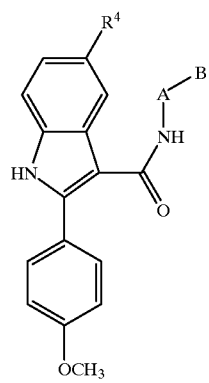

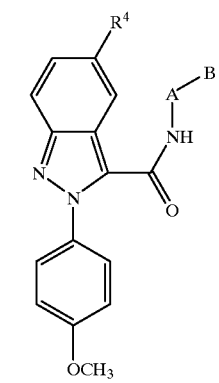

e₁ R⁴ = OCH₃
e₂ R⁴ = CO₂CH₃
e₃ R⁴ = CH₂OCH₃
e₄ R⁴ = CH₃
e₅ R⁴ = CF₃
e₆ R⁴ = Cl
e₇ R⁴ = F f₁ R⁴ = OCH₃
f₂ R⁴ = CO₂CH₃
f₃ R⁴ = CH₂OCH₃
f₄ R⁴ = CH₃
f₅ R⁴ = CF₃
f₆ R⁴ = Cl
f₇ R⁴ = F

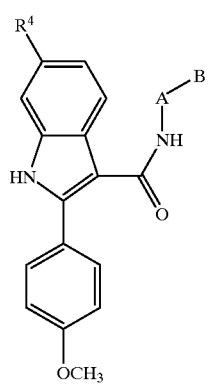

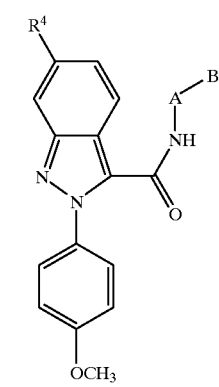

g₁ R⁴ = OCH₃
g₂ R⁴ = CO₂CH₃
g₃ R⁴ = CH₂OCH₃
g₄ R⁴ = CH₃
g₅ R⁴ = CF₃
g₆ R⁴ = Cl
g₇ R⁴ = F h₁ R⁴ = OCH₃
h₂ R⁴ = CO₂CH₃
h₃ R⁴ = CH₂OCH₃
h₄ R⁴ = CH₃
h₅ R⁴ = CF₃
h₆ R⁴ = Cl
h₇ R⁴ = F

TABLE 6-continued

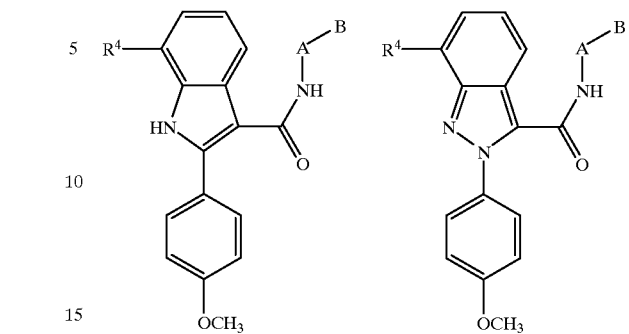

i₁ R⁴ = OCH₃
i₂ R⁴ = CO₂CH₃
i₃ R⁴ = CH₂OCH₃
i₄ R⁴ = CH₃
i₅ R⁴ = CF₃
i₆ R⁴ = Cl
i₇ R⁴ = F j₁ R⁴ = OCH₃
j₂ R⁴ = CO₂CH₃
j₃ R⁴ = CH₂OCH₃
j₄ R⁴ = CH₃
j₅ R⁴ = CF₃
j₆ R⁴ = Cl
j₇ R⁴ = F

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF₃-tetrazol-2-yl)phenyl |
| 7 | phenyl | 4-morpholinocarbonyl |
| 8 | 2-pyridyl | 2-(aminosulfonyl)phenyl |
| 9 | 2-pyridyl | 2-(methylaminosulfonyl)phenyl |
| 10 | 2-pyridyl | 1-pyrrolidinocarbonyl |
| 11 | 2-pyridyl | 2-(methylsulfonyl)phenyl |
| 12 | 2-pyridyl | 4-morpholino |
| 13 | 2-pyridyl | 2-(1'-CF₃-tetrazol-2-yl)phenyl |
| 14 | 2-pyridyl | 4-morpholinocarbonyl |
| 15 | 3-pyridyl | 2-(aminosulfonyl)phenyl |
| 16 | 3-pyridyl | 2-(methylaminosulfonyl)phenyl |
| 17 | 3-pyridyl | 1-pyrrolidinocarbonyl |
| 18 | 3-pyridyl | 2-(methylsulfonyl)phenyl |
| 19 | 3-pyridyl | 4-morpholino |
| 20 | 3-pyridyl | 2-(1'-CF₃-tetrazol-2-yl)phenyl |
| 21 | 3-pyridyl | 4-morpholinocarbonyl |
| 22 | 2-pyrimidyl | 2-(aminosulfonyl)phenyl |
| 23 | 2-pyrimidyl | 2-(methylaminosulfonyl)phenyl |
| 24 | 2-pyrimidyl | 1-pyrrolidinocarbonyl |
| 25 | 2-pyrimidyl | 2-(methylsulfonyl)phenyl |
| 26 | 2-pyrimidyl | 4-morpholino |
| 27 | 2-pyrimidyl | 2-(1'-CF₃-tetrazol-2-yl)phenyl |
| 28 | 2-pyrimidyl | 4-morpholinocarbonyl |
| 29 | 5-pyrimidyl | 2-(aminosulfonyl)phenyl |
| 30 | 5-pyrimidyl | 2-(methylaminosulfonyl)phenyl |
| 31 | 5-pyrimidyl | 1-pyrrolidinocarbonyl |
| 32 | 5-pyrimidyl | 2-(methylsulfonyl)phenyl |
| 33 | 5-pyrimidyl | 4-morpholino |
| 34 | 5-pyrimidyl | 2-(1'-CF₃-tetrazol-2-yl)phenyl |
| 35 | 5-pyrimidyl | 4-morpholinocarbonyl |
| 36 | 2-Cl-phenyl | 2-(aminosulfonyl)phenyl |
| 37 | 2-Cl-phenyl | 2-(methylaminosulfonyl)phenyl |
| 38 | 2-Cl-phenyl | 1-pyrrolidinocarbonyl |
| 39 | 2-Cl-phenyl | 2-(methylsulfonyl)phenyl |
| 40 | 2-Cl-phenyl | 4-morpholino |
| 41 | 2-Cl-phenyl | 2-(1'-CF₃-tetrazol-2-yl)phenyl |
| 42 | 2-Cl-phenyl | 4-morpholinocarbonyl |
| 43 | 2-F-phenyl | 2-(aminosulfonyl)phenyl |
| 44 | 2-F-phenyl | 2-(methylaminosulfonyl)phenyl |
| 45 | 2-F-phenyl | 1-pyrrolidinocarbonyl |
| 46 | 2-F-phenyl | 2-(methylsulfonyl)phenyl |
| 47 | 2-F-phenyl | 4-morpholino |
| 48 | 2-F-phenyl | 2-(1'-CF₃-tetrazol-2-yl)phenyl |
| 49 | 2-F-phenyl | 4-morpholinocarbonyl |
| 50 | 2,5-diF-phenyl | 2-(aminosulfonyl)phenyl |
| 51 | 2,5-diF-phenyl | 2-(methylaminosulfonyl)phenyl |
| 52 | 2,5-diF-phenyl | 1-pyrrolidinocarbonyl |

TABLE 6-continued

| | | |
|---|---|---|
| 53 | 2,5-diF-phenyl | 2-(methylsulfonyl)phenyl |
| 54 | 2,5-diF-phenyl | 4-morpholino |
| 55 | 2,5-diF-phenyl | 2-(1'-CF$_3$-tetrazol-2-yl)phenyl |
| 56 | 2,5-diF-phenyl | 4-morpholinocarbonyl |

TABLE 7

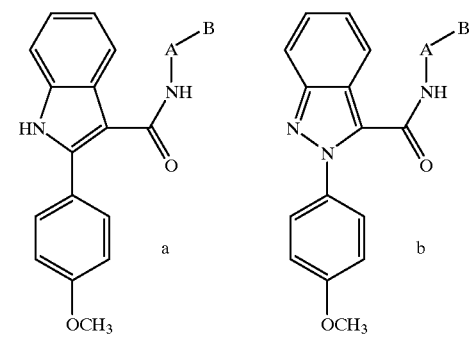

a / b

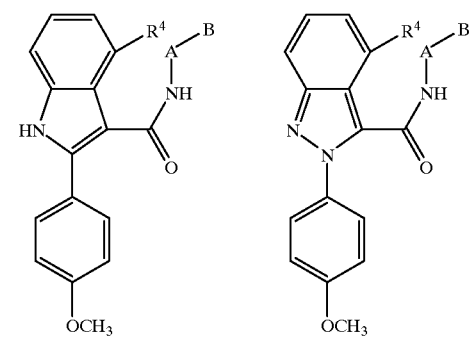

$c_1$ R$^4$ = OCH$_3$
$c_2$ R$^4$ = CO$_2$CH$_3$
$c_3$ R$^4$ = CH$_2$OCH$_3$
$c_4$ R$^4$ = CH$_3$
$c_5$ R$^4$ = CF$_3$
$c_6$ R$^4$ = Cl
$c_7$ R$^4$ = F $d_1$ R$^4$ = OCH$_3$
$d_2$ R$^4$ = CO$_2$CH$_3$
$d_3$ R$^4$ = CH$_2$OCH$_3$
$d_4$ R$^4$ = CH$_3$
$d_5$ R$^4$ = CF$_3$
$d_6$ R$^4$ = Cl
$d_7$ R$^4$ = F

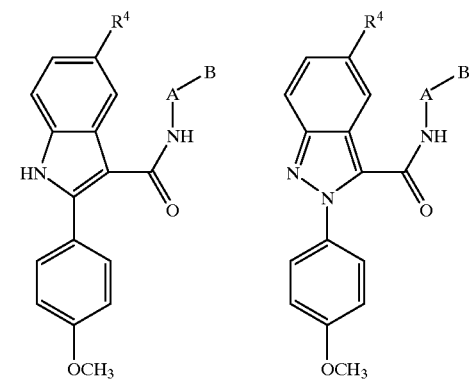

$e_1$ R$^4$ = OCH$_3$
$e_2$ R$^4$ = CO$_2$CH$_3$
$e_3$ R$^4$ = CH$_2$OCH$_3$
$e_4$ R$^4$ = CH$_3$
$e_5$ R$^4$ = CF$_3$
$e_6$ R$^4$ = Cl
$e_7$ R$^4$ = F $f_1$ R$^4$ = OCH$_3$
$f_2$ R$^4$ = CO$_2$CH$_3$
$f_3$ R$^4$ = CH$_2$OCH$_3$
$f_4$ R$^4$ = CH$_3$
$f_5$ R$^4$ = CF$_3$
$f_6$ R$^4$ = Cl
$f_7$ R$^4$ = F

TABLE 7-continued $g_1$ R$^4$ = OCH$_3$
$g_2$ R$^4$ = CO$_2$CH$_3$
$g_3$ R$^4$ = CH$_2$OCH$_3$
$g_4$ R$^4$ = CH$_3$
$g_5$ R$^4$ = CF$_3$
$g_6$ R$^4$ = Cl
$g_7$ R$^4$ = F $h_1$ R$^4$ = OCH$_3$
$h_2$ R$^4$ = CO$_2$CH$_3$
$h_3$ R$^4$ = CH$_2$OCH$_3$
$h_4$ R$^4$ = CH$_3$
$h_5$ R$^4$ = CF$_3$
$h_6$ R$^4$ = Cl
$h_7$ R$^4$ = F $i_1$ R$^4$ = OCH$_3$
$i_2$ R$^4$ = CO$_2$CH$_3$
$i_3$ R$^4$ = CH$_2$OCH$_3$
$i_4$ R$^4$ = CH$_3$
$i_5$ R$^4$ = CF$_3$
$i_6$ R$^4$ = Cl
$i_7$ R$^4$ = F $j_1$ R$^4$ = OCH$_3$
$j_2$ R$^4$ = CO$_2$CH$_3$
$j_3$ R$^4$ = CH$_2$OCH$_3$
$j_4$ R$^4$ = CH$_3$
$j_5$ R$^4$ = CF$_3$
$j_6$ R$^4$ = Cl
$j_7$ R$^4$ = F

| Ex # | A | B |
|---|---|---|
| 1 | phenyl | 2-((Me)$_2$N-methyl)phenyl |
| 2 | phenyl | 2-((Me)NH-methyl)phenyl |
| 3 | phenyl | 2-(H$_2$N-methyl)phenyl |
| 4 | phenyl | 2-HOCH$_2$-phenyl |
| 5 | 2-F-phenyl | 2-((Me)$_2$N-methyl)phenyl |
| 6 | 2-F-phenyl | 2-((Me)NH-methyl)phenyl |
| 7 | 2-F-phenyl | 2-(H$_2$N-methyl)phenyl |
| 8 | 2-F-phenyl | 2-HOCH$_2$-phenyl |
| 9 | phenyl | 2-methylimidazol-1-yl |
| 10 | phenyl | 2-ethylimidazol-1-yl |
| 11 | phenyl | 2-((Me)$_2$N-methyl)imidazol-1-yl |
| 12 | phenyl | 2-CH$_3$SO$_2$-imidazol-1-yl |
| 13 | phenyl | 2-CH$_3$OCH$_2$-imidazol-1-yl |
| 14 | 2-F-phenyl | 2-methylimidazol-1-yl |
| 15 | 2-F-phenyl | 2-ethylimidazol-1-yl |
| 16 | 2-F-phenyl | 2-((Me)$_2$N-methyl)imidazol-1-yl |
| 17 | 2-F-phenyl | 2-CH$_3$SO$_2$-imidazol-1-yl |
| 18 | 2-F-phenyl | 2-CH$_3$OCH$_2$-imidazol-1-yl |
| 19 | 2-Cl-phenyl | 2-methylimidazol-1-yl |
| 20 | 2-Cl-phenyl | 2-ethylimidazol-1-yl |
| 21 | 2-Cl-phenyl | 2-((Me)$_2$N-methyl)imidazol-1-yl |
| 22 | 2-Cl-phenyl | 2-CH$_3$SO$_2$-imidazol-1-yl |
| 23 | 2-Cl-phenyl | 2-CH$_3$OCH$_2$-imidazol-1-yl |
| 24 | 2-(Me)$_2$N-phenyl | 2-methylimidazol-1-yl |
| 25 | 2-(Me)$_2$N-phenyl | 2-ethylimidazol-1-yl |
| 26 | 2-(Me)$_2$N-phenyl | 2-((Me)$_2$N-methyl)imidazol-1-yl |

TABLE 7-continued

| | | |
|---|---|---|
| 27 | 2-(Me)$_2$N-phenyl | 2-CH$_3$SO$_2$-imidazol-1-yl |
| 28 | 2-(Me)$_2$N-phenyl | 2-CH$_3$OCH$_2$-imidazol-1-yl |
| 29 | phenyl | N-methylimidazol-2-yl |
| 30 | phenyl | 4-methylimidazol-5-yl |
| 31 | phenyl | 5-CF$_3$-pyrazol-1-yl |
| 32 | 2-F-phenyl | N-methylimidazol-2-yl |
| 33 | 2-F-phenyl | 4-methylimidazol-5-yl |
| 34 | 2-F-phenyl | 5-CF$_3$-pyrazol-1-yl |
| 35 | phenyl | guanidino |
| 36 | phenyl | 2-thiazolin-2-ylamine |
| 37 | phenyl | N-methyl-2-imidazolin-2-yl |
| 38 | phenyl | N-methyl-1,4,5,6-tetrahydropyrimid-2-yl |
| 39 | phenyl | N-methylimidazol-2-ylthiol |
| 40 | phenyl | t-butoxycarbonylamine |
| 41 | phenyl | (N-pyrrolidino)formylimino |
| 42 | phenyl | (N-pyrrolidino)formyl-N-methanesulfamoyl)imino |
| 43 | 2-F-phenyl | guanidino |
| 44 | 2-F-phenyl | 2-thiazolin-2-ylamine |
| 45 | 2-F-phenyl | N-methyl-2-imidazolin-2-yl |
| 46 | 2-F-phenyl | N-methyl-1,4,5,6-tetrahydropyrimid-2-yl |
| 47 | 2-F-phenyl | N-methylimidazol-2-ylthio |
| 48 | 2-F-phenyl | t-butoxycarbonylamine |
| 49 | 2-F-phenyl | (N-pyrrolidino)formylimino |
| 50 | 2-F-phenyl | (N-pyrrolidino)formyl-N-methanesulfamoyl)imino |
| 51 | 2-CH$_3$O-phenyl | (N-pyrrolidino)formylimino |
| 52 | 2-CH$_3$O-phenyl | (N-pyrrolidino)formyl-N-(methanesulfamoyl)imino |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i\,(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of ≦15 μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometricaily. Addition of an inhibitor to the assay mixture results in decreased absorbance and is indicative of thrombin inhibition Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 15 μm, thereby confirming the utility of the compounds of the present invention as effective Xa inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitcellulose, aga methyl cellulose, agar, bezntonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier zo interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

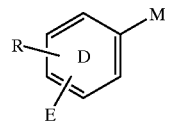

or a stereoisomer or pharmaceutically acceptable salt form thereof, wherein;

ring D is phenyl or pyridyl:

E is selected from F, Cl, Br, I, OH, $C_{1-3}$ alkoxy, SH, $C_{1-3}$ alkyl-S, $S(O)R^{3b}$, $S(O)_2R^{3a}$, $S(O)_2NR^2R^{2a}$, and $OCF_3$;

R is selected from H, F, Cl, Br, I, $OR^3$, $SR^3$, $CO_2R^3$, $NO_2$, and $CH_2OR^3$;

alternatively, E and R combine to form methylenedioxy or ethylenedioxy;

M is selected from the group:

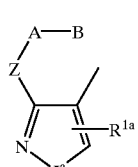

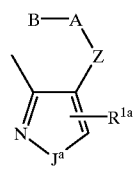

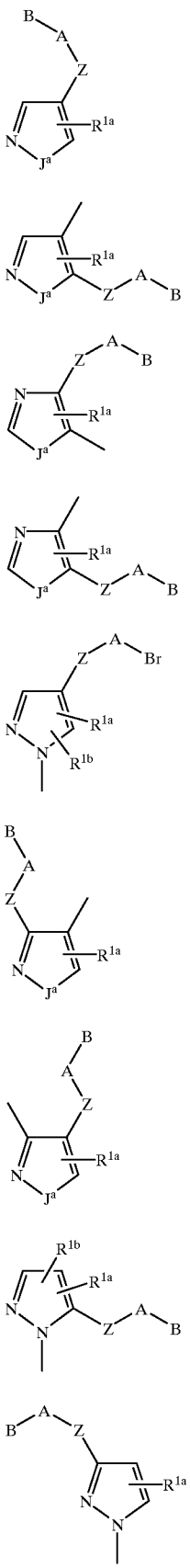

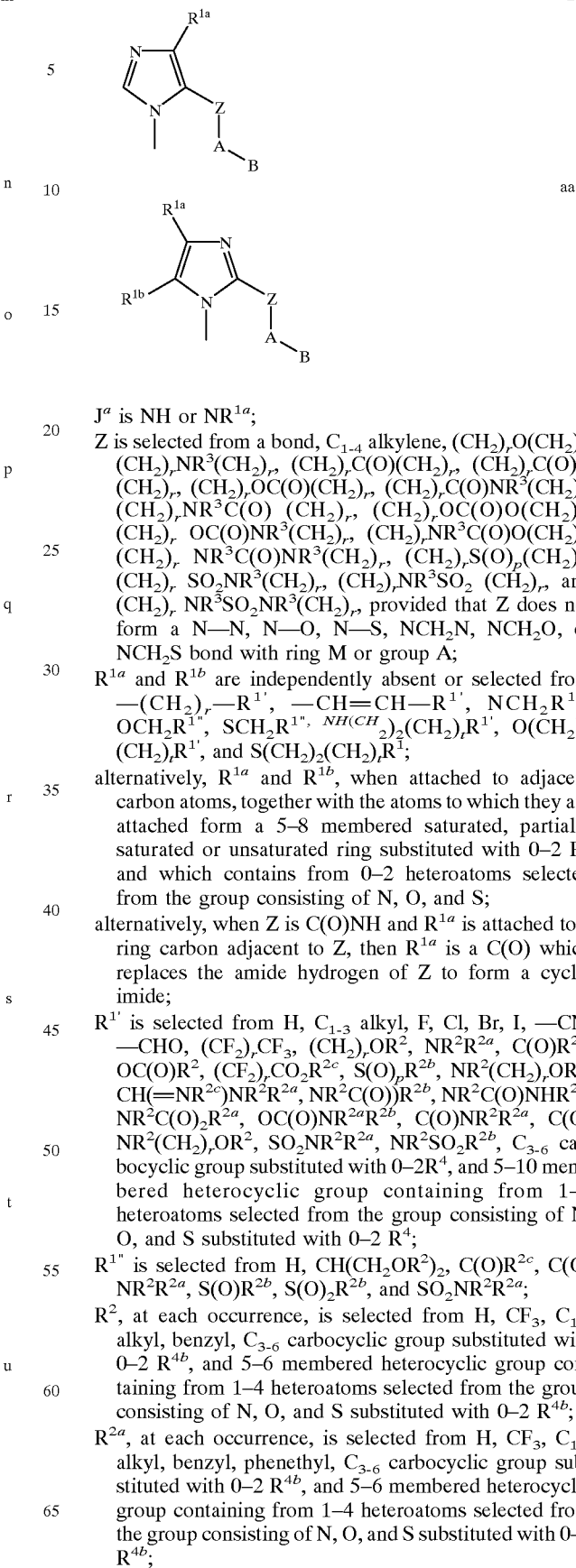

$J^a$ is NH or $NR^{1a}$;

Z is selected from a bond, $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_rNR^3C(O)$ $(CH_2)_r$, $(CH_2)_rOC(O)O(CH_2)_r$, $(CH_2)_r$ $OC(O)NR^3(CH_2)_r$, $(CH_2)_rNR^3C(O)O(CH_2)_r$, $(CH_2)_r$ $NR^3C(O)NR^3(CH_2)_r$, $(CH_2)_rS(O)_p(CH_2)_r$, $(CH_2)_r$ $SO_2NR^3(CH_2)_r$, $(CH_2)_rNR^3SO_2$ $(CH_2)_r$, and $(CH_2)_r$ $NR^3SO_2NR^3(CH_2)_r$, provided that Z does not form a N—N, N—O, N—S, $NCH_2N$, $NCH_2O$, or $NCH_2S$ bond with ring M or group A;

$R^{1a}$ and $R^{1b}$ are independently absent or selected from $-(CH_2)_r-R^{1'}$, $-CH=CH-R^{1'}$, $NCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$;

alternatively, $R^{1a}$ and $R^{1b}$, when attached to adjacent carbon atoms, together with the atoms to which they are attached form a 5–8 membered saturated, partially saturated or unsaturated ring substituted with 0–2 $R^4$ and which contains from 0–2 heteroatoms selected from the group consisting of N, O, and S;

alternatively, when Z is C(O)NH and $R^{1a}$ is attached to a ring carbon adjacent to Z, then $R^{1a}$ is a C(O) which replaces the amide hydrogen of Z to form a cyclic imide;

$R^{1'}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $CH(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic group substituted with 0–2 $R^4$, and 5–10 membered heterocyclic group containing from 1–4 heteroatoms selected from the group consisting of N, O, and S substituted with 0–2 $R^4$;

$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic group substituted with 0–2 $R^{4b}$, and 5–6 membered heterocyclic group containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, phenethyl, $C_{3-6}$ carbocyclic group substituted with 0–2 $R^{4b}$, and 5–6 membered heterocyclic group containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic group substituted with 0–2 $R^{4b}$, and 5–6 membered heterocyclic group containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic group substituted with 0–2 $R^{4b}$, and 5–6 membered heterocyclic group containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is selected from:
$C_{3-10}$ carbocyclic group substituted with 0–2 $R^4$, and 5–10 membered heterocyclic group containing from 1–4 heteroatoms selected from the group consisting of N, O, and S substituted with 0–2 $R^4$;

provided that A does not include a β-lactam;

B is selected from: H, Y, and X—Y;

X is selected from $C_{1-4}$ alkylene, —$CR^2(CR^2R^{2b})(CH_2)_t$—, —C(O)—, —C(=$NR^{1"}$)—, —$CR^2(NR^{1"}R^2)$—, —$CR^2(OR^2)$—, —$CR^2(SR^2)$—, —C(O)$CR^2R^{2a}$—, —$CR^2R^{2a}$C(O), —S(O)$_p$—, —S(O)$_p$$CR^2R^{2a}$—, —$CR^2R^{2a}$S(O)$_p$—, —S(O)$_2$$NR^2$—, —$NR^2$S(O)$_2$—, —$NR^2$S(O)$_2$$CR^2R^{2a}$—, —$CR^2R^{2a}$S(O)$_2$$NR^2$—, —$NR^2$S(O)$_2$$NR^2$—, —C(O)$NR^2$—, —$NR^2$C(O)—, —C(O)$NR^2CR^2R^{2a}$—, —$NR^2$C(O)$CR^2R^{2a}$—, —$CR^2R^{2a}$C(O)$NR^2$—, —$CR^2R^{2a}$$NR^2$C(O)—, —$NR^2$C(O)O—, —OC(O)$NR^2$—, —$NR^2$C(O)$NR^2$—, —$NR^2$—, —$NR^2CR^2R^{2a}$—, —$CR^2R^{2a}$$NR^2$—, O, —$CR^2R^{2a}$O—, and —OCR$^2$R$^{2a}$—;

Y is selected from:
$(CH_2)_rNR^2R^{2a}$, provided that X—Y do not form a N—N, O—N, or S—N bond,
$C_{3-10}$ carbocyclic group substituted with 0–2 $R^{4a}$, and 5–10 membered heterocyclic group containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $CH(=NR^2)NR^2R^{2a}$, $CH(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1"}$, $OCH_2R^{1"}$, $SCH_2R^{1"}$, $N(CH_2)_2(CH_2)_rR^{1'}$, $O(CH_2)_2(CH_2)_rR^{1'}$, and $S(CH_2)_2(CH_2)_rR^{1'}$, alternatively, one $R^4$ is a 5–6 membered aromatic heterocycle containing from 1–4 heteroatoms selected from the group consisting of N, O, and S;

provided that if B is H, then $R^4$ is other than tetrazole, C(O)-alkoxy, and $C(O)NR^2R^{2a}$;

$R^{4a}$, at each occurrence, is selected from H, =O, $(CH_2)_rOR^2$, $(CH_2)_r$—F, $(CH_2)_r$—Br, $(CH_2)_r$—Cl, I, $C_{1-4}$ alkyl, —CN, $NO_2$, $(CH_2)_rNR^2R^{2a}$, $(CH_2)_rNR^2R^{2b}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S and substituted with 0–1 $R^5$;

$R^{4b}$ at each occurrence, is selected from H, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NR^3)NR^3R^{3a}$, $NH^3C(=NR^3)NR^3R^{3a}$, $SO_2NR^3R^{3a}$, $NR_3SO_2NR^3R^{3a}$, $NR^3SO_2$—$C_{1-4}$ alkyl, $NR^3SO_2CF_3$, $NR^3SO_2$—phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, F, Cl, Br, I, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

n is selected from 0, 1, 2, and 3;
m is selected from 0, 1, and 2;
p is selected from 0, 1, and 2;
r is selected from 0, 1, 2, and 3;
s is selected from 0, 1, and 2; and,
t is selected from 0 and 1.

2. A compound according to claim 1, wherein M is selected from the group:

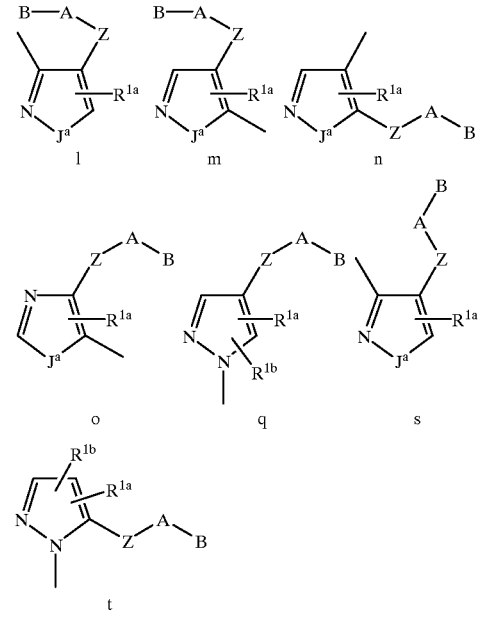

Z is selected from $(CH_2)_rC(O)(CH_2)_r$, $(CH_2)_rC(O)O(CH_2)_r$, $(CH_2)_rC(O)NR^3(CH_2)_r$, $(CH_2)_rS(O)_p(CH_2)_r$, and $(CH_2)_rSO_2NR^3(CH_2)_r$; and, Y is selected from one of the following carbocyclic and heterocyclic groups which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

Y may also be selected from the following bicyclic heteroaryl ring groups:

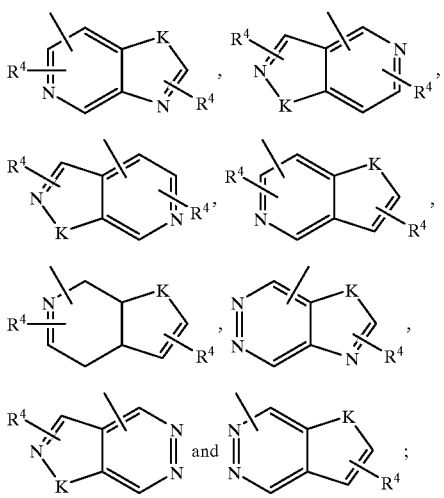

K is selected from O, S, NH, and N.

3. A compound according to claim 2, wherein the compound is of formula Ia or Ib:

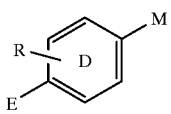

Ia

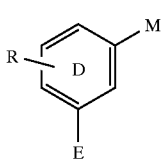

Ib wherein;

ring D is phenyl or pyridyl:

E is selected from F, Cl, Br, and $C_{1-3}$ alkoxy;

R is selected from H, F, Cl, Br, $OR^3$, and $CH_2OR^3$;

M is selected from the group:

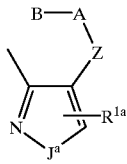

l

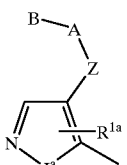

m

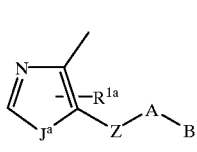

n

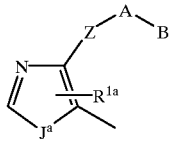

q

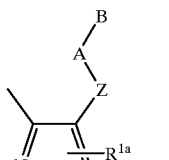

s

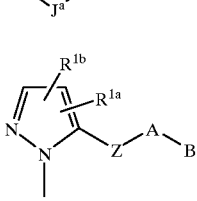

t

Z is selected from $(CH_2)_rC(O)(CH_2)_r$ and $(CH_2)_rC(O)NR^3(CH_2)_r$; and,

Y is selected from one of the following carbocyclic and heterocyclic groups which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole.

4. A compound according to claim 3, wherein;

ring D is phenyl;

E is selected from F, Cl, Br, and $OCH_3$;

R is selected from H, F, Cl, and Br;

M is selected from the group:

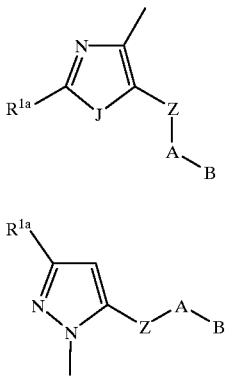

A is selected from:
C$_{5-6}$ carbocyclic group substituted with 0–2 R$^4$, and
5–6 membered heterocyclic group containing from 1–4 heteroatoms selected from the group consisting of N, O, and S substituted with 0–2 R$^4$;

Y is selected from one of the following carbocyclic and heterocyclic groups which are substituted with 0–2 R$^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole;

R$^2$, at each occurrence, is selected from H, CF$_3$, C$_{1-6}$ alkyl, benzyl, C$_{5-6}$ carbocyclic group substituted with 0–2 R$^{4b}$, and 5–6 membered heterocyclic group containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{5-6}$ carbocyclic group substituted with 0–2 R$^{4b}$, and 5–6 membered heterocyclic group containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{5-6}$ carbocyclic group substituted with 0–2 R$^{4b}$, and 5–6 membered heterocyclic group containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{5-6}$ carbocyclic group substituted with 0–2 R$^{4b}$, and 5–6 membered heterocyclic group containing from 1–4 heteroatoms selected from the group consisting of N, O, and S substituted with 0–2 R$^{4b}$; alternatively, R$^2$ and R$^{2a}$, together with the atom to which they are attached, combine to form a ring selected from imidazolyl, morpholino, piperazinyl, pyridyl, and pyrrolidinyl, substituted with 0–2 R$^{4b}$;

R$^4$, at each occurrence, is selected from H, =O, OR$^2$, CH$_2$OR$^2$, F, Cl, C$_{1-4}$ alkyl, NR$^2$R$^{2a}$, CH$_2$NR$^2$R$^{2a}$, C(O)R$^{2c}$, CH$_2$C(O)R$^{2c}$, C(O)NR$^2$R$^{2a}$, CH(=NR$^2$)NR$^2$R$^{2a}$, CH(=NS(O)$_2$R$^5$)NR$^2$R$^{2a}$, SO$_2$NR$^2$R$^{2a}$, NR$^2$SO$_2$—C$_{1-4}$ alkyl, S(O)$_2$R$^5$, and CF$_3$ provided that if B is H, then R$^4$ is other than tetrazole, C(O)-alkoxy, and C(O)NR$^2$R$^{2a}$;

R$^{4a}$, at each occurrence, is selected from H, =O, (CH$_2$)$_r$OR$^2$, F, Cl, C$_{1-4}$ alkyl, NR$^2$R$^{2a}$, CH$_2$NR$^2$R$^{2a}$, NR$^2$R$^{2b}$, CH$_2$NR$^2$R$^{2b}$, (CH$_2$)$_r$C(O)R$^{2c}$, NR$^2$C(O)R$^{2b}$, C(O)NR$^2$R$^{2a}$, C(O)NH(CH$_2$)$_2$NR$^2$R$^{2a}$, NR$^2$C(O)NR$^2$R$^{2a}$, SO$_2$NR$^2$R$^{2a}$, S(O)$_2$R$^5$, and CF$_3$; and, R$^{4b}$, at each occurrence, is selected from H, =O, (CH$_2$)$_r$OR$^3$, F, Cl, C$_{1-4}$ alkyl, NR$^3$R$^{3a}$, CH$_2$NR$^3$R$^{3a}$, C(O)R$^3$, CH$_2$C(O)R$^3$, C(O)OR$^{3c}$, C(O)NR$^3$R$^{3a}$, CH(=NR$^3$) NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_2$CF$_3$, S(O)$_2$—C$_{1-4}$ alkyl, S(O)$_2$-phenyl, and CF$_3$.

5. A compound according to claim 1, wherein compound is selected from:
3-Methyl-1-phenyl-1H-pyrazole-5-(N-(2'-aminosulfonyl-[1,1']-biphen-4-yl))carboxyamide;
3-Methyl-1-(2-methoxy)phenyl-1H-pyrazole-5-(N-(2'-aminosulfonyl -[1,1']-biphen-4-yl)carboxyamide;
3-Methyl-1-(3-methoxy)phenyl-1H-pyrazole-5-(N-(2'-aminosulfonyl -[1,1']-biphen-4-yl)carboxyamide;
3-Methyl-1-(4-methoxy)phenyl-1H-pyrazole-5-(N-(2'-aminosulfonyl -[1,1']-biphen-4-yl)carboxyamide;
3-Methyl-1-(2-hydroxy)phenyl-1H-pyrazole-5-(N-(2'-aminosulfonyl -[1,1']-biphen-4-yl)carboxyamide;
3-Methyl-1-(3-hydroxy)phenyl-1H-pyrazole-5-(N-(2'-aminosulfonyl -[1,1']-biphen-4-yl)carboxyamide;
3-Methyl-1-(4-hydroxy)phenyl-1H-pyrazole-5-(N-(2'-aminosulfonyl -[1,1']-biphen-4-yl)carboxyamide;
3-Methyl-1-(4-methoxyphenyl)-1H-pyrazole-5-(N-(3-fluoro-(2'-aminosulfonyl-[1,1']-biphen-4-yl) carboxyamide;
3-Methyl-1-(4-methoxyphenyl)-1H-pyrazole-5-(N-(3-bromo-4-(2'-aminosulfonyl-[1,1']-biphen-4-yl) carboxyamide;
3-Methyl-1-(4-methoxyphenyl)-1H-pyrazole-5-(N-(3-iodo-(2'-aminosulfonyl-[1,1']-biphen-4-yl)carboxyamide;
3-Methyl-1-(4-methoxyphenyl)-1H-pyrazole-5-(N-(3-methyl-(2'-aminosulfonyl-[1,1']-biphen-4-yl) carboxyamide;
3-Methyl-1-(4-methoxyphenyl)-1H-pyrazole-5-(N-(4-N-carboxyldimethylamine)phenyl)carboxyamide;
3-Methyl-1-(4-methoxyphenyl)-1H-pyrazole-5-(N-(4-N-pyrrolidinocarbonyl)phenyl)carboxyamide;
3-Methyl-1-(4-methoxyphenyl)-1H-pyrazole-5-(N-(4-a-methyl-N-pyrrolidino)phenyl)carboxyamide;
3-Trifluoromethyl-1-(4-methoxyphenyl)-1H-pyrazole-5-(N-(2'-aminosulfonyl-[1,1']-biphen-4-yl)carboxyamide;
3-Trifluoromethyl-1-(4-methoxyphenyl)-1H-pyrazole-5-(N-(4-N-pyrrolidinocarbonyl)phenyl)carboxyamide;
3-Trifluoromethyl-1-(4-methoxyphenyl)-1H-pyrazole-5-(N-(5-(2-methanesulfonyl)phenyl)pyridin-2-yl) carboxyamide;
3-Trifluoromethyl-1-(4-methoxyphenyl)-1H-pyrazole-5-(N-(5-N-pyrrolidinocarbonyl)pyridin-2-yl) carboxyamide;
3-Methyl-1-(4-methoxyphenyl)-1H-pyrazole-5-(N-(5-N-pyrrolidinocarbonyl)pyridin-2-yl)carboxyamide;
3-Methyl-1-(4-methoxyphenyl)-1H-pyrazole-5-(N-(5-(2-sulfonamido)phenyl)pyridin-2-yl)carboxyamide;
3-Methyl-1-(4-methoxyphenyl)-1H-pyrazole-5-N-(4-(N-carboxyl-3-hydroxypyrrolidino)phenyl)carboxyamide;
[2-Amino-4-(4-methoxyphenyl)-5-[(2'-aminosulfonyl-[1,1']-biphen-4-yl)aminocarbonyl]thiazole;
2-Bromo-4-(4-methoxyphenyl)-5-[(2'-aminosulfonyl-[1,1']-biphen-4-yl)aminocarbonyl]thiazole;
2-Chloro-4-(4-methoxyphenyl)-5-[(2'-aminosulfonyl-[1,1']-biphen-4-yl)aminocarbonyl]thiazole;

2-Chloro-4-(4-phenoxy)-5-[(2'-aminosulfonyl-[1,1']-biphen-4-yl)aminocarbonyl]thiazole;
2-Methoxy-4-(4-methoxyphenyl)-5-[(2'-aminosulfonyl-[1,1']-biphen-4-yl)aminocarbonyl]thiazole;
2-Thiomethyl-4-(4-methoxyphenyl)-5-[(2'-aminosulfonyl-[1,1']-biphen-4-yl)aminocarbonyl]thiazole;
2-Methylsulfoxide-4-(4-methoxyphenyl)-5-[(2'-aminosulfonyl-[1,1']-biphen-4-yl)aminocarbonyl]thiazole;
2-Methylsulfone-4-(4-methoxyphenyl)-5-[(2'-aminosulfonyl-[1,1']-biphen-4-yl)aminocarbonyl]thiazole;
2-Cyano-4-(4-methoxyphenyl)-5-[(2'-aminosulfonyl-[1,1']-biphen-4-yl)aminocarbonyl]thiazole;
2-N,N-Dimethylamino-4-(4-methoxyphenyl)-5-[(2'-aminosulfonyl-[1,1']-biphen-4-yl)aminocarbonyl]thiazole;
2-(1-Pyrrole)-4-(4-methoxyphenyl)-5-[(2'-aminosulfonyl-[1,1']-biphen-4-yl)aminocarbonyl]thiazole;
3-(4-Methoxyphenyl)-5-[5-(2'-aminosulfonylphenyl-1-yl)pyridin-2-yl]aminocarbonyl-5-carbomethoxymethyl-isoxazoline;
3-(4-Methoxyphenyl)-5-[5-(2'-aminosulfonylphenyl-1-yl)pyridin-2-yl]aminocarbonyl-5-carboxymethyl-isoxazoline;
3-(4-Methoxyphenyl)-5-[5-(2'-aminosulfonylphenyl-1-yl)pyridin-2-yl]aminocarbonyl-5-(N-carbomethoxymethyl)carboxamidomethyl-isoxazoline;
3-(4-Methoxyphenyl)-5-[5-(2'-aminosulfonylphenyl-1-yl)pyridin-2-yl]aminocarbonyl-5-(1,2,4-triazol-1-yl)methyl-isoxazoline;
1-(4-Methoxyphenyl)-5-[(2'-aminosulfonyl-[1,1']-biphen-4-yl)aminocarbonyl]tetrazole;]
3-Methyl-1-(4-methoxy-3-chloro)phenyl-1H-pyrazole-5-(N-(2'-aminosulfonyl-[1,1']-biphen-4-yl)carboxyamide;
3-Methyl-1-(4-trifluoroimethoxy)phenyl-1H-pyrazole-5-(N-(2'-aminosulfonyl-[1,1']-biphen-4-yl)carboxyamide;
1-(3-Bromophenyl)-3-methyl-1H-pyrazole-5-[(2'-aminosulfonyl-[1,1']-biphen-4-yl)carboxyamide;
1-(3-Iodophenyl)-3-methyl-1H-pyrazole-5-[(2'-aminosulfonyl-[1,1']-biphen-4-yl)carboxyamide;
1-(3,4-Methylenedioxanephenyl)-3-methyl-1H-pyrazole-5-[(2'-aminosulfonyl-[1,1']-biphen-4-yl)carboxyamide;
1-(4-Methoxyphenyl)-3-hydroxylmethylene-1H-pyrazole-5-(4'-pyrrolidinocarbonyl)anilide;
1-(4-Methoxyphenyl)-3-formaldehyde-1H-pyrazole-5-(4'-pyrrolidinocarbonyl)anilide;
1-(4-Methoxyphenyl)-5-(4'-pyrrolidinocarbonyl)anilide-3-pyrazolecarboxylic acid;
1-(4-Methoxyphenyl)-3-methylcarboxylate-1H-pyrazole-5-(4'-pyrrolidinocarbonyl)anilide;
1-(4'-Chlorophenyl)-3-methyl-1H-pyrazole-5-[(2'-aminosulfonyl-[1,1']-biphen-4-yl)carboxyamide;
1-(4'-Chlorophenyl)-3-methyl-1H-pyrazole-5-[(2'-aminosulfonyl-[1-pyridyl-1'-phenyl]-4-yl)carboxyamide;
1-(3',4'-Dichlorophenyl)-3-methyl-1H-pyrazole-5-[(2'-aminosulfonyl-[1,1']-biphen-4-yl)carboxyamide;
1-(3'-Chlorophenyl)-3-methyl-1H-pyrazole-5-[(2'-aminosulfonyl-[1,1']-biphen-4-yl) carboxyamide;
[2-Amino-4-phenyl-5-[(2'-aminosulfonyl-[1,1']-biphen-4-yl)aminocarbonyl]thiazole;
2-Chloro-4-phenyl-5-[(2'-aminosulfonyl-[1,1']-biphen-4-yl)aminocarbonyl]thiazole;
2-Amino-4-[3-(bromo)-4-(fluoro)-phenyl]-5-[(2'-aminosulfonyl-[1,1']-biphen-4-yl)aminocarbonyl]thiazole;
2-Amino-4-[4-fluorophenyl]-5-[(2'-aminosulfonyl-[1,1']-biphen-4-yl)aminocarbonyl]thiazole;
2-Amino-4-[3-bromophenyl]-5-[(2'-aminosulfonyl-[1,1']-biphen-4-yl)aminocarbonyl]thiazole;
2-Chloro-4-[3-bromophenyl]-5-[(2'-aminosulfonyl-[1,1']-biphen-4-yl)aminocarbonyl]thiazole;]
N-(2'-Aminosulfonyl-[1,1']-biphen-4-yl)-1-(4-methoxyphenyl)-3-(methylthio)pyrazole-5-carboxamide;
1-(4-Methoxyphenyl)-3-(methylsulfonyl)-N-(5-(2'-methylsulfonylphenyl)pyrimid-2-yl)pyrazole-5-carboxamide;
N-(2'-Aminosulfonyl-[1,1']-biphen-4-yl)-1-(4-methoxyphenyl)-3-(methylsulfonyl)-1H-pyrazole-5-carboxamide;
N-(4-Benzoylpyrrolidino)-1-(4-methoxyphenyl)-3-(methylthio)-1H-pyrazole-5-carboxamide;
1-(4-Methoxyphenyl)-N-(5-(2'-methylsulfonylphenyl)pyrimid-2-yl)-3-(methylthio)-1H-pyrazole-5-carboxamide;
N-(4-Benzoylpyrrolidino)-1-(4-methoxyphenyl)-3-(methylsulfonyl)-1H-pyrazole-5-carboxamide;
N-(2'-Aminosulfonyl-[1,1']-biphen-4-yl)-1-(4-methoxyphenyl)-3-(methoxymethyl)-1H-pyrazole-5-carboxamide;
N-(2'-Aminosulfonyl-[1,1']-biphen-4-yl)-1-(4-methoxyphenyl)-3-carbomethoxy-1H-pyrazole-5-carboxamide;
N-(2'-Aminosulfonyl-[1,1']-biphen-4-yl)-1-(4-methoxyphenyl)-3-(methylsulfonylmethyl)-1H-pyrazole-5-carboxamide;
3-Trifluoromethyl-1-(4-methoxyphenyl)-1H-pyrazole-5-(N-(5-(2-methanesulfonyl)phenyl)pyrimidin-2-yl)carboxyamide;
3-Methyl-1-(4-methoxyphenyl)-1H-pyrazole-5-N-(4-(N-carboxyl-2-carbomethoxypyrrolidino)phenyl)carboxyamide;
3-Methyl-1-(4-methoxyphenyl)-1H-pyrazole-5-N-(4-(N-carboxyl-3-aminopyrrolidino)phenyl)carboxyamide;
3-Methyl-1-(4-methoxyphenyl)-1H-pyrazole-5-N-(4-(N-carboxyl-3-methoxypyrrolidino)phenyl)carboxyamide;
3-Trifluoromethyl-1-(4-methoxyphenyl)-1H-pyrazole-5-(N-(5-(2-aminosulfonyl)phenyl)pyridin-2-yl)carboxyamide;
3-Trifluoromethyl-1-(4-methoxyphenyl)-1H-pyrazole-5-(N-(4-amidino)phenyl)carboxyamide;
3-Trifluoromethyl-1-(4-methoxyphenyl)-1H-pyrazole-5-(N-(4-(N-pyrrolidino)formylimino)phenyl)carboxyamide;
3-Trifluoromethyl-5-(N-(2'-aminosulfonyl-[1,1']-biphen-4-yl))-1-(4-methoxyphenyl)pyrrolo[3,4-d]pyrazole-4,6-(1H,5H)-dione;
3-Trifluoromethyl-1-(4-methoxyphenyl)-1H-pyrazole-5-carbomethoxy-(N-(2'-aminosulfonyl-[1,1']-biphen-4-yl))carboxyamide;
3-Trifluoromethyl-1-(4-methoxyphenyl)-1H-pyrazole-5-hydoxymethyl-(N-(2'-aminosulfonyl-[1,1']-biphen-4-yl))carboxyamide;
3-Trifluoromethyl-1-(4-methoxyphenyl)-1H-pyrazole-5-(N-2-fluoro(4-(N-pyrrolidino)formylimino)phenyl)carboxyamide;
3-Trifluoromethyl-1-(4-methoxyphenyl)-1H-pyrazole-5-(N-(4-(N-pyrrolidino)formyl-N-((2-propyl)methylcarbamoyl)imino)phenyl)carboxyamide;
3-Trifluoromethyl-1-(4-methoxyphenyl)-1H-pyrazole-5-(N-(4-(N-pyrrolidino)formyl-N-(methanesulfamoyl)imino)phenyl)carboxyamide;
3-Trifluoromethyl-1-(4-methoxyphenyl)-1H-pyrazole-5-(N-((4-amidino)phenyl)methyl)carboxyamide;
3-Trifluoromethyl-1-(4-methoxyphenyl)-1H-pyrazole-5-(N-((4-(N-pyrrolidino)formylimino)phenyl)methyl)carboxyamide;

3-Trifluoromethyl-1-(4-methoxyphenyl)-1H-pyrazole-5-(N-((1-benzyl)piperidin-4-yl)carboxyamide;

3-Trifluoromethyl-1-(4-methoxyphenyl)-1H-pyrazole-5-(N-((1-(pyridin-2-yl)methyl)piperidin-4-yl)carboxyamide;

3-Trifluoromethyl-1-(4-methoxyphenyl)-1H-pyrazole-5-(N-(4-(2-methylimidazo-1-yl))phenyl)carboxyamide;

3-Methyl-(4-methoxy)phenyl-1H-pyrazole-5-(N-{4-(5-methyl-imidazol-1-yl}phenyl)carboxyamide;

3-Methyl-(4-methoxy)phenyl-1H-pyrazole-5-(N-{4-(4-methyl-imidazol-1-yl}phenyl)carboxyamide;

3-Trifluoromethyl-(4-methoxy)phenyl-1H-pyrazole-5-(N-{4-(5-carbomethoxy-imicdazol-1-yl}phenyl)carboxyamide;

3-Trifluoromethyl-(4-methoxy)phenyl-1H-pyrazole-5-(N-{4-(5-carboxy-imidazol-1-yl}phenyl)carboxyamide;

1-(4'-Methoxyphenyl)-3-hydroxylmethyl-1H-pyrazole-5-N-(4'-pyrrolidinocarbonyl)phenyl)carboxyamide;

1-(4'-Methoxyphenyl)-3-formaldehyde-1H-pyrazole-5-N-(4'-(pyrrolidinocarbonyl)phenyl)carboxyamide;

1-(4'-Methoxyphenyl)-5-N-(4'-(pyrrolidinocarbonyl)anilide)-1H-pyrazol-3-yl-carboxylic acid;

1-(4'-Methoxyphenyl)-3-methylcarboxylate-1H-pyrazole-5-N-(4'-pyrrolidinocarbonyl)phenyl)carboxyamide;

1-(4'-Methoxyphenyl)-3-cyanomethyl-1H-pyrazole-5-N-(4'-pyrrolidinocarbonyl)phenyl)carboxyamide;

2-(1'-(4"-Methoxyphenyl)-5'-(4"-pyrrolidinyl-one)anilide-1H-pyrazol-3'-yl)acetic acid;

1-(4'-Methoxyphenyl)-3-bromomethyl-1H-pyrazole-5-N-(2'-aminosulfonyl-[1,1']-biphen-4-yl)carboxyamide;

1-(4'-Methoxyphenyl)-3-aminomethyl-1H-pyrazole-5-N-(2'-aminosulfonyl-[1,1']-biphen-4-yl)carboxyamide;

1-(4'-Methoxyphenyl)-3-(N-methylsulfonylamino)methyl-1H-pyrazole-5-N-(2'-aminosulfonyl-[1,1']-biphen-4-yl)carboxyamide;

1-(4'-Methoxyphenyl)-3-(imidazol-1-yl)methyl-1H-pyrazole-5-N-(2'-aminosulfonyl-[1,1']-biphen-4-yl)carboxyamide;

1-(4'-Methoxyphenyl)-3-hydroxylmethyl-1H-pyrazole-5-N-(2'-aminosulfonyl-[1,1']-biphen-4-yl)carboxyamide;

1-(4'-Methoxyphenyl)-3-trifluoroacetylhydroxylmethyl-1H-pyrazole-5-N-(2'-aminosulfonyl-[1,1']-biphen-4-yl)carboxyamide;

1-(4'-Methoxy-2'-methoxycarbonylphenyl)-3-trifluoromethyl-1H-pyrazole-5-N-(2'-methylsulfonyl-[1,1']-biphen-4-yl)carboxyamide;

1-(4'-Methoxy-2'-hydroxycarbonylphenyl)-3-trifluoromethyl-1H-pyrazole-5-N-(2'-methylsulfonyl-[1,1']-biphen-4-yl)carboxyamide;

1-(4'-Methoxy-2'-methoxycarbonylphenyl)-3-trifluoromethyl-1H-pyrazole-5-N-(2'-aminosulfonyl-[1,1']-biphen-4-yl)carboxyamide;

1-(4'-Methoxy-2'-hydroxycarbonylphenyl)-3-trifluoromethyl-1H-pyrazole-5-N-(2'-tert-butylaminosulfonyl-[1,1']-biphenyl)carboxyamnide;

1-(4'-Methoxy-2'-hydroxycarbonylphenyl)-3-trifluoromethyl-1H-pyrazole-5-N-(2'-aminosulfonyl-[1,1']-biphen-4-yl)carboxyamide;

1-(4'-Methoxy-2'-hydroxylmethylphenyl)-3-trifluoromethyl-1H-pyrazole-5-N-(2'-aminosulfonyl-[1,1']-biphen-4-yl)carboxyamide;

1-(4'-Methoxyphenyl)-3-methyl-1H-pyrazole-5-N-(4'-sec-butyl)phenyl)carboxyamide;

1-(4'-Methoxyphenyl)-3-methyl-1H-pyrazole-5-N-(4'-(3"-methyl-3"-pyrazolin-5"-one-2"-yl)phenyl)carboxyamide;

1-(4'-Methoxyphenyl)-3-methyl-1H-pyrazole-5-N-(4'-(6"-methylbenzothiazol-2"-yl)phenyl)carboxyamide;

1-(4'-Methoxyphenyl)-3-methyl-1H-pyrazole-5-N-(3',4'-dibromophenyl)carboxyamide;

1-(4'-Methoxyphenyl)-3-methyl-1H-pyrazole-5-N-(4'-n-butyl)phenyl)carboxyamide;

1-(4'-Methoxyphenyl)-3-methyl-1H-pyrazole-5-N-(4'-(4"-methylpiperidino)phenyl)carboxyamide;

1-(4'-Methoxyphenyl)-3-methyl-1H-pyrazole-5-N-(4'-(2"-methylimidazol-1"-yl)phenyl)carboxyamide;

3-Trifluoromethyl-1-(4-methoxyphenyl)-1H-pyrazole-5-(N-(4-carboxy(N-methylimidazo-2-yl)phenyl)carboxyamide;

3-Trifluoromethyl-1-(4-methoxyphenyl)-1H-pyrazole-5-(N-(4-hydroxymethyl(2-(imidazol-2-yl)phenyl)))carboxyamide;

3-Trifluoromethyl-1-(4-methoxyphenyl)-1H-pyrazole-5-(N-(4-hydroxymethyl(2-(1-benzyl-imidazol-2-yl)phenyl)))carboxyamide;

1-(4-Methoxyphenyl)-3-trifluoromethyl-1H-pyrazole-5-(N-(4-(2-carboxy(imidazol-2-yl)phenyl)))carboxyamide;

3-Trifluoromethyl-1-(4-methoxyphenyl)-1H-pyrazole-5-(N-(4-(N-(4-methoxyphenyl)amino-(2-thiazolyl)methyl)phenyl)))carboxyamide;

1-(4-Methoxyphenyl)-3-trifluoromethyl-1H-pyrazole-5-(N-(4-(2-carboxy-(4,5-dihyrothiazol-2-yl)phenyl)))carboxyamide;

1-(4-Methoxyphenyl)-3-trifluoromethyl-1H-pyrazole-5-N-4-(2-(4',5'-dihydro-1'H-imidazol-2'yl)phenyl)carboxyamide;

1-(4-Methoxyphenyl)-3-trifluoromethyl-1H-pyrazole-5-N-(4-(N-2'-aminoethylenecarboxyamide)phenyl)carboxyamide;

1-(4-Methoxyphenyl)-3-trifluoromethyl-1H-pyrazole-5-[4-(1,4,5,6-tetrahydro-pyrimid-2-yl)-phenyl]carboxyamide;

1-(4-Methoxyphenyl)-3-trifluoromethyl-1H-pyrazole-5-[4-(N-methyl-4,5,6-trihydro-pyrimid-2-yl)-phenyl]carboxyamide;

1-(4-Methoxyphenyl)-3-trifluoromethyl-1H-pyrazole-5-N-1-(2-fluoro-4-imadazolinephenyl)carboxyamide;

1-(4-Methoxyphenyl)-3-1-trifluoromethyl-1H-pyrazole-5-N-1-(2-fluoro-4-N-methylimadazolinephenyl)carboxyamide;

1-(4-Methoxyphenyl)-3-trifluoromethyl-1H-pyrazole-5-N-[4-(4,5-dihydro-1-N-methyl-imidazo-2-yl)phenyl]carboxyamide;

1-(4-Methoxyphenyl)-3-trifluoromethyl-1H-pyrazole-5-N-[4-carbonylguanidine)phenyl]carboxyamide;

1-(4-Methoxyphenyl)-3-trifluoromethyl-1H-pyrazole-5-N-[4-(pyrimidin-2-yl)phenyl]carboxyamide;

[2-(Carboxyamide)-4-[(4-methoxy)phenyl]-5-[(2'-aminosulfonyl-[1,1']-biphen-4-yl)carboxyamide]thiazole;

2-(2-Methoxyethylamino)-4-[(4-methoxy)phenyl]-5-[(2'-aminosulfonyl-[1,1']-biphen-4-yl)carboxyamide]thiazole;

2-(3-Hydroxypropylamino)-4-[(4-methoxy)phenyl]-5-[(2'-aminosulfonyl-[1,1']-biphen-4-yl)carboxyamide]thiazole;

2-(2-Cyanoethylamino)-4-[(4-methoxy)phenyl]-5-[(2'-aminosulfonyl-[1,1']-biphen-4-yl)carboxyamidelthiazole;

2-(3-Methoxypropylamino)-4-[(4-methoxy)phenyl]-5-[(2'-aminosulfonyl-[1,1']-biphen-4-yl)carboxyamide]thiazole;

2-(N-b-Alanyl)-4-[(4-methoxy)phenyl]-5-[(2'-aminosulfonyl-[1,1']-biphen-4-yl)carboxyamide]thiazole;

2-(Isopropylamino)-4-[(4-methoxy)phenyl]-5-[(2'-aminosulfonyl-[1,1']-biphen-4-yl)carboxyamide]thiazole;

2-(1,3-Dihydroxy-2-propylamino)-4-[(4-methoxy)phenyl]-5-[(2'-aminosulfonyl-[1,1']-biphen-4-yl)carboxyamide]thiazole;

2-[(Methoxycarbonyl)methylamino]-4-[(4-methoxy)phenyl]-5-[(2'-aminosulfonyl-[1,1']-biphen-4-yl)carboxyamide]thiazole;

2-(N-Glycyl)-4-[(4-methoxy)phenyl]-5-[(2'-aminosulfonyl-[1,1']-biphen-4-yl)carboxyamide]thiazole;]

1-[(4-Methoxy)phenyl]-3-(ethoxycarbonyl)-1H-pyrazole-5-[(4-(N-pyrrolidinocarbonyl)phenyl)carboxyamide;

1-[(4-Methoxy)phenyl]-3-(carboxyamide)-1H-pyrazole-5-[(4-(N-pyrrolidinocarbonyl)phenyl)carboxyamide;

1-[(4-Methoxy)phenyl]-3-[(2-hydroxyethyl)carboxyamide]-1H-pyrazole-5-[(4-(N-pyrrolidinocarbonyl)phenyl)carboxyamide;

1-[(4-Methoxy)phenyl]-1H-pyrazole-5-[(4-(N-pyrrolidinocarbonyl)phenyl)carboxyamide-3-hydroxamic acid;

1-[(4-Methoxy)phenyl]-3-[phenylcarboxyamide]-1H-pyrazole-5-[(4-(N-pyrrolidinocarbonyl)phenyl)carboxyamide;

1-[(4-Methoxy)phenyl]-3-[(3-hydroxypropyl)carboxyamide]-1H-pyrazole-5-[(4-(N-pyrrolidinocarbonyl)phenyl)carboxyamide;

1-[(4-Methoxy)phenyl]-3-[methylcarboxyamide]-1H-pyrazole-5-[(4-(N-pyrrolidinocarbonyl)phenyl)carboxyamide;

1-[(4-Methoxy)phenyl]-3-[(benzyl)carboxyamide]-1H-pyrazole-5-[(4-(N-pyrrolidinocarbonyl)phenyl)carboxyamide;

1-[(4-Methoxy)phenyl]-3-[(dimethyl)carboxyamide]-1H-pyrazole-5-[(4-(N-pyrrolidinocarbonyl)phenyl)carboxyamide;

1-[(4-Methoxy)phenyl]-3-[(phenylethyl)carboxyamide]-1H-pyrazole-5-[(4-(N-pyrrolidinocarbonyl)phenyl)carboxyamide;

1-[(4-Methoxy)phenyl]-3-[(2-hydroxyphenyl)carboxyamide]-1H-pyrazole-5-[(4-(N-pyrrolidinocarbonyl)phenyl)carboxyamide;

1-[(4-Methoxy)phenyl]-3-[(3-hydroxyphenyl)carboxyamide]-1H-pyrazole-5-[(4-(N-pyrrolidinocarbonyl)phenyl)carboxyamide;

1-[(4-Methoxy)phenyl]-3-[(4-hydroxyphenyl)carboxyamide]-1H-pyrazole-5-[(4-(N-pyrrolidinocarbonyl)phenyl)carboxyamide;

1-[(4-Methoxy)phenyl]-3-[(methoxycarbonyl)amino]-1H-pyrazole-5-[(2'-aminosulfonyl-[1,1']-biphen-4-yl)carboxyamide;

1-[(4-Methoxy)phenyl]-3-amino-1H-pyrazole-5-[(2'-aminosulfonyl-[1,1']-biphen-4-yl)carboxyamide;

1-[(4-Methoxy)phenyl]-3-[(methoxycarbonyl)methylamino]-1H-pyrazole-5-[(2'-aminosulfonyl-[1,1']-biphen-4-yl)carboxyamide;

1-[(4-Methoxy)phenyl]-3-[(2-hydroxy)ethylamino]-1H-pyrazole-5-[(2'-aminosulfonyl-[1,1']-biphen-4-yl)carboxyamide;

1-[(4-Methoxy)phenyl]-3-[E-2-(methoxycarbonyl)ethenyl]-1H-pyrazole-5-[(2'-aminosulfonyl-[1,1']-biphen-4-yl)carboxyamide;

1-[(4-Methoxy)phenyl]-3-[2-(methoxycarbonyl)ethyl]-1H-pyrazole-5-[(2'-aminosulfonyl-[1,1']-biphen-4-yl)carboxyamide;

1-[(4-Methoxy)phenyl]-3-[E-2-(carboxy)ethenyl]-1H-pyrazole-5-[(2'-aminosulfonyl-[1,1']-biphen-4-yl)carboxyamide;

1-[(4-Methoxy)phenyl]-3-[2-(carboxy)ethyl]-1H-pyrazole-5-[(2'-aminosulfonyl-[1,1']-biphen-4-yl)carboxyamide;

1-[(4-Methoxy)phenyl]-3-[E-2-(carboxyamide)ethenyl]-1H-pyrazole-5-[(2'-aminosulfonyl-[1,1']-biphen-4-yl)carboxyamide;

1-[(4-Methoxy)phenyl]-3-[E-2-(hydroxymethyl)ethenyl]-1H-pyrazole-5-[(2'-aminosulfonyl-[1,1']-biphen-4-yl)carboxyamide;

1-[(4-Methoxy)phenyl]-3-(3-hydroxypropyl)-1H-pyrazole-5-[(2'-aminosulfonyl-[1,1']-biphen-4-yl)carboxyamide;

1-[(4-Methoxy)phenyl]-3-propyl-1H-pyrazole-5-[(2'-aminosulfonyl-[1,1']-biphen-4-yl)carboxyamide;

1-[(4-Methoxy)phenyl]-3-(trifluoromethyl)-4-cyano-1H-pyrazole-5-[(2'-methylsulfonyl-3-fluoro-[1,1']-biphen-4-yl)carboxyamide;

1-[(4-Methoxy)phenyl]-3-(trifluoromethyl)-4-(amidino)-1H-pyrazole-5-[(2'-methylsulfonyl-3-fluoro-[1,1']-biphen-4-yl)carboxyamide;

1-[(4-Methoxy)phenyl]-3-(trifluoromethyl)-4-(N-hydroxyamidino)-1H-pyrazole-5-[(2'-methylsulfonyl-3-fluoro-[1,1']-biphen-4-yl)carboxyamide;

1-[(4-Methoxy)phenyl]-3-(trifluoromethyl)-4-(ethoxycarbonyl)-1H-pyrazole-5-[(2'-methylsulfonyl-3-fluoro-[1,1']-biphen-4-yl)carboxyamide; and, 1-[(4-Methoxy)phenyl]-3-(trifluoromethyl)-1H-pyrazole-5-[(2'-methylsulfonyl-3-fluoro-[1,1']-biphen-4-yl)carboxyamide-4-carboxylic acid; and pharmaceutically acceptable salts thereof.

6. A compound of formula II:

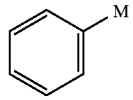

II or a stereoisomer or pharmaceutically acceptable salt form thereof, wherein;

M is selected from the group:

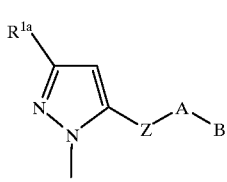

$t_1$

Z is selected from C(O)CH$_2$ and C(O)NR$^3$;

R$^{1a}$ is —(CH$_2$)$_r$—R$^{1'}$;

R$^{1'}$ is selected from H, C$_{1-3}$ alkyl, F, Cl, Br, CH(CH$_2$OR$^2$)$_2$, (CF$_2$)$_r$CF$_3$, (CH$_2$)$_r$OR$^2$, NR$^2$R$^{2a}$, S(O)$_p$R$^{2b}$, NR$^2$(CH$_2$)$_r$OR$^2$, NR$^2$C(O)R$^{2b}$, C(O)NR$^2$R$^{2a}$, C(O)NR$^2$(CH$_2$)$_r$OR$^2$, and SO$_2$NR$^2$R$^{2a}$;

R$^2$, at each occurrence, is selected from H, CF$_3$, C$_{1-6}$ alkyl, benzyl, C$_{3-6}$ carbocyclic group substituted with 0–2 R$^4$, and 5–6 membered heterocyclic group containing from 1–4 heteroatoms selected from the group consisting of N, O, and S substituted with 0–2 R$^4$;

R$^{2a}$, at each occurrence, is selected from H, CF$_3$, C$_{1-6}$ alkyl, benzyl, C$_{3-6}$ carbocyclic group substituted with 0–2 R$^4$, and 5–6 membered heterocyclic group containing from 1–4 heteroatoms selected from the group consisting of N, O, and S substituted with 0–2 R$^4$;

R$^{2b}$, at each occurrence, is selected from CF$_3$, C$_{1-4}$ alkoxy, C$_{1-6}$ alkyl, C$_{3-6}$ carbocyclic group substituted with 0–2 R$^4$, and 5–6 membered heterocyclic group containing from 1–4 heteroatoms selected from the group consisting of N, O, and S substituted with 0–2 R$^4$;

alternatively, R$^2$ and R$^{2a}$, together with the atom to which they are attached, combine to form a 5 or 6 membered saturated, partially saturated or unsaturated ring substituted with 0–2 R⁴ which contains from 0–1 additional heteroatoms selected from the group consisting of N, O, and S;

R³, at each occurrence, is selected from H, $C_{1-4}$ alkyl, and phenyl;

A is selected from phenyl, pyridyl, and pyrimidyl, and A is substituted with 0–2 R⁴;

B is selected from: H and Y;

Y is selected from phenyl, pyridyl, tetrazolyl, and morpholino, and Y is substituted with 0–2 $R^{4a}$;

R⁴, at each occurrence, is selected from F, Cl, Sr, I, $C(O)NR^2R^{2a}$, and $(CF_2)_rCF_3$;

$R^{4a}$, at each occurrence, is selected from F, Cl, Br, I, $C_{1-4}$ alkyl, $C(O)NR^2R^{2a}$, $SO_2NR^2R^{2a}$, $NR^2SO_2$—$C_{1-4}$ alkyl, $S(O)_pR^5$, and $(CF_2)_rCF_3$;

R⁵, at each occurrence, is selected from $CF_3$, $C_{1-6}$ alkyl, phenyl, and benzyl;

p is selected from 0, 1, and 2; and, r is selected from 0, 1, 2, and 3.

7. A compound according to claim 6, wherein the compound is selected from:

3-Methyl-1-phenyl-1H-pyrazole-5-(N-(2-aminosulfonyl-[1,1']-biphen-4-yl)carboxyamide;

[2-Amino-4-phenyl-5-[(2'-aminosulfonyl-[1,1']-biphen-4-yl)aminocarbonyl]thiazole; and, 2-Chloro-4-phenyl-5-[(2'-aminosulfonyl-[1,1']-biphen-4-yl) aminocarbonyl[thiazole;]

and pharmaceutically acceptable salts thereof.

8. A pharmaceutical composition, comprising: a pharmaceutically acceptable carrier and a therapeutically effective amount of a compound according to claim 1 or a pharmaceutically acceptable salt thereof.

9. A pharmaceutical composition, comprising: a pharmaceutically acceptable carrier and a therapeutically effective amount of a compound according to claim 2 or a pharmaceutically acceptable salt thereof.

10. A pharmaceutical composition, comprising: a pharmaceutically acceptable carrier and a therapeutically effective amount of a compound according to claim 3 or a pharmaceutically acceptable salt thereof.

11. A pharmaceutical composition, comprising: a pharmaceutically acceptable carrier and a therapeutically effective amount of a compound according to claim 4 or a pharmaceutically acceptable salt thereof.

12. A pharmaceutical composition, comprising: a pharmaceutically acceptable carrier and a therapeutically effective amount of a compound according to claim 5 or a pharmaceutically acceptable salt thereof.

13. A pharmaceutical composition, comprising: a pharmaceutically acceptable carrier and a therapeutically effective amount of a compound according to claim 6 or a pharmaceutically acceptable salt thereof.

14. A pharmaceutical composition, comprising: a pharmaceutically acceptable carrier and a therapeutically effective amount of a compound according to claim 7 or a pharmaceutically acceptable salt thereof.

15. A method for treating a thromboembolic disorder, comprising: administering to a patient in need thereof a therapeutically effective amount of a compound according to claim 1 or a pharmaceutically acceptable salt thereof.

16. A method for treating a thromboembolic disorder, comprising: administering to a patient in need thereof a therapeutically effective amount of a compound according to claim 2 or a pharmaceutically acceptable salt thereof.

17. A method for treating a thromboembolic disorder, comprising: administering to a patient in need thereof a therapeutically effective amount of a compound according to claim 3 or a pharmaceutically acceptable salt thereof.

18. A method for treating a thromboembolic disorder, comprising: administering to a patient in need thereof a therapeutically effective amount of a compound according to claim 4 or a pharmaceutically acceptable salt thereof.

19. A method for treating a thromboembolic disorder, comprising: administering to a patient in need thereof a therapeutically effective amount of a compound according to claim 5 or a pharmaceutically acceptable salt thereof.

20. A method for treating a thromboembolic disorder, comprising: administering to a patient in need thereof a therapeutically effective amount of a compound according to claim 6 or a pharmaceutically acceptable salt thereof.

21. A method for treating a thromboembolic disorder, comprising: administering to a patient in need thereof a therapeutically effective amount of a compound according to claim 7 or a pharmaceutically acceptable salt thereof.

22. A compound according to claim 5, wherein the pharmaceutically acceptable salt is selected from: hydrochloric acid salt, hydrobromic acid salt, sulfuric acid salt, phosphoric acid salt, acetic acid salt, succinic acid salt, glycolic acid salt, stearic acid salt, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

23. A compound according to claim 7, wherein the pharmaceutically acceptable salt is selected from: hydrochloric acid salt, hydrobromic acid salt, sulfuric acid salt, phosphoric acid salt, acetic acid salt, succinic acid salt, glycolic acid salt, stearic acid salz, lactic acid salt, malic acid salt, tartaric acid salt, citric acid salt, ascorbic acid salt, maleic acid salt, fumaric acid salt, toluenesulfonic acid salt, methanesulfonic acid salt, and oxalic acid salt.

* * * * *